United States Patent
Aitman et al.

(10) Patent No.: US 6,322,976 B1
(45) Date of Patent: Nov. 27, 2001

(54) COMPOSITIONS AND METHODS OF DISEASE DIAGNOSIS AND THERAPY

(75) Inventors: Timothy J. Aitman; James Scott, both of London (GB); Lawrence W. Stanton, Redwood City, CA (US)

(73) Assignees: Medical Research Council, London (GB); SCIOS, Inc., Sunnyvale, CA (US)

( * ) Notice: Subject to any disclaimer, the term of this patent is extended or adjusted under 35 U.S.C. 154(b) by 0 days.

(21) Appl. No.: 09/270,542

(22) Filed: Mar. 17, 1999

Related U.S. Application Data

(63) Continuation-in-part of application No. 09/221,222, filed on Dec. 23, 1998, which is a continuation-in-part of application No. 09/167,750, filed on Oct. 7, 1998, which is a continuation-in-part of application No. 09/086,047, filed on May 28, 1998.

(51) Int. Cl.$^7$ .......................... C12Q 1/68; G01N 33/574; C07H 21/02; C07H 21/04; C07H 21/00
(52) U.S. Cl. .......................... 435/6; 435/7.23; 536/23.1; 536/24.3; 536/24.31
(58) Field of Search ..................... 435/6, 7.23; 536/23.5, 536/23.1, 24.3, 24.31

(56) References Cited

U.S. PATENT DOCUMENTS

| | | | |
|---|---|---|---|
| 5,190,856 | 3/1993 | Borresen | 435/6 |
| 5,338,839 | * 8/1994 | McCay et al. | 536/23.5 |
| 5,420,030 | * 5/1995 | Reitz et al. | 435/235.1 |
| 5,506,126 | * 4/1996 | Seed et al. | 435/6 |
| 5,580,859 | 12/1996 | Felgner et al. | 514/14 |
| 5,629,158 | * 5/1997 | Uhlen | 435/6 |
| 5,834,183 | * 11/1998 | Orr et al. | 435/6 |
| 5,837,832 | * 11/1998 | Chee et al. | 536/22.1 |
| 5,871,931 | * 2/1999 | Kleyn et al. | 435/6 |
| 5,992,926 | * 3/1999 | Amara et al. | 435/325.1 |

FOREIGN PATENT DOCUMENTS

| | | |
|---|---|---|
| 2019408 | 10/1979 | (GB) . |
| WO84/03564 | 9/1984 | (WO) . |
| 95/11995 | * 4/1995 | (WO) . |

OTHER PUBLICATIONS

Abel, et al., *Genomics*, 17:632–641 (1993).
Abumrad, et al., *J. Biol. Chem.*, 24:17665–17668 (1993).
Abumrad, et al., *Am. J. Physiol.*, 261:E76–E86 (1991).
Ahlbom, et al., *Hum. Genet.*, 99:186–190 (1997).
Aitman, et al., *Arterioscler. Thromb. Vasc. Biol.*, 17:748–754 (1997).
Aitman, et al., *Nature Genetics*, 16:197–201 (1997).
Armesilla and Vega, *J. Biol. Chem.*, 269:18385–18991 (1994).
Arnheiter, et al., *Nature*, 294:278–280 (1981).
Beckers, et al., *Genomics*, 23:685–690 (1994).
Benham, et al., *Genomics*, 4:509–517 (1989).
Boersma and Van Leeuwen, *J. Neurosci. Methods*, 51:317 (1994).
Bottger, et al., *J. Clin. Invest.*, 98:856–862 (1996).
Burmesiter, et al., *Genomics*, 9:19–30 (1991).
Butler, *Methods Enzymol*, 73:482–523 (1981).
Casadaban and Cohen, *Proc. Natl. Acad. Sci. USA*, 76:4530 (1979).
Casadaban, et al., *J. Bacteriol.*, 143:971 (1980).
Castro–Cabezas, et al., *J. Clin. Invest.*, 92:160–168 (1993).
Cecchereini, et al., *Proc. Natl. Acad. Sci. USA*, 89:104–108 (1992).
Chagnon and Bouchard, *Trends Genet.*, 12:441–444 (1996).
Chiappe de Cingolani, *Metabolism*, 37:318–322 (1988).
Chin, et al., *Genomics*, 13:1325–1327 (1992).
Clarke and Woodland, *Rheumatol. Rehabil.*, 14:47–49 (1975).
Cohen, et al., *Science*, 274:1185–1188 (1996).
Contreras, et al., *Methods Enzymol.*, 92:277–292 (1983).
Cox, et al., *Science*, 250:245–250 (1990).
Curtis and Aster, *Transfusion*, 36:331–334 (1996).
Dohi, et al., *Hypertension*, 28:732–737 (1996).
Drmanac, et al., *Science*, 260(5114):1649–1652 (1993).
Dubay, et al., *Nature Genetics*, 3:354–357 (1993).
Dymecki, et al., *J. Biol. Chem.*, 267:4815–4823 (1992).
Ellison, et al., *Biotechniques*, 15:684 (1993).
Elsner, et al., *Curr. Opin. Card.*, 10:153–159 (1995).
Endemann, et al., *J. Biol. Chem.*, 268:11811–11816 (1993).
Evans, et al., *J. Clin. Invest.*, 74:1515–1525.
Faham, et al., *Genome Res.*, 5:474 (1995).
Feldman, et al., *Circ. Res.*, 73:184–192 (1993).
Felley–Bosco, et al., *Nucleic Acids Res.*, 19:2913–2919 (1991).
Ferrannini, et al., *N. Engl. J. Med.*, 317:350–357.
Galli, et al., *Nature Genetics*, 12:31–37 (1996).
Gauguier, et al., *Nature Genetics*, 12:38–43 (1996).
Glavac, et al., *Hum. Mut.*, 2:404 (1993).
Goldmuntz, et al., *Mamm. Genome*, 6:459–463 (1995).
Gossler, et al., *Science*, 244:463 (1989).
Pourzand and Cerutti, *Mutat. Res.*, 288(1):113–121 (1993).

(List continued on next page.)

*Primary Examiner*—Andrew Wang
*Assistant Examiner*—Jane Zara
(74) *Attorney, Agent, or Firm*—Palmer & Dodge, LLP; Kathleen M. Williams

(57) ABSTRACT

The invention pertains to isolated nucleic acid molecules containing sequences specified herein, to mutant CD36 genes and their encoded gene products, to methods of screening blood or a blood product by detecting a CD36 gene mutation, methods of administering blood or a blood product based on the presence or absence of a CD36 gene mutation, to methods of matching a biological sample donor with a recipient based on detection of a mutation in the CD36 gene, methods of determining the resistance of a patient to infection by a parasite by detecting a CD36 gene mutation, methods of diagnosing a disease associated with a defect in insulin action, glucose metabolism, fatty acid metabolism, and/or catecholamine action by detecting a mutation in the CD36 gene, and methods of disease treatment by altering the mutation(s).

18 Claims, 30 Drawing Sheets

OTHER PUBLICATIONS

Figure 1:
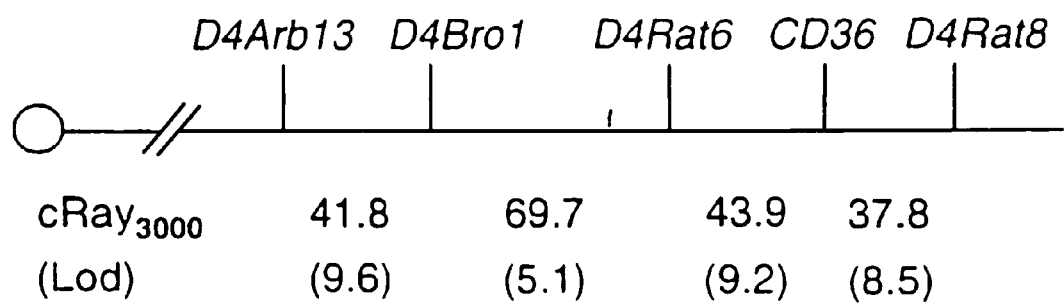

Pravenac, et al., *J. Clin. Invest.*, 96:1973–1978 (1995).
Rao, *Diabetes*, 42:1364–1371 (1993).
Reaven, et al., *Diabetes*, 38:1155–1160 (1989c).
Reaven, et al., *N. Engl. J. Med.*, 334:374–381 (1996).
Reaven, et al., *Diabetes*, 37:1020–1024 (1988b).
Reaven, *Diabetes*, 37:1595–1607 (1988a).
Reynisdottir, et al., *J. Clin. Invest.*, 95:2163–2169 (1995).
Reynisdottir, et al., *Diabetologia*, 37:428–435 (1994).
Richard, et al., *Am. J. Hum. Genet.*, 49:1189–1196 (1991).
Reiss, et al., *Genomics*, 19:298–302 (1994).
Roberge, et al., *Science*, 269:202 (1995).
Rodbell, *J. Biol. Chem.*, 239:375–380 (1964).
Scherrer, *J. Clin. Invest.*, 94:2511–2515 (1994).
Schmitt, et al., *Genomics*, 34:193–197 (1996).
Sheffield, et al., *Genomics*, 16:325 (1993).
Sikes, et al., *Human Gene Ther.*, 5:837–844 (1994).
Simon, et al., *Mamm. Genome*, 7:380–382 (1996).
Skarnes, *Biotechnology*, 8:827 (1990).
Stanton, et al., *J. Biol. Chem.*, 267:22446–22451 (1992).
Stoffers, et al., *Nature Genetics*, 15:106–110.
Sullivan, *J. Invest. Dermatol.*, 103:85S–98S (1994).
Talle, et al., *Cellular Immunol.*, 78:83–99 (1983).
Tontonoz, et al., *Cell*, 93:241–252 (1998).
Tontonoz, et al., *Cell*, 79:1147–1156 (1994).
Usman, et al., *Curr. Opin. Struct. Biol.*, 6:527–533 (1996).
van Nieuwenhoven, et al., *BBRC*, 207:747–752 (1995).
Vesselinovitch and Wissler, *Adv. Exp. Med. Biol.*, 82:614–622 (1977).
Vile, et al., *Cancer Res.*, 53:962–967 (1993).
Voller, et al., *J. Clin. Pathol.*, 31:507–520 (1978).
Warrington, et al., *Genomics*, 13:803–808 (1992).
Warrington, et al., *Genomics*, 11:701–708 (1991).
Wolff, et al., *Science*, 247:1465–1468 (1990).
Yamada, et al, *Mamm. Genome*, 5:63–83 (1994).
Green, et al., *Cell*, 28:477–487 (1982).
Greenwalt, et al., *Blood*, 80:1105 (1992).
Handunnetti, et al., *Blood*, 80:2097 (1992).
Hengge, et al., *Nature Genet.*, 10:161–166 (1995).
Hickman, et al., *Human Gene Therapy*, 5:1477–1483 (1994).
Hongo, et al., *Trends Cardiovasc. Med.*, 7:161–167 (1997).
Huang, et al., *Nature*, 377:239–242 (1995).
Hubbard, et al., *J. Clin. Invest.*, 84:1349–1354 (1989).
Hubner, et al., *Mamm. Genome*, 6:758–759 (1995).
Hunt, et al., *Arteriosclerosis*, 9:335–344 (1989).
Ibrahimi, et al., *Proc. Natl. Acad. Sci. USA*, 93:2646–2651 (1996).
Jacob, et al., *Cell*, 67:213–224.
Kanehisa, *Nucleic Acid Res.*, 12:203 (1984).
Kaplan, *Arch. Intern. Med.*, 149:1514–1520 (1989).
Khrapko, et al., *Nucleic Acids Res.*, 22[3]:364 (1994).
Klocke, et al., *Genomics*, 18:568–574 (1993).
Kovacs and Koting, *Arch. Biochem. Biophys.*, 354:139–143 (1998).
Levak–Frank, et al., *J. Clin. Invest.*, 96:976–986 (1995).
Lipsky, et al., *Hum. Mol. Genet.*, 3:217 (1994).
Lisitsyn, et al., *Nature Genet.*, 6:57 (1993).
Lisitsyn, et al. *Science*, 259:946 (1993).
Makino, et al., *PCR Methods Appl.*, 2:10 (1992).
Martin and Jensen, *J. Clin. Invest.*, 88:609–613.
McGarry, *Science*, 258:766–770 (1992).
Meyer, et al., *Gene Therapy*, 2:450–460 (1995).
Mugasimangalam, et al., *Nucleic Acids Res.*, 25:800–805 (1997).
Mullis and Faloona, *Methods Enzymol.*, 155:335–350 (1987).
Nagy, et al., *Cell*, 93:229–240 (1998).
Oquendo, et al., *Cell*, 58:95 (1989).
Paternosro, *Cardiovasc. Res.*, 30:205–211 (1995).
Pfeffer, et al., *Circ. Res.*, 44:503–512 (1979).
Polonsky, et al., *N. Engl. J. Med.*, 334:777–783 (1995).

* cited by examiner

| Best Order | log(LR)<1 | log(LR)<2 | log(LR)<3 | |
|---|---|---|---|---|
| ILG6 | 27 | 27 | 27 | 27 |
| D4Rat133 | 26 | 26 | 26 | 26 |
| D4Rat4 | 25 | 25 | 25 | 25 |
| D4Arb13 | 24 | 24 | 24 | 24 |
| D4Rat139 | 23 | 23 | 23 | 23 |
| D4Rat2 | 22 | 22 | 22 | 22 |
| D4Rat3 | 21 | 21 | 21 | 21 |
| D4Rat142 | 20 | 20 | 20 | 20 |
| Slc4a2 | 19 | 19 | 19 | 19 |
| D9Bro1 | 18 | 18 | 18 | 18 |
| Nos3 | 17 | 17 | 17 | 17 |
| D4Rat1 | 16 | 16 | 16 | 16 |
| D4Rat136Psmc2 | 15 | 15 | 15 | 15 |
| Fgl2 | 14 | 14 | 14 | 14 |
| D4Rat5 | 13 | 13 | 13 | 13 |
| D4Rat6 | 12 | 12 | 12 | 12 |
| D4Rat7 | 11 | 11 | 11 | 11 |
| D4Rat8 | 10 | 10 | 10 | 10 |
| D4Mgh1 | 9 | 9 | 9 | 9 |
| Cacna2 | 8 | 8 | 8 | 8 |
| D4Rat149 | 7 | 7 | 7 | 7 |
| D4Rat150 | 6 | 6 | 6 | 6 |
| D4Rat125 | 5 | 5 | 5 | 5 |
| Pgy1 | 4 | 4 | 4 | 4 |
| D4Rat9 | 3 | 3 | 3 | 3 |
| D4Rat126 | 2 | 2 | 2 | 2 |
| D4Rat10 | 1 | 1 | 1 | 1 |

FIG. 7

FIG. 9A

| | |
|---|---|
| Tyr Leu Ala Lys Glu Asn Ile Thr Gln | [SEQ ID NO: 2] |
| Tyr Leu Ala Lys Glu Asn Ile Thr Gln | [SEQ ID NO: 4] |
| Tyr Leu Ala Lys Glu Ser Ile Thr Gln | [SEQ ID NO: 6] |
| Thr Gln Asp Pro Lys Asp Ser Thr Val | [SEQ ID NO: 8] |
| Thr Gln Asp Pro Lys Asp Ser Thr Val | [SEQ ID NO: 10] |
| Thr Gln Asp Pro Lys Asp Ser Thr Val | [SEQ ID NO: 12] |
| Leu Ala Val Ala Ala Ala Pro His Ile Tyr | [SEQ ID NO: 14] |
| Leu Ala Val Ala Ala Ala Pro His Ile Tyr | [SEQ ID NO: 16] |
| Leu Ala Val Ala Ala Val Pro His Ile Tyr | [SEQ ID NO: 18] |
| His Ile Tyr Thr Asn Ser Phe Val Gln | [SEQ ID NO: 20] |
| His Ile Tyr Thr Asn Ser Phe Val Gln | [SEQ ID NO: 22] |
| His Ile Tyr Gln Asn Ser Phe Phe Gln | [SEQ ID NO: 24] |
| Gln Thr His Leu Phe Lys Val Cys Ser | [SEQ ID NO: 26] |
| Gln Thr His Leu Phe Lys Val Cys Ser | [SEQ ID NO: 28] |
| Gln Asn Ser Phe Phe Gln Gly Val Leu Asn | [SEQ ID NO: 30] |
| Val Leu Asn Ser Leu Ile Lys Lys Ser | [SEQ ID NO: 32] |
| Val Leu Asn Ser Leu Ile Lys Lys Ser | [SEQ ID NO: 34] |
| Val Leu Asn Ile Phe Ile Lys Lys Ser | [SEQ ID NO: 36] |
| Val Leu Asn Ser Leu Ile Lys Lys Ser | [SEQ ID NO: 38] |
| Val Leu Asn Ser Leu Ile Lys Lys Ser | [SEQ ID NO: 40] |
| Val Leu Asn Ile Phe Ile Lys Lys Ser | [SEQ ID NO: 42] |

FIG. 9B

```
Phe Gln Thr Arg Ser Leu Lys Glu Leu Leu    [SEQ ID NO: 44]

Phe Gln Thr Arg Ser Leu Lys Glu Leu Leu    [SEQ ID NO: 46]

Phe Gln Thr Arg Ser Leu Lys Glu Leu Leu    [SEQ ID NO: 48]

Glu Leu Leu Trp Gly Tyr Lys Asp Pro        [SEQ ID NO: 50]

Glu Leu Leu Trp Gly Tyr Lys Asp Pro        [SEQ ID NO: 52]

Glu Leu Leu Trp Gly Tyr Glu Asp Pro        [SEQ ID NO: 54]

Glu Leu Leu Trp Gly Tyr Lys Asp Pro        [SEQ ID NO: 56]

Glu Leu Leu Trp Gly Tyr Lys Asp Pro        [SEQ ID NO: 58]

Glu Leu Leu Trp Gly Tyr Glu Asp Pro        [SEQ ID NO: 60]

Leu Ser Leu Val Pro Tyr Pro Ile Ser        [SEQ ID NO: 62]

Leu Ser Leu Val Pro Tyr Pro Ile Ser        [SEQ ID NO: 64]

Leu Ser Leu Ile Pro Tyr Pro Ile Ser        [SEQ ID NO: 66]

Gly Lys Asp Asn Ile Ser Lys Val Ala        [SEQ ID NO: 68]

Gly Lys Asp Asn Ile Ser Lys Val Ala        [SEQ ID NO: 70]

Gly Lys Asp Asn Ile Ser Lys Val Ala        [SEQ ID NO: 72]

Ser Tyr Trp Glu Ser Tyr Cys Asp Met        [SEQ ID NO: 74]

Ser Tyr Trp Glu Ser Tyr Cys Asp Met        [SEQ ID NO: 76]

Ser Tyr Trp Lys Ser Tyr Cys Asp Met        [SEQ ID NO: 78]

Lys Ser Arg Thr Leu Arg Phe Phe Ser Ser    [SEQ ID NO: 80]

Lys Ser Arg Thr Leu Arg Phe Phe Ser Ser    [SEQ ID NO: 82]

Lys Ser Gln Thr Leu Arg Phe Phe Ser Ser    [SEQ ID NO: 84]
```

Arg Lys Ile Glu Ala Leu Lys Asn Leu        [SEQ ID NO: 166]

Arg Lys Ile Glu Pro Leu Lys Asn Leu        [SEQ ID NO: 168]

Cys Ala Cys Arg Ser Lys Asn Gly Lys        [SEQ ID NO: 177]

Cys Ala Cys Arg Phe Lys Asn Gly Lys        [SEQ ID NO: 141]

FIG. 9C

[SEQ ID NO: 101]                                                  FIG. 10A

```
GGATCCACTCATTTCACAAACTGTATTCTTTCTTCCAATCTTTTTTTTTTTTGAGATG
GAGTTTCACCTCTTGTTGCCCAGGCTGGAGTGCAATGGCATGATCTCGGCTCACCACAAC
CTCCGCCTCCTGGGTTCAAGCGATTCTCCTGCCTCAGCCTCCGGAGTAGCTTGGGATTAC
AAGCATGTGCCACCAAGCCCGGCTAACTTTGTATGTTTAGTAGAGATGGGGTTTCTCTGT
GTTGGTCGGGCTGGTCTCAAACTCCCAACCTCAGGTGATCCACCCGCCTCAGCCTTCCAA
AGTGCTAGGATGACAGGTGTGAGCCACCACGCCCGGCTCTCCCAATCTTTATATAATAAT
CACATACTATGGCTGGGCATGGTGGCTCACGCCTGTCATCCCAGCACTTTGGGAGGCTGA
GGTGGGTGGATCACGAGGTCAGGAGTTCGAGACCAGCCTGACCAACATGGTGAAACCCCA
TCTCTACTGAAAATACAAAAATTAACCAGGCATGGTGGCGTGCACCTGTAATCCCAGCTA
CACAGGAGGCTGAGTCAGGAGAATTGCTTGAACCCAGGAGGCAGAGGTTGCAGTGAGCCG
AGATCGTGCCACTGCACTCCAGCCTGGGTGACAGAGAAAGACTCCGTCTCAAAAAAATAA
TAATAATCACATACTTTATGAAGACACCAAACATTAGATTGACAAATATATACTAACACA
AACATCCTAATTTTAACAGAATTAGCATGAATCAACTGCAAATGACAAACTATATTGTAG
TTGAATGTGCAGGGAAAAAATTCTTCAGTAAGAGAGCAATGCCATGGTTGAAACAAGACA
TCCTCTACATTTTATATTTACTTCAAATTCTTTATACCTGTAGTCTATCCAAAGTCGTCA
ATAAAACTGAAAGTAAGATACTCTTATTTTAAAAATTCCATGTTTTAAACAGCTTTTAGG
ACAAGCCCTTCAGGCCTGAACTCAGTATTCATGAAATTAGACTTTCTTTTAACAGTTAT
TTTAAGTATGGTGATATTAGAGAGTGTCCCAGTATAAAATTTCTGAGAATTTTTTTCTA
TTTACCCATGCTTTCTTATTTTCACAGATAGCTTTCCAATGATTAGACGAATTGATTCT
TTCTGTGACTCATCAGTTCATTTCCTGTAAAATTCATGTCTTGCTGTTGATTTGTGAATA
AGGTATCGTAAATAAAACATCTGTTACCATACTTGCTTATCATTTAATGGAAAACACATC
AGTCAACCCACATTCTGTTCGCAGGAGAGCTCCAGAAGGGGTGTGGAAGGTTGTGTTGGG
TGGAGAAACCAGATAGTGAGGATGCAACTAAGTTGCTGAGACAAGGGAAGAGAGATGAGG
GTGAGAGTTCTCCTTAGATAAGATTTCAATATGTTAATCATGTGTAGAAAGAAAATTAAA
AAGGAGGAATATGAAGAAATTCAGATATGACATTATTAGTTCTGCCACTGGTAGGCATTA
GAAGCAAGAAAAGGGAGACGGACCGAGGAAGCCACTTTGGTGAAACGAAAAGCATTTGTT
TATTTAGAACGGGCAAAATGATACGTTTCAGTGGGGGTTTTCTTTGTACTTTGATCTTTT
TGTACTGATATTTAAGCTTCTGTTTTATGATCTCTTTCTAATGATAGAACCAGAGCTTGT
AGAAACCACTTTAATCATATCCAGGAGTTTGCAAGAAACAGGTGCTTAACACTAATTCAC
CTCCTGAACAAGAAAATGGGCTGTGACCGGAACTGTGGGCTCATCGCTGGGGCTGTCAT
TGGTGCTGTCCTGGCTGTGTTTGGAGGTATTCTAATGCCAGTTGGAGACCTGCTTATCCA
GAAGACAATTAAAAAGGTACAAGTAGTCCAAAGAATATGCCTTCTCATTTTGATTGATTC
TAACTTCTCTTTTTTTGCTTTGTATTTACCTGCTTTATATTTCATGGTAACTGCTAATTT
TGTATCTTTGACATAAAGGTAATTATGAACCACTGCAACTCTATATGATGTGACTTTATG
TGAAATGTTATAAGTATAATGTATATTTAACATGACTCCATTGCTGTCTTAAATATAAAT
ACCAAATTCTATTAAAAGCTGTCTACAGGTATGCATGTTAGTAGAAATAATTGTTTTAAG
TTATGTCCAAGAGCATGTTGGCATGCTTTTGAATAGGAAATAAGTGAGTATATTTTGTA
AAAGCACATTTATAAAGAAGTTGCACTTTAGTTAATACTGAGAAAAGTAAAACTGTGTG
TGTGTGTGTGTGTGTAATGTGTTTAATATTGAAACATAAATCCTTATTAAATTGTA
GGTAAACTTGTTTGGTAATACACTGTTTAGTAATCCACTATTTTTATATATGTGTAATAA
TCTCATCTCATAAATATTTTCTATTTGTGAAGCTTCATATTGGAATCTTAGAAAATACTT
```

[SEQ ID NO: 101, cont'd.]
TCAGAAATATGCAGAACATGTCTTAGTATAAAACAAATTGACTGTAGTGTGAAAAAACAG
AATGATTGAATAGATGGGCTTTGCACAACAACCTAGAATTC

[SEQ ID NO: 102]
TATTTACCCATGCTTTTCTTATTTTCACAGATAGCTTTCCAATGATTAGACGAATTGATT
CTTTCTGTGACTCATCAGTTCCTTTCCTGTAAAATTCATGTCTTGCTGTTGATTTGTGAA
TAAGGTATCGTAAATAAAACATCTGTTACCATAC

[SEQ ID NO: 103]
CTAATCATTTGCCACTCGATTTTTAAACAGATGCAGCCTCATTTCCACCTTTTGTTGAGA
AAAGCCAGGTATTGCAGTTCTTTTCTTCTGATATTTGCAGGTAAGACAGATACTGAAGTA
TAAGTATGCT

[SEQ ID NO: 104]
AAGTAACATTTTCCCATACATATATTTCAGTACAACAATACTGCAGATGGAGTTTATAAA
GTTTTCAATGGAAAAGATAACATAAGTAAAGTTGCCATAATCGACACATATAAAGGTAAA
AGGTAAGTATTCTGGTAAAATGTGCATGTATG

[SEQ ID NO: 105]
TTGTCTTAAACAGTGACTTTGTTTTTGTAGGCTGCATCCCATATCTATCAAAATCAATTT
GTTCAAATGATCCTCAATTCACTTATTAACAAGTCAAAATCTTCTATGTTCCAAGTCAGA
ACTTTGAGAGAACTGTTATGGGGCTATAGGGATCCATTTTTGAGTTTGGTTCCGTACCCT
GTTACTACCACAGTTGGTCTGTTTTATCCTGTAAGTACCAAATATGAATGGCAATATTAT

[SEQ ID NO: 106]
TTTGAATTTTGTTTACTGCTGTTTCTTTAGAGTTCGTTTTCTAGCCAAGGAAAATGTAAC
CCAGGACGCTGAGGACAACACAGTCTCTTTCCTGCAGCCCAATGGTGCCATCTTCGAACC
TTCACTATCAGTTGGAACAGAGGCTGACAACTTCACAGTTCTCAATCTGGCTGTGGCAGT
GAGTAGACAAACAACAAAGTTATCTATT

[SEQ ID NO: 107]
CATAACCCAAACTTATTTTCTTTTCCATAGCAAGTTGTCCTCGAAGAAGGTACAATTGCT
TTTAAAAATTGGGTTAAAACAGGCACAGAAGTTTACAGACAGTTTTGGATCTTTGATGTG
CAAAATCCACAGGAAGTGATGATGAACAGCAGCAACATTCAAGTTAAGCAAAGAGGTCCT
TATACGTACAGGTGAGTGAGTGCCCACAAATATGAGACACT

FIG. 10B

FIG. 10C

[SEQ ID NO: 108]
AAATAATGTTGATTATTAACTTGATTACAGACTGGGACCATTGGTGATGAGAAGGCAAAC
ATGTTCAGAAGTCAAGTAACTGGAAAAATAAACCTCCTTGGCCTGATAGAAATGATCTTA
CTCAGTGTTGGTGTGGTGATGTTTGTTGCTTTTATGATTTCATATTGTGCATGCAGATCG
AAAACAATAAAATAAGTAAGTATGTACCAAAAAATATTGCTTCAATAATATTAGCTTATA
TATTACTTGTTTTCACTTTATCAAAGAGAAGTTACATATTAGGCCATATATATTTCTAGA
CATGTCTAGCCACTGATCATTTTAAATATAGGTAAATAAACCTATAAATATTATCACGC
AGATCACTAAAGTATATCTTTAATTCTGGGAGAAATGAGATAAAAGATGTACTTGTGACC
ATTGTAACAATAGCACAAATAAAGCACTTGTGCCAAAGTTGTCCAAAATTGACTGGTTCA
TTTCTCAATTATAT

[SEQ ID NO: 109]
GTTCATAATTATTTTCAACGTATTACAGAGTATTAAAGAATCTGAAGAGGAACTATATTG
TGCCTATTCTTTGGCTTAATGAGGTTTGTATTTGCAGCTGTTAGTCATTAAAA

[SEQ ID NO: 110]
TTGGTAATTATTTAGTTGTTCTCTTTTTAGATAACTGGATTCACTTTACAATTTGCAAAA
CGGCTGCAGGTCAACCTATTGGTCAAGCCATCAGAAAAAATTCAGTGAGTCTCTTGAAAA
TGGTTATTTTGATA

[SEQ ID NO: 111]
TTCCAATTGACTCTTAAAACTTGTCTTCAGGGAGACCTGTGTACATTTCACTTCCTCATT
TTCTGTATGCAAGTCCTGATGTTTCAGAACCTATTGATGGATTAAACCCAAATGAAGAAG
AACATAGGACATACTTGGATATTGAACCTGTAAGAAAACACCTTATTGATCTGATTTGG

[SEQ ID NO: 112]
TGGAATGCAGCTCTTTTTTCTCTGTATTTAGGTCAATCTATGCTGTATTTGAATCCGACG
TTAATCTGAAAGGAATCCCTGTGTATAGATTTGTTCTTCCATCCAAGGCCTTTGCCTCTC
CAGTTGAAAACCCAGACAACTATTGTTTCTGCACAGAAAAATTATCTCAAAAATTGTA
CATCATATGGTGTGCTAGACATCAGCAAATGCAAGAAGGTGAGTAAATAACCTCAGTAG
CACAGTCCAT

[SEQ ID NO: 113]
GAGGACTGCAGTGTAGGACTTTCCTGCAGAATACCATTTGATCCTATTAAGAATTGTCCA
AATGTTGGAGCATTTGATTGAAAATCCTTCTTAGCCATTTTAAAGGTAAGTTGTATGAT
TTTTCTTTAAATAAAG

[SEQ ID NO: 114]
TGTTTATTCATTGTCTTTTTCTATTCCTAGGAATCTGTCCTATTGGGAAAGTCACTGCGA
CATGATTAATGGTACAGGTAAGAATATTTGTTTTGTGGTCATCACAG

FIG. 10D

[SEQ ID NO: 115]
CCACAACTGAATTGATTTCCGTTTCTACAGACCTGGCTCAAGCACAAACCAATTTGTGTT
GTTCTGATTCAATAATTGGTTTCTGGGTGGCCAATTCAGAAGAAGAGTGTACATGCTCAA
CAAATCCTAGGCCCTGCATTCCTGTCATCCTCATCCGGGGGAAACACCATCATCCCAGTA
GCTGCCCTATTCAACTGCAACAGTCTCCAGGACCATCAGTATACTGCATTTCATGTGCAC
CAAATATTTTGAAAGACATTTATAAATAATTGGCTTATGACTCATATTTCTCTATGAATA
CCTTCATACAGCAGGTATAACTCTTTTCTTTATGGGCTTAAATATTTTGTCACTGATCCT
GCAAATGGACATCATTTTAGCACACTAGCGGTTTATATTTAAGGACCTTCATTCTCTGT
TCTGCACCTCTTCTGGAAATTGAGTAAATTTGCTTTTTTTTTTTACTCAGTTGCAACT
TACGCTTGGCATCTTCAGAATGCTTTTCTAGCATTAAGAGATGTAAATGATAAAGGAATT
ATTGTATGAAATATTACAAAGCGTAGACTATGCATTGTTATTCATTATAATATTTTTGC
TGTCATAATCGCCTCATAAAGACAGGTTTCAACCATTAAAATATGTTCTTCCTTAAATTC
CTGTGCTTTTTCTAGTTCCTCTTG

[SEQ ID NO: 116]
TTTCACTTCCTCATTTCTGTATGCAAGTCCTGATGTTTCAGAACCTATTGATGGATTAA
ACCCAAATNAAGAAGAACATAGGACATACTTGGATATTGAACCTATAACTGGATTCACTT
NACANTTTGCAAAACGGCTGCAGGTCAACCTATTGGTCAAGCCATCAGAAAAAATTCAAG
TATTAAAGAATCTANGNGGGA

[SEQ ID NO: 117]
AAGGNAGANCATATTTTAATGGNTGAAACCTGTCTTTATGAGGCGATTATGACAGCAAAA
AATATTATAATGAATANCAATGCATAGTCTACGCTTTGTAATATTTCATACAATAATTCC
TTTATCAGTTACANCTCTTAATGCTAGAAAAGCATTCTGAAGATGCCAAGCGTAAGTNGC
AACTGAGTAAAAAAAAAAAAGCAAAATTTACTCAATTTCC

[SEQ ID NO: 118]
CTTGAGCAGGGGTTCACTTATTCTGAGAGCATTAGTTCTCCTAAAAAGCTCCAGCATAGA
AAGGGAAGATAAACCAAATTCTAGCTTGTGTTTTACCCACAGAAGGATACAGGACAAAGG
AATAGTAACTGGCCTGTTTGGATACTAAAATTGAAAATAACTTTTAGCCTCCTCCTTATG
ATAGCCGCCAGAGTAAATGTTGAGCATTACTACAGAAAAGCCACAAACCAAGNATCTACC
TGTTTGGAAAGATCTTTTGCATCTCTGAAGGTGCTTAAAGCATACTTAGTGNCTTTCCTT
TTAACTCGG

[SEQ ID NO: 119]
GGATCCACTCATTTCACAAACTGTATTCTTTCTTCCAATCTTTTTTTTTTTTGAGATG
GAGTTTCACCTCTTGTTGCCCAGGCTGGAGTGCAATGGCATGATCTCGGCTCACCACAAC
CTCCGCCTCCTGGGTTCAAGCGATTCTCCTGCCTCAGCCTCCGGAGTAGCTTGGGATTAC
AAGCATGTGCCACCAAGCCCGGCTAACTTTGTATGTTTAGTAGAGATGGGGTTTCTCTGT
GTTGGTCGGGCTGGTCTCAAACTCCCAACCTCAGGTGATCCACCCGCCTCAGCCTTCCAA
AGTGCTAGGATGACAGGTGTGAGCCACCACGCCCGGCTCTCCCAATCTTTATATAATAAT
CACATACTATGGCTGGGCATGGTGGCTCACGCCTGTCATCCCAGCACTTTGGGAGGCTGA

FIG. 10E

[SEQ ID NO: 119, cont'd.]
GGTGGGTGGATCACGAGGTCAGGAGTTCGAGACCAGCCTGACCAACATGGTGAAACCCCA
TCTCTACTGAAAATACAAAAATTAACCAGGCATGGTGGCGTGCACCTGTAATCCCAGCTA
CACAGGAGGCTGAGTCAGGAGAATTGCTTGAACCCAGGAGGCAGAGGTTGCAGTGAGCCG
AGATCGTGCCACTGCACTCCAGCCTGGGTGACAGAGAAAGACTCCGTCTCAAAAAAATAA
TAATAATCACATACTTTATGAAGACACCAAACATTAGATTGACAAATATATACTAACACA
AACATCCTAATTTTAACAGAATTAGCATGAATCAACTGCAAATGACAAACTATATTGTAG
TTGAATGTGCAGGGAAAAAATTCTTCAGTAAGAGAGCAATGCCATGGTTGAAACAAGACA
TCCTCTACATTTTATATTTACTTCAAATTCTTTATACCTGTAGTCTATCCAAAGTCGTCA
ATAAAACTGAAAGTAAGATACTCTTATTTTAAAAATTCCATGTTTTAAACAGCTTTTAGG
ACAAGCCCTTCAGGCCTGAACTCAGTATTCATGAAAATTAGACTTTCTTTTAACAGTTAT
TTTAAGTATGGTGATATTAGAGAGTGTCCCAGTATAAAATTTCTGAGAATTTTTTTCTA
TTTACCCATGCTTTTCTTATTTTCACAGATAGCTTTCCAATGATTAGACGAATTGATTCT
TTCTGTGACTCATCAGTTCATTTCCTGTAAAATTCATGTCTTGCTGTTGATTTGTAATA
AGGTATCGTAAATAAAACATCTGTTACCATACTTGCTTATCATTTAATGGAAAACACATC
AGTCAACCCACATTCTGTTCGCAGGAGAGCTCCAGAAGGGGTGTGGAAGGTTGTGTTGGG
TGGAGAAACCAGATAGTGAGGATGCAACTAAGTTGCTGAGACAAGGGAAGAGAGATGAGG
GTGAGAGTTCTCCTTAGATAAGATTTCAATATGTTAATCATGTGTAGAAAGAAAATTAAA
AAGGAGGAATATGAAGAAATTCAGATATGACATTATTAGTTCTGCCACTGGTAGGCATTA
GAAGCAAGAAAAGGGAGACGGACCGAGGAAGCCACTTTGGTGAAACGAAAGCATTTGTT
TATTTAGAACGGGCAAAATGATACGTTTCAGTGGGGGTTTTCTTTGTACTTTGATCTTTT
TGTACTGATATTTAAGCTTCTGTTTTATGATCTCTTTCTAATGATAGAACCAGAGCTTGT
AGAAACCACTTTAATCATATCCAGGAGTTTGCAAGAAACAGGTGCTTAACACTAATTCAC
CTCCTGAACAAGAAAAATGGGCTGTGACCGGAACTGTGGGCTCATCGCTGGGGCTGTCAT
TGGTGCTGTCCTGGCTGTGTTTGGAGGTATTCTAATGCCAGTTGGAGACCTGCTTATCCA
GAAGACAATTAAAAAGGTACAAGTAGTCCAAGAATATGCCTTCTCATTTTGATTGATTC
TAACTTCTCTTTTTTTGCTTTGTATTTACCTGCTTTATATTTCATGGTAACTGCTAATTT
TGTATCTTTGACATAAAGGTAATTATGAACCACTGCAACTCTATATGATGTGACTTTATG
TGAAATGTTATAAGTATAATGTATATTTAACATGACTCCATTGCTGTCTTAAATATAAAT
ACCAAATTCTATTAAAAGCTGTCTACAGGTATGCATGTTAGTAGAAATAATTGTTTAAG
TTATGTCCAAAGAGCATGTTGGCATGCTTTTGAATAGGAAATAAGTGAGTATATTTGTA
AAAGCACATTTATAAAAGAAGTTGCACTTTAGTTAATACTGAGAAAAGTAAAACTGTGTG
TGTGTGTGTGTGTGTAATGTGTTTAATATTGAAACATAAATCCTTATTAAATTGTA
GGTAAACTTGTTTGGTAATACACTGTTTAGTAATCCACTATTTTATATATGTGTAATAA
TCTCATCTCATAAATATTTTCTATTTGTGAAGCTTCATATTGGAATCTTAGAAAATACTT
TCAGAAATATGCAGAACATGTCTTAGTATAAAACAAATTGACTGTAGTGTGAAAAAACAG
AATGATTGAATAGATGGGCTTTGCACAACAACCTAGAATTC

[SEQ ID NO: 120]
GTTCCTTTCCTGTAAAATTCATGTCTTGCTGTTGATTTGTAATAAGAACCAGAGCTTGT
AGAAACCACTTTAATCATATCCAGGAGTTTGCAAGAAACAGGTGCTTAACACTAATTCAC
CTCCTGAACAAGAAAAATGGGCTGTGACCGGAACTGTGGGCTCATCGCTGGGGCTGTCAT

FIG. 10F

[SEQ ID NO: 120, cont'd.]
TGGTGCTGTCCTGGCTGTGTTTGGAGGTATTCTAATGCCAGTTGGAGACCTGCTTATCCA
GAAGACAATTAAAAAGCAAGTTGTCCGCGAAGAAGGTACAATTGCTTTTAAAAATTGGGT
TAAAACAGGCACAGAAGTTTACAGACAGTTTTGGATCTTTGATGTGCAAAATCCACAGGA
AGTGATGATGAACAGCAGCAACATTCAAGTTAAGCAAAGAGGTCCTTATACGTACAGAGT
TCGTTTTCTAGCCAAGGAAAATGTAACCCAGGACGCTGAGGACAACACAGTCTCTTTCCT
GCAGCCCAATGGTGCCATCTTCGAACCTTCACTATCAGTTGGAACAGAGGCTGACAACTT
CACAGTTCTAATCTGGCTGTGGCAGCTGCATCCCATATCTATCAAAATCAATTTGTTCA
AATGATCCTCAATTCACTTATTAACAAGTCAAAATCTTCTATGTTCCAAGTCAGAACTTT
GAGAGAACTGTTATGGGGCTATAGGGATCCATTTTGAGTTTGGTTCCGTACCCTGTTAC
TACCACAGTTGGTCTGTTTTATCCTTACAACAATACTGCAGATGGAGTTTATAAAGTTTT
CAATGGAAAAGATAACATAAGTAAAGTTGCCATAATCGACACATATAAAGGTAAAAGGAA
TCTGTCCGATTGGGAAAGTCACTGCGACATGATTAATGGTACAGATGCAGCCTCATTTCC
ACCTTTTGTTGAGAAAAGCCAGGTATTGCAGTTCTTTTCTTCTGATATTTGCAGGTCAAT
CTATGCTGTATTTGAATCCGACGTTAATCTGAAAGGAATCCCTGTGTATAGATTTGTTCT
TCCATCCAAGGCCTTTGCCTCTCCAGTTGAAAACCCAGACAACTATTGTTTCTGCACAGA
AAAAATTATCTCAAAAAATTGTACATCATATGGTGTGCTAGACATCAGCAAATGCAAAGA
AGGGAGACCTGTGTACATTTCACTTCCTCATTTTCTGTATGCAAGTCCTGATGTTTCAGA
ACCTATTGATGGATTAAACCCAAATGAAGAAGAACATAGGACATACTTGGATATTGAACC
TATAACTGGATTCACTTTACAATTTGCAAAACGGCTGCAGGTCAACCTATTGGTCAAGCC
ATCAGAAAAAATTCAAGTATTAAAGAATCTGAAGAGGAACTATATTGTGCCTATTCTTTG
GCTTAATGAGACTGGGACCATTGGTGATGAGAAGGCAAACATGTTCAGAAGTCAAGTAAC
TGGAAAAATAAACCTCCTTGGCCTGATAGAAATGATCTTACTCAGTGTTGGTGTGGTGAT
GTTTGTTGCTTTTATGATTTCATATTGTGCATGCAGATCGAAAACAATAAAATAAGTAAG
TATGTACCAAAAAATATTGCTTCAATAATATTAGCTTATATATTACTTGTTTTCACTTTA
TCAAGAGAGAAGGTTACATATTAGGCC

[SEQ ID NO: 121]
GTATTAAGCTCAATATTAGCATTAATCCATTTATTTGTTAAAATCTAATATTGTATTCTT
GTCTTAAACAGTGACTTTGTTTTTGTAGGCTGCATCCCATATCTATCAAAATCAATTTGT
TCAAATGATCCTCAATTCACTTATTAACAAGTCAAAATCTTCTATGTTCCAAGTCAGAAC
TTTGAGAGAACTGTTATGGGGCTATAGGGATCCATTTTGAGTTTGGTTCCGTACCCTGT
TACTACCACAGTTGGTCTGTTTTATCCTGTAAGTACCAAATATGAATGGCAATATTATTA
CATTTTAATTTAATTAATTCAATGGCATTGGCAAGGCATAATTTTATAATTTAGCTCATT
AGCTATGCT

[SEQ ID NO: 122]
TTCTGTTTTATGATCTCTTTCTAATGATAGAACCAGAGCTTGTAGAAACCACTTTAATCA
TATCCAGGAGTTTGCAAGAAACAGGTGCTTAACACTAATTCACCTCCTGAACAAGAAAAA
TGGGCTGTGACCGGAACTGTGGGCTCATCGCTGGGGCTGTCATTGGTGCTGTCCTGGCTG
TGTTTGGAGGTATTCTAATGCCAGTTGGAGACCTGCTTATCCAGAAGACAATTAAAAGG
TACAAGTAGTCAAAGAATATCCTCTCATT

[SEQ ID NO: 123]

FIG. 10G

GTATTAAGCTCAATATTAGCATTAATCCATTTATTTGTTAAAATCTAATATTGTATTCTT
GTCTTAAACAGTGACTTTGTTTTTGTAGGCTGCATCCCATATCTATCAAAATCAATTTGT
TCAAATGATCCTCAATTCACTTATTAACAAGTCAAAATCTTCTATGTTCCAAGTCAGAAC
TTTGAGAGAACTGTTATGGGGCTATAGGGATCCATTTTTGAGTTTGGTTCCGTACCCTGT
TACTACCACAGTTGGTCTGTTTTATCCTGTAAGTACCAAATATGAATGGCAATATTATTA
CATTTTAATTTAATTAATTCAATGGCATTGGCAAGGCATAATTTTATAATTTAGCTCATT
AGCTATGCT

[SEQ ID NO: 124]
CGTCGCCGTCCCCGTCTCCTGCCAGGCGCGGAGCCCTGCGAGCCGCGGGTGGGCCCCAGG
CGCGCAGACATGGGCTGCTCCGCCAAAGCGCGCTGGGCTGCCGGGGCGCTGGGCGTCGCG
GGGCTACTGTGCGCTGTGCTGGGCGCTGTCATGATCGTGATGGTGCCGTCGCTCATCAAG
CAGCAGGTCCTTAAGAACGTGCGCATCGACCCCAGTAGCCTGTCCTTCAACATGTGGAAG
GAGATCCCTATCCCCTTCTATCTCTCCGTCTACTTCTTTGACGTCATGAACCCCAGCGAG
ATCCTGAAGGGCGAGAAGCCGCAGGTGCGGGAGCGCGGGCCCTACGTGTACAGGGAGTCC
AGGCACAAAAGCAACATCACCTTCAACAACAACGACACCGTGTCCTTCCTCGAGTACCGC
ACCTTCCAGTTCCAGCCCTCCAAGTCCCACGGCTCGGAGAGCGACTACATCGTCATGCCC
AACATCCTGGTCTTGGGTGCGGCGGTGATGATGGAGAATAAGCCCATGACCCTGAAGCTC
ATCATGACCTTGGCATTCACCACCCTCGGCGAACGTGCCTTCATGAACCGCACTGTGGGT
GAGATCATGTGGGCTACAAGGACCCCCTTGTGAATCTCATCAACAAGTACTTTCCAGGC
ATGTTCCCCTTCAAGGACAAGTTCGGATTATTTGCTGAGCTCAACAACTCCGACTCTGGG
CTCTTCACGGTGTTCACGGGGGTCCAGAACATCAGCAGGATCCACCTCGTGGACAAGTGG
AACGGGCTGAGCAAGGTTGACTTCTGGCATTCCGATCAGTGCAACATGATCAATGGAACT
TCTGGGCAAATGTGGCCGCCCTTCATGACTCCTGAGTCCTCGCTGGAGTTCTACAGCCCG
GAGGCCTGCCGATCCATGAAGCTAATGTACAAGGAGTCAGGGGTGTTTGAAGGCATCCCC
ACCTATCGCTTCGTGGCTCCCAAAACCCTGTTTGCCAACGGGTCCATCTACCCACCCAAC
GAAGGCTTCTGCCCGTGCCTGGAGTCTGGAATTCAGAACGTCAGCACCTGCAGGTTCAGT
GCCCCCTTGTTTCTCTCCCATCCTCACTTCCTCAACGCCGACCCGGTTCTGGCAGAAGCG
GTGACTGGCCTGCACCCTAACCAGGAGGCACACTCCTTGTTCCTGGACATCCACCCGGTC
ACGGGAATCCCCATGAACTGCTCTGTGAAACTGCAGCTGAGCCTCTACATGAAATCTGTC
GCAGGCATTGGACAAACTGGGAAGATTGAGCCTGTGGTCCTGCCGCTGCTCTGGTTTGCA
GAGAGCGGGGCCATGGAGGGGGAGACTCTTCACACATTCTACACTCAGCTGGTGTTGATG
CCCAAGGTGATGCACTATGCCCAGTACGTCCTCCTGGCGCTGGGCTGCGTCCTGCTGCTG
GTCCCTGTCATCTGCCAAATCCGGAGCCAAGAGAAATGCTATTTATTTTGGAGTAGTAGT
AAAAAGGGCTCAAAGGATAAGGAGGCCATTCAGGCCTATTCTGAATCCCTGATGACATCA
GCTCCCAAGGGCTCTGTGCTGCAGGAAGCAAAACTGTAGGGTCCTGAGGACACCGTGAGC
CAGCCAGGCCTGGCCGCTGGGCCTGACCGGCCCCCAGCCCCTACACCCCGCTTCTCCCG
GACTCTCCCAGCAGACAGCCCCCCAGCCCCACAGCCTGAGCCTCCCAGCTGCCATGTGCC
TGTTGCACACCTGCACACACGCCCTGGCACACATACACACATGCGTGCAGGCTTGTGCAG
ACACTCAGGGATGGAGCTGCTGCTGAAGGGACTTGTAGGGAGAGGCTCGTCAACAAGCAC
TGTTCTGGAACCTTCTCTCCACGTGGCCCACAGGCTGACCACAGGGGCTGTGGGTCCTGC

FIG. 10H

[SEQ ID NO: 124, cont'd.]
GTCCCCTTCCTCGGGTGAGCCTGGCCTGTCCCGTTCAGCCGTTGGGCCAGGCTTCCTCCC
CTCCAAGGTGAAACACTGCAGTCCCGGTGTGGTGGCTCCCCATGCAGGACGGGCCAGGCT
GGGAGTGCCGCCTTCCTGTGCCAAATTCAGTGGGGACTCAGTGCCCAGGCCCTGGCACGA
GCTTTGGCCTTGGTCTACCTGCCAGGCCAGGCAAAGCGCCTTTACACAGGCCTCGGAAAA
CAATGGAGTGAGCACAAGATGCCCTGTGCAGCTGCCCGAGGGTCTCCGCCCACCCCGGCC
GGACTTTGATCCCCCCGAAGTCTTCACAGGCACTGCATCGGGTTGTCTGGCGCCCTTTTC
CTCCAGCCTAAACTGACATCATCCTATGGACTGAGCCGGCCACTCTCTGGCCGAAGTGGC
GCAGGCTGTGCCCCGAGCTGCCCCCACCCCCTCACAGGGTCCCTCAGATTATAGGTGCC
CAGGCTGAGGTGAAGAGGCCTGGGGGCCCTGCCTTCCGGGCGCTCCTGGACCCTGGGGCA
ACCTGTGACCCTTTTCTACTGGAATAGAAATGAGTTTTATCATCTTTGAAAAATAATTC
ACTCTTGAAGTAATAAACGTTTAAAAAATGGAAAAAAAAAAAAAAA

[SEQ ID NO: 125]
AAGGAAGAACATATTTTAATGGTTGAAACCTGTCTTTATGAGGCGATTATGACAGCAAAA
AATATTATAATGAATAACAATGCATAGTCTACGCTTTGTAATATTTCATACAATAATTCC
TTTATCATTTACATCTCTTAATGCTAGAAAAGCATTCTGAAGATGCCAAGCGTAAGTNGC
AACTGAGTAAAAAAAAAAAAGCAAAATTTACTCAATTTCCAGANGAGGTGCAGAACAGAG
AATGAAGGTCCTTAAAATATAANCCGCTAGTGTGCTTAAAATGNTGTCCATTTGCAGGNT
CCAGT

[SEQ ID NO: 126]
ATTTGATCCTATTAAGAATTGTCCAAATGTTGGAGCATTTGATTGAAAAATCCTTCTTAG
CCATTTTAAAGATAGCTTTCCAATGATTAGACGAATTGATTCTTTCTGTGACTCATCAGT
TCCTTTCCTGTAAAATTCATGTCTTGCTGTTGATTTGTGAATAAGAACCAGAGCTTGTAG
AAACCACTTTAATCATATCCAGGAGTTTGCAAGAAACAGGTGCTTAACACTAATTCACCT
CCTGAACAAGAAAATGGGCTGTGACCGGAACTGTGGGCTCATCGCTGGGGCTGTCATTG
GTGCTGTCCTGGCTGTGTTTGGAGGTATTCTAATGCCAGTTGGAGACCTGCTTATCCAGA
AGACAATTAAAAAGCAAGTTGTCCTCGAAGAAGGTACAATTGCTTTTAAAAATTGGGTTA
AAACAGGCACAGAAGTTTACAGACAGTTTTGGATCTTTGATGTGCAAAATCCACAGGAAG
TGATGATGAACAGCAGCAACATTCAAGTTAAGCAAAGAGGTCCTTATACGTACAGAGTTC
GTTTTCTAGCCAAGGAAAATGTAACCCAGGACGCTGAGGACAACACAGTCTCTTTCCTGC
AGCCCAATGGTGCCATCTTCGAACCTTCACTATCAGTTGGAACAGAGGCTGACAACTTCA
CAGTTCTCAATCTGGCTGTGGCAGCTGCATCCCATATCTATCAAAATCAATTTGTTCAAA
TGATCCTCAATTCACTTATTAACAAGTCAAAATCTTCTATGTTCCAAGTCAGAACTTTGA
GAGAACTGTTATGGGGCTATAGGGATCCATTTTTGAGTTTGGTTCCGTACCCTGTTACTA
CCACAGTTGGTCTGTTTTATCCTTACAACAATACTGCAGATGGAGTTTATAAAGTTTCA
ATGGAAAAGATAACATAAGTAAAGTTGCCATAATCGACACATATAAAGGTAAAAGGAATC
TGTCCTATTGGGAAAGTCACTGCGACATGATTAATGGTACAGATGCAGCCTCATTTCCAC
CTTTTGTTGAGAAAAGCCAGGTATTGCAGTTCTTTTCTTCTGATATTTGCAGGTCAATCT
ATGCTGTATTTGAATCCGACGTTAATCTGAAAGGAATCCCTGTGTATAGATTTGTTCTTC
CATCCAAGGCCTTTGCCTCTCCAGTTGAAAACCCAGACAACTATTGTTTCTGCACAGAAA

FIG. 10I

[SEQ ID NO: 126, cont'd.]
AAATTATCTCAAAAAATTGTACATCATATGGTGTGCTAGACATCAGCAAATGCAAAGAAG
GGAGACCTGTGTACATTTCACTTCCTCATTTTCTGTATGCAAGTCCTGATGTTTCAGAAC
CTATTGATGGATTAAACCCAAATGAAGAAGAACATAGGACATACTTGGATATTGAACCTA
TAACTGGATTCACTTTACAATTTGCAAAACGGCTGCAGGTCAACCTATTGGTCAAGCCAT
CAGAAAAAATTCAAGTATTAAAGAATCTGAAGAGGAACTATATTGTGCCTATTCTTTGGC
TTAATGAGACTGGGACCATTGGTGATGAGAAGGCAAACATGTTCAGAAGTCAAGTAACTG
GAAAAATAAACCTCCTTGGCCTGATAGAAATGATCTTACTCAGTGTTGGTGTGGTGATGT
TTGTTGCTTTTATGATTTCATATTGTGCATGCAGATCGAAAACAATAAAATAAACCTGGC
TCAAGCACAAACCAATTTGTGTTGTTCTGATTCAATAATTGGTTTCTGGGTGGCCAATTC
AGAAGAAGAGTGTACATGCTCAACAGTCTCCAGGACCATCAGTATACTGCATTTCATGTG
CACCAAATATTTTGAAAGACATTTATAAATAATTGGCTTATGACTCATATTTCTCTATGA
ATACCTTCATACAGCAGGTATAACTCTTTTCTTTATGGGCTTAAATATTTGTCACTGAT
CCTGCAAATGGACATCATTTTAGCACACTAGCGGTTTATATTTTAAGGACCTTCATTCTC
TGTTCTGCACCTCTTCTGGAAATTGAGTAAATTTTGCTTTTTTTTTTACTCAGTTGCAA
CTTACGCTTGGCATCTTCAGAATGCTTTTCTAGCATTAAGAGATGTAAATGATAAAGGAA
TTATTGTATGAAATATTACAAAGCGTAGACTATGCATTGTTATTCATTATAATATTTTTT
GCTGTCATAATCGCCTCATAAAGACAGGTTTCAACCATTAAAATATGTTCTTCCTT

[SEQ ID NO: 127]
ATTTGATCCTATTAAGAATTGTCCAAATGTTGGAGCATTTGATTGAAAAATCCTTCTTAG
CCATTTTAAAGATAGCTTTCCAATGATTAGACGAATTGATTCTTTCTGTGACTCATCAGT
TCCTTTCCTGTAAAATTCATGTCTTGCTGTTGATTTGTGAATAAGAACCAGAGCTTGTAG
AAACCACTTTAATCATATCCAGGAGTTTGCAAGAAACAGGTGCTTAACACTAATTCACCT
CCTGAACAAGAAAATGGGCTGTGACCGGAACTGTGGGCTCATCGCTGGGGCTGTCATTG
GTGCTGTCCTGGCTGTGTTTGGAGGTATTCTAATGCCAGTTGGAGACCTGCTTATCCAGA
AGACAATTAAAAAGCAAGTTGTCCTCGAAGAAGGTACAATTGCTTTTAAAAATTGGGTTA
AAACAGGCACAGAAGTTTACAGACAGTTTTGGATCTTTGATGTGCAAAATCCACAGGAAG
TGATGATGAACAGCAGCAACATTCAAGTTAAGCAAAGAGGTCCTTATACGTACAGAGTTC
GTTTTCTAGCCAAGGAAAATGTAACCCAGGACGCTGAGGACAACACAGTCTCTTTCCTGC
AGCCCAATGGTGCCATCTTCGAACCTTCACTATCAGTTGGAACAGAGGCTGACAACTTCA
CAGTTCTCAATCTGGCTGTGGCAGCTGCATCCCATATCTATCAAAATCAATTTGTTCAAA
TGATCCTCAATTCACTTATTAACAAGTCAAAATCTTCTATGTTCCAAGTCAGAACTTTGA
GAGAACTGTTATGGGGCTATAGGGATCCATTTTGAGTTTGGTTCCGTACCCTGTTACTA
CCACAGTTGGTCTGTTTATCCTTACAACAATACTGCAGATGGAGTTTATAAAGTTTTCA
ATGGAAAAGATAACATAAGTAAAGTTGCCATAATCGACACATATAAAGGTAAAAGGAATC
TGTCCTATTGGGAAAGTCACTGCGACATGATTAATGGTACAGATGCAGCCTCATTTCCAC
CTTTTGTTGAGAAAAGCCAGGTATTGCAGTTCTTTTCTTCTGATATTTGCAGGTCAATCT
ATGCTGTATTTGAATCCGACGTTAATCTGAAAGGAATCCCTGTGTATAGATTTGTTCTTC
CATCCAAGGCCTTTGCCTCTCCAGTTGAAAACCCAGACAACTATTGTTTCTGCACAGAAA
AAATTATCTCAAAAAATTGTACATCATATGGTGTGCTAGACATCAGCAAATGCAAAGAAG
GGAGACCTGTGTACATTTCACTTCCTCATTTTCTGTATGCAAGTCCTGATGTTTCAGAAC

FIG. 10J

[SEQ ID NO: 127, cont'd.]
CTATTGATGGATTAAACCCAAATGAAGAAGAACATAGGACATACTTGGATATTGAACCTA
TAACTGGATTCACTTTACAATTTGCAAAACGGCTGCAGGTCAACCTATTGGTCAAGCCAT
CAGAAAAAATTCAAGTATTAAAGAATCTGAAGAGGAACTATATTGTGCCTATTCTTTGGC
TTAATGAGACTGGGACCATTGGTGATGAGAAGGCAAACATGTTCAGAAGTCAAGTAACTG
GAAAAATAAACCTCCTTGGCCTGATAGAAATGATCTTACTCAGTGTTGGTGTGGTGATGT
TTGTTGCTTTTATGATTTCATATTGTGCATGCAGATCGAAAACAATAAAATAAGTAAGTA
TGTACCAAAAATATTGCTTCAATAATATTAGCTTATATATTACTTGTTTTCACTTTATC
AAAGAGAAGTTACATATTAGGCCATATATATTTCTAGACATGTCTAGCCACTGATCATTT
TTAAATATAGGTAAATAAACCTATAAATATTATCACGCAGATCACTAAAGTATATCTTTA
ATTCTGGGAGAAATGAGATAAAAGATGTACTTGTGACCATTGTAACAATAGCACAAATAA
AGCACTTGTGCCAAAGTTGTCC

[SEQ ID NO: 128]
GAAAAATCCTTCTTAGCCATTTTAAAGATAGCTTTCCAATGATTAGACGAATTGATTCTT
TCTGTGACTCATCAGTTCCTTTCCTGTAAAATTCATGTCTTGCTGTTGATTTGTGAATAA
GAACCAGAGCTTGTAGAAACCACTTTAATCATATCCAGGAGTTTGCAAGAAACAGGTGCT
TAACACTAATTCACCTCCTGAACAAGAAAAATGGGCTGTGACCGGAACTGTGGGCTCATC
GCTGGGGCTGTCATTGGTGCTGTCCTGGCTGTGTTTGGAGGTATTCTAATGCCAGTTGGA
GACCTGCTTATCCAGAAGACAATTAAAAAGCAAGTTGTCCTCGAAGAAGGTACAATTGCT
TTTAAAAATTGGGTTAAAACAGGCACAGAAGTTTACAGACAGTTTTGGATCTTTGATGTG
CAAAATCCACAGGAAGTGATGATGAACAGCAGCAACATTCAAGTTAAGCAAAGAGGTCCT
TATACGTACAGAGTTCGTTTTCTAGCCAAGGAAAATGTAACCCAGGACGCTGAGGACAAC
ACAGTCTCTTTCCTGCAGCCCAATGGTGCCATCTTCGAACCTTCACTATCAGTTGGAACA
GAGGCTGACAACTTCACAGTTCTCAATCTGGCTGTGGCAGCTGCATCCCATATCTATCAA
AATCAATTTGTTCAAATGATCCTCAATTCACTTATTAACAAGTCAAAATCTTCTATGTTC
CAAGTCAGAACTTTGAGAGAACTGTTATGGGGCTATAGGGATCCATTTTTGAGTTTGGTT
CCGTACCCTGTTACTACCACAGTTGGTCTGTTTTATCCTTACAACAATACTGCAGATGGA
GTTTATAAAGTTTTCAATGGAAAAGATAACATAAGTAAAGTTGCCATAATCGACACATAT
AAAGGTAAAAGGAATCTGTCCTATTGGGAAAGTCACTGCGACATGATTAATGGTACAGAT
GCAGCCTCATTTCCACCTTTTGTTGAGAAAAGCCAGGTATTGCAGTTCTTTTCTTCTGAT
ATTTGCAGGTCAATCTATGCTGTATTTGAATCCGACGTTAATCTGAAAGGAATCCCTGTG
TATAGATTTGTTCTTCCATCCAAGGCCTTTGCCTCTCCAGTTGAAAACCCAGACAACTAT
TGTTTCTGCACAGAAAAATTATCTCAAAAATTGTACATCATATGGTGTGCTAGACATC
AGCAAATGCAAAGAAGGGAGACCTGTGTACATTTCACTTCCTCATTTTCTGTATGCAAGT
CCTGATGTTTCAGAACCTATTGATGGATTAAACCCAAATGAAGAAGAACATAGGACATAC
TTGGATATTGAACCTATAACTGGATTCACTTTACAATTTGCAAAACGGCTGCAGGTCAAC
CTATTGGTCAAGCCATCAGAAAAAATTCAAGTATTAAAGAATCTGAAGAGGAACTATATT
GTGCCTATTCTTTGGCTTAATGAGACTGGGACCATTGGTGATGAGAAGGCAAACATGTTC
AGAAGTCAAGTAACTGGAAAAATAAACCTCCTTGGCCTGATAGAAATGATCTTACTCAGT
GTTGGTGTGGTGATGTTTGTTGCTTTTATGATTTCATATTGTGCATGCAGATCGAAAACA
ATAAAATAAGTATGTACCAAAAATATTGCTTCAATAATATTAGCTTATATATTACTTGT

[SEQ ID NO: 128, cont'd.]
TTTCACTTTATCAAAGAGAAGTTACATATTAGGCCATATATATTTCTAGACATGTCTAGC
CACTGATCATTTTTAAATATAGGTAAATAAACCTATAAATATTATCACGCAGATCACTAA
AGTATATCTTTAATTCTGGGAGAAATGAGATAAAAGATGTACTTGTGACCATTGTAACAA
TAGCACAAAT

[SEQ ID NO: 129]
GGGGATGCAACTAAGTTGCTGAGACAAGGGAAGAGAGATGAGGAACCAGAGCTTGTAGAA
ACCACTTTAATCATATCCAGGAGTTTGCAAGAAACAGGTGCTTAACACTAATTCACCTCC
TGAACAAGAAAAATGGGCTGTGACCGGAACTGTGGGCTCATCGCTGGGGCTGTCATTGGT
GCTGTCCTGGCTGTGTTTGGAGGTATTCTAATGCCAGTTGGAGACCTGCTTATCCAGAAG
ACAATTAAAAGCAAGTTGTCCTCGAAGAAGGTACAATTGCTTTTAAAAATTGGGTTAAA
ACAGGCACAGAAGTTTACAGACAGTTTTGGATCTTTGATGTGCAAAATCCACAGGAAGTG
ATGATGAACAGCAGCAACATTCAAGTTAAGCAAAGAGGTCCTTATACGTACAGAGTTCGT
TTTCTAGCCAAGGAAAATGTAACCCAGGACGCTGAGGACAACACAGTCTCTTTCCTGCAG
CCCAATGGTGCCATCTTCGAACCTTCACTATCAGTTGGAACAGAGGCTGACAACTTCACA
GTTCTCAATCTGGCTGTGGCAGCTGCATCCCATATCTATCAAAATCAATTTGTTCAAATG
ATCCTCAATTCACTTATTAACAAGTCAAAATCTTCTATGTTCCAAGTCAGAACTTTGAGA
GAACTGTTATGGGGCTATAGGGATCCATTTTTGAGTTTGGTTCCGTACCCTGTTACTACT
ACAGTTGGTCTGTTTTATCCTTACAACAATACTGCAGATGGAGTTTATAAAGTTTTCAAT
GGAAAAGATAACATAAGTAAAGTTGCCATAATCGACACATATAAAGGTAAAAGGAATCTG
TCCTATTGGGAAAGTCACTGCGACATGATTAATGGTACAGATGCAGCCTCATTTCCACCT
TTTGTTGAGAAAAGCCAGGTATTGCAGTTCTTTTCTTCTGATATTTGCAGGTCAATCTAT
GCTGTATTTGAATCCGACGTTAATCTGAAAGGAATCCCTGTGTATAGATTCGTTCTTCCA
TCCAAGGCCTTTGCCTCTCCAGTTGAAAACCCAGACAACTATTGTTTCTGCACAGAAAAA
ATTATCTCAAAAAATTGTACATCATATGGTGTGCTAGACATCAGCAAATGCAAAGAAGGG
AGACCTGTGTACATTTCACTTCCTCATTTTCTGTATGCAAGTCCTGATGTTTCAGAACCT
ATTGATGGATTAAACCCAAATGAAGAAGAACATAGGACATACTTGGATATTCAACCTATA
ACTGGATTCACTTTACAATTTGCAAAACGGCTGCAGGTCAACCTATTGGTCAAGCCATCA
GAAAAAATTCAAGTATTAAAGAATCTGAAGAGGAACTATATTGTGCCTATTCTTTGGCTT
AATGAGACTGGGACCATTGGTGATGAGAAGGCAAACATGTTCAGAAGTCAAGTAACTGGA
AAAATAAACCTCCTTGGCCTGATAGAAATGATCTTACTCAGTGTTGGTGTGGTGATGTTT
GTTGCTTTTATGATTTCATATTGTGCATGCAGATCGAAAACAATAAAATAAGTATGTACC
AAAAAATATTGCTTCAATAATATTAGCTTATATATTACTTGTTTTCACTTTATCAAAGAG
AAGTTACATATTAGGCCATATATATTTCTAGACATGTCTAGCCACTGATCATTTTTAAAT
ATAGGTAAATAAACCTATAAATATTATCACGCAGATCACTAAAGTATATCTTTAATTCTG
GGAGAAATGAGATAAAAGATGTACTTGTGACCATTGTAACAATAGCACAATAAAGCACTG
TGCCAAAGTTGTCCAAAAAA

FIG. 10K

FIG. 11

```
CGGCATTGTAATTGTACCTGTGAGTTGGCAAGAAGCAAGTGCTCTTCCTTGATTCTGCTG
CACGAGGAGGAGAATGGGCTGCGATCGGAACTGTGGGCTCATTACTGGAGCCGTTATTGG
TGCTGTCCTGGCTGTGTTTGGAGGCATTCTCATGCCGGTTGGAGACCTACTCATTGAGAA
GACAATCAAAAGGGAAGTTGTCCTTGAAGAAGGAACCATTGCTTTCAAAAACTGGGTGAA
AACGGGCACCACTGTGTACAGACAGTTTTGGGTCTTTGACGTGCAAAACCCAGAGGAAGT
GGCAAAGAATAGCAGCAAGATCAAGGTTATACAGAGAGGTCCTTACACATACAGAGTTCG
CTATTTAGCCAAGGAAAATATAACTCAGGACCCCAAGGACAGCACTGTCTCTTTTGTACA
ACCCAATGGAGCCATCTTTGAGCCTTCACTGTCTGTTGGCACAGAGAATGACAACTTCAC
AGTTCTCAATCTGGCTGTGGCAGCTGCACCACATATCTACACAAACTCATTTGTTCAAGG
TGTGCTCAACAGCCTTATCAAAAAGTCCAAGTCTTCTATGTTCCAAACACGAAGTTTGAA
GGAACTCTTGTGGGGTTACAAAGATCCATTCTTGAGTTTGGTTCCATATCCTATAAGTAC
CACAGTTGGTGTGTTTTATCCTTACAATAACACTGTAGATGGAGTTTATAAAGTTTCCAA
TGGAAAGGATAACATAAGCAAGGTTGCCATAATTGATACCTATAAAGGGAAAAGGAATTT
GTCCTATTGGGAAAGTTATTGCGACATGATTAATGGCACAGATGCAGCCTCCTTTCCACC
TCTTGGTGAGAAGTCTCGAACACTGAGGTTCTTTTCCTCTGACATTTGCAGGTCCATCTA
TGCTGTGTTTGAATCTGAAGTGAACCTTAAAGGAATCCCCGTATACAGATTTGTTCTTCC
AGCCAACGCCTTTGCCTCCCCACTCCAGAACCCAGACAACCACTGTTTCTGCACTGAAAA
AGTAATCTCAAATAACTGTACGTCGTATGGTGTGCTGGACATTGGCAAGTGCAAAGAAGG
GAAACCTGTGTACAATTCTCTTCCACATTTCCTACATGCAAGTCCTGATGTCTCAGAACC
TATCGAAGGCTTGAATCCTACCGAAGATGAGCATAGGACATACTTGGATGTGGAACCCAT
AACTGGATTCACTCTACAGTTTTCCAAACGACTGCAGGTCAACATACTGGTCAAGCCAGC
TAGAAAAATAGAAGCACTGAAGAATCTGAAGAGACCTTACATTGTACCTATACTGTGGCT
AAATGAGACTGGGACCATCGGCGATGAGAAAGCAGAAATGTTCAGAAACCAAGTGACCGG
GAAAATAAAGCTCCTGGGCCTGGTTGAGATGGTCTTACTTGGTGTTGGAGTAGTGATGTT
TGTTGCTTTTATGATTTCATACTGTGCTTGCAGATCTAAGAATGGAAAATAAGTAGTGGA
TGAGCCTACATTATGCACTAGCTACATTTTTGGTAAAACCAATCTCCAAAACGAAGACTT
AAGACATGCTTGTTTTATAAAACACACCTATCTGTAGTTGAAGAAACGGTGGTGTGCGC
GCTCTCTCTCTTATTGCAGATATATATTCATTCATATATTGCAATAAGCCACAGCATATT
TTGACAAGATCAATATGTCACTAAGCCTATATTTTAATAAAATCTTGTATTTTGTTAAG
TCCATCATCTGCAACTGAGTGGACTTCAATTTCTGCAGAACTAATTATCTTTTTGGTTC
TGATTTACTGATTTTTTTTCCTGTTGCCAAATTTCAAGAATGTATATATTCTAAGAAAC
GCTTTGTTCCTCATCGAAGTAAACTGTTATCATGTCTGGGGTGACCCTTTCATTTATAGC
AAATGTTCCTTGTGACTGTCAGCACATGATATGTCATTTATTACATCATTTTAAAGATTT
AAGGATGAAAAATGAACAATTCACATATGAACCATTGCTAATATATTGTTTAAGCCTCTC
CCTCTCTGGTGTCCTTGGCAACAACAAGGCCAGGTATCACAGATATTTTTCTTTTACT
TTCTTAACACAGAGCTTAATATGTTCTGTTCCTCGCCATGAAATGAACTATTTTTAGCAC
ATTTTAGCTCTTGAATTTAAGTATGTTGTCAAGTTCCAGGCTGCCTAGCTCTTTTGAAA
ACTGAGTAGGTTTTTCTCTTTCTGCTCAGCCACAACTAATGTAACTTCAGAGAGCTGTTA
TAGTGGTAAAAGATGTAATTTATAATAAATGGATTATGATATAGAATCTTACAAAAGCTA
GAATTGGCTTTAAATATGTATTTGTGGTAATATATTCTGCTTTTATAATCACCCAGAAAT
AACTGGTTTCTAACATTAAAGATGTTCTTAAATTCC
```

MGCDRNCGLITGAVIGAVLAVFGGILMPVGDLLIEKTIKREVVLEEGTIAFKNWVKTGTT
VYRQFWVFDVQNPEEVAKNSSKIKVIQRGPYTYRVRYLAKENITQDPKDSTVSFVQPNGA
IFEPSLSVGTENDNFTVLNLAVAAAPHIYTNSFVQGVLNSLIKKSKSSMFQTRSLKELLW
GYKDPFLSLVPYPISTTVGVFYPYNNTVDGVYKVSNGKDNISKVAIIDTYKGKRNLSYWE
SYCDMINGTDAASFPPLGEKSRTLRFFSSDICRSIYAVFESEVNLKGIPVYRFVLPANAF
ASPLQNPDNHCFCTEKVISNNCTSYGVLDIGKCKEGKPVYNSLPHFLHASPDVSEPIEGL
NPTEDEHRTYLDVEPITGFTLQFSKRLQVNILVKPARKIEALKNLKRPYIVPILWLNETG
TIGDEKAEMFRNQVTGKIKLLGLVEMVLLGVGVVMFVAFMISYCACRSKNGK

FIG. 12

SHR *Cd36* [SEQ ID NO: 87]

```
AGCAAGTGCTCTTCCTTGATTCTGCTGCACGAGGAGGAGAATGGGCTGCGATCGGAACTG
TGGGCTCATTACTGGAGCCGTTATTGGTGCTGTCCTGGCTGTGTTTGGAGGCATTCTCAT
GCCGGTTGGAGACCTACTCATTGAGAAGACAATCAAAAGGGAAGTTGTCCTTGAAGAAGG
AACCATTGCTTTCAAAAACTGGGTGAAAACGGGCACCACTGTGTACAGACAGTTTTGGAT
CTTTGACGTGCAAAACCCAGAGGAAGTGGCAAAGAATAGCAGCAAGATCAAGGTTAAACA
GAGAGGTCCTTACACATACAGAGTTCGTTATTTAGCCAAGGAAAGTATAACTCAGGACCC
CAAAGACAGCACTGTCTCTTTTGTACAACCCAATGGAGCCATCTTTGAGCCTTCACTGTC
TGTTGGAACAGAGAATGACAACTTCACAGTTCTCAATCTGGCTGTGGCAGCTGTACCACA
TATCTACCAAAACTCATTTTTTCAAGGTGTGCTCAACATATTTATCAAAAAGTCCAAGTN
TTCTANGTTNCAAACACGAAGTTTGAAAGAACTCTTGTGGGGTTATGAAGATCCATTCTT
GAGTTTGATTCCATATCCTATAAGTACCACAGTTGGTGTGTTTATCCTTACAATAACAC
TGTAGATGGAGTTTATAAAGTTTTCAATGGAAAGGATAACATAAGCAAAGTTGCCATAAT
TGATACCTATAAAGGGAAAAGGAATTTGTCCTATTGGAAAAGTTATTGCGACATGATTAA
TGGCACAGATGCAGCCTCCTTTCCACCTTTTGTTGAGAAGTCTCAAACACTGAGGTTTTT
TTCCTCTGACATTTGCAGGTCCATCTATGCTGTGTTTGAATCTGAAGTGAACCTTAAAGG
AATCCCCGTATACAGATTTGTTCTTCCAGCCAACGCCTTTGCCTCCCCACTCCAGAACCC
AGACAACCACTGTTTCTGCACTGAAAAAGTAATCTCAAATAACTGTACGTCGTATGGTGT
GCTGGACATTGGCAAGTGCAAAGAAGGAAAGCCTGTGTACATTTCTCTTCCACATTTCCT
ACATGCAAGTCCTGATGTCTCAGAACCTATCGAAGGCTTGAATCCTAACGAAGATGAGCA
TAGGACATACTTGGATGTGGAACCCATAACTGGATTCACTCTACAGTTTGCAAAACGACT
GCAGGTCAACATACTGGTCAAGCCAGCTAGAAAAATAGAACCACTGAAGAATCTGAAGAG
ACCTTACATTGTACCTATACTGTGGCTAAATGAGACTGGGACCATTGGCGATGAGAAAGC
AGAAATGTTCAGAAACCAAGTGACCGGGAAAATAAAGCTCCTGGGCCTGGTTGAGATGGT
CTTACTTGGTGTTGGAGTAGTGATGTTTGTTGCTTTCATGATTTCATACTGTGCTTGCAG
ATTTAAGAATGGAAAATAAGTAAGTGCTCATCAAAGTATGTATCATTTCATCAAAGTATG
TTTTCATCTCATCGAGAAGGGATTATACATTAAAGCACATATATACATTTCTGCACATGT
TTAGCCAGCTATAATGTCTTAATATATCCCAACTTTTGATGTTATTGTTGTAAAGAAAAT
TGAGAAGCAAATGATTATTGAAATCATCATTACCACAGGGAAATGAACACAATTATAATT
TTTGTCCAAATTAAAAAAAAAAAAAAAAA
```

FIG. 13

MGCDRNCGLI TGAVIGAVLA VFGGILMPVG DLLIEKTIKR EVVLEEGTIA

FKNWVKTGTT VYRQFWIFDV QNPEEVAKNS SKIKVKQRGP YTYRVRYLAK

ESITQDPKDS TVSFVQPNGA IFEPSLSVGT ENDNFTVLNL AVAAVPHIYQ

NSFFQGVLNI FIKKSKXSXX QTRSLKELLW GYEDPFLSLI PYPISTTVGV

FYPYNNTVDG VYKVFNGKDN ISKVAIIDTY KGKRNLSYWK SYCDMINGTD

AASFPPFVEK SQTLRFFSSD ICRSIYAVFE SEVNLKGIPV YRFVLPANAF

ASPLQNPDNH CFCTEKVISN NCTSYGVLDI GKCKEGKPVY ISLPHFLHAS

PDVSEPIEGL NPNEDEHRTY LDVEPITGFT LQFAKRLQVN ILVKPARKIE

PLKNLKRPYI VPILWLNETG TIGDEKAEMF RNQVTGKIKL LGLVEMVLLG

VGVVMFVAFM ISYCACRFKN GK

FIG. 14

```
AGCAAGTGCTCTTCCTTGATTCTGCTGCACGAGGAGGAGAATGGGCTGCGATCGGAACTG
TGGGCTCATTACTGGAGCCGTTATTGGTGCTGTCCTGGCTGTGTTTGGAGGCATTCTCAT
GCCGGTTGGAGACCTACTCATTGAGAAGACAATCAAAAGGGAAGTTGTCCTTGAAGAAGG
AACCATTGCTTTCAAAAACTGGGTGAAAACGGGCACCACTGTGTACAGACAGTTTTGGAT
CTTTGACGTGCAAAACCCAGAGGAAGTGGCAAAGAATAGCAGCAAGATCAAGGTTAAACA
GAGAGGTCCTTACACATACAGAGTTCGTTATTTAGCCAAGGAAAATATAACTCAGGACCC
CAAGGACAGCACTGTCTCTTTTGTACAACCCAATGGAGCCATCTTTGAGCCTTCACTGTC
TGTTGGAACAGAGAATGACAACTTCACAGTTCTCAATCTGGCTGTGGCAGCTGCACCACA
TATCTACACAAACTCATTTGTTCAAGGTGTGCTCAACAGCCTTATCAAAAAGTCCAAGTC
TTCTATGTTCCAAACACGAAGTTTGAAGGAACTCTTGTGGGGTTACAAAGATCCATTCTT
GAGTTTGGTTCCATATCCTATAAGTACCACAGTTGGTGTGTTTATCCTTACAATAACAC
TGTAGATGGAGTTTATAAAGTTTTCAATGGAAAGGATAACATAAGCAAGGTTGCCATAAT
TGATACCTATAAAGGGAAAAGGAATTTGTCCTATTGGGAAAGTTATTGCGACATGATTAA
TGGCACAGATGCAGCCTCCTTTCCACCTTTTGTTGAGAAATCTCAAACACTGAGGTTCTT
TTCCTCTGACATTTGCAGGTCCATCTATGCTGTGTTTGAATCTGAAGTGAACCTTAAAGG
AATCCCCGTATACAGATTTGTTCTTCCAGCCAACGCCTTTGCCTCCCCACTCCAGAACCC
AGACAACCACTGTTTCTGCACTGAAAAAGTAATCTCAAATAACTGTACGTCGTATGGTGT
GCTGGACATTGGCAAGTGCAAAGAAGGAAAGCCTGTGTACATTTCTCTTCCACATTTCCT
ACATGCAAGTCCTGATGTCTCAGAACCTATCGAAGGCTTGAATCCTAACGAAGATGAGCA
TAGGACATACTTGGATGTGGAACCCATAACTGGATTCACTCTACAGTTTGCAAAACGACT
GCAGGTCAACATACTGGTCAAGCCAGCTAGAAAATAGAAGCACTGAAGAATCTGAAGAG
ACCTTACATTGTACCTATACTGTGGCTAAATGAGACTGGGACCATCGGCGATGAGAAAGC
AGAAATGTTCAGAAACCAAGTGACCGGGAAAATAAAGCTCCTGGGCCTGGTTGAGATGGT
CTTACTTGGTGTTGGAGTAGTGATGTTTGTTGCTTTTATGATTTCATACTGTGCTTGCAG
ATCTA
```

FIG. 15

```
Met Gly Cys Asp Arg Asn Cys Gly Leu Ile Thr Gly Ala Val Ile
Gly Ala Val Leu Ala Val Phe Gly Gly Ile Leu Met Pro Val Gly
Asp Leu Leu Ile Glu Lys Thr Ile Lys Arg Glu Val Val Leu Glu
Glu Gly Thr Ile Ala Phe Lys Asn Trp Val Lys Thr Gly Thr Thr
Val Tyr Arg Gln Phe Trp Ile Phe Asp Val Gln Asn Pro Glu Glu
Val Ala Lys Asn Ser Ser Lys Ile Lys Val Lys Gln Arg Gly Pro
Tyr Thr Tyr Arg Val Arg Tyr Leu Ala Lys Glu Asn Ile Thr Gln
Asp Pro Lys Asp Ser Thr Val Ser Phe Val Gln Pro Asn Gly Ala
Ile Phe Glu Pro Ser Leu Ser Val Gly Thr Glu Asn Asp Asn Phe
Thr Val Leu Asn Leu Ala Val Ala Ala Ala Pro His Ile Tyr Thr
Asn Ser Phe Val Gln Gly Val Leu Asn Ser Leu Ile Lys Lys Ser
Lys Ser Ser Met Phe Gln Thr Arg Ser Leu Lys Glu Leu Leu Trp
Gly Tyr Lys Asp Pro Phe Leu Ser Leu Val Pro Tyr Pro Ile Ser
Thr Thr Val Gly Val Phe Tyr Pro Tyr Asn Asn Thr Val Asp Gly
Val Tyr Lys Val Phe Asn Gly Lys Asp Asn Ile Ser Lys Val Ala
Ile Ile Asp Thr Tyr Lys Gly Lys Arg Asn Leu Ser Tyr Trp Glu
Ser Tyr Cys Asp Met Ile Asn Gly Thr Asp Ala Ala Ser Phe Pro
Pro Phe Val Glu Lys Ser Gln Thr Leu Arg Phe Phe Ser Ser Asp
Ile Cys Arg Ser Ile Tyr Ala Val Phe Glu Ser Glu Val Asn Leu
Lys Gly Ile Pro Val Tyr Arg Phe Val Leu Pro Ala Asn Ala Phe
Ala Ser Pro Leu Gln Asn Pro Asp Asn His
```

FIG. 16

```
TCTTCCTTGATTCTGCTGCACGAGGAGGAGAATGGGCTGCGATCGGAACTGTGGGCTCAT
TACTGGAGCCGTTATTGGTGCTGTCCTGGCTGTGTTTGGAGGCATTCTCATGCCGGTTGG
AGACCTACTCATTGAGAAGACAATCAAAAGGGAAGTTGTCCTTGAAGAAGGAACCATTGC
TTTCAAAAACTGGGTGAAAACGGGCACCACTGTGTACAGACAGTTTTGGATCTTTGACGT
GCAAAACCCAGAGGAAGTGGCAAAGAATAGCAGCAAGATCAAGGTTAAACAGAGAGGTCC
TTACACATACAGAGTTCGTTATTTAGCCAAGGAAAATATAACTCAGGACCCCAAGGACAG
CACTGTCTCTTTTGTACAACCCAATGGAGCCATCTTTGAGCCTTCACTGTCTGTTGGAAC
AGAGAATGACAACTTCACAGTTCTCAATCTGGCTGTGGCAGCTGCACCACATATCTACAC
AAACTCATTTGTTCAAGGTGTGCTCAACAGCCTTATCAAAAGTCCAAGTCTTCTATGTT
CCAAACACGAAGTTTGAAGGAACTCTTGTGGGGTTACAAAGATCCATTCTTGAGTTTGGT
TCCATATCCTATAAGTACCACAGTTGGTGTGTTTATCCTTACAATAACACTGTAGATGG
AGTTTATAAAGTTTTCAATGGAAAGGATAACATAAGCAAGGTTGCCATAATTGATACCTA
TAAAGGGAAAAGGAATTTGTCCTATTGGGAAAGTTATTGCGACATGATTAATGGCACAGA
TGCAGCCTCCTTTCCACCTTTTGTTGAGAAGTCTCGAACACTGAGGTTCTTTTCCTCTGA
CATTTGCAGGTCCATCTATGCTGTGTTTGGATCTGAAGTGAACCTTAAAGGAATCCCCGT
GTACAGATTTGTTCTTCCAGCCAACGCCTTTGCCTCCCCACTCCAGAACCCAGACAACCA
CTGTTTCTGCACTGAAAAAGTAATCTCAAATAACTGTACGTCGTATGGTGTGCTGGACAT
TGGCAAGTGCAAAGAAGGAAAGCCTGTGTACATTTCTCTTCCACATTTCCTACATGCAAG
TCCTGATGTCTCAGAACCTATCGAAGGCTTGAATCCTAACGAAGATGAGCATAGGACATA
CTTGGATGTGGAACCCATAACTGGATTCACTCTACAGTTTGCAAAACGACTGCAGGTCAA
CATACTGGTCAAGCCAGCTAGAAAAATAGAAGCACTGAAGAATCTGAAGAGACCTTACAT
TGTACCTATACTGTGGCTAAATGAGACTGGGACCATCGGCGATGAGAAAGCAGAAATGTT
CAGAAACCAAGTGACCGGGAAAATAAAGCTCCTGGGCCTGGTTGAGATGGTCTTACTTGG
TGTTGGAGTAGTGATGTTTGTTGCTTTTATGATTTCATACTGTGCTTGCAGATCTA
```

FIG. 17

```
Met Gly Cys Asp Arg Asn Cys Gly Leu Ile Thr Gly Ala Val Ile
Gly Ala Val Leu Ala Val Phe Gly Gly Ile Leu Met Pro Val Gly
Asp Leu Leu Ile Glu Lys Thr Ile Lys Arg Glu Val Val Leu Glu
Glu Gly Thr Ile Ala Phe Lys Asn Trp Val Lys Thr Gly Thr Thr
Val Tyr Arg Gln Phe Trp Ile Phe Asp Val Gln Asn Pro Glu Glu
Val Ala Lys Asn Ser Ser Lys Ile Lys Val Lys Gln Arg Gly Pro
Tyr Thr Tyr Arg Val Arg Tyr Leu Ala Lys Glu Asn Ile Thr Gln
Asp Pro Lys Asp Ser Thr Val Ser Phe Val Gln Pro Asn Gly Ala
Ile Phe Glu Pro Ser Leu Ser Val Gly Thr Glu Asn Asp Asn Phe
Thr Val Leu Asn Leu Ala Val Ala Ala Ala Pro His Ile Tyr Thr
Asn Ser Phe Val Gln Gly Val Leu Asn Ser Leu Ile Lys Lys Ser
Lys Ser Ser Met Phe Gln Thr Arg Ser Leu Lys Glu Leu Leu Trp
Gly Tyr Lys Asp Pro Phe Leu Ser Leu Val Pro Tyr Pro Ile Ser
Thr Thr Val Gly Val Phe Tyr Pro Tyr Asn Asn Thr Val Asp Gly
Val Tyr Lys Val Phe Asn Gly Lys Asp Asn Ile Ser Lys Val Ala
Ile Ile Asp Thr Tyr Lys Gly Lys Arg Asn Leu Ser Tyr Trp Glu
Ser Tyr Cys Asp Met Ile Asn Gly Thr Asp Ala Ala Ser Phe Pro
Pro Phe Val Glu Lys Ser Arg Thr Leu Arg Phe Phe Ser Ser Asp
Ile Cys Arg Ser Ile Tyr Ala Val Phe Gly Ser Glu Val Asn Leu
Lys Gly Ile Pro Val Tyr Arg Phe Val Leu Pro Ala Asn Ala Phe
Ala Ser Pro Leu Gln Asn Pro Asp Asn His Cys Phe Cys Thr Glu
Lys Val Ile Ser Asn Asn Cys Thr Ser Tyr Gly Val Leu Asp Ile
Gly Lys Cys Lys Glu Gly Lys Pro Val Tyr Ile Ser Leu Pro His
Phe Leu His Ala Ser Pro Asp Val Ser Glu Pro Ile Glu Gly Leu
Asn Pro Asn Glu Asp Glu His Arg Thr Tyr Leu Asp Val Glu Pro
Ile Thr Gly Phe Thr Leu Gln Phe Ala Lys Arg Leu Gln Val Asn
Ile Leu Val Lys Pro Ala Arg Lys Ile Glu Ala Leu Lys Asn Leu
Lys Arg Pro Tyr Ile Val Pro Ile Leu Trp Leu Asn Glu Thr Gly
Thr Ile Gly Asp Glu Lys Ala Glu Met Phe Arg Asn Gln Val Thr
Gly Lys Ile Lys Leu Leu Gly Leu Val Glu Met Val Leu Leu Gly
Val Gly Val Val Met Phe Val Ala Phe Met Ile Ser Tyr Cys Ala
Cys Arg Ser
```

FIG. 18

SEQUENCE LISTING

<160> NUMBER OF SEQ ID NOS: 207

<210> SEQ ID NO 1
<211> LENGTH: 29
<212> TYPE: DNA
<213> ORGANISM: Rattus norvegicus

<400> SEQUENCE: 1
tatttagcca aggaaaatat aactcagga                                          29

<210> SEQ ID NO 2
<211> LENGTH: 9
<212> TYPE: PRT
<213> ORGANISM: Rattus norvegicus

<400> SEQUENCE: 2

Tyr Leu Ala Lys Glu Asn Ile Thr Gln
 1               5

<210> SEQ ID NO 3
<211> LENGTH: 29
<212> TYPE: DNA
<213> ORGANISM: Rattus norvegicus

<400> SEQUENCE: 3
tatttagcca aggaaaatat aactcagga                                          29

<210> SEQ ID NO 4
<211> LENGTH: 9
<212> TYPE: PRT
<213> ORGANISM: Rattus norvegicus

<400> SEQUENCE: 4

Tyr Leu Ala Lys Glu Asn Ile Thr Gln
 1               5

<210> SEQ ID NO 5
<211> LENGTH: 29
<212> TYPE: DNA
<213> ORGANISM: Rattus norvegicus

<400> SEQUENCE: 5
tatttagcca aggaaagtat aactcagga                                          29

<210> SEQ ID NO 6
<211> LENGTH: 9
<212> TYPE: PRT
<213> ORGANISM: Rattus norvegicus

<400> SEQUENCE: 6

Tyr Leu Ala Lys Glu Ser Ile Thr Gln
 1               5

<210> SEQ ID NO 7
<211> LENGTH: 30
<212> TYPE: DNA
<213> ORGANISM: Rattus norvegicus

<400> SEQUENCE: 7
taactcagga ccccaaggac agcactgtct                                         30

<210> SEQ ID NO 8

```
<211> LENGTH: 9
<212> TYPE: PRT
<213> ORGANISM: Rattus norvegicus

<400> SEQUENCE: 8

Thr Gln Asp Pro Lys Asp Ser Thr Val
  1               5

<210> SEQ ID NO 9
<211> LENGTH: 30
<212> TYPE: DNA
<213> ORGANISM: Rattus norvegicus

<400> SEQUENCE: 9
taactcagga ccccaaggac agcactgtct                                    30

<210> SEQ ID NO 10
<211> LENGTH: 9
<212> TYPE: PRT
<213> ORGANISM: Rattus norvegicus

<400> SEQUENCE: 10

Thr Gln Asp Pro Lys Asp Ser Thr Val
  1               5

<210> SEQ ID NO 11
<211> LENGTH: 30
<212> TYPE: DNA
<213> ORGANISM: Rattus norvegicus

<400> SEQUENCE: 11
taactcagga ccccaaagac agcactgtct                                    30

<210> SEQ ID NO 12
<211> LENGTH: 9
<212> TYPE: PRT
<213> ORGANISM: Rattus norvegicus

<400> SEQUENCE: 12

Thr Gln Asp Pro Lys Asp Ser Thr Val
  1               5

<210> SEQ ID NO 13
<211> LENGTH: 30
<212> TYPE: DNA
<213> ORGANISM: Rattus norvegicus

<400> SEQUENCE: 13
ctggctgtgg cagctgcacc acatatctac                                    30

<210> SEQ ID NO 14
<211> LENGTH: 10
<212> TYPE: PRT
<213> ORGANISM: Rattus norvegicus

<400> SEQUENCE: 14

Leu Ala Val Ala Ala Ala Pro His Ile Tyr
  1               5                  10

<210> SEQ ID NO 15
<211> LENGTH: 30
<212> TYPE: DNA
<213> ORGANISM: Rattus norvegicus

<400> SEQUENCE: 15
```

```
ctggctgtgg cagctgcacc acatatctac                                              30
```

<210> SEQ ID NO 16
<211> LENGTH: 10
<212> TYPE: PRT
<213> ORGANISM: Rattus norvegicus

<400> SEQUENCE: 16

```
Leu Ala Val Ala Ala Ala Pro His Ile Tyr
  1               5                  10
```

<210> SEQ ID NO 17
<211> LENGTH: 30
<212> TYPE: DNA
<213> ORGANISM: Rattus norvegicus

<400> SEQUENCE: 17

```
ctggctgtgg cagctgtacc acatatctac                                              30
```

<210> SEQ ID NO 18
<211> LENGTH: 10
<212> TYPE: PRT
<213> ORGANISM: Rattus norvegicus

<400> SEQUENCE: 18

```
Leu Ala Val Ala Ala Val Pro His Ile Tyr
  1               5                  10
```

<210> SEQ ID NO 19
<211> LENGTH: 30
<212> TYPE: DNA
<213> ORGANISM: Rattus norvegicus

<400> SEQUENCE: 19

```
acatatctac acaaactcat ttgttcaagg                                              30
```

<210> SEQ ID NO 20
<211> LENGTH: 9
<212> TYPE: PRT
<213> ORGANISM: Rattus norvegicus

<400> SEQUENCE: 20

```
His Ile Tyr Thr Asn Ser Phe Val Gln
  1               5
```

<210> SEQ ID NO 21
<211> LENGTH: 30
<212> TYPE: DNA
<213> ORGANISM: Rattus norvegicus

<400> SEQUENCE: 21

```
acatatctac acaaactcat ttgttcaagg                                              30
```

<210> SEQ ID NO 22
<211> LENGTH: 9
<212> TYPE: PRT
<213> ORGANISM: Rattus norvegicus

<400> SEQUENCE: 22

```
His Ile Tyr Thr Asn Ser Phe Val Gln
  1               5
```

<210> SEQ ID NO 23

-continued

```
<211> LENGTH: 30
<212> TYPE: DNA
<213> ORGANISM: Rattus norvegicus

<400> SEQUENCE: 23
acatatctac caaaactcat tttttcaagg                                              30

<210> SEQ ID NO 24
<211> LENGTH: 9
<212> TYPE: PRT
<213> ORGANISM: Rattus norvegicus

<400> SEQUENCE: 24

His Ile Tyr Gln Asn Ser Phe Phe Gln
 1               5

<210> SEQ ID NO 25
<211> LENGTH: 30
<212> TYPE: DNA
<213> ORGANISM: Rattus norvegicus

<400> SEQUENCE: 25
acaaactcat tgttcaagg tgtgctcaac                                               30

<210> SEQ ID NO 26
<211> LENGTH: 9
<212> TYPE: PRT
<213> ORGANISM: Rattus norvegicus

<400> SEQUENCE: 26

Gln Thr His Leu Phe Lys Val Cys Ser
 1               5

<210> SEQ ID NO 27
<211> LENGTH: 30
<212> TYPE: DNA
<213> ORGANISM: Rattus norvegicus

<400> SEQUENCE: 27
acaaactcat tgttcaagg tgtgctcaac                                               30

<210> SEQ ID NO 28
<211> LENGTH: 9
<212> TYPE: PRT
<213> ORGANISM: Rattus norvegicus

<400> SEQUENCE: 28

Gln Thr His Leu Phe Lys Val Cys Ser
 1               5

<210> SEQ ID NO 29
<211> LENGTH: 30
<212> TYPE: DNA
<213> ORGANISM: Rattus norvegicus

<400> SEQUENCE: 29
caaaactcat tttttcaagg tgtgctcaac                                              30

<210> SEQ ID NO 30
<211> LENGTH: 10
<212> TYPE: PRT
<213> ORGANISM: Rattus norvegicus

<400> SEQUENCE: 30
```

Gln Asn Ser Phe Phe Gln Gly Val Leu Asn
 1               5                   10

<210> SEQ ID NO 31
<211> LENGTH: 30
<212> TYPE: DNA
<213> ORGANISM: Rattus norvegicus

<400> SEQUENCE: 31
tgtgctcaac agccttatca aaaagtccaa                                30

<210> SEQ ID NO 32
<211> LENGTH: 9
<212> TYPE: PRT
<213> ORGANISM: Rattus norvegicus

<400> SEQUENCE: 32

Val Leu Asn Ser Leu Ile Lys Lys Ser
 1               5

<210> SEQ ID NO 33
<211> LENGTH: 30
<212> TYPE: DNA
<213> ORGANISM: Rattus norvegicus

<400> SEQUENCE: 33
tgtgctcaac agccttatca aaaagtccaa                                30

<210> SEQ ID NO 34
<211> LENGTH: 9
<212> TYPE: PRT
<213> ORGANISM: Rattus norvegicus

<400> SEQUENCE: 34

Val Leu Asn Ser Leu Ile Lys Lys Ser
 1               5

<210> SEQ ID NO 35
<211> LENGTH: 30
<212> TYPE: DNA
<213> ORGANISM: Rattus norvegicus

<400> SEQUENCE: 35
tgtgctcaac atatttatca aaaagtccaa                                30

<210> SEQ ID NO 36
<211> LENGTH: 9
<212> TYPE: PRT
<213> ORGANISM: Rattus norvegicus

<400> SEQUENCE: 36

Val Leu Asn Ile Phe Ile Lys Lys Ser
 1               5

<210> SEQ ID NO 37
<211> LENGTH: 30
<212> TYPE: DNA
<213> ORGANISM: Rattus norvegicus

<400> SEQUENCE: 37
tgtgctcaac agccttatca aaaagtccaa                                30

<210> SEQ ID NO 38
<211> LENGTH: 9

```
<212> TYPE: PRT
<213> ORGANISM: Rattus norvegicus

<400> SEQUENCE: 38

Val Leu Asn Ser Leu Ile Lys Lys Ser
 1               5

<210> SEQ ID NO 39
<211> LENGTH: 30
<212> TYPE: DNA
<213> ORGANISM: Rattus norvegicus

<400> SEQUENCE: 39
tgtgctcaac agccttatca aaaagtccaa                                        30

<210> SEQ ID NO 40
<211> LENGTH: 9
<212> TYPE: PRT
<213> ORGANISM: Rattus norvegicus

<400> SEQUENCE: 40

Val Leu Asn Ser Leu Ile Lys Lys Ser
 1               5

<210> SEQ ID NO 41
<211> LENGTH: 30
<212> TYPE: DNA
<213> ORGANISM: Rattus norvegicus

<400> SEQUENCE: 41
tgtgctcaac atatttatca aaaagtccaa                                        30

<210> SEQ ID NO 42
<211> LENGTH: 9
<212> TYPE: PRT
<213> ORGANISM: Rattus norvegicus

<400> SEQUENCE: 42

Val Leu Asn Ile Phe Ile Lys Lys Ser
 1               5

<210> SEQ ID NO 43
<211> LENGTH: 30
<212> TYPE: DNA
<213> ORGANISM: Rattus norvegicus

<400> SEQUENCE: 43
ttccaaacac gaagtttgaa ggaactcttg                                        30

<210> SEQ ID NO 44
<211> LENGTH: 10
<212> TYPE: PRT
<213> ORGANISM: Rattus norvegicus

<400> SEQUENCE: 44

Phe Gln Thr Arg Ser Leu Lys Glu Leu Leu
 1               5                  10

<210> SEQ ID NO 45
<211> LENGTH: 30
<212> TYPE: DNA
<213> ORGANISM: Rattus norvegicus

<400> SEQUENCE: 45
```
ttccaaacac gaagtttgaa ggaactcttg                                         30

<210> SEQ ID NO 46
<211> LENGTH: 10
<212> TYPE: PRT
<213> ORGANISM: Rattus norvegicus

<400> SEQUENCE: 46

Phe Gln Thr Arg Ser Leu Lys Glu Leu Leu
 1               5                  10

<210> SEQ ID NO 47
<211> LENGTH: 30
<212> TYPE: DNA
<213> ORGANISM: Rattus norvegicus

<400> SEQUENCE: 47
ttccaaacac gaagtttgaa agaactcttg                                         30

<210> SEQ ID NO 48
<211> LENGTH: 10
<212> TYPE: PRT
<213> ORGANISM: Rattus norvegicus

<400> SEQUENCE: 48

Phe Gln Thr Arg Ser Leu Lys Glu Leu Leu
 1               5                  10

<210> SEQ ID NO 49
<211> LENGTH: 30
<212> TYPE: DNA
<213> ORGANISM: Rattus norvegicus

<400> SEQUENCE: 49
ggaactcttg tggggttaca aagatccatt                                         30

<210> SEQ ID NO 50
<211> LENGTH: 9
<212> TYPE: PRT
<213> ORGANISM: Rattus norvegicus

<400> SEQUENCE: 50

Glu Leu Leu Trp Gly Tyr Lys Asp Pro
 1               5

<210> SEQ ID NO 51
<211> LENGTH: 30
<212> TYPE: DNA
<213> ORGANISM: Rattus norvegicus

<400> SEQUENCE: 51
ggaactcttg tggggttaca aagatccatt                                         30

<210> SEQ ID NO 52
<211> LENGTH: 9
<212> TYPE: PRT
<213> ORGANISM: Rattus norvegicus

<400> SEQUENCE: 52

Glu Leu Leu Trp Gly Tyr Lys Asp Pro
 1               5

<210> SEQ ID NO 53
<211> LENGTH: 30

-continued

<210> SEQ ID NO 54
<211> LENGTH: 9
<212> TYPE: PRT
<213> ORGANISM: Rattus norvegicus

<400> SEQUENCE: 53
agaactcttg tggggttatg aagatccatt                30

<210> SEQ ID NO 54
<211> LENGTH: 9
<212> TYPE: PRT
<213> ORGANISM: Rattus norvegicus

<400> SEQUENCE: 54

Glu Leu Leu Trp Gly Tyr Glu Asp Pro
 1               5

<210> SEQ ID NO 55
<211> LENGTH: 30
<212> TYPE: DNA
<213> ORGANISM: Rattus norvegicus

<400> SEQUENCE: 55
ggaactcttg tggggttaca aagatccatt                30

<210> SEQ ID NO 56
<211> LENGTH: 9
<212> TYPE: PRT
<213> ORGANISM: Rattus norvegicus

<400> SEQUENCE: 56

Glu Leu Leu Trp Gly Tyr Lys Asp Pro
 1               5

<210> SEQ ID NO 57
<211> LENGTH: 30
<212> TYPE: DNA
<213> ORGANISM: Rattus norvegicus

<400> SEQUENCE: 57
ggaactcttg tggggttaca aagatccatt                30

<210> SEQ ID NO 58
<211> LENGTH: 9
<212> TYPE: PRT
<213> ORGANISM: Rattus norvegicus

<400> SEQUENCE: 58

Glu Leu Leu Trp Gly Tyr Lys Asp Pro
 1               5

<210> SEQ ID NO 59
<211> LENGTH: 30
<212> TYPE: DNA
<213> ORGANISM: Rattus norvegicus

<400> SEQUENCE: 59
agaactcttg tggggttatg aagatccatt                30

<210> SEQ ID NO 60
<211> LENGTH: 9
<212> TYPE: PRT
<213> ORGANISM: Rattus norvegicus

<400> SEQUENCE: 60

Glu Leu Leu Trp Gly Tyr Glu Asp Pro

-continued

<210> SEQ ID NO 61
<211> LENGTH: 30
<212> TYPE: DNA
<213> ORGANISM: Rattus norvegicus

<400> SEQUENCE: 61
cttgagtttg gttccatatc ctataagtac                             30

<210> SEQ ID NO 62
<211> LENGTH: 9
<212> TYPE: PRT
<213> ORGANISM: Rattus norvegicus

<400> SEQUENCE: 62

Leu Ser Leu Val Pro Tyr Pro Ile Ser
  1               5

<210> SEQ ID NO 63
<211> LENGTH: 30
<212> TYPE: DNA
<213> ORGANISM: Rattus norvegicus

<400> SEQUENCE: 63
cttgagtttg gttccatatc ctataagtac                             30

<210> SEQ ID NO 64
<211> LENGTH: 9
<212> TYPE: PRT
<213> ORGANISM: Rattus norvegicus

<400> SEQUENCE: 64

Leu Ser Leu Val Pro Tyr Pro Ile Ser
  1               5

<210> SEQ ID NO 65
<211> LENGTH: 30
<212> TYPE: DNA
<213> ORGANISM: Rattus norvegicus

<400> SEQUENCE: 65
cttgagtttg attccatatc ctataagtac                             30

<210> SEQ ID NO 66
<211> LENGTH: 9
<212> TYPE: PRT
<213> ORGANISM: Rattus norvegicus

<400> SEQUENCE: 66

Leu Ser Leu Ile Pro Tyr Pro Ile Ser
  1               5

<210> SEQ ID NO 67
<211> LENGTH: 30
<212> TYPE: DNA
<213> ORGANISM: Rattus norvegicus

<400> SEQUENCE: 67
tggaaaggat aacataagca aggttgccat                             30

<210> SEQ ID NO 68
<211> LENGTH: 9
<212> TYPE: PRT

-continued

<213> ORGANISM: Rattus norvegicus

<400> SEQUENCE: 68

Gly Lys Asp Asn Ile Ser Lys Val Ala
 1               5

<210> SEQ ID NO 69
<211> LENGTH: 30
<212> TYPE: DNA
<213> ORGANISM: Rattus norvegicus

<400> SEQUENCE: 69
tggaaaggat aacataagca aggttgccat                                      30

<210> SEQ ID NO 70
<211> LENGTH: 9
<212> TYPE: PRT
<213> ORGANISM: Rattus norvegicus

<400> SEQUENCE: 70

Gly Lys Asp Asn Ile Ser Lys Val Ala
 1               5

<210> SEQ ID NO 71
<211> LENGTH: 30
<212> TYPE: DNA
<213> ORGANISM: Rattus norvegicus

<400> SEQUENCE: 71
tggaaaggat aacataagca aagttgccat                                      30

<210> SEQ ID NO 72
<211> LENGTH: 9
<212> TYPE: PRT
<213> ORGANISM: Rattus norvegicus

<400> SEQUENCE: 72

Gly Lys Asp Asn Ile Ser Lys Val Ala
 1               5

<210> SEQ ID NO 73
<211> LENGTH: 30
<212> TYPE: DNA
<213> ORGANISM: Rattus norvegicus

<400> SEQUENCE: 73
gtcctattgg gaaagttatt gcgacatgat                                      30

<210> SEQ ID NO 74
<211> LENGTH: 9
<212> TYPE: PRT
<213> ORGANISM: Rattus norvegicus

<400> SEQUENCE: 74

Ser Tyr Trp Glu Ser Tyr Cys Asp Met
 1               5

<210> SEQ ID NO 75
<211> LENGTH: 30
<212> TYPE: DNA
<213> ORGANISM: Rattus norvegicus

<400> SEQUENCE: 75
gtcctattgg gaaagttatt gcgacatgat                                      30

<210> SEQ ID NO 76
<211> LENGTH: 9
<212> TYPE: PRT
<213> ORGANISM: Rattus norvegicus

<400> SEQUENCE: 76

Ser Tyr Trp Glu Ser Tyr Cys Asp Met
 1               5

<210> SEQ ID NO 77
<211> LENGTH: 30
<212> TYPE: DNA
<213> ORGANISM: Rattus norvegicus

<400> SEQUENCE: 77
gtcctattgg aaaagttatt gcgacatgat                                    30

<210> SEQ ID NO 78
<211> LENGTH: 9
<212> TYPE: PRT
<213> ORGANISM: Rattus norvegicus

<400> SEQUENCE: 78

Ser Tyr Trp Lys Ser Tyr Cys Asp Met
 1               5

<210> SEQ ID NO 79
<211> LENGTH: 30
<212> TYPE: DNA
<213> ORGANISM: Rattus norvegicus

<400> SEQUENCE: 79
aaatctcaaa cactgaggtt cttttcctct                                    30

<210> SEQ ID NO 80
<211> LENGTH: 10
<212> TYPE: PRT
<213> ORGANISM: Rattus norvegicus

<400> SEQUENCE: 80

Lys Ser Arg Thr Leu Arg Phe Phe Ser Ser
 1               5                   10

<210> SEQ ID NO 81
<211> LENGTH: 30
<212> TYPE: DNA
<213> ORGANISM: Rattus norvegicus

<400> SEQUENCE: 81
aagtctcgaa cactgaggtt cttttcctct                                    30

<210> SEQ ID NO 82
<211> LENGTH: 10
<212> TYPE: PRT
<213> ORGANISM: Rattus norvegicus

<400> SEQUENCE: 82

Lys Ser Arg Thr Leu Arg Phe Phe Ser Ser
 1               5                   10

<210> SEQ ID NO 83
<211> LENGTH: 30
<212> TYPE: DNA

<213> ORGANISM: Rattus norvegicus

<400> SEQUENCE: 83
aagtctcaaa cactgaggtt tttttcctct                    30

<210> SEQ ID NO 84
<211> LENGTH: 10
<212> TYPE: PRT
<213> ORGANISM: Rattus norvegicus

<400> SEQUENCE: 84

Lys Ser Gln Thr Leu Arg Phe Phe Ser Ser
 1               5                  10

<210> SEQ ID NO 85
<211> LENGTH: 2436
<212> TYPE: DNA
<213> ORGANISM: Rattus norvegicus

<400> SEQUENCE: 85

| | | | |
|---|---|---|---|
| cggcattgta attgtacctg tgagttggca agaagcaagt gctcttcctt gattctgctg | 60 |
| cacgaggagg agaatgggct gcgatcggaa ctgtgggctc attactggag ccgttattgg | 120 |
| tgctgtcctg gctgtgtttg gaggcattct catgccggtt ggagacctac tcattgagaa | 180 |
| gacaatcaaa agggaagttg tccttgaaga aggaaccatt gctttcaaaa actgggtgaa | 240 |
| aacgggcacc actgtgtaca gacagttttg ggtcttttgac gtgcaaaacc cagaggaagt | 300 |
| ggcaaagaat agcagcaaga tcaaggttat acagagaggt ccttacacat acagagttcg | 360 |
| ctatttagcc aaggaaaaata taactcagga ccccaaggac agcactgtct cttttgtaca | 420 |
| acccaatgga gccatctttg agccttcact gtctgttggc acagagaatg acaacttcac | 480 |
| agttctcaat ctggctgtgg cagctgcacc acatatctac acaaactcat ttgttcaagg | 540 |
| tgtgctcaac agccttatca aaagtccaa gtcttctatg ttccaaacac gaagtttgaa | 600 |
| ggaactcttg tggggttaca agatccatt cttgagtttg gttccatatc ctataagtac | 660 |
| cacagttggt gtgttttatc cttacaataa cactgtagat ggagtttata agtttccaa | 720 |
| tggaaaggat aacataagca aggttgccat aattgatacc tataagggaa aaggaatttt | 780 |
| gtcctattgg gaaagttatt gcgacatgat taatggcaca gatgcagcct cctttccacc | 840 |
| tcttggtgag aagtctcgaa cactgaggtt cttttcctct gacatttgca ggtccatcta | 900 |
| tgctgtgttt gaatctgaag tgaaccttaa aggaatcccc gtatacagat tgttcttcc | 960 |
| agccaacgcc tttgcctccc cactccagaa cccagacaac cactgtttct gcactgaaaa | 1020 |
| agtaatctca ataactgta cgtcgtatgg tgtgctggac attggcaagt gcaaagaagg | 1080 |
| gaaacctgtg tacaattctc ttccacattt cctacatgca agtcctgatg tctcagaacc | 1140 |
| tatcgaaggc ttgaatccta ccgaagatga gcataggaca tacttggatg tggaacccat | 1200 |
| aactggattc actctacagt tttccaaacg actgcaggtc aacatactgg tcaagccagc | 1260 |
| tagaaaaata gaagcactga gaatctgaa gagaccttac attgtaccta tactgtggct | 1320 |
| aaatgagact gggaccatcg gcgatgagaa agcagaaatg ttcagaaacc aagtgaccgg | 1380 |
| gaaaataaag ctcctgggcc tggttgagat ggtcttactt ggtgttggag tagtgatgtt | 1440 |
| tgttgctttt atgatttcat actgtgcttg cagatctaag aatggaaaat aagtagtgga | 1500 |
| tgagcctaca ttatgcacta gctacatttt tggtaaaacc aatctccaaa cgaagactt | 1560 |
| aagacatgct tgttttata aaacacacct atctgtagtt gaagaaacgg tggtgtgcgc | 1620 |

-continued

```
gctctctctc ttattgcaga tatatattca ttcatatatt gcaataagcc acagcatatt      1680
ttgacaagat caatatgtca ctaagcctat attttaata aaatcttgta ttttgttaag      1740
tccatcatct gcaactgagt ggacttcaat ttctgcagaa ctaattatct tttttggttc      1800
tgatttactg attttttttt cctgttgcca aatttcaaga atgtatatat tctaagaaac      1860
gctttgttcc tcatcgaagt aaactgttat catgtctggg gtgaccctt catttatagc      1920 aaatgttcct tgtgactgtc agcacatgat atgtcattta ttacatcatt ttaaagattt      1980
aaggatgaaa aatgaacaat tcacatatga accattgcta atatattgtt taagcctctc      2040
cctctctggt gtccttggca acaacaaggc caggtatcac agatatttt tcttttact       2100 ttcttaacac agagcttaat atgttctgtt cctcgccatg aaatgaacta tttttagcac      2160
attttagctc ttgaatttta agtatgttgt caagttccag gctgcctagc tcttttgaaa      2220
actgagtagg ttttctctt tctgctcagc cacaactaat gtaacttcag agagctgtta      2280
tagtggtaaa agatgtaatt tataataaat ggattatgat atagaatctt acaaaagcta      2340
gaattggctt taaatatgta tttgtggtaa tatattctgc ttttataatc acccagaaat      2400
aactggtttc taacattaaa gatgttctta aattcc                                2436
```

<210> SEQ ID NO 86
<211> LENGTH: 472
<212> TYPE: PRT
<213> ORGANISM: Rattus norvegicus

<400> SEQUENCE: 86

```
Met Gly Cys Asp Arg Asn Cys Gly Leu Ile Thr Gly Ala Val Ile Gly
  1               5                  10                  15

Ala Val Leu Ala Val Phe Gly Gly Ile Leu Met Pro Val Gly Asp Leu
                 20                  25                  30

Leu Ile Glu Lys Thr Ile Lys Arg Glu Val Val Leu Glu Glu Gly Thr
             35                  40                  45

Ile Ala Phe Lys Asn Trp Val Lys Thr Gly Thr Thr Val Tyr Arg Gln
         50                  55                  60

Phe Trp Val Phe Asp Val Gln Asn Pro Glu Glu Val Ala Lys Asn Ser
 65                  70                  75                  80

Ser Lys Ile Lys Val Ile Gln Arg Gly Pro Tyr Thr Tyr Arg Val Arg
                 85                  90                  95

Tyr Leu Ala Lys Glu Asn Ile Thr Gln Asp Pro Lys Asp Ser Thr Val
                100                 105                 110

Ser Phe Val Gln Pro Asn Gly Ala Ile Phe Glu Pro Ser Leu Ser Val
            115                 120                 125

Gly Thr Glu Asn Asp Asn Phe Thr Val Leu Asn Leu Ala Val Ala Ala
        130                 135                 140

Ala Pro His Ile Tyr Thr Asn Ser Phe Val Gln Gly Val Leu Asn Ser
145                 150                 155                 160

Leu Ile Lys Lys Ser Lys Ser Ser Met Phe Gln Thr Arg Ser Leu Lys
                165                 170                 175

Glu Leu Leu Trp Gly Tyr Lys Asp Pro Phe Leu Ser Leu Val Pro Tyr
            180                 185                 190

Pro Ile Ser Thr Thr Val Gly Val Phe Tyr Pro Tyr Asn Asn Thr Val
        195                 200                 205

Asp Gly Val Tyr Lys Val Ser Asn Gly Lys Asp Asn Ile Ser Lys Val
    210                 215                 220

Ala Ile Ile Asp Thr Tyr Lys Gly Lys Arg Asn Leu Ser Tyr Trp Glu
```

-continued

```
                225                 230                 235                 240

Ser Tyr Cys Asp Met Ile Asn Gly Thr Asp Ala Ala Ser Phe Pro Pro
                245                 250                 255

Leu Gly Glu Lys Ser Arg Thr Leu Arg Phe Phe Ser Ser Asp Ile Cys
                260                 265                 270

Arg Ser Ile Tyr Ala Val Phe Glu Ser Glu Val Asn Leu Lys Gly Ile
                275                 280                 285

Pro Val Tyr Arg Phe Val Leu Pro Ala Asn Ala Phe Ala Ser Pro Leu
                290                 295                 300

Gln Asn Pro Asp Asn His Cys Phe Cys Thr Glu Lys Val Ile Ser Asn
305                 310                 315                 320

Asn Cys Thr Ser Tyr Gly Val Leu Asp Ile Gly Lys Cys Lys Glu Gly
                325                 330                 335

Lys Pro Val Tyr Asn Ser Leu Pro His Phe Leu His Ala Ser Pro Asp
                340                 345                 350

Val Ser Glu Pro Ile Glu Gly Leu Asn Pro Thr Glu Asp Glu His Arg
                355                 360                 365

Thr Tyr Leu Asp Val Glu Pro Ile Thr Gly Phe Thr Leu Gln Phe Ser
                370                 375                 380

Lys Arg Leu Gln Val Asn Ile Leu Val Lys Pro Ala Arg Lys Ile Glu
385                 390                 395                 400

Ala Leu Lys Asn Leu Lys Arg Pro Tyr Ile Val Pro Ile Leu Trp Leu
                405                 410                 415

Asn Glu Thr Gly Thr Ile Gly Asp Glu Lys Ala Glu Met Phe Arg Asn
                420                 425                 430

Gln Val Thr Gly Lys Ile Lys Leu Leu Gly Leu Val Glu Met Val Leu
                435                 440                 445

Leu Gly Val Gly Val Val Met Phe Val Ala Phe Met Ile Ser Tyr Cys
                450                 455                 460

Ala Cys Arg Ser Lys Asn Gly Lys
465                 470
```

<210> SEQ ID NO 87
<211> LENGTH: 1709
<212> TYPE: DNA
<213> ORGANISM: Rattus norvegicus
<220> FEATURE:
<221> NAME/KEY: unsure
<222> LOCATION: (540)..(550)
<223> OTHER INFORMATION: The N at positions 540, 546, and 550 can be
      any nucleotide because the author is unsure of the
      exact sequence at these positions.

<400> SEQUENCE: 87

```
agcaagtgct cttccttgat tctgctgcac gaggaggaga atgggctgcg atcggaactg      60
tgggctcatt actggagccg ttattggtgc tgtcctggct gtgtttggag gcattctcat     120
gccggttgga gacctactca ttgagaagac aatcaaaagg gaagttgtcc ttgaagaagg     180
aaccattgct ttcaaaaact gggtgaaaac gggcaccact gtgtacagac agttttggat     240
ctttgacgtg caaaacccag aggaagtggc aaagaatagc agcaagatca aggttaaaca     300
gagaggtcct tacacataca gagttcgtta tttagccaag gaaagtataa ctcaggaccc     360
caaagacagc actgtctctt tgtacaacc caatggagcc atctttgagc cttcactgtc     420
tgttggaaca gagaatgaca acttcacagt tctcaatctg gctgtggcag ctgtaccaca     480
tatctaccaa aactcatttt ttcaaggtgt gctcaacata tttatcaaaa agtccaagtn     540
```

```
ttctangttn caaacacgaa gtttgaaaga actcttgtgg ggttatgaag atccattctt    600
gagtttgatt ccatatccta taagtaccac agttggtgtg ttttatcctt acaataacac    660
tgtagatgga gtttataaag ttttcaatgg aaaggataac ataagcaaag ttgccataat    720
tgatacctat aaagggaaaa ggaatttgtc ctattggaaa agttattgcg acatgattaa    780
tggcacagat gcagcctcct ttccaccttt tgttgagaag tctcaaacac tgaggttttt    840
ttcctctgac atttgcaggt ccatctatgc tgtgtttgaa tctgaagtga accttaaagg    900
aatccccgta tacagatttg ttcttccagc caacgccttt gcctcccac tccagaaccc    960 agacaaccac tgtttctgca ctgaaaaagt aatctcaaat aactgtacgt cgtatggtgt   1020
gctggacatt ggcaagtgca aagaaggaaa gcctgtgtac atttctcttc cacatttcct   1080
acatgcaagt cctgatgtct cagaacctat cgaaggcttg aatcctaacg aagatgagca   1140
taggacatac ttggatgtgg aacccataac tggattcact ctacagtttg caaaacgact   1200
gcaggtcaac atactggtca agccagctag aaaaatagaa ccactgaaga atctgaagag   1260
accttacatt gtacctatac tgtggctaaa tgagactggg accattggcg atgagaaagc   1320
agaaatgttc agaaaccaag tgaccgggaa aataaagctc ctgggcctgg ttgagatggt   1380
cttacttggt gttggagtag tgatgtttgt tgctttcatg atttcatact gtgcttgcag   1440
atttaagaat ggaaaataag taagtgctca tcaaagtatg tatcatttca tcaaagtatg   1500
ttttcatctc atcgagaagg gattatacat taaagcacat atacacattt ctgcacatgt   1560
ttagccagct ataatgtctt aatatatccc aacttttgat gttattgttg taaagaaaat   1620
tgagaagcaa atgattattg aaatcatcat taccacaggg aaatgaacac aattataatt   1680
tttgtccaaa ttaaaaaaaa aaaaaaaaa                                      1709
```

<210> SEQ ID NO 88
<211> LENGTH: 472
<212> TYPE: PRT
<213> ORGANISM: Rattus norvegicus
<220> FEATURE:
<221> NAME/KEY: UNSURE
<222> LOCATION: (169)..(170)
<223> OTHER INFORMATION: The Xaa at positions 167, 169, and 170 can be
      any amino acid because the author is unsure of the
      exact sequence at these positions.

<400> SEQUENCE: 88

```
Met Gly Cys Asp Arg Asn Cys Gly Leu Ile Thr Gly Ala Val Ile Gly
 1               5                  10                  15

Ala Val Leu Ala Val Phe Gly Gly Ile Leu Met Pro Val Gly Asp Leu
                20                  25                  30

Leu Ile Glu Lys Thr Ile Lys Arg Glu Val Val Leu Glu Glu Gly Thr
            35                  40                  45

Ile Ala Phe Lys Asn Trp Val Lys Thr Gly Thr Thr Val Tyr Arg Gln
        50                  55                  60

Phe Trp Ile Phe Asp Val Gln Asn Pro Glu Glu Val Ala Lys Asn Ser
    65                  70                  75                  80

Ser Lys Ile Lys Val Lys Gln Arg Gly Pro Tyr Thr Tyr Arg Val Arg
                85                  90                  95

Tyr Leu Ala Lys Glu Ser Ile Thr Gln Asp Pro Lys Asp Ser Thr Val
               100                 105                 110

Ser Phe Val Gln Pro Asn Gly Ala Ile Phe Glu Pro Ser Leu Ser Val
           115                 120                 125

Gly Thr Glu Asn Asp Asn Phe Thr Val Leu Asn Leu Ala Val Ala Ala
```

```
        130                 135                 140
Val Pro His Ile Tyr Gln Asn Ser Phe Phe Gln Gly Val Leu Asn Ile
145                 150                 155                 160
Phe Ile Lys Lys Ser Lys Xaa Ser Xaa Xaa Gln Thr Arg Ser Leu Lys
                165                 170                 175
Glu Leu Leu Trp Gly Tyr Glu Asp Pro Phe Leu Ser Leu Ile Pro Tyr
            180                 185                 190
Pro Ile Ser Thr Thr Val Gly Val Phe Tyr Pro Tyr Asn Asn Thr Val
            195                 200                 205
Asp Gly Val Tyr Lys Val Phe Asn Gly Lys Asp Asn Ile Ser Lys Val
        210                 215                 220
Ala Ile Ile Asp Thr Tyr Lys Gly Lys Arg Asn Leu Ser Tyr Trp Lys
225                 230                 235                 240
Ser Tyr Cys Asp Met Ile Asn Gly Thr Asp Ala Ala Ser Phe Pro Pro
                245                 250                 255
Phe Val Glu Lys Ser Gln Thr Leu Arg Phe Phe Ser Ser Asp Ile Cys
            260                 265                 270
Arg Ser Ile Tyr Ala Val Phe Glu Ser Glu Val Asn Leu Lys Gly Ile
            275                 280                 285
Pro Val Tyr Arg Phe Val Leu Pro Ala Asn Ala Phe Ala Ser Pro Leu
        290                 295                 300
Gln Asn Pro Asp Asn His Cys Phe Cys Thr Glu Lys Val Ile Ser Asn
305                 310                 315                 320
Asn Cys Thr Ser Tyr Gly Val Leu Asp Ile Gly Lys Cys Lys Glu Gly
                325                 330                 335
Lys Pro Val Tyr Ile Ser Leu Pro His Phe Leu His Ala Ser Pro Asp
            340                 345                 350
Val Ser Glu Pro Ile Glu Gly Leu Asn Pro Asn Glu Asp Glu His Arg
            355                 360                 365
Thr Tyr Leu Asp Val Glu Pro Ile Thr Gly Phe Thr Leu Gln Phe Ala
        370                 375                 380
Lys Arg Leu Gln Val Asn Ile Leu Val Lys Pro Ala Arg Lys Ile Glu
385                 390                 395                 400
Pro Leu Lys Asn Leu Lys Arg Pro Tyr Ile Val Pro Ile Leu Trp Leu
                405                 410                 415
Asn Glu Thr Gly Thr Ile Gly Asp Glu Lys Ala Glu Met Phe Arg Asn
            420                 425                 430
Gln Val Thr Gly Lys Ile Lys Leu Leu Gly Leu Val Glu Met Val Leu
        435                 440                 445
Leu Gly Val Gly Val Val Met Phe Val Ala Phe Met Ile Ser Tyr Cys
    450                 455                 460
Ala Cys Arg Phe Lys Asn Gly Lys
465                 470

<210> SEQ ID NO 89
<211> LENGTH: 1445
<212> TYPE: DNA
<213> ORGANISM: Rattus norvegicus

<400> SEQUENCE: 89
agcaagtgct cttccttgat tctgctgcac gaggaggaga atgggctgcg atcggaactg      60
tgggctcatt actggagccg ttattggtgc tgtcctggct gtgtttggag cattctcat     120 gccggttgga gacctactca ttgagaagac aatcaaaagg gaagttgtcc ttgaagaagg    180
```

```
aaccattgct ttcaaaaact gggtgaaaac gggcaccact gtgtacagac agttttggat      240
ctttgacgtg caaaacccag aggaagtggc aaagaatagc agcaagatca aggttaaaca      300
gagaggtcct tacacataca gagttcgtta tttagccaag gaaaatataa ctcaggaccc      360
caaggacagc actgtctctt ttgtacaacc caatggagcc atctttgagc cttcactgtc      420
tgttggaaca gagaatgaca acttcacagt tctcaatctg gctgtggcag ctgcaccaca      480
tatctacaca aactcatttg ttcaaggtgt gctcaacagc cttatcaaaa gtccaagtc       540 ttctatgttc caaacacgaa gtttgaagga actcttgtgg ggttacaaag atccattctt      600
gagtttggtt ccatatccta taagtaccac agttggtgtg ttttatcctt acaataacac      660
tgtagatgga gtttataaag ttttcaatgg aaaggataac ataagcaagg ttgccataat      720 tgataccttat aaagggaaaa ggaatttgtc ctattgggaa agttattgcg acatgattaa     780
tggcacagat gcagcctcct ttccaccttt tgttgagaaa tctcaaacac tgaggttctt      840
ttcctctgac atttgcaggt ccatctatgc tgtgtttgaa tctgaagtga accttaaagg      900
aatccccgta tacagatttg ttcttccagc caacgccttt gcctcccac tccagaaccc       960 agacaaccac tgtttctgca ctgaaaaagt aatctcaaat aactgtacgt cgtatggtgt     1020
gctggacatt ggcaagtgca aagaaggaaa gcctgtgtac atttctcttc cacatttcct     1080
acatgcaagt cctgatgtct cagaacctat cgaaggcttg aatcctaacg aagatgagca     1140
taggacatac ttggatgtgg aacccataac tggattcact ctacagtttg caaaacgact     1200
gcaggtcaac atactggtca agccagctag aaaaatagaa gcactgaaga atctgaagag     1260
accttacatt gtacctatac tgtggctaaa tgagactggg accatcggcg atgagaaagc     1320
agaaatgttc agaaaccaag tgaccgggaa aataaagctc ctgggcctgg ttgagatggt     1380
cttacttggt gttggagtag tgatgtttgt tgcttttatg atttcatact gtgcttgcag     1440
atcta                                                                 1445
```

<210> SEQ ID NO 90
<211> LENGTH: 310
<212> TYPE: PRT
<213> ORGANISM: Rattus norvegicus

<400> SEQUENCE: 90

```
Met Gly Cys Asp Arg Asn Cys Gly Leu Ile Thr Gly Ala Val Ile Gly
  1               5                  10                  15

Ala Val Leu Ala Val Phe Gly Gly Ile Leu Met Pro Val Gly Asp Leu
             20                  25                  30

Leu Ile Glu Lys Thr Ile Lys Arg Glu Val Val Leu Glu Glu Gly Thr
         35                  40                  45

Ile Ala Phe Lys Asn Trp Val Lys Thr Gly Thr Thr Val Tyr Arg Gln
     50                  55                  60

Phe Trp Ile Phe Asp Val Gln Asn Pro Glu Glu Val Ala Lys Asn Ser
 65                  70                  75                  80

Ser Lys Ile Lys Val Lys Gln Arg Gly Pro Tyr Thr Tyr Arg Val Arg
                 85                  90                  95

Tyr Leu Ala Lys Glu Asn Ile Thr Gln Asp Pro Lys Asp Ser Thr Val
            100                 105                 110

Ser Phe Val Gln Pro Asn Gly Ala Ile Phe Glu Pro Ser Leu Ser Val
        115                 120                 125

Gly Thr Glu Asn Asp Asn Phe Val Leu Asn Leu Ala Val Ala Ala
    130                 135                 140
```

-continued

```
Ala Pro His Ile Tyr Thr Asn Ser Phe Val Gln Gly Val Leu Asn Ser
145                 150                 155                 160

Leu Ile Lys Lys Ser Lys Ser Ser Met Phe Gln Thr Arg Ser Leu Lys
                165                 170                 175

Glu Leu Leu Trp Gly Tyr Lys Asp Pro Phe Leu Ser Leu Val Pro Tyr
            180                 185                 190

Pro Ile Ser Thr Thr Val Gly Val Phe Tyr Pro Tyr Asn Asn Thr Val
        195                 200                 205

Asp Gly Val Tyr Lys Val Phe Asn Gly Lys Asp Asn Ile Ser Lys Val
    210                 215                 220

Ala Ile Ile Asp Thr Tyr Lys Gly Lys Arg Asn Leu Ser Tyr Trp Glu
225                 230                 235                 240

Ser Tyr Cys Asp Met Ile Asn Gly Thr Asp Ala Ala Ser Phe Pro Pro
                245                 250                 255

Phe Val Glu Lys Ser Gln Thr Leu Arg Phe Phe Ser Ser Asp Ile Cys
            260                 265                 270

Arg Ser Ile Tyr Ala Val Phe Glu Ser Glu Val Asn Leu Lys Gly Ile
        275                 280                 285

Pro Val Tyr Arg Phe Val Leu Pro Ala Asn Ala Phe Ala Ser Pro Leu
    290                 295                 300

Gln Asn Pro Asp Asn His
305                 310

<210> SEQ ID NO 91
<211> LENGTH: 1436
<212> TYPE: DNA
<213> ORGANISM: Rattus norvegicus

<400> SEQUENCE: 91
tcttccttga ttctgctgca cgaggaggag aatgggctgc gatcggaact gtgggctcat      60
tactggagcc gttattggtg ctgtcctggc tgtgtttgga ggcattctca tgccggttgg     120
agacctactc attgagaaga caatcaaaag ggaagttgtc cttgaagaag gaaccattgc     180
tttcaaaaac tgggtgaaaa cgggcaccac tgtgtacaga cagttttgga tctttgacgt     240
gcaaaaccca gaggaagtgg caaagaatag cagcaagatc aaggttaaac agagaggtcc     300
ttacacatac agagttcgtt atttagccaa ggaaaatata actcaggacc ccaaggacag     360
cactgtctct tttgtacaac ccaatggagc catctttgag ccttcactgt ctgttggaac     420
agagaatgac aacttcacag ttctcaatct ggctgtggca gctgcaccac atatctacac     480
aaactcattt gttcaaggtg tgctcaacag ccttatcaaa agtccaagt cttctatgtt      540 ccaaacacga gtttgaagg aactcttgtg gggttacaaa gatccattct tgagtttggt     600
tccatatcct ataagtacca cagttggtgt gttttatcct tacaataaca ctgtagatgg     660
agtttataaa gttttcaatg gaaggataa cataagcaag gttgccataa ttgataccta     720
taaagggaaa aggaatttgt cctattggga aagttattgc gacatgatta atggcacaga     780
tgcagcctcc tttccacctt ttgttgagaa gtctcgaaca ctgaggttct tttcctctga     840
catttgcagg tccatctatg ctgtgtttgg atctgaagtg aaccttaaag gaatccccgt     900
gtacagattt gttcttccag ccaacgcctt tgcctcccca ctccagaacc cagacaacca     960
ctgtttctgc actgaaaaag taatctcaaa taactgtacg tcgtatggtg tgctggacat    1020
tggcaagtgc aaagaaggaa agcctgtgta catttctctt ccacatttcc tacatgcaag    1080
tcctgatgtc tcagaaccta tcgaaggctt gaatcctaac gaagatgagc ataggacata    1140
```

-continued

```
cttggatgtg gaacccataa ctggattcac tctacagttt gcaaaacgac tgcaggtcaa    1200
catactggtc aagccagcta gaaaaataga agcactgaag aatctgaaga gaccttacat    1260
tgtacctata ctgtggctaa atgagactgg gaccatcggc gatgagaaag cagaaatgtt    1320
cagaaaccaa gtgaccggga aaataaagct cctgggcctg gttgagatgg tcttacttgg    1380
tgttggagta gtgatgtttg ttgcttttat gatttcatac tgtgcttgca gatcta        1436
```

<210> SEQ ID NO 92
<211> LENGTH: 468
<212> TYPE: PRT
<213> ORGANISM: Rattus norvegicus

<400> SEQUENCE: 92

```
Met Gly Cys Asp Arg Asn Cys Gly Leu Ile Thr Gly Ala Val Ile Gly
 1               5                  10                  15

Ala Val Leu Ala Val Phe Gly Gly Ile Leu Met Pro Val Gly Asp Leu
                20                  25                  30

Leu Ile Glu Lys Thr Ile Lys Arg Glu Val Val Leu Glu Glu Gly Thr
            35                  40                  45

Ile Ala Phe Lys Asn Trp Val Lys Thr Gly Thr Thr Val Tyr Arg Gln
        50                  55                  60

Phe Trp Ile Phe Asp Val Gln Asn Pro Glu Glu Val Ala Lys Asn Ser
 65                  70                  75                  80

Ser Lys Ile Lys Val Lys Gln Arg Gly Pro Tyr Thr Tyr Arg Val Arg
                85                  90                  95

Tyr Leu Ala Lys Glu Asn Ile Thr Gln Asp Pro Lys Asp Ser Thr Val
            100                 105                 110

Ser Phe Val Gln Pro Asn Gly Ala Ile Phe Glu Pro Ser Leu Ser Val
        115                 120                 125

Gly Thr Glu Asn Asp Asn Phe Thr Val Leu Asn Leu Ala Val Ala Ala
    130                 135                 140

Ala Pro His Ile Tyr Thr Asn Ser Phe Val Gln Gly Val Leu Asn Ser
145                 150                 155                 160

Leu Ile Lys Lys Ser Lys Ser Ser Met Phe Gln Thr Arg Ser Leu Lys
                165                 170                 175

Glu Leu Leu Trp Gly Tyr Lys Asp Pro Phe Leu Ser Leu Val Pro Tyr
            180                 185                 190

Pro Ile Ser Thr Thr Val Gly Val Phe Tyr Pro Tyr Asn Asn Thr Val
        195                 200                 205

Asp Gly Val Tyr Lys Val Phe Asn Gly Lys Asp Asn Ile Ser Lys Val
    210                 215                 220

Ala Ile Ile Asp Thr Tyr Lys Gly Lys Arg Asn Leu Ser Tyr Trp Glu
225                 230                 235                 240

Ser Tyr Cys Asp Met Ile Asn Gly Thr Asp Ala Ala Ser Phe Pro Pro
                245                 250                 255

Phe Val Glu Lys Ser Arg Thr Leu Arg Phe Phe Ser Ser Asp Ile Cys
            260                 265                 270

Arg Ser Ile Tyr Ala Val Phe Gly Ser Glu Val Asn Leu Lys Gly Ile
        275                 280                 285

Pro Val Tyr Arg Phe Val Leu Pro Ala Asn Ala Phe Ala Ser Pro Leu
    290                 295                 300

Gln Asn Pro Asp Asn His Cys Phe Cys Thr Glu Lys Val Ile Ser Asn
305                 310                 315                 320

Asn Cys Thr Ser Tyr Gly Val Leu Asp Ile Gly Lys Cys Lys Glu Gly
```

```
                    325                 330                 335
Lys Pro Val Tyr Ile Ser Leu Pro His Phe Leu His Ala Ser Pro Asp
                340                 345                 350

Val Ser Glu Pro Ile Glu Gly Leu Asn Pro Asn Glu Asp Glu His Arg
            355                 360                 365

Thr Tyr Leu Asp Val Glu Pro Ile Thr Gly Phe Thr Leu Gln Phe Ala
        370                 375                 380

Lys Arg Leu Gln Val Asn Ile Leu Val Lys Pro Ala Arg Lys Ile Glu
385                 390                 395                 400

Ala Leu Lys Asn Leu Lys Arg Pro Tyr Ile Val Pro Ile Leu Trp Leu
                405                 410                 415

Asn Glu Thr Gly Thr Ile Gly Asp Glu Lys Ala Glu Met Phe Arg Asn
            420                 425                 430

Gln Val Thr Gly Lys Ile Lys Leu Leu Gly Leu Val Glu Met Val Leu
        435                 440                 445

Leu Gly Val Gly Val Val Met Phe Val Ala Phe Met Ile Ser Tyr Cys
    450                 455                 460

Ala Cys Arg Ser
465

<210> SEQ ID NO 93
<211> LENGTH: 20
<212> TYPE: DNA
<213> ORGANISM: Rattus norvegicus

<400> SEQUENCE: 93
tgagttccag gatacccagg                                                    20

<210> SEQ ID NO 94
<211> LENGTH: 22
<212> TYPE: DNA
<213> ORGANISM: Rattus norvegicus

<400> SEQUENCE: 94
aagcggagtc aaaatacttt gc                                                 22

<210> SEQ ID NO 95
<211> LENGTH: 20
<212> TYPE: DNA
<213> ORGANISM: Rattus norvegicus

<400> SEQUENCE: 95
acgttcctcc tcagccctgg                                                    20

<210> SEQ ID NO 96
<211> LENGTH: 21
<212> TYPE: DNA
<213> ORGANISM: Rattus norvegicus

<400> SEQUENCE: 96
gtgcatgtct gcataaacat g                                                  21

<210> SEQ ID NO 97
<211> LENGTH: 20
<212> TYPE: DNA
<213> ORGANISM: Rattus norvegicus

<400> SEQUENCE: 97
tataggtgga gcctaatgag                                                    20
```

<210> SEQ ID NO 98
<211> LENGTH: 20
<212> TYPE: DNA
<213> ORGANISM: Rattus norvegicus

<400> SEQUENCE: 98
actcacgact gatcaaagtg                                                    20

<210> SEQ ID NO 99
<211> LENGTH: 20
<212> TYPE: DNA
<213> ORGANISM: Rattus norvegicus

<400> SEQUENCE: 99
agctgctgtg agcttgtgag                                                    20

<210> SEQ ID NO 100
<211> LENGTH: 20
<212> TYPE: DNA
<213> ORGANISM: Rattus norvegicus

<400> SEQUENCE: 100
gacagcagtc agcatggaga                                                    20

<210> SEQ ID NO 101
<211> LENGTH: 2561
<212> TYPE: DNA
<213> ORGANISM: Rattus norvegicus

<400> SEQUENCE: 101
ggatccactc atttcacaaa ctgtattctt tcttccaatc tttttttttt ttttgagatg      60
gagtttcacc tcttgttgcc caggctggag tgcaatggca tgatctcggc tcaccacaac     120
ctccgcctcc tgggttcaag cgattctcct gcctcagcct ccggagtagc ttgggattac     180
aagcatgtgc caccaagccc ggctaacttt gtatgtttag tagagatggg gtttctctgt     240
gttggtcggc tggtctcaa actcccaacc tcaggtgatc cacccgcctc agccttccaa      300
agtgctagga tgacaggtgt gagccaccac gcccggctct cccaatcttt atataataat     360
cacatactat ggctgggcat ggtggctcac gcctgtcatc ccagcacttt gggaggctga     420
ggtgggtgga tcacgaggtc aggagttcga gaccagcctg accaacatgg tgaaacccca     480
tctctactga aaatacaaaa attaaccagg catggtggcg tgcacctgta atcccagcta     540
cacaggaggc tgagtcagga gaattgcttg aacccaggag gcagaggttg cagtgagccg     600
agatcgtgcc actgcactcc agcctgggtg acagagaaag actccgtctc aaaaaaataa     660
taataatcac atactttatg aagacaccaa acattagatt gacaaatata tactaacaca     720
aacatcctaa ttttaacaga attagcatga atcaactgca aatgcaaaac tatattgtag     780
ttgaatgtgc agggaaaaaa ttcttcagta agagagcaat gccatggttg aaacaagaca     840
tcctctacat tttatattta cttcaaattc tttatacctg tagtctatcc aaagtcgtca     900
ataaaactga agtaagata ctcttatttt aaaaattcca tgttttaaac agcttttagg      960
acaagccctt caggcctgaa ctcagtattc atgaaaatta gactttcttt taacagttat    1020
tttaagtatg gtgatattag agagtgtccc agtataaaat ttctgagaat ttttttttcta   1080 tttacccatg ctttttcttat tttcacagat agctttccaa tgattagacg aattgattct    1140
ttctgtgact catcagttca tttcctgtaa aattcatgtc ttgctgttga tttgtgaata    1200
aggtatcgta aataaaacat ctgttaccat acttgcttat catttaatgg aaaacacatc    1260

| | |
|---|---|
| agtcaaccca cattctgttc gcaggagagc tccagaaggg gtgtggaagg ttgtgttggg | 1320 |
| tggagaaacc agatagtgag gatgcaacta agttgctgag acaagggaag agagatgagg | 1380 |
| gtgagagttc tccttagata agatttcaat atgttaatca tgtgtagaaa gaaaattaaa | 1440 |
| aaggaggaat atgaagaaat tcagatatga cattattagt tctgccactg gtaggcatta | 1500 |
| gaagcaagaa aagggagacg gaccgaggaa gccactttgg tgaaacgaaa agcatttgtt | 1560 |
| tatttagaac gggcaaaatg atacgtttca gtgggggttt tctttgtact ttgatctttt | 1620 |
| tgtactgata tttaagcttc tgtttttatga tctctttcta atgatagaac cagagcttgt | 1680 |
| agaaaccact ttaatcatat ccaggagttt gcaagaaaca ggtgcttaac actaattcac | 1740 |
| ctcctgaaca agaaaaatgg gctgtgaccg gaactgtggg ctcatcgctg gggctgtcat | 1800 |
| tggtgctgtc ctggctgtgt ttggaggtat tctaatgcca gttggagacc tgcttatcca | 1860 |
| gaagacaatt aaaaaggtac aagtagtcca agaatatgc cttctcattt tgattgattc | 1920 |
| taacttctct ttttttgctt tgtatttacc tgctttatat ttcatggtaa ctgctaattt | 1980 |
| tgtatctttg acataaaggt aattatgaac cactgcaact ctatatgatg tgactttatg | 2040 |
| tgaaatgtta taagtataat gtatatttaa catgactcca ttgctgtctt aaatataaat | 2100 |
| accaaattct attaaaagct gtctacaggt atgcatgtta gtagaaataa ttgttttaag | 2160 |
| ttatgtccaa agagcatgtt ggcatgcttt tgaataggaa ataagtgagt atattttgta | 2220 |
| aaagcacatt tataaaagaa gttgcacttt agttaatact gagaaaagta aaactgtgtg | 2280 |
| tgtgtgtgtg tgtgtgtgta atgtgtttaa tattgaaaca taaatcctta ttaaattgta | 2340 |
| ggtaaacttg tttggtaata cactgtttag taatccacta tttttatata tgtgtaataa | 2400 |
| tctcatctca taaatatttt ctatttgtga agcttcatat tggaatctta gaaaatactt | 2460 |
| tcagaaatat gcagaacatg tcttagtata aaacaaattg actgtagtgt gaaaaaacag | 2520 |
| aatgattgaa tagatgggct ttgcacaaca acctagaatt c | 2561 |

<210> SEQ ID NO 102
<211> LENGTH: 154
<212> TYPE: DNA
<213> ORGANISM: Rattus norvegicus

<400> SEQUENCE: 102

| | |
|---|---|
| tatttacccca tgcttttctt attttcacag atagctttcc aatgattaga cgaattgatt | 60 |
| cttttctgtga ctcatcagtt cctttcctgt aaaattcatg tcttgctgtt gatttgtgaa | 120 |
| taaggtatcg taaataaaac atctgttacc atac | 154 |

<210> SEQ ID NO 103
<211> LENGTH: 130
<212> TYPE: DNA
<213> ORGANISM: Rattus norvegicus

<400> SEQUENCE: 103

| | |
|---|---|
| ctaatcattt gccactcgat ttttaaacag atgcagcctc atttccacct tttgttgaga | 60 |
| aaagccaggt attgcagttc ttttcttctg atatttgcag gtaagacaga tactgaagta | 120 |
| taagtatgct | 130 |

<210> SEQ ID NO 104
<211> LENGTH: 152
<212> TYPE: DNA
<213> ORGANISM: Rattus norvegicus -continued

```
<400> SEQUENCE: 104
aagtaacatt ttcccataca tatatttcag tacaacaata ctgcagatgg agtttataaa      60
gttttcaatg gaaaagataa cataagtaaa gttgccataa tcgacacata taaaggtaaa     120
aggtaagtat tctggtaaaa tgtgcatgta tg                                   152

<210> SEQ ID NO 105
<211> LENGTH: 240
<212> TYPE: DNA
<213> ORGANISM: Rattus norvegicus

<400> SEQUENCE: 105
ttgtcttaaa cagtgacttt gtttttgtag gctgcatccc atatctatca aaatcaattt      60
gttcaaatga tcctcaattc acttattaac aagtcaaaat cttctatgtt ccaagtcaga     120
actttgagag aactgttatg gggctatagg gatccatttt tgagtttggt tccgtaccct     180
gttactacca cagttggtct gttttatcct gtaagtacca aatatgaatg gcaatattat     240

<210> SEQ ID NO 106
<211> LENGTH: 208
<212> TYPE: DNA
<213> ORGANISM: Rattus norvegicus

<400> SEQUENCE: 106
tttgaatttt gtttactgct gtttctttag agttcgtttt ctagccaagg aaaatgtaac      60
ccaggacgct gaggacaaca cagtctcttt cctgcagccc aatggtgcca tcttcgaacc     120
ttcactatca gttggaacag aggctgacaa cttcacagtt ctcaatctgg ctgtggcagt     180
gagtagacaa acaacaaagt tatctatt                                        208

<210> SEQ ID NO 107
<211> LENGTH: 221
<212> TYPE: DNA
<213> ORGANISM: Rattus norvegicus

<400> SEQUENCE: 107
cataacccaa acttattttc ttttccatag caagttgtcc tcgaagaagg tacaattgct      60
tttaaaaatt gggttaaaac aggcacagaa gttttacagac agttttggat ctttgatgtg    120
caaaatccac aggaagtgat gatgaacagc agcaacattc aagttaagca aagaggtcct    180
tatacgtaca ggtgagtgag tgcccacaaa tatgagacac t                         221

<210> SEQ ID NO 108
<211> LENGTH: 494
<212> TYPE: DNA
<213> ORGANISM: Rattus norvegicus

<400> SEQUENCE: 108
aaataatgtt gattattaac ttgattacag actgggacca ttggtgatga gaaggcaaac      60
atgttcagaa gtcaagtaac tggaaaaata aacctccttg gcctgataga aatgatctta     120
ctcagtgttg gtgtggtgat gtttgttgct tttatgattt catattgtgc atgcagatcg     180
aaaacaataa aataagtaag tatgtaccaa aaaatattgc ttcaataata ttagcttata    240
tattacttgt tttcactta tcaaagagaa gttacatatt aggccatata tatttctaga     300
catgtctagc cactgatcat ttttaaatat aggtaaataa acctataaat attatcacgc    360
agatcactaa agtatatctt taattctggg agaaatgaga taaagatgt acttgtgacc    420
attgtaacaa tagcacaaat aaagcacttg tgccaaagtt gtccaaaatt gactggttca    480
```

```
tttctcaatt atat                                                      494

<210> SEQ ID NO 109
<211> LENGTH: 113
<212> TYPE: DNA
<213> ORGANISM: Rattus norvegicus

<400> SEQUENCE: 109
gttcataatt attttcaacg tattacagag tattaaagaa tctgaagagg aactatattg    60
tgcctattct ttggcttaat gaggtttgta tttgcagctg ttagtcatta aaa          113

<210> SEQ ID NO 110
<211> LENGTH: 134
<212> TYPE: DNA
<213> ORGANISM: Rattus norvegicus

<400> SEQUENCE: 110
ttggtaatta tttagttgtt ctcttttttag ataactggat tcactttaca atttgcaaaa   60
cggctgcagg tcaacctatt ggtcaagcca tcagaaaaaa ttcagtgagt ctcttgaaaa   120
tggttatttt gata                                                     134

<210> SEQ ID NO 111
<211> LENGTH: 179
<212> TYPE: DNA
<213> ORGANISM: Rattus norvegicus

<400> SEQUENCE: 111
ttccaattga ctcttaaaac ttgtcttcag ggagacctgt gtacatttca cttcctcatt    60
ttctgtatgc aagtcctgat gtttcagaac ctattgatgg attaaaccca aatgaagaag   120
aacataggac atacttggat attgaacctg taagaaaaca ccttattgat ctgatttgg    179

<210> SEQ ID NO 112
<211> LENGTH: 250
<212> TYPE: DNA
<213> ORGANISM: Rattus norvegicus

<400> SEQUENCE: 112
tggaatgcag ctctttttc tctgtattta ggtcaatcta tgctgtattt gaatccgacg     60
ttaatctgaa aggaatccct gtgtatagat ttgttcttcc atccaaggcc tttgcctctc   120
cagttgaaaa cccagacaac tattgttct gcacagaaaa aattatctca aaaaattgta    180
catcatatgg tgtgctagac atcagcaaat gcaaagaagg tgagtaaata acctcagtag   240
cacagtccat                                                          250

<210> SEQ ID NO 113
<211> LENGTH: 136
<212> TYPE: DNA
<213> ORGANISM: Rattus norvegicus

<400> SEQUENCE: 113
gaggactgca gtgtaggact ttcctgcaga ataccatttg atcctattaa gaattgtcca    60
aatgttggag catttgattg aaaaatcctt cttagccatt ttaaaggtaa gttgtatgat   120
ttttctttaa ataaag                                                   136

<210> SEQ ID NO 114
<211> LENGTH: 107
<212> TYPE: DNA
```

<213> ORGANISM: Rattus norvegicus

<400> SEQUENCE: 114

```
tgtttattca ttgtctttttt ctattcctag gaatctgtcc tattgggaaa gtcactgcga      60
catgattaat ggtacaggta agaatatttg ttttgtggtc atcacag                    107
```

<210> SEQ ID NO 115
<211> LENGTH: 684
<212> TYPE: DNA
<213> ORGANISM: Rattus norvegicus

<400> SEQUENCE: 115

```
ccacaactga attgatttcc gtttctacag acctggctca agcacaaacc aatttgtgtt      60
gttctgattc aataattggt ttctgggtgg ccaattcaga agaagagtgt acatgctcaa     120
caaatcctag gccctgcatt cctgtcatcc tcatccgggg gaaacaccat catcccagta     180
gctgccctat tcaactgcaa cagtctccag gaccatcagt atactgcatt tcatgtgcac     240
caaatatttt gaaagacatt tataaataat tggcttatga ctcatatttc tctatgaata     300
ccttcataca gcaggtataa ctcttttctt tatgggctta aatattttgt cactgatcct     360
gcaaatggac atcattttag cacactagcg gtttatattt taaggacctt cattctctgt     420
tctgcacctc ttctggaaat tgagtaaatt ttgctttttt ttttttactc agttgcaact     480
tacgcttggc atcttcagaa tgcttttcta gcattaagag atgtaaatga taaaggaatt     540
attgtatgaa atattacaaa gcgtagacta tgcattgtta ttcattataa tattttttgc     600
tgtcataatc gcctcataaa gacaggtttc aaccattaaa atatgttctt ccttaaattc     660
ctgtgctttt tctagttcct cttg                                            684
```

<210> SEQ ID NO 116
<211> LENGTH: 201
<212> TYPE: DNA
<213> ORGANISM: Rattus norvegicus
<220> FEATURE:
<221> NAME/KEY: unsure
<222> LOCATION: (69)..(197)
<223> OTHER INFORMATION: The N at positions 69, 121, 125, 195 and 197
      can be any nucleotide because the author is unsure of
      the exact sequence at these positions.

<400> SEQUENCE: 116

```
tttcacttcc tcattttctg tatgcaagtc ctgatgtttc agaacctatt gatggattaa      60
acccaaatna agaagaacat aggacatact tggatattga acctataact ggattcactt     120
nacantttgc aaacggctg caggtcaacc tattggtcaa gccatcagaa aaaattcaag     180
tattaaagaa tctangnggg a                                               201
```

<210> SEQ ID NO 117
<211> LENGTH: 220
<212> TYPE: DNA
<213> ORGANISM: Rattus norvegicus
<220> FEATURE:
<221> NAME/KEY: unsure
<222> LOCATION: (5)..(178)
<223> OTHER INFORMATION: The N at positions 5, 9, 23, 77, 134 and 178
      can be any nucleotide because the author is unsure of
      the exact sequence at these positions.

<400> SEQUENCE: 117

```
aaggnaganc atattttaat ggntgaaacc tgtctttatg aggcgattat gacagcaaaa      60
aatattataa tgaatancaa tgcatagtct acgctttgta atatttcata caataattcc     120
```

```
tttatcagtt acanctctta atgctagaaa agcattctga agatgccaag cgtaagtngc      180
aactgagtaa aaaaaaaaaa gcaaaattta ctcaatttcc                            220
```

<210> SEQ ID NO 118
<211> LENGTH: 309
<212> TYPE: DNA
<213> ORGANISM: Rattus norvegicus
<220> FEATURE:
<221> NAME/KEY: unsure
<222> LOCATION: (233)..(292)
<223> OTHER INFORMATION: The N at positions 233 and 292 can be any
      nucleotide because the author is unsure of the
      exact sequence at these positions.

<400> SEQUENCE: 118

```
cttgagcagg ggttcactta ttctgagagc attagttctc ctaaaaagct ccagcataga       60
aagggaagat aaaccaaatt ctagcttgtg ttttacccac agaaggatac aggacaaagg      120
aatagtaact ggcctgtttg gatactaaaa ttgaaaataa cttttagcct cctccttatg      180
atagccgcca gagtaaatgt tgagcattac tacagaaaag ccacaaacca agnatctacc      240
tgtttggaaa gatcttttgc atctctgaag gtgcttaaag catacttagt gnctttcctt      300
ttaactcgg                                                             309
```

<210> SEQ ID NO 119
<211> LENGTH: 2561
<212> TYPE: DNA
<213> ORGANISM: Rattus norvegicus

<400> SEQUENCE: 119

```
ggatccactc atttcacaaa ctgtattctt tcttccaatc tttttttttt ttttgagatg       60
gagtttcacc tcttgttgcc caggctggag tgcaatggca tgatctcggc tcaccacaac      120
ctccgcctcc tgggttcaag cgattctcct gcctcagcct ccggagtagc ttgggattac      180
aagcatgtgc caccaagccc ggctaacttt gtatgtttag tagagatggg gtttctctgt      240
gttggtcggg ctggtctcaa actcccaacc tcaggtgatc cacccgcctc agccttccaa      300
agtgctagga tgacaggtgt gagccaccac gcccggctct cccaatcttt atataataat      360
cacatactat ggctgggcat ggtggctcac gcctgtcatc ccagcacttt gggaggctga      420
ggtgggtgga tcacgaggtc aggagttcga ccagcctg accaacatgg tgaaacccca      480
tctctactga aaatacaaaa attaaccagg catggtggcg tgcacctgta atcccagcta      540
cacaggaggc tgagtcagga gaattgcttg aacccaggag gcagaggttg cagtgagccg      600
agatcgtgcc actgcactcc agcctgggtg acagagaaag actccgtctc aaaaaaataa      660
taataatcac atactttatg aagacaccaa acattagatt gacaaatata tactaacaca      720
aacatcctaa ttttaacaga attagcatga atcaactgca aatgacaaac tatattgtag      780
ttgaatgtgc agggaaaaaa ttcttcagta agagagcaat gccatggttg aaacaagaca      840
tcctctacat tttatattta cttcaaattc tttatacctg tagtctatcc aaagtcgtca      900
ataaaactga agtaagata ctcttatttt aaaaattcca tgttttaaac agcttttagg      960
acaagccctt caggcctgaa ctcagtattc atgaaaatta gactttcttt taacagttat     1020
tttaagtatg gtgatattag agagtgtccc agtataaaat ttctgagaat ttttttttcta     1080 tttacccatg ctttttcttat tttcacagat agctttccaa tgattagacg aattgattct     1140
ttctgtgact catcagttca tttcctgtaa aattcatgtc ttgctgttga tttgtgaata     1200
```

```
aggtatcgta aataaaacat ctgttaccat acttgcttat catttaatgg aaaacacatc    1260
agtcaaccca cattctgttc gcaggagagc tccagaaggg gtgtggaagg ttgtgttggg    1320
tggagaaacc agatagtgag gatgcaacta agttgctgag acaagggaag agagatgagg    1380
gtgagagttc tccttagata agatttcaat atgttaatca tgtgtagaaa gaaaattaaa    1440
aaggaggaat atgaagaaat tcagatatga cattattagt tctgccactg gtaggcatta    1500
gaagcaagaa aagggagacg gaccgaggaa gccactttgg tgaaacgaaa agcatttgtt    1560
tatttagaac gggcaaaatg atacgtttca gtgggggttt tctttgtact ttgatctttt    1620
tgtactgata tttaagcttc tgttttatga tctctttcta atgatagaac cagagcttgt    1680
agaaaccact ttaatcatat ccaggagttt gcaagaaaca ggtgcttaac actaattcac    1740
ctcctgaaca agaaaaatgg gctgtgaccg gaactgtggg ctcatcgctg gggctgtcat    1800
tggtgctgtc ctggctgtgt ttggaggtat tctaatgcca gttggagacc tgcttatcca    1860
gaagacaatt aaaaaggtac aagtagtcca agaatatgc cttctcattt tgattgattc    1920
taacttctct ttttttgctt tgtatttacc tgctttatat ttcatggtaa ctgctaattt    1980
tgtatctttg acataaaggt aattatgaac cactgcaact ctatatgatg tgactttatg    2040
tgaaatgtta taagtataat gtatatttaa catgactcca ttgctgtctt aaatataaat    2100
accaaattct attaaaagct gtctacaggt atgcatgtta gtagaaataa ttgttttaag    2160
ttatgtccaa agagcatgtt ggcatgcttt tgaataggaa ataagtgagt atattttgta    2220
aaagcacatt tataaaagaa gttgcacttt agttaatact gagaaaagta aaactgtgtg    2280
tgtgtgtgtg tgtgtgtgta atgtgtttaa tattgaaaca taaatcctta ttaaattgta    2340
ggtaaacttg tttggtaata cactgtttag taatccacta tttttatata tgtgtaataa    2400
tctcatctca taaatatttt ctatttgtga agcttcatat tggaatctta gaaaatactt    2460
tcagaaatat gcagaacatg tcttagtata aaacaaattg actgtagtgt gaaaaaacag    2520
aatgattgaa tagatgggct ttgcacaaca acctagaatt c                        2561
```

<210> SEQ ID NO 120
<211> LENGTH: 1647
<212> TYPE: DNA
<213> ORGANISM: Rattus norvegicus

<400> SEQUENCE: 120

```
gttccttttcc tgtaaaattc atgtcttgct gttgatttgt gaataagaac cagagcttgt      60
agaaaccact ttaatcatat ccaggagttt gcaagaaaca ggtgcttaac actaattcac     120
ctcctgaaca agaaaaatgg gctgtgaccg gaactgtggg ctcatcgctg gggctgtcat     180
tggtgctgtc ctggctgtgt ttggaggtat tctaatgcca gttggagacc tgcttatcca     240
gaagacaatt aaaaagcaag ttgtccgcga agaaggtaca attgctttta aaaattgggt     300
taaaacaggc acagaagttt acagacagtt ttggatcttt gatgtgcaaa atccacagga     360
agtgatgatg aacagcagca acattcaagt taagcaaaga ggtccttata cgtacagagt     420 tcgtttttcta gccaaggaaa atgtaaccca ggacgctgag acaacacag tctctttcct     480 gcagcccaat ggtgccatct tcgaaccttc actatcagtt ggaacagagg ctgacaactt     540
cacagttctc aatctggctg tggcagctgc atcccatatc tatcaaaatc aatttgttca     600
aatgatcctc aattcactta ttaacaagtc aaaatcttct atgttccaag tcagaacttt     660
gagagaactg ttatggggct atagggatcc attttttgagt ttggttccgt accctgttac     720
taccacagtt ggtctgtttt atccttacaa caatactgca gatggagttt ataaagtttt     780
```

```
caatggaaaa gataacataa gtaaagttgc cataatcgac acatataaag gtaaaaggaa      840
tctgtccgat tgggaaagtc actgcgacat gattaatggt acagatgcag cctcatttcc      900 acctttgtt gagaaaagcc aggtattgca gttcttttct tctgatattt gcaggtcaat       960
ctatgctgta tttgaatccg acgttaatct gaaaggaatc cctgtgtata gatttgttct     1020
tccatccaag gcctttgcct ctccagttga aacccagac aactattgtt tctgcacaga      1080
aaaaattatc tcaaaaaatt gtacatcata tggtgtgcta gacatcagca aatgcaaaga     1140
agggagacct gtgtacattt cacttcctca ttttctgtat gcaagtcctg atgtttcaga     1200
acctattgat ggattaaacc caatgaaga agaacatagg acatacttgg atattgaacc      1260
tataactgga ttcactttac aatttgcaaa acggctgcag gtcaacctat tggtcaagcc    1320
atcagaaaaa attcaagtat taaagaatct gaagaggaac tatattgtgc ctattctttg    1380
gcttaatgag actgggacca ttggtgatga aaggcaaac atgttcagaa gtcaagtaac    1440
tggaaaaata aacctccttg gcctgataga aatgatctta ctcagtgttg gtgtggtgat    1500
gtttgttgct tttatgattt catattgtgc atgcagatcg aaaacaataa aataagtaag    1560
tatgtaccaa aaaatattgc ttcaataata ttagcttata tattacttgt tttcacttta    1620
tcaagagaga aggttacata ttaggcc                                         1647

<210> SEQ ID NO 121
<211> LENGTH: 369
<212> TYPE: DNA
<213> ORGANISM: Rattus norvegicus

<400> SEQUENCE: 121
gtattaagct caatattagc attaatccat ttatttgtta aaatctaata ttgtattctt       60
gtcttaaaca gtgactttgt ttttgtaggc tgcatcccat atctatcaaa atcaatttgt      120
tcaaatgatc ctcaattcac ttattaacaa gtcaaaatct tctatgttcc aagtcagaac     180
tttgagagaa ctgttatggg gctatagga tccattttg agtttggttc cgtaccctgt       240
tactaccaca gttggtctgt tttatcctgt aagtaccaaa tatgaatggc aatattatta    300
cattttaatt taattaattc aatggcattg gcaaggcata attttataat ttagctcatt    360
agctatgct                                                             369

<210> SEQ ID NO 122
<211> LENGTH: 269
<212> TYPE: DNA
<213> ORGANISM: Rattus norvegicus

<400> SEQUENCE: 122
ttctgtttta tgatctcttt ctaatgatag aaccagagct tgtagaaacc actttaatca       60
tatccaggag tttgcaagaa acaggtgctt aacactaatt cacctcctga acaagaaaaa      120
tgggctgtga ccggaactgt gggctcatcg ctggggctgt cattggtgct gtcctggctg     180
tgtttggagg tattctaatg ccagttggag acctgcttat ccagaagaca attaaaaagg     240
tacaagtagt caaagaatat cctctcatt                                        269

<210> SEQ ID NO 123
<211> LENGTH: 369
<212> TYPE: DNA
<213> ORGANISM: Rattus norvegicus

<400> SEQUENCE: 123
```

```
gtattaagct caatattagc attaatccat ttatttgtta aaatctaata ttgtattctt      60
gtcttaaaca gtgactttgt ttttgtaggc tgcatcccat atctatcaaa atcaatttgt     120
tcaaatgatc ctcaattcac ttattaacaa gtcaaaatct tctatgttcc aagtcagaac     180
tttgagagaa ctgttatggg gctataggga tccattttg agtttggttc cgtaccctgt      240
tactaccaca gttggtctgt tttatcctgt aagtaccaaa tatgaatggc aatattatta     300
cattttaatt taattaattc aatggcattg gcaaggcata attttataat ttagctcatt     360
agctatgct                                                             369

<210> SEQ ID NO 124
<211> LENGTH: 2566
<212> TYPE: DNA
<213> ORGANISM: Rattus norvegicus

<400> SEQUENCE: 124
cgtcgccgtc cccgtctcct gccaggcgcg gagccctgcg agccgcgggt gggccccagg      60
cgcgcagaca tgggctgctc cgccaaagcg cgctgggctg ccggggcgct gggcgtcgcg     120
gggctactgt gcgctgtgct gggcgctgtc atgatcgtga tggtgccgtc gctcatcaag     180
cagcaggtcc ttaagaacgt gcgcatcgac cccagtagcc tgtccttcaa catgtggaag     240
gagatcccta tccccttcta tctctccgtc tacttctttg acgtcatgaa ccccagcgag     300
atcctgaagg gcgagaagcc gcaggtgcgg gagcgcgggc cctacgtgta cagggagtcc     360
aggcacaaaa gcaacatcac cttcaacaac aacgacaccg tgtccttcct cgagtaccgc     420
accttccagt tccagccctc caagtcccac ggctcggaga gcgactacat cgtcatgccc     480
aacatcctgg tcttgggtgc ggcggtgatg atggagaata gcccatgac  cctgaagctc     540 atcatgacct tggcattcac caccctcggc gaacgtgcct tcatgaaccg cactgtgggt     600
gagatcatgt ggggctacaa ggaccccctt gtgaatctca tcaacaagta ctttccaggc     660
atgttcccct tcaaggacaa gttcggatta tttgctgagc tcaacaactc cgactctggg     720
ctcttcacgg tgttcacggg ggtccagaac atcagcagga tccacctcgt ggacaagtgg     780
aacgggctga gcaaggttga cttctggcat tccgatcagt gcaacatgat caatggaact     840
tctgggcaaa tgtggccgcc cttcatgact cctgagtcct cgctggagtt ctacagcccg     900
gaggcctgcc gatccatgaa gctaatgtac aaggagtcag gggtgtttga aggcatcccc     960
acctatcgct tcgtggctcc caaaaccctg tttgccaacg ggtccatcta cccacccaac    1020
gaaggcttct gcccgtgcct ggagtctgga attcagaacg tcagcacctg caggttcagt    1080
gcccccttgt ttctctccca tcctcacttc ctcaacgccg accgggttct ggcagaagcg    1140
gtgactggcc tgcaccctaa ccaggaggca cactccttgt tcctggacat ccacccggtc    1200
acgggaatcc ccatgaactg ctctgtgaaa ctgcagctga gcctctacat gaaatctgtc    1260
gcaggcattg gacaaactgg gaagattgag cctgtggtcc tgccgctgct ctggtttgca    1320
gagagcgggg ccatggaggg ggagactctt cacacattct acactcagct ggtgttgatg    1380
cccaaggtga tgcactatgc ccagtacgtc ctcctggcgc tgggctgcgt cctgctgctg    1440
gtccctgtca tctgccaaat ccggagccaa gagaaatgct atttattttg gagtagtagt    1500
aaaaagggct caaaggataa ggaggccatt caggcctatt ctgaatccct gatgacatca    1560
gctcccaagg gctctgtgct gcaggaagca aaactgtagg gtcctgagga caccgtgagc    1620
cagccaggcc tggccgctgg gcctgaccgg ccccccagcc cctacacccc gcttctcccg    1680
gactctccca gcagacagcc ccccagcccc acagcctgag cctcccagct gccatgtgcc    1740
```

```
tgttgcacac ctgcacacac gccctggcac acatacacac atgcgtgcag gcttgtgcag     1800
acactcaggg atggagctgc tgctgaaggg acttgtaggg agaggctcgt caacaagcac     1860
tgttctggaa ccttctctcc acgtggccca caggctgacc acagggctg tgggtcctgc      1920 gtcccttcc tcgggtgagc ctggcctgtc ccgttcagcc gttgggccag gcttcctccc      1980
ctccaaggtg aaacactgca gtcccggtgt ggtggctccc catgcaggac gggccaggct     2040
gggagtgccg ccttcctgtg ccaaattcag tggggactca gtgcccaggc cctggcacga     2100
gctttggcct tggtctacct gccaggccag gcaaagcgcc tttacacagg cctcggaaaa     2160
caatggagtg agcacaagat gccctgtgca gctgcccgag ggtctccgcc caccccggcc     2220
ggactttgat ccccccgaag tcttcacagg cactgcatcg ggttgtctgg cgccttttc     2280 ctccagccta aactgacatc atcctatgga ctgagccggc cactctctgg ccgaagtggc    2340
gcaggctgtg cccccgagct gcccccaccc cctcacaggg tccctcagat tataggtgcc    2400
caggctgagg tgaagaggcc tggggggccct gccttccggg cgctcctgga ccctggggca  2460
aacctgtgac ccttttctac tggaatagaa atgagttta tcatctttga aaataattc       2520 actcttgaag taataaacgt ttaaaaaaat ggaaaaaaa aaaaaa                     2566

<210> SEQ ID NO 125
<211> LENGTH: 305
<212> TYPE: DNA
<213> ORGANISM: Rattus norvegicus
<220> FEATURE:
<221> NAME/KEY: unsure
<222> LOCATION: (178)..(299)
<223> OTHER INFORMATION: The N at positions 178, 224, 263, 284 and 299
      can be any nucleotide because the author is unsure of
      the exact sequence at these positions

<400> SEQUENCE: 125
aaggaagaac atattttaat ggttgaaacc tgtctttatg aggcgattat gacagcaaaa      60
aatattataa tgaataacaa tgcatagtct acgctttgta atatttcata caataattcc     120
tttatcattt acatctctta atgctagaaa agcattctga agatgccaag cgtaagtngc     180
aactgagtaa aaaaaaaaaa gcaaaattta ctcaatttcc agangaggtg cagaacagag     240
aatgaaggtc cttaaaatat aanccgctag tgtgcttaaa atgntgtcca tttgcaggnt     300
ccagt                                                                 305

<210> SEQ ID NO 126
<211> LENGTH: 2216
<212> TYPE: DNA
<213> ORGANISM: Rattus norvegicus

<400> SEQUENCE: 126
atttgatcct attaagaatt gtccaaatgt tggagcattt gattgaaaaa tccttcttag      60
ccattttaaa gatagctttc caatgattag acgaattgat tctttctgtg actcatcagt    120
tcctttcctg taaaattcat gtcttgctgt tgatttgtga ataagaacca gagcttgtag    180
aaaccacttt aatcatatcc aggagtttgc aagaaacagg tgcttaacac taattcacct    240
cctgaacaag aaaaatgggc tgtgaccgga actgtgggct catcgctggg gctgtcattg    300
gtgctgtcct ggctgtgttt ggaggtattc taatgccagt tggagacctg cttatccaga    360
agacaattaa aaagcaagtt gtcctcgaag aaggtacaat tgcttttaaa aattgggtta    420
aaacaggcac agaagtttac agacagtttt ggatctttga tgtgcaaaat ccacaggaag    480
```

-continued

```
tgatgatgaa cagcagcaac attcaagtta agcaaagagg tccttatacg tacagagttc      540
gttttctagc caaggaaaat gtaacccagg acgctgagga caacacagtc tctttcctgc      600
agcccaatgg tgccatcttc gaaccttcac tatcagttgg aacagaggct gacaacttca      660
cagttctcaa tctggctgtg gcagctgcat cccatatcta tcaaaatcaa tttgttcaaa      720
tgatcctcaa ttcacttatt aacaagtcaa aatcttctat gttccaagtc agaactttga      780
gagaactgtt atggggctat agggatccat ttttgagttt ggttccgtac cctgttacta      840
ccacagttgg tctgttttat ccttacaaca atactgcaga tggagtttat aaagttttca      900
atggaaaaga taacataagt aaagttgcca taatcgacac atataaaggt aaaaggaatc      960
tgtcctattg ggaaagtcac tgcgacatga ttaatggtac agatgcagcc tcatttccac     1020
cttttgttga gaaaagccag gtattgcagt tcttttcttc tgatatttgc aggtcaatct     1080
atgctgtatt tgaatccgac gttaatctga aggaatccc tgtgtataga tttgttcttc      1140
catccaaggc ctttgcctct ccagttgaaa acccagacaa ctattgtttc tgcacagaaa     1200
aaattatctc aaaaaattgt acatcatatg gtgtgctaga catcagcaaa tgcaaagaag     1260
ggagacctgt gtacatttca cttcctcatt ttctgtatgc aagtcctgat gtttcagaac     1320
ctattgatgg attaaaccca aatgaagaag aacataggac atacttggat attgaaccta     1380
taactggatt cactttacaa tttgcaaaac ggctgcaggt caacctattg gtcaagccat     1440
cagaaaaaat tcaagtatta aagaatctga agaggaacta tattgtgcct attctttggc     1500
ttaatgagac tgggaccatt ggtgatgaga aggcaaacat gttcagaagt caagtaactg     1560
gaaaaataaa cctccttggc ctgatagaaa tgatcttact cagtgttggt gtggtgatgt     1620
ttgttgcttt tatgatttca tattgtgcat gcagatcgaa aacaataaaa taaacctggc     1680
tcaagcacaa accaatttgt gttgttctga ttcaataatt ggtttctggg tggccaattc     1740
agaagaagag tgtacatgct caacagtctc caggaccatc agtatactgc atttcatgtg     1800
caccaaatat tttgaaagac atttataaat aattggctta tgactcatat ttctctatga     1860
ataccttcat acagcaggta taactctttt ctttatgggc ttaaatattt tgtcactgat     1920
cctgcaaatg gacatcattt tagcacacta gcggtttata ttttaaggac cttcattctc     1980
tgttctgcac ctcttctgga aattgagtaa attttgcttt ttttttttac tcagttgcaa     2040
cttacgcttg gcatcttcag aatgcttttc tagcattaag agatgtaaat gataaaggaa     2100
ttattgtatg aaatattaca aagcgtagac tatgcattgt tattcattat aatattttt      2160 gctgtcataa tcgcctcata aagacaggtt tcaaccatta aaatatgttc ttcctt         2216
```

<210> SEQ ID NO 127
<211> LENGTH: 1942
<212> TYPE: DNA
<213> ORGANISM: Rattus norvegicus

<400> SEQUENCE: 127

```
atttgatcct attaagaatt gtccaaatgt tggagcattt gattgaaaaa tccttcttag       60
ccatttaaaa gatagctttc caatgattag acgaattgat tctttctgtg actcatcagt      120 tccttcctg taaaattcat gtcttgctgt tgatttgtga ataagaacca gagcttgtag       180
aaaccacttt aatcatatcc aggagtttgc aagaaacagg tgcttaacac taattcacct      240
cctgaacaag aaaatgggc tgtgaccgga actgtgggct catcgctggg gctgtcattg       300
gtgctgtcct ggctgtgttt ggaggtattc taatgccagt tggagacctg cttatccaga      360
agacaattaa aaagcaagtt gtcctcgaag aaggtacaat tgcttttaaa aattgggtta      420
```

```
aaacaggcac agaagtttac agacagtttt ggatctttga tgtgcaaaat ccacaggaag    480
tgatgatgaa cagcagcaac attcaagtta agcaaagagg tccttatacg tacagagttc    540
gttttctagc caaggaaaat gtaacccagg acgctgagga caacacagtc tctttcctgc    600
agcccaatgg tgccatcttc gaaccttcac tatcagttgg aacagaggct gacaacttca    660
cagttctcaa tctggctgtg gcagctgcat cccatatcta tcaaaatcaa tttgttcaaa    720
tgatcctcaa ttcacttatt aacaagtcaa atcttctat gttccaagtc agaactttga     780
gagaactgtt atggggctat agggatccat ttttgagttt ggttccgtac cctgttacta    840
ccacagttgg tctgttttat ccttacaaca atactgcaga tggagtttat aaagttttca    900
atggaaaaga taacataagt aaagttgcca taatcgacac atataaaggt aaaaggaatc    960
tgtcctattg ggaaagtcac tgcgacatga ttaatggtac agatgcagcc tcatttccac   1020
cttttgttga gaaagccag gtattgcagt tcttttcttc tgatatttgc aggtcaatct    1080
atgctgtatt tgaatccgac gttaatctga aggaatccc tgtgtataga tttgttcttc    1140
catccaaggc ctttgcctct ccagttgaaa acccagacaa ctattgtttc tgcacagaaa   1200
aaattatctc aaaaaattgt acatcatatg gtgtgctaga catcagcaaa tgcaaagaag   1260
ggagacctgt gtacatttca cttcctcatt ttctgtatgc aagtcctgat gtttcagaac   1320
ctattgatgg attaaaccca aatgaagaag aacataggac atacttggat attgaaccta   1380
taactggatt cactttacaa tttgcaaaac ggctgcaggt caacctattg gtcaagccat   1440
cagaaaaaat tcaagtatta aagaatctga agaggaacta tattgtgcct attctttggc   1500
ttaatgagac tgggaccatt ggtgatgaga aggcaaacat gttcagaagt caagtaactg   1560
gaaaaataaa cctccttggc ctgatagaaa tgatcttact cagtgttggt gtggtgatgt   1620
ttgttgcttt tatgatttca tattgtgcat gcagatcgaa aacaataaaa taagtaagta   1680
tgtaccaaaa aatattgctt caataatatt agcttatata ttacttgttt tcactttatc   1740
aaagagaagt tacatattag gccatatata tttctagaca tgtctagcca ctgatcattt   1800
ttaaatatag gtaaataaac ctataaatat tatcacgcag atcactaaag tatatcttta   1860
attctgggag aaatgagata aaagatgtac ttgtgaccat tgtaacaata gcacaaataa   1920
agcacttgtg ccaaagttgt cc                                            1942
```

<210> SEQ ID NO 128
<211> LENGTH: 1870
<212> TYPE: DNA
<213> ORGANISM: Rattus norvegicus

<400> SEQUENCE: 128

```
gaaaaatcct tcttagccat tttaaagata gctttccaat gattagacga attgattctt     60
tctgtgactc atcagttcct ttcctgtaaa attcatgtct tgctgttgat ttgtgaataa    120
gaaccagagc ttgtagaaac cactttaatc atatccagga gtttgcaaga aacaggtgct    180
taacactaat tcacctcctg aacaagaaaa atgggctgtg accggaactg tgggctcatc    240
gctggggctg tcattggtgc tgtcctggct gtgtttggag gtattctaat gccagttgga    300
gacctgctta tccagaagac aattaaaaag caagttgtcc tcgaagaagg tacaattgct    360
tttaaaaatt gggttaaaac aggcacagaa gtttacagac agttttggat ctttgatgtg    420
caaaatccac aggaagtgat gatgaacagc agcaacattc aagttaagca aagaggtcct    480
tatacgtaca gagttcgttt tctagccaag gaaaatgtaa cccaggacgc tgaggacaac    540
```

| | |
|---|---|
| acagtctctt tcctgcagcc caatggtgcc atcttcgaac cttcactatc agttggaaca | 600 |
| gaggctgaca acttcacagt tctcaatctg gctgtggcag ctgcatccca tatctatcaa | 660 |
| aatcaatttg ttcaaatgat cctcaattca cttattaaca agtcaaaatc ttctatgttc | 720 |
| caagtcagaa ctttgagaga actgttatgg ggctataggg atccattttt gagtttggtt | 780 |
| ccgtaccctg ttactaccac agttggtctg ttttatcctt acaacaatac tgcagatgga | 840 |
| gtttataaag ttttcaatgg aaaagataac ataagtaaag ttgccataat cgacacatat | 900 |
| aaaggtaaaa ggaatctgtc ctattgggaa agtcactgcg acatgattaa tggtacagat | 960 |
| gcagcctcat ttccaccttt tgttgagaaa agccaggtat tgcagttctt ttcttctgat | 1020 |
| atttgcaggt caatctatgc tgtatttgaa tccgacgtta atctgaaagg aatccctgtg | 1080 |
| tatagatttg ttcttccatc caaggccttt gcctctccag ttgaaaaccc agacaactat | 1140 |
| tgtttctgca cagaaaaaat tatctcaaaa aattgtacat catatggtgt gctagacatc | 1200 |
| agcaaatgca agaagggag acctgtgtac atttcacttc ctcatttct gtatgcaagt | 1260 |
| cctgatgttt cagaacctat tgatggatta acccaaatg aagaagaaca taggacatac | 1320 |
| ttggatattg aacctataac tggattcact ttacaatttg caaacggct gcaggtcaac | 1380 |
| ctattggtca agccatcaga aaaaattcaa gtattaaaga atctgaagag gaactatatt | 1440 |
| gtgcctattc tttggcttaa tgagactggg accattggtg atgagaaggc aaacatgttc | 1500 |
| agaagtcaag taactggaaa aataaacctc cttggcctga tagaaatgat cttactcagt | 1560 |
| gttggtgtgg tgatgtttgt tgcttttatg atttcatatt gtgcatgcag atcgaaaaca | 1620 |
| ataaaataag tatgtaccaa aaaatattgc ttcaataata ttagcttata tattacttgt | 1680 |
| tttcactta tcaaagagaa gttacatatt aggcccatata tatttctaga catgtctagc | 1740 |
| cactgatcat tttaaaatat aggtaaataa acctataaat attatcacgc agatcactaa | 1800 |
| agtatatctt taattctggg agaaatgaga taaaagatgt acttgtgacc attgtaacaa | 1860 |
| tagcacaaat | 1870 |

<210> SEQ ID NO 129
<211> LENGTH: 1820
<212> TYPE: DNA
<213> ORGANISM: Rattus norvegicus

<400> SEQUENCE: 129

| | |
|---|---|
| ggggatgcaa ctaagttgct gagacaaggg aagagagatg aggaaccaga gcttgtagaa | 60 |
| accactttaa tcatatccag gagtttgcaa gaaacaggtg cttaacacta attcacctcc | 120 |
| tgaacaagaa aaatgggctg tgaccggaac tgtgggctca tcgctgggc tgtcattggt | 180 |
| gctgtcctgg ctgtgtttgg aggtattcta atgccagttg gagacctgct tatccagaag | 240 |
| acaattaaaa agcaagttgt cctcgaagaa ggtacaattg cttttaaaaa ttgggttaaa | 300 |
| acaggcacag aagtttacag acagttttgg atctttgatg tgcaaaatcc acaggaagtg | 360 |
| atgatgaaca gcagcaacat tcaagttaag caaagaggtc cttatacgta cagagttcgt | 420 |
| tttctagcca aggaaaatgt aacccaggac gctgaggaca acacagtctc tttcctgcag | 480 |
| cccaatggtg ccatcttcga accttcacta tcagttggaa cagaggctga caacttcaca | 540 |
| gttctcaatc tggctgtggc agctgcatcc catatctatc aaaatcaatt tgttcaaatg | 600 |
| atcctcaatt cacttattaa caagtcaaaa tcttctatgt tccaagtcag aactttgaga | 660 |
| gaactgttat ggggctatag ggatccattt ttgagtttgg ttccgtaccc tgttactact | 720 |
| acagttggtc tgttttatcc ttacaacaat actgcagatg gagtttataa agttttcaat | 780 |

```
ggaaaagata acataagtaa agttgccata atcgacacat ataaaggtaa aaggaatctg        840
tcctattggg aaagtcactg cgacatgatt aatggtacag atgcagcctc atttccacct        900
tttgttgaga aaagccaggt attgcagttc ttttcttctg atatttgcag gtcaatctat        960
gctgtatttg aatccgacgt taatctgaaa ggaatccctg tgtatagatt cgttcttcca       1020
tccaaggcct ttgcctctcc agttgaaaac ccagacaact attgtttctg cacagaaaaa       1080
attatctcaa aaaattgtac atcatatggt gtgctagaca tcagcaaatg caaagaaggg       1140
agacctgtgt acatttcact tcctcatttt ctgtatgcaa gtcctgatgt ttcagaacct       1200
attgatggat taaacccaaa tgaagaagaa cataggacat acttggatat tcaacctata       1260
actggattca ctttacaatt tgcaaaacgg ctgcaggtca accattggt caagccatca        1320 gaaaaaattc aagtattaaa gaatctgaag aggaactata ttgtgcctat tctttggctt       1380
aatgagactg ggaccattgg tgatgagaag gcaaacatgt tcagaagtca agtaactgga       1440
aaaataaacc tccttggcct gatagaaatg atcttactca gtgttggtgt ggtgatgttt       1500
gttgctttta tgatttcata ttgtgcatgc agatcgaaaa caataaaata gtatgtacc        1560 aaaaaatatt gcttcaataa tattagctta tatattactt gttttcactt tatcaaagag       1620
aagttacata ttaggccata tatttctta gacatgtcta gccactgatc attttttaaat       1680 ataggtaaat aaacctataa atattatcac gcagatcact aaagtatatc tttaattctg       1740
ggagaaatga gataaaagat gtacttgtga ccattgtaac aatagcacaa taaagcactg       1800
tgccaaagtt gtccaaaaaa                                                   1820

<210> SEQ ID NO 130
<211> LENGTH: 35
<212> TYPE: DNA
<213> ORGANISM: Rattus norvegicus

<400> SEQUENCE: 130
acakmyttat caaagagtcc aagtcttcta tgttc                                    35

<210> SEQ ID NO 131
<211> LENGTH: 20
<212> TYPE: DNA
<213> ORGANISM: Rattus norvegicus

<400> SEQUENCE: 131
accaactgtg gtacttatcg                                                     20

<210> SEQ ID NO 132
<211> LENGTH: 30
<212> TYPE: DNA
<213> ORGANISM: Rattus norvegicus

<400> SEQUENCE: 132
gctttctctt ctcttttttt ggggggggga                                          30

<210> SEQ ID NO 133
<211> LENGTH: 29
<212> TYPE: DNA
<213> ORGANISM: Rattus norvegicus

<400> SEQUENCE: 133
gctttctctt ctctttttg ggggggggga                                           29

<210> SEQ ID NO 134
```

```
<211> LENGTH: 30
<212> TYPE: DNA
<213> ORGANISM: Rattus norvegicus

<400> SEQUENCE: 134
gctttctctt ctctttttt gggggggga                                    30

<210> SEQ ID NO 135
<211> LENGTH: 30
<212> TYPE: DNA
<213> ORGANISM: Rattus norvegicus

<400> SEQUENCE: 135
gctttctctt ctctttttt tggggggga                                    30

<210> SEQ ID NO 136
<211> LENGTH: 30
<212> TYPE: DNA
<213> ORGANISM: Rattus norvegicus

<400> SEQUENCE: 136
ctgtgactca tcagttcctt tcctgtaaaa                                   30

<210> SEQ ID NO 137
<211> LENGTH: 30
<212> TYPE: DNA
<213> ORGANISM: Rattus norvegicus

<400> SEQUENCE: 137
ctgtgactca tcagttcatt tcctgtaaaa                                   30

<210> SEQ ID NO 138
<211> LENGTH: 30
<212> TYPE: DNA
<213> ORGANISM: Rattus norvegicus

<400> SEQUENCE: 138
actgtgcttg cagatttaag aatggaaaat                                   30

<210> SEQ ID NO 139
<211> LENGTH: 40
<212> TYPE: DNA
<213> ORGANISM: Rattus norvegicus

<400> SEQUENCE: 139
attgtaacaa tagcacaaat aaagcacttg tgccaaagtt                        40

<210> SEQ ID NO 140
<211> LENGTH: 24
<212> TYPE: DNA
<213> ORGANISM: Rattus norvegicus

<400> SEQUENCE: 140
attgtaacaa tatgtgccaa agtt                                         24

<210> SEQ ID NO 141
<211> LENGTH: 9
<212> TYPE: PRT
<213> ORGANISM: Rattus norvegicus

<400> SEQUENCE: 141

Cys Ala Cys Arg Phe Lys Asn Gly Lys
 1               5
```

<210> SEQ ID NO 142
<211> LENGTH: 30
<212> TYPE: DNA
<213> ORGANISM: Rattus norvegicus

<400> SEQUENCE: 142
gaatccctgt gtatagattt gttcttccat            30

<210> SEQ ID NO 143
<211> LENGTH: 30
<212> TYPE: DNA
<213> ORGANISM: Rattus norvegicus

<400> SEQUENCE: 143
gaatccctgt gtatagattc gttcttccat            30

<210> SEQ ID NO 144
<211> LENGTH: 30
<212> TYPE: DNA
<213> ORGANISM: Rattus norvegicus

<400> SEQUENCE: 144
ctgtgactca tcagttcctt tcctgtaaaa            30

<210> SEQ ID NO 145
<211> LENGTH: 30
<212> TYPE: DNA
<213> ORGANISM: Rattus norvegicus

<400> SEQUENCE: 145
ctgtgactca tcagttcatt tcctgtaaaa            30

<210> SEQ ID NO 146
<211> LENGTH: 30
<212> TYPE: DNA
<213> ORGANISM: Rattus norvegicus

<400> SEQUENCE: 146
tgatacgttt cagtgggtgt tttctttgta            30

<210> SEQ ID NO 147
<211> LENGTH: 30
<212> TYPE: DNA
<213> ORGANISM: Rattus norvegicus

<400> SEQUENCE: 147
tgatacgttt cagtggatgt tttctttgta            30

<210> SEQ ID NO 148
<211> LENGTH: 30
<212> TYPE: DNA
<213> ORGANISM: Rattus norvegicus

<400> SEQUENCE: 148
ggttattttg atatgatctg tagtatcgta            30

<210> SEQ ID NO 149
<211> LENGTH: 30
<212> TYPE: DNA
<213> ORGANISM: Rattus norvegicus

<400> SEQUENCE: 149
ggttattttg atatgatcta tagtatcgta            30

<210> SEQ ID NO 150
<211> LENGTH: 20
<212> TYPE: DNA
<213> ORGANISM: Rattus norvegicus

<400> SEQUENCE: 150
ctcctcctgc cctcctcatt                                               20

<210> SEQ ID NO 151
<211> LENGTH: 20
<212> TYPE: DNA
<213> ORGANISM: Rattus norvegicus

<400> SEQUENCE: 151
ttgaagcact ttactgcagg                                               20

<210> SEQ ID NO 152
<211> LENGTH: 20
<212> TYPE: DNA
<213> ORGANISM: Rattus norvegicus

<400> SEQUENCE: 152
tctgctgtcc tcttaagcct                                               20

<210> SEQ ID NO 153
<211> LENGTH: 20
<212> TYPE: DNA
<213> ORGANISM: Rattus norvegicus

<400> SEQUENCE: 153
tccaacacaa cagagcacag                                               20

<210> SEQ ID NO 154
<211> LENGTH: 20
<212> TYPE: DNA
<213> ORGANISM: Rattus norvegicus

<400> SEQUENCE: 154
caggaactgg agagtcaggt                                               20

<210> SEQ ID NO 155
<211> LENGTH: 20
<212> TYPE: DNA
<213> ORGANISM: Rattus norvegicus

<400> SEQUENCE: 155
gcccctggat ctggtccttt                                               20

<210> SEQ ID NO 156
<211> LENGTH: 20
<212> TYPE: DNA
<213> ORGANISM: Rattus norvegicus

<400> SEQUENCE: 156
gaacttgaag aggaccttaa                                               20

<210> SEQ ID NO 157
<211> LENGTH: 20
<212> TYPE: DNA
<213> ORGANISM: Rattus norvegicus

<400> SEQUENCE: 157

-continued ttgcccatct ttgagaagtt                                              20

<210> SEQ ID NO 158
<211> LENGTH: 20
<212> TYPE: DNA
<213> ORGANISM: Rattus norvegicus

<400> SEQUENCE: 158
tgccttgcaa gctgtaacca                                              20

<210> SEQ ID NO 159
<211> LENGTH: 20
<212> TYPE: DNA
<213> ORGANISM: Rattus norvegicus

<400> SEQUENCE: 159
gtctggcagc agtgtagtca                                              20

<210> SEQ ID NO 160
<211> LENGTH: 20
<212> TYPE: DNA
<213> ORGANISM: Rattus norvegicus

<400> SEQUENCE: 160
ccggattacc taggtgcgga                                              20

<210> SEQ ID NO 161
<211> LENGTH: 20
<212> TYPE: DNA
<213> ORGANISM: Rattus norvegicus

<400> SEQUENCE: 161
tccagagctc ggatgggctt                                              20

<210> SEQ ID NO 162
<211> LENGTH: 24
<212> TYPE: DNA
<213> ORGANISM: Rattus norvegicus

<400> SEQUENCE: 162
caggaatatc tagatgttct gtgg                                         24

<210> SEQ ID NO 163
<211> LENGTH: 19
<212> TYPE: DNA
<213> ORGANISM: Rattus norvegicus

<400> SEQUENCE: 163
tccactggac ttgctttgc                                               19

<210> SEQ ID NO 164
<211> LENGTH: 30
<212> TYPE: DNA
<213> ORGANISM: Rattus norvegicus

<400> SEQUENCE: 164 tagaaaata gaagcactga agaatctgaa                                    30

<210> SEQ ID NO 165
<211> LENGTH: 30
<212> TYPE: DNA
<213> ORGANISM: Rattus norvegicus

<400> SEQUENCE: 165

```
tagaaaaata gaagcactga agaatctgaa                                    30
```

<210> SEQ ID NO 166
<211> LENGTH: 9
<212> TYPE: PRT
<213> ORGANISM: Rattus norvegicus

<400> SEQUENCE: 166

```
Arg Lys Ile Glu Ala Leu Lys Asn Leu
 1               5
```

<210> SEQ ID NO 167
<211> LENGTH: 30
<212> TYPE: DNA
<213> ORGANISM: Rattus norvegicus

<400> SEQUENCE: 167

```
tagaaaaata gaaccactga agaatctgaa                                    30
```

<210> SEQ ID NO 168
<211> LENGTH: 9
<212> TYPE: PRT
<213> ORGANISM: Rattus norvegicus

<400> SEQUENCE: 168

```
Arg Lys Ile Glu Pro Leu Lys Asn Leu
 1               5
```

<210> SEQ ID NO 169
<211> LENGTH: 30
<212> TYPE: DNA
<213> ORGANISM: Rattus norvegicus

<400> SEQUENCE: 169

```
aaatgagact gggaccatcg gcgatgagaa                                    30
```

<210> SEQ ID NO 170
<211> LENGTH: 30
<212> TYPE: DNA
<213> ORGANISM: Rattus norvegicus

<400> SEQUENCE: 170

```
aaatgagact gggaccatcg gcgatgagaa                                    30
```

<210> SEQ ID NO 171
<211> LENGTH: 30
<212> TYPE: DNA
<213> ORGANISM: Rattus norvegicus

<400> SEQUENCE: 171

```
aaatgagact gggaccattg gcgatgagaa                                    30
```

<210> SEQ ID NO 172
<211> LENGTH: 30
<212> TYPE: DNA
<213> ORGANISM: Rattus norvegicus

<400> SEQUENCE: 172

```
tgttgctttt atgatttcat actgtgcttg                                    30
```

<210> SEQ ID NO 173
<211> LENGTH: 30
<212> TYPE: DNA

```
<213> ORGANISM: Rattus norvegicus

<400> SEQUENCE: 173
tgttgctttt atgatttcat actgtgcttg                                30

<210> SEQ ID NO 174
<211> LENGTH: 30
<212> TYPE: DNA
<213> ORGANISM: Rattus norvegicus

<400> SEQUENCE: 174
tgttgctttc atgatttcat actgtgcttg                                30

<210> SEQ ID NO 175
<211> LENGTH: 30
<212> TYPE: DNA
<213> ORGANISM: Rattus norvegicus

<400> SEQUENCE: 175
actgtgcttg cagatctaag aatggaaaat                                30

<210> SEQ ID NO 176
<211> LENGTH: 30
<212> TYPE: DNA
<213> ORGANISM: Rattus norvegicus

<400> SEQUENCE: 176
actgtgcttg cagatctaag aatggaaaat                                30

<210> SEQ ID NO 177
<211> LENGTH: 9
<212> TYPE: PRT
<213> ORGANISM: Rattus norvegicus

<400> SEQUENCE: 177

Cys Ala Cys Arg Ser Lys Asn Gly Lys
 1               5

<210> SEQ ID NO 178
<211> LENGTH: 30
<212> TYPE: DNA
<213> ORGANISM: Rattus norvegicus

<400> SEQUENCE: 178
gaatccgacg ttaatctgaa aggaatccct                                30

<210> SEQ ID NO 179
<211> LENGTH: 29
<212> TYPE: DNA
<213> ORGANISM: Rattus norvegicus

<400> SEQUENCE: 179
gaatccgacg ttaatctaaa ggaatccct                                 29

<210> SEQ ID NO 180
<211> LENGTH: 30
<212> TYPE: DNA
<213> ORGANISM: Rattus norvegicus

<400> SEQUENCE: 180
aaaaattgta catcatatgg tgtgctagac                                30

<210> SEQ ID NO 181
```

```
<211> LENGTH: 30
<212> TYPE: DNA
<213> ORGANISM: Rattus norvegicus

<400> SEQUENCE: 181
aaaaattgta catcataggg tgtgctagac                                    30

<210> SEQ ID NO 182
<211> LENGTH: 30
<212> TYPE: DNA
<213> ORGANISM: Rattus norvegicus

<400> SEQUENCE: 182
taaaggtaaa aggtaagtat tctggtaaaa                                    30

<210> SEQ ID NO 183
<211> LENGTH: 34
<212> TYPE: DNA
<213> ORGANISM: Rattus norvegicus

<400> SEQUENCE: 183
taaaggtaaa aggtaagtaa gtattctggt aaaa                               34

<210> SEQ ID NO 184
<211> LENGTH: 33
<212> TYPE: DNA
<213> ORGANISM: Rattus norvegicus

<400> SEQUENCE: 184
tctatttacc catgcttttc ttattttcac aga                                33

<210> SEQ ID NO 185
<211> LENGTH: 32
<212> TYPE: DNA
<213> ORGANISM: Rattus norvegicus

<400> SEQUENCE: 185
ctatttaccc atgcttttct tattttcaca ga                                 32

<210> SEQ ID NO 186
<211> LENGTH: 16
<212> TYPE: DNA
<213> ORGANISM: Rattus norvegicus

<400> SEQUENCE: 186
cctattcttt ggctta                                                   16

<210> SEQ ID NO 187
<211> LENGTH: 30
<212> TYPE: DNA
<213> ORGANISM: Rattus norvegicus

<400> SEQUENCE: 187
cctattctat tgtgcctatt ctttggctta                                    30

<210> SEQ ID NO 188
<211> LENGTH: 30
<212> TYPE: DNA
<213> ORGANISM: Rattus norvegicus

<400> SEQUENCE: 188
tccctgtgta tagatttgtt cttccatcca                                    30
```

-continued

```
<210> SEQ ID NO 189
<211> LENGTH: 30
<212> TYPE: DNA
<213> ORGANISM: Rattus norvegicus

<400> SEQUENCE: 189
tccctgtgta tagattcgtt cttccatcca                                    30

<210> SEQ ID NO 190
<211> LENGTH: 8
<212> TYPE: DNA
<213> ORGANISM: Rattus norvegicus

<400> SEQUENCE: 190 atctaaag                                                             8

<210> SEQ ID NO 191
<211> LENGTH: 12
<212> TYPE: DNA
<213> ORGANISM: Rattus norvegicus

<400> SEQUENCE: 191
taatctaaag ga                                                       12

<210> SEQ ID NO 192
<211> LENGTH: 16
<212> TYPE: DNA
<213> ORGANISM: Rattus norvegicus

<400> SEQUENCE: 192
gttaatctaa aggaat                                                   16

<210> SEQ ID NO 193
<211> LENGTH: 9
<212> TYPE: DNA
<213> ORGANISM: Rattus norvegicus

<400> SEQUENCE: 193 catagggtg                                                            9

<210> SEQ ID NO 194
<211> LENGTH: 13
<212> TYPE: DNA
<213> ORGANISM: Rattus norvegicus

<400> SEQUENCE: 194
atcatagggt gtg                                                      13

<210> SEQ ID NO 195
<211> LENGTH: 17
<212> TYPE: DNA
<213> ORGANISM: Rattus norvegicus

<400> SEQUENCE: 195
acatcatagg gtgtgct                                                  17

<210> SEQ ID NO 196
<211> LENGTH: 8
<212> TYPE: DNA
<213> ORGANISM: Rattus norvegicus

<400> SEQUENCE: 196 gtaagtat                                                             8
```

```
<210> SEQ ID NO 197
<211> LENGTH: 12
<212> TYPE: DNA
<213> ORGANISM: Rattus norvegicus

<400> SEQUENCE: 197
aagtaagtat tc                                                    12

<210> SEQ ID NO 198
<211> LENGTH: 16
<212> TYPE: DNA
<213> ORGANISM: Rattus norvegicus

<400> SEQUENCE: 198
gtaagtaagt attctg                                                16

<210> SEQ ID NO 199
<211> LENGTH: 8
<212> TYPE: DNA
<213> ORGANISM: Rattus norvegicus

<400> SEQUENCE: 199 ctatttac                                                          8

<210> SEQ ID NO 200
<211> LENGTH: 12
<212> TYPE: DNA
<213> ORGANISM: Rattus norvegicus

<400> SEQUENCE: 200
ctatttaccc at                                                    12

<210> SEQ ID NO 201
<211> LENGTH: 16
<212> TYPE: DNA
<213> ORGANISM: Rattus norvegicus

<400> SEQUENCE: 201
ctatttaccc atgctt                                                16

<210> SEQ ID NO 202
<211> LENGTH: 14
<212> TYPE: DNA
<213> ORGANISM: Rattus norvegicus

<400> SEQUENCE: 202
attgtgccta ttct                                                  14

<210> SEQ ID NO 203
<211> LENGTH: 22
<212> TYPE: DNA
<213> ORGANISM: Rattus norvegicus

<400> SEQUENCE: 203
ttctattgtg cctattcttt gg                                         22

<210> SEQ ID NO 204
<211> LENGTH: 26
<212> TYPE: DNA
<213> ORGANISM: Rattus norvegicus

<400> SEQUENCE: 204
tattctattg tgcctattct ttggct                                     26
```

```
<210> SEQ ID NO 205
<211> LENGTH: 9
<212> TYPE: DNA
<213> ORGANISM: Rattus norvegicus

<400> SEQUENCE: 205 gattcgttc                                                              9

<210> SEQ ID NO 206
<211> LENGTH: 13
<212> TYPE: DNA
<213> ORGANISM: Rattus norvegicus

<400> SEQUENCE: 206
tagattcgtt ctt                                                         13

<210> SEQ ID NO 207
<211> LENGTH: 17
<212> TYPE: DNA
<213> ORGANISM: Rattus norvegicus

<400> SEQUENCE: 207
tatagattcg ttcttcc                                                     17
```

COMPOSITIONS AND METHODS OF DISEASE DIAGNOSIS AND THERAPY

This application is a continuation-in-part application of U.S. Ser. No. 09/221,222, filed Dec. 23, 1998, which is a continuation-in-part application of U.S. Ser. No. 09/167,750, filed Oct. 7, 1998, which is a continuation-in-part application of U.S. Ser. No. 09/086,047, filed May 28, 1998.

FIELD OF THE INVENTION

The invention relates in general to the discovery of the mechanisms underlying disease.

BACKGROUND OF THE INVENTION

Coronary heart disease, hypertension, non-insulin-dependent diabetes, insulin resistance or -insensitivity and obesity are major causes of ill health in industrial societies. Disturbances of carbohydrate and lipid metabolism are a common feature of those disorders (Evans et al., 1984, *J. Clin. Tnvest.*, 74: 1515–1525; Ferrannini et al., 1987, *N. Engl. J. Med.*, 317: 350–357; Reaven, 1988a, *Diabetes*, 37: 1595–1607; Hunt et al., 1989, *Arteriosclerosis*, 9: 335–344; Kaplan, 1989, *Arch. Intern. Med.*, 149: 1514–1520; McGarry, 1992, *Science*, 258: 766–770; Cohen et al., 1996, *Science*, 274: 1185–1188; Polonsky et al., 1995, *N. Engl. J. Med.*, 334: 777–783; Reaven et al., 1996, *N. Engl. J. Med.*, 334: 374–381). Specifically, disturbances in carbohydrate- and fatty acid metabolism associated with defects in insulin and catecholamine action are characteristic of non-insulin-dependent diabetes, metabolic Syndrome X, obesity, familial dyslipidemic hypertension and familial combined hyperlipidemia (Reaven, 1988a, supra; Reaven et al., 1988b, *Diabetes*, 37: 1020–1024; Martin and Jensen, 1991, *J. Clin. Invest.*, 88: 609–613; Hunt et al., 1989, supra; Castro Cabezas et al, 1993, *J. Clin. Invest.*, 92: 160–168; Aitman et al., 1997, *Arterioscler. Thromb. Vasc. Biol.*, 17: 748–754; Reynisdottir et al., 1994, *Diabetologia*, 37: 428–435; Reynisdottir et al., 1995, *J. Clin. Invest.*, 95: 2163–2169). These conditions are treatable by modifications of patient lifestyle (e.g., diet and exercise) and/or with medication. If the presence- or risk of developing such a condition is identified early, a therapeutic or prophylactic regimen may be begun before the well-being of the patient has been compromised, either at all or to an appreciable extent.

There is need in the art for methods of diagnosing an individual having a propensity for one or more of heart disease, hypertension, non-insulin-dependent diabetes, metabolic Syndrome X, combined hyperlipidemia and/or obesity.

It has been suggested in the art that certain parasites utilize the CD36 protein as a ligand for infection of the host cell (Oquendo et al., 1989, Cell 58:95). An example is *Plasmodium falciparum*, a causative agent of malaria. Thus, hosts that express a variant of CD36 protein, or fail to express CD36, may have a greater resistance to infection by such parasites. A significant fraction of individuals lacking CD36 protein have been identified in populations of Asian and African origin, whose ancestry suggests that the phenotype became commonplace due to selection pressure from frequent malarial infection. Curtis, B. R., and Aster, R. H., 1996, *Transfusion* 36: 331–334.

There is a need in the art for methods of determining resistance or susceptibility to infection by *Plasmodium falciparum*.

It has been suggested that some apparently normal individuals lack GPIV, and thus are at risk of producing antibodies against the protein when they receive blood transfusions. Curtis et al., 1996, supra; Greenwalt et al., 1992, *Blood* 80:1105; Yamamoto et al., 1990, *Blood* 76:1698.

There is a need in the art for detecting CD36 gene mutations that give rise to CD36 deficiency for purposes of tissue screening and donation.

SUMMARY OF THE INVENTION

The invention provides a method of identifying an agent which modulates a defect in insulin action and/or glucose metabolism and/or fatty acid metabolism and/or catecholamine action, the method comprising the step of determining in an assay system whether an activity of a gene regulating insulin action and/or glucose metabolism and/or fatty acid metabolism and/or catecholamine action is altered in the presence of a candidate modulator, wherein alteration of the activity of the gene in the presence of the candidate modulator is indicative of efficacy of the candidate modulator in modulating defective insulin action and/or glucose metabolism and/or fatty acid metabolism and/or catecholamine action.

As used herein, the term "agent" refers to a biochemical substance selected from the group that includes, but is not limited to, proteins, peptides or amino acids; nucleic acids such as DNA, such as full-length genes or fragments thereof derived from genomic, cDNA or artificial coding sequences, gene regulatory elements, RNA, including mRNA, tRNA, ribosomal RNA, ribozymes and antisense RNA, oligonucleotides and oligoribonucleotides, deoxyribonucleotides and ribonucleotides; carbohydrates; lipids; proteoglycans; such agents may exist as isolated (purified) compounds or in crude mixtures, such as in a tissue, cell or cell lysate. In addition, such agents may be naturally occurring or may be synthetic. The term "agent" additionally refers to small molecules, such as organic and inorganic compounds.

As used herein, the term "gene" refers to a nucleic acid sequence which comprises one or more of an exon, which exon may encode a protein or an RNA molecule, an intron, a 5'-untranslated region, a 3'-untranslated region and a regulatory sequence, which regulatory sequence may be located either 5' to- or 3' of the exon, either in a transcribed- or a non-transcribed sequence.

As used herein with regard to the expression or activity of a gene or protein, the term "modulate" refers to the effect of an agent (such as a drug or other pharmacological composition) or condition (such as an environmental change or a genetic mutation) either to stimulate, enhance or otherwise increase- or to inhibit, repress, depress or otherwise decrease expression of that gene (whether expression is detected via the RNA, protein, or gene product activity) or protein by at least 10% relative to its basal level of expression. An agent which modulates the expression or activity of a gene or protein is herein referred to as a "modulator". The percent change in expression or activity relative to the basal level or to a control which has not been contacted with a modulator or candidate modulator may be greater than 10%, such as 20–50%, or 75–100%. Alternatively, a modulator may effect a change in activity or expression of greater than 100%, for example 2- to 10-fold, 20- to 100-fold, 1000-fold, or even 10,000- to-100,000-fold above or below the basal level of expression or activity or that observed in a control which has not received or been contacted by the modulator (i.e., an untreated control).

As used herein in reference to the expression or activity of a gene or protein, the term "basal level" refers to the level of expression or activity of that gene or protein in an organism, cell lysate or other system or relative to its level of expression in a control organism, cell, cell lysate or other system which has not been treated with- or exposed or otherwise subjected to the candidate modulating agent or condition, or to its level of expression in the subject organism prior to such treatment or exposure.

As used herein, the terms "defect" and "deficiency" refer to an increase or decrease in the activity or expression of a gene or protein or in the efficiency of a metabolic process which increase or decrease is may produce a clinical pathology in an organism, e.g., a mammal.

It is contemplated that a defect or deficiency results from a mutation in a gene associated with an Insulin Resistance Locus, as described below, in particular the CD36 gene. In particular, mutations in the CD36 gene of humans are useful as diagnostic markers for the testing of individuals for the presence or risk of diseases associated with defects in one or more of insulin action, glucose metabolism or uptake, fatty acid metabolism or uptake or catecholamine action, as well as for targets for drug screening or disease treatment.

Mutations in the CD36 gene are also useful for detecting a CD36 protein deficiency. Many such mutations result in expression of proteins whose CD36 function is reduced or eliminated, or they result in expression of truncated CD36 protein or no expression of CD36 protein at all. A CD36 protein deficiency is a condition resulting in a functional or physical reduction of CD36 protein by at least 30%, at least 50%, at least 60%, at least 70%, at least 80%, at least 90%, at least 95%, at least 98%, or at least 99–100%. A mutation is indicative of or results in a CD36 protein deficiency if the mutation results in alteration or inhibition of transcription of the CD36 gene, or alteration or inhibition of processing or translation of a CD36 gene product.

As used herein with regard to a gene or protein, the terms "activity" or "expression" refer to one or more of transcription, mRNA processing or stability and translation of the encoded product or of structural, enzymatic or other biological function. The terms "activity" or "expression" may additionally refer to the effect of one or more products of the gene (e.g., RNA or protein) in a cell (e.g., as a structural component, enzyme and/or member of a pathway, such as a signalling or metabolic pathway) or on a substrate or downstream target (either a protein or nucleic acid molecule, such as to regulate a gene). An effect on a downstream component of a pathway may be direct (e.g., through direct protein:protein, protein:nucleic acid or nucleic acid:nucleic acid interactions) or indirect, such as through interactions with intermediate molecules.

As used herein, the term "alteration" refers to a change of at least 10%, preferably 20% or more, such as 30–50%, 75%, 100% or several fold, in activity or expression of a gene or protein relative to a basal state, wild-type or control.

As used herein, the term "assay system" refers to an organism, cell, cell lysate or cell-free system (i.e., a buffer or other medium, such as a nucleic acid or peptide microarray, which permits the biological process being assayed to progress, such as an in vitro transcription and/or translation, an enzymatic reaction, or protein:protein, protein:nucleic acid or nucleic acid:nucleic acid binding, such as comprises a physiological buffer or other reaction medium, enzymes, enzyme substrates and, optionally, an indicator compound, e.g. a dye or label). An assay system comprises, at a minimum, a test organism, cell, cell lysate or cell-free system and, preferably, additionally comprises a control organism, cell, cell lysate or cell-free system. An assay system may be naturally occurring or may comprise synthetic, investigator-assembled or engineered components (e.g., a microarray, a mixture of biochemical molecules, a transgenic animal or tissue or cells therefrom, or a transformed or transfected cell or lysate derived therefrom).

As used herein, the term "insulin action" refers to insulin-mediated glucose uptake by a cell.

As used herein, the term "glucose metabolism" refers to the uptake of glucose by a cell, either in culture or in an organism.

It is contemplated that a defect in the metabolic process of glucose metabolism according to the invention is a reduction in the amount of glucose taken up by a cell of at least 10%, preferably of at least 15%, or even a failure of a cell to take up glucose, either in the basal unstimulated state or in response to insulin.

As used herein, the term "fatty acid metabolism" refers to the breakdown of triglycerides into glycerol and fatty acids.

It is contemplated that a defect in fatty acid metabolism according to the invention is a decrease of at least 10%, preferably of at least 15%, in fatty acid secretion from fat cells.

As used herein, the term "catecholamine action" refers to the effect of a catecholamine molecule on a fat cell which induces fatty acid metabolism, as evidenced by the release of fatty acids and glycerol from the cell. A catecholamine which is particularly useful in the assays of the invention is isoproterenol.

It is contemplated that a defect in catecholamine action according to the invention is decreased sensitivity of a fat cell to the effect of a catecholamine on fatty acid metabolism by at least 10%, and preferably by at least 15%.

Preferably, the gene is selected from the group consisting of CD36 or Cd36.

It is preferred that in the assay system, there is a deficiency in insulin action and/or glucose metabolism and/or fatty acid metabolism and/or catecholamine action.

Likewise, it is further contemplated that a "deficiency" or defect in insulin action according to the invention is a decreased sensitivity of a fat cell to the effect of insulin on glucose metabolism by at least 10%, preferably by at least 15%.

As used herein, the term "insulin resistance" refers to a reduction of at least 10%, and preferably 15% or more, in insulin action, as measured in isolated fat tissue, skeletal muscle or vascular tissue in vitro, or in whole animals in vivo, the latter by means of an assay selected from the group which includes, but is not limited to, a euglycemic clamp, an insulin tolerance test, a hyperglycemic clamp, an intravenous glucose tolerance test and a measurement of the distribution of radioactive glucose in an animal to which it has been administered.

Another aspect of the invention is a method of identifying an agent which modulates an activity of the CD36 gene, comprising performing a detection step to detect an alteration in CD36 activity in the presence of a candidate modulator, wherein detection of an alteration is indicative of efficacy of said candidate modulator at modulating an activity of said CD36 gene.

Preferably, in the assay system of the above methods, there is a deficiency of CD36 activity.

The invention additionally encompasses a method of identifying an agent for the treatment of a disease associated with insulin action and/or glucose metabolism and/or fatty acid metabolism and/or catecholamine action, comprising the steps of contacting an assay system comprising a CD36 gene with a candidate agent, wherein the CD36 gene is expressed in the assay system, and performing a detection step to detect a change in the assay system relative to a first control system comprising a CD36 gene, wherein the gene is expressed in the first control system and wherein the first control system has not been contacted with the candidate agent, and relative to a second control system, wherein a CD36 gene is not expressed in the second system and wherein the second system has been contacted with the candidate agent, wherein a change in the assay system relative to the first and second control systems is indicative that the candidate agent is efficacious for the treatment of the disease.

As used herein, the term "disease" refers to the overt presentation of symptoms (i.e., illness) or the manifestation of abnormal clinical indicators (e.g., biochemical indicators), resulting from defects in one or more of the metabolic processes of insulin action, glucose metabolism or uptake, fatty acid metabolism or uptake or catechdlamine action. Alternatively, the term "disease" refers to a genetic or environmental risk of- or propensity for developing such symptoms or abnormal clinical indicators.

Diseases associated with defects in insulin action and fatty acid metabolism or uptake include, but are not limited to, the common insulin resistance syndromes including, but not limited to, metabolic syndrome X, and cardiomyopathy.

Diseases associated with insulin action include, but are not limited to, non-insulin- dependent diabetes (NIDDM), combined hyperlipidemia (including, but not limited to, familial combined hyperlipidemia) and essential hypertension.

Diseases associated with cardiomyopathy include, but are not limited to, hereditary hypertrophic-, dilated-, pressure overload- and idiopathic cardiomyopathy.

As used herein, the term "hypertension" refers to an elevation in resting blood pressure of at least 10% relative to that of normal individuals of comparable age, height and weight.

As used herein, the term "non-insulin-dependent diabetes" refers to type 2 diabetes, which is characterized by insulin resistance, impaired glucose tolerance and impaired fasting glycemia.

As used herein, the term "metabolic Syndrome X" refers to a disease characterized by spontaneous hypertension, dyslipidemia, insulin resistance, hyperinsulinemia, increased abdominal fat and increased risk of coronary heart disease.

As used herein, the term "obesity" refers to a condition in which the body weight of a mammal exceeds medically-recommended limits, based upon age and skeletal size, by at least 20%.

As used herein, the term "mammal" refers to a member of the class Mammalia, including a human.

Another aspect of the invention is a method of identifying an agent for the treatment of a disease associated with insulin action and/or glucose metabolism and/or fatty acid metabolism and/or catecholamine action, comprising the steps of contacting an assay system comprising a CD36 gene with a candidate agent, wherein the CD36 gene is expressed in the assay system, and performing a detection step to detect a change in the assay system relative to a first control system comprising a CD36 gene, wherein the gene is expressed in the first control system and wherein the first control system has not been contacted with the candidate agent, and relative to a second control system, wherein a CD36 gene is not expressed in the second system and wherein the second system has been contacted with the candidate agent, wherein a change in the assay system relative to the first and second control systems is observed, and administering the candidate agent to an animal exhibiting a clinical indicator of the disease, wherein improvement in the clinical indicator is indicative that the candidate agent is efficacious for the treatment of the disease.

The invention further provides a method of identifying an agent for the treatment of a disease associated with insulin action and/or glucose metabolism and/or fatty acid metabolism and/or catecholamine action, comprising the steps of contacting an assay system comprising a CD36 gene with a candidate agent, wherein the CD36 gene is expressed in the assay system, and performing a detection step to detect a change in the assay system relative to a first control system comprising a CD36 gene, wherein the gene is expressed in the first control system and wherein the first control system has not been contacted with the candidate agent, and relative to a second control system, wherein a CD36 gene is not expressed in the second system and wherein the second system has been contacted with the candidate agent, wherein a change in the assay system relative to the first and second control systems is observed, administering the candidate agent to an animal exhibiting a clinical indicator of the disease, performing a detection step to detect a change in the clinical indicator, wherein improvement in the clinical indicator is detected, and producing a kit comprising the candidate agent and a physiologically compatible carrier and packaging therefor, wherein the improvement in the clinical indicator is indicative that the candidate agent is efficacious for the treatment of the disease.

Another aspect of the invention is a method of identifying an agent for the treatment of a disease associated with insulin action and/or glucose metabolism and/or fatty acid metabolism and/or catecholamine action, comprising the steps of contacting an assay system comprising a CD36 protein with a candidate agent, and performing a detection step to detect a change in the assay system relative to a first control system, wherein the first control system comprises a CD36 protein and has not been contacted with the candidate agent, and a second control system, wherein the second control system does not comprise a CD36 protein and has been contacted with the candidate agent, wherein a change in the assay system relative to the first and second control systems is indicative that the candidate agent is efficacious for the treatment of the disease.

The invention additionally encompasses a method of identifying an agent for the treatment of a disease associated with insulin action and/or glucose metabolism and/or fatty acid metabolism and/or catecholamine action, comprising the steps of contacting an assay system comprising a CD36 protein with a candidate agent, performing a detection step to detect a change in the assay system relative to a first control system, wherein the first control system comprises a CD36 protein and has not been contacted with the candidate agent, and a second control system, wherein the second control system does not comprise a CD36 protein and has been contacted with the candidate agent, wherein a change in the assay system relative to the first and second control systems is detected, and administering the candidate agent to an animal exhibiting a clinical indicator of the disease, wherein improvement in the clinical indicator is indicative that the candidate agent is efficacious for the treatment of the disease.

Another aspect of the invention is a method of identifying an agent for the treatment of a disease associated with insulin action and/or glucose metabolism and/or fatty acid metabolism and/or catecholamine action, comprising the steps of contacting an assay system comprising a CD36 protein with a candidate agent, performing a detection step to detect a change in the assay system relative to a first control system, wherein the first control system comprises a CD36 protein and has not been contacted with the candidate agent, and a second control system, wherein the second control system does not comprise a CD36 protein and has been contacted with the candidate agent, wherein a change in the assay system relative to the first and second control systems is detected, administering the candidate agent to an animal exhibiting a clinical indicator of the disease, performing a detection step to detect a change in the clinical indicator, wherein improvement in the clinical indicator is detected, and producing a kit comprising the candidate agent and a physiologically compatible carrier and packaging therefor, wherein improvement in the clinical indicator is indicative that the candidate agent is efficacious for the treatment of the disease.

Preferably, in the above methods, the assay and control systems comprise an animal.

It is preferred that the animal is a mammal.

Preferably, the assay and control systems comprise cultured cells.

In another preferred embodiment, the assay and control systems comprise a cell lysate.

Preferably, in said assay and control systems, there is a deficiency in CD36 activity.

It is preferred that the above methods further comprise, after the step of administering the candidate agent to an animal exhibiting a clinical indicator of the disease a step of performing a detection step to detect an improvement in the clinical indicator in the animal.

The invention of diagnosing a disease associated with a defect in insulin action and/or glucose metabolism and/or fatty acid metabolism and/or catecholamine action in a mammal, comprising the steps of measuring expression levels of CD36 in biological samples from a test mammal and from a normal mammal, and comparing the levels of CD36 expression measured in the biological sample from the test mammal and in the biological sample from the normal mammal, wherein a difference between the levels is indicative of the presence of the disease in the test mammal.

Preferably, the step of measuring expression comprises performing a step to detect CD36 mRNA.

In another preferred embodiment, the step of measuring expression comprises performing a step to detect CD36 protein.

It is preferred that the test and normal mammals are human.

It is additionally preferred that a difference of at least two-fold in CD36 expression levels is observed between the test and normal subjects.

The invention further provides a method of treating a disease associated with insulin resistance, comprising administering to a subject in need thereof an effective amount of a modulator of CD36 activity.

It is preferred that the modulator decreases CD36 activity.

According to another preferred embodiment, the modulator increases CD36 activity.

It is preferred that the modulator is a polypeptide, more preferred that the polypeptide is selected from the group consisting of a CD36 protein and a CD36 peptide, and highly preferred that the polypeptide is human.

Preferably, the polypeptide comprises an amino acid sequence encoded by a nucleic acid sequence selected from the group consisting of [SEQ ID NO: 101], [SEQ ID NO: 102], [SEQ ID NO: 103], [SEQ ID NO: 104], [SEQ ID NO: 105], [SEQ ID NO: 106], [SEQ ID NO: 107], [SEQ ID NO: 108], [SEQ ID NO: 109], [SEQ ID NO: 110], [SEQ ID NO: 111], [SEQ ID NO: 112], [SEQ ID NO: 113], [SEQ ID NO: 114], [SEQ ID NO: 115], [SEQ ID NO: 116], [SEQ ID NO: 117], [SEQ ID NO: 118], [SEQ ID NO: 119], [SEQ ID NO: 120], [SEQ ID NO: 121], [SEQ ID NO: 122], [SEQ ID NO: 123], [SEQ ID NO: 124], [SEQ ID NO: 125], [SEQ ID NO: 126], [SEQ ID NO: 127], [SEQ ID NO: 128] and [SEQ ID NO: 129].

It is preferred that the polypeptide is expressed by a recombinant nucleic acid molecule.

It is additionally preferred that the recombinant nucleic acid molecule comprises a sequence selected from the group consisting of [SEQ ID NO: 101], [SEQ ID NO: 102], [SEQ ID NO: 103], [SEQ ID NO: 104], [SEQ ID NO: 105], [SEQ ID NO: 106], [SEQ ID NO: 107], [SEQ ID NO: 108], [SEQ ID NO: 109], [SEQ ID NO: 110], [SEQ ID NO: 111], [SEQ ID NO: 112], [SEQ ID NO: 113], [SEQ ID NO: 114], [SEQ ID NO: 115], [SEQ ID NO: 116], [SEQ ID NO: 117], [SEQ ID NO: 118], [SEQ ID NO: 119], [SEQ ID NO: 120], [SEQ ID NO: 121], [SEQ ID NO: 122], [SEQ ID NO: 123], [SEQ ID NO: 124], [SEQ ID NO: 125], [SEQ ID NO: 126], [SEQ ID NO: 127], [SEQ ID NO: 128], [SEQ ID NO: 129], [SEQ ID NO: 132], [SEQ ID NO: 133], [SEQ ID NO: 134], [SEQ ID NO: 135], [SEQ ID NO: 136], [SEQ ID NO: 137], [SEQ ID NO: 139], [SEQ ID NO: 140], [SEQ ID NO: 142], [SEQ ID NO: 143], [SEQ ID NO: 144], [SEQ ID NO: 145], [SEQ ID NO: 146], [SEQ ID NO: 147], [SEQ ID NO: 148] and [SEQ ID NO: 149].

Preferably, the modulator is a nucleic acid molecule.

It is preferred that the nucleic acid molecule comprises a sequence selected from the group consisting of [SEQ ID NO: 101], [SEQ ID NO: 102], [SEQ ID NO: 103], [SEQ ID NO: 104], [SEQ ID NO: 105], [SEQ ID NO: 106], [SEQ ID NO: 107], [SEQ ID NO: 108], [SEQ ID NO: 109], [SEQ ID NO: 110], [SEQ ID NO: 111], [SEQ ID NO: 112], [SEQ ID NO: 113], [SEQ ID NO: 114], [SEQ ID NO: 115], [SEQ ID NO: 116], [SEQ ID NO: 117], [SEQ ID NO: 118], [SEQ ID NO: 119], [SEQ ID NO: 120], [SEQ ID NO: 121], [SEQ ID NO: 122], [SEQ ID NO: 123], [SEQ ID NO: 124], [SEQ ID NO: 125], [SEQ ID NO: 126], [SEQ ID NO: 127], [SEQ ID NO: 128], [SEQ ID NO: 129], [SEQ ID NO: 132], [SEQ ID NO: 133], [SEQ ID NO: 134], [SEQ ID NO: 135], [SEQ ID NO: 136], [SEQ ID NO: 137], [SEQ ID NO: 139], [SEQ ID NO: 140], [SEQ ID NO: 142], [SEQ ID NO: 143], [SEQ ID NO: 144], [SEQ ID NO: 145], [SEQ ID NO: 146], [SEQ ID NO: 147], [SEQ ID NO: 148] and [SEQ ID NO: 149].

Preferably, the nucleic acid molecule expresses in a host cell a polypeptide selected from the group consisting of a CD36 protein and a fragment thereof.

More preferably, the nucleic acid molecule self-replicates in said host cell.

It is preferred that a host cell is transformed with the nucleic acid molecule.

Preferably, the host cell is a human cell.

Host cells which are advantageously used in the invention include, but are not limited to, a human cell cardiac muscle cell, particularly a left ventricle cell, a fat cell, an endothelial cell, a vascular smooth muscle cell, a macrophage, a cell of a macrophage cell line, a peripheral monocyte and a cell of a monocyte cell lines. Particularly preferred in screening assays of the invention are a macrophage, a cell of a macrophage cell line, a peripheral monocyte and a cell of a monocyte cell line.

Preferably, the modulator is selected from the group consisting of a peptide, a phosphopeptide, a small organic molecule, a small inorganic molecule, an antibody and an epitope-binding fragment of an antibody.

In another preferred embodiment, the modulator is selected from the group consisting of an antisense nucleic acid molecule, a ribozyme and a triple helix nucleic acid molecule.

Preferably, the modulator is an anti-CD36 antibody.

It is preferred that the modulator is an organic molecule which binds CD36 protein.

It is additionally preferred that the subject is a human.

The invention additionally encompasses an isolated nucleic acid sequence comprising a nucleic acid sequence selected from the group consisting of [SEQ ID NO: 132], [SEQ ID NO: 133], [SEQ ID NO: 134], [SEQ ID NO: 135], [SEQ ID NO: 136], [SEQ ID NO: 137], [SEQ ID NO: 139], [SEQ ID NO: 140], [SEQ ID NO: 142], [SEQ ID NO: 143], [SEQ ID NO: 144], [SEQ ID NO: 145], [SEQ ID NO: 146], [SEQ ID NO: 147], [SEQ ID NO: 148] and [SEQ ID NO: 149].

The invention further provides an isolated nucleic acid molecule comprising a nucleic acid sequence selected from the group consisting of [SEQ ID NO: 5], [SEQ ID NO: 11], [SEQ ID NO: 17], [SEQ ID NO: 23], [SEQ ID NO: 29], [SEQ ID NO: 35], [SEQ ID NO: 41], [SEQ ID NO: 47], [SEQ ID NO: 53], [SEQ ID NO: 59], [SEQ ID NO: 65], [SEQ ID NO: 71], [SEQ ID NO: 77], [SEQ ID NO: 83], [SEQ ID NO: 87], [SEQ ID NO: 167], [SEQ ID NO: 171], [SEQ ID NO: 174] and [SEQ ID NO: 138].

The invention additionally encompasses a polypeptide comprising an amino acid sequence selected from the group consisting of [SEQ ID NO: 6], [SEQ ID NO: 12], [SEQ ID NO: 18], [SEQ ID NO: 24], [SEQ ID NO: 29], [SEQ ID NO: 36], [SEQ ID NO: 42], [SEQ ID NO: 48], [SEQ ID NO: 54], [SEQ ID NO: 60], [SEQ ID NO: 66], [SEQ ID NO: 72], [SEQ ID NO: 78], [SEQ ID NO: 84], [SEQ ID NO: 88], [SEQ ID NO: 168], and [SEQ ID NO: 141].

Another aspect of the invention is an isolated nucleic acid sequence comprising an antisense oligonucleotide which hybridizes to CD36 MRNA.

The invention provides a nucleic acid vector which expresses an antisense RNA which hybridizes to CD36 mNRA.

The invention addtionally encompasses a host cell which comprises a nucleic acid vector, wherein said vector expresses in said cell an antisense RNA which antisense RNA hybridizes to CD36 mNRA.

Preferably, the host cell is a human cell.

In preferred embodiments, the human cell is a cardiac muscle cell, preferably a left ventricle cell, a fat cell, an endothelial cell, a vascular smooth muscle cell, a macrophage, a cell of a macrophage cell line, a peripheral monocyte or a cell of a monocyte cell line.

Another aspect of the invention is a method of diagnosing a disease associated with a defect in insulin action and/or glucose metabolism and/or fatty acid metabolism and/or catecholamine action in an individual suspected of being at risk for such a disease, comprising the step of performing a detection step to detect a mutation in the Cd36 gene, wherein detection of a mutation is indicative of the presence of a disease associated with a defect in insulin action and/or glucose metabolism and/or fatty acid metabolism and/or catecholamine action in the individual.

The invention provides a method for identifying a gene associated with one or more of the metabolic processes of glucose metabolism, fatty acid metabolism, insulin action and catecholamine action in a mammal, comprising determining whether a candidate gene maps to a chromosomal location of an Insulin Resistance locus of a Spontaneously Hypertensive Rat, wherein mapping of the candidate gene to that locus indicates an association between the gene and one or more of the metabolic processes of glucose metabolism, fatty acid metabolism, insulin action and catecholamine action.

Another aspect of the invention is a method for identifying a gene associated with one or more of the metabolic processes of glucose metabolism, fatty acid metabolism, insulin action and catecholamine action in a mammal, comprising the steps of mapping the position of a candidate gene in a mammalian genome so as to provide a map position, and comparing the map position so obtained to a map position of an Insulin Resistance locus of a Spontaneously Hypertensive Rat, wherein coincidence of the map positions indicates an association between the gene and one or more of the metabolic processes of glucose metabolism, fatty acid metabolism, insulin action or catecholamine action.

The invention additionally encompasses a method for identifying a gene associated with one or more of the metabolic processes of glucose metabolism, fatty acid metabolism and catecholamine activity in a mammal, comprising determining whether a candidate gene maps to a chromosomal location of one of Insulin Resistance loci 1, 2, 3 and 4, wherein mapping of the candidate gene to one of these loci indicates an association between the gene and one or more of the metabolic processes of glucose metabolism, fatty acid metabolism, insulin action and catecholamine action.

The invention also provides a method for identifying a gene associated with one or more of the metabolic processes of glucose metabolism, fatty acid metabolism, insulin action and catecholamine action in a mammal, comprising the steps of mapping the position of a candidate gene in a mammalian genome so as to provide a map position, and comparing the map position so obtained to a map position of one or more of Insulin Resistance loci 1, 2, 3 and 4, wherein coincidence of the map positions indicates an association between the gene and one or more of the metabolic processes of glucose metabolism, fatty acid metabolism or catecholamine activity.

As used herein, the term "Insulin-Resistance locus of a Spontaneously Hypertensive Rat" refers to a chromosomal segment, genetic linkage group or gene to which a defect in one or more of glucose- or fatty acid metabolism, insulin action or catecholamine action maps, which segment, linkage group or gene is selected from the group which includes, but is not limited to, Insulin-Resistance loci 1, 2, 3 and 4, each as defined below. For example, defects in one or more of glucose- or fatty acid metabolism, insulin action or catecholamine action characteristic of the Spontaneous Hypertensive Rat (SHR) are found in the rat genome.

As used herein, the term "Insulin Resistance loci 1, 2, 3 and 4" refers to Insulin Resistance loci of the Spontaneously Hypertensive Rat, as defined above, including Insulin Resistance Locus 1, Insulin Resistance Locus 2, Insulin Resistance Locus 3 and Insulin Resistance Locus 4 of the Spontaneously Hypertensive Rat and mammalian, including human, homologs of these rat loci, as defined below.

As used herein, the term "Insulin Resistance Locus 1" refers to an Insulin Resistance locus of a Hypertensive Rat, as defined above, having a peak of linkage spanning approximately 4 centiMorgans (cM) of chromosome 4 of the rat comprising the D4Arb13, D4Ae2 and D4Rt8 markers (hereinafter referred to without the designation "D4"), and encompassing about 10 cM to either side of the peak of linkage, to which locus defects of the Spontaneous Hypertensive Rat in glucose metabolism, fatty acid metabolism, insulin action and catecholamine action map. The gene(s) responsible for the observed phenotypes may be located between the end of the chromosome (which is 2–3 cM from the peak of linkage) and a site about 7 cM from the peak of linkage in the direction away from the telomere. The term "Insulin-Resistance Locus 1" also refers to a chromosomal locus in another mammal, which locus corresponds (e.g., by synteny or nucleic acid sequence similarity) to Insulin Resistance Locus 1 of the rat genome.

As used herein with regard to any measurement in centiMorgans (cM), the terms "about" and "approximately" refer to a margin of 10% above and below the recited numerical value.

As used herein, the term "Insulin Resistance Locus 2" refers to an Insulin Resistance locus of a Spontaneously Hypertensive Rat, as defined above, having a peak of linkage spanning approximately 20 cM of chromosome 12 of the rat between- and comprising the D12Mit8 and D12Mgh1 markers, with strongest linkage in the 4 cM of this region proximal to the D12Mit8 marker, and encompassing 10 cM to either side of the peak of linkage, to which locus a defect of the Spontaneously Hypertensive Rat in glucose metabolism maps. The gene(s) responsible for the observed phenotype may be located within 5 cM or even within 2 cM of either terminus of the peak of linkage. The term "Insulin-Resistance Locus 2" also refers to a chromosomal locus in another mammal, which locus corresponds (e.g., by synteny or nucleic acid sequence similarity) to Insulin Resistance Locus 2 of the rat genome.

As used herein, the term "Insulin-Resistance Locus 3" refers to an Insulin Resistance locus of a Spontaneously Hypertensive Rat, as defined above, on chromosome 7 of the rat, having a peak of linkage at the D7Cebr179s7 marker, and encompassing 15 cM to either side of the peak of linkage, and to which locus a defect of the Spontaneously Hypertensive Rat in glucose metabolism maps. The gene(s) responsible for the observed phenotype may be located within 10 cM, or even within 5 cM, of either side of the peak of linkage. The term "Insulin-Resistance Locus 3" also refers to a chromosomal locus in another mammal, which locus corresponds (e.g., by synteny or nucleic acid sequence similarity) to Insulin Resistance Locus 3 of the rat genome.

As used herein, the term "Insulin-Resistance Locus 4" refers to an Insulin Resistance locus of a Spontaneously Hypertensive Rat, as defined above, on chromosome 16 of the rat having a peak of linkage at the D16Mit3 marker and encompassing 10 cM to either side of the peak of linkage, to which locus a defect of the Spontaneously Hypertensive Rat in glucose metabolism maps. The gene(s) responsible for the observed phenotype may be located within 5 cM or even within 2 cM of either side of the peak of linkage. The term "Insulin-Resistance Locus 4" also refers to a chromosomal locus in another mammal, which locus corresponds (e.g., by synteny or nucleic acid sequence similarity) to Insulin Resistance Locus 4 of the rat genome.

As used herein, the term "synteny" refers to the chromosomal positions of genes which are conserved between two populations or species throughout evolutionary time, such that the genes of one population or species are found at positions relative to established markers which correspond to those of the homologous genes in the other population or species.

As used herein with regard to Insulin-Resistance loci 1, 2, 3 and 4, the term "nucleic acid similarity" refers to those sequences which display at least 60%, preferably 70% and more preferably 80% sequence identity.

As used herein, the phrase "maps to a chromosomal location", refers either to a statistically-significant linkage between a candidate gene and a marker, which marker may be within an Insulin-Resistance locus of a Spontaneously Hypertensive Rat, within one of Insulin-Resistance loci 1, 2, 3 or 4, or may be another marker, such that it is probable that the candidate gene and the marker are within a distance of 15, preferably 10, more preferably 5 and, most preferably, 2 centiMorgans (cM) of each other. Such a result may be obtained through genetic linkage analysis or radiation hybrid mapping, as described below. The phrase "maps to a chromosomal location" also refers to a non-probabilistic localization of a gene on a chromosome based upon a technique such as in situ nucleic acid hybridization, in which a signal indicating the physical position of a gene on a chromosome is observed.

A candidate gene is said to map to a chromosomal map position of an Insulin-Resistance locus of a Spontaneously Hypertensive Rat or one of Insulin-Resistance loci 1, 2, 3 or 4 if linkage analysis between the candidate gene and an Insulin-Resistance locus results in a lod score of 3, or if mapping using a radiation hybrid panel results in a lod score of 4. In mapping a phenotype, e.g. a defect in glucose metabolism, fatty acid metabolism, insulin action or catecholamine action, to a new genetic marker (i.e. a candidate gene) in order to compare the chromosomal map position of that marker to that of an Insulin-Resistance locus of a Spontaneously Hypertensive rat and/or of one or more of Insulin-Resistance loci 1, 2, 3 and 4 according to the invention, linkage analysis between the phenotype and the candidate gene must result, in a first set of genetic crosses or in a first pedigree analysis, in a P value$<10^{-4}$ and, in a second set of crosses or in a second pedigree analysis performed to confirm the results of either of the first, in a P value$<5\times10^{-2}$.

As used herein, the term "coincidence" refers to the mapping, to within a distance of 15 centiMorgans (cM) of a candidate gene to a second gene or other marker. Preferably, the candidate gene maps to within 10, more preferably to within 5 or even to within 2 cM of the second gene or other marker.

As used herein in reference to the relationship between a defect in a metabolic process and a disease state, the term "association" refers to the coincidence of the defect and the disease, whether the defect causes or contributes to the development of the disease, is a result of the disease, or is neither causative of- nor brought about by the disease, but is merely observed to accompany it (e.g., if both the defect and the disease arise independently of each other by a common mechanism).

It is preferred that the above methods further comprise the step of measuring the effect of the candidate gene on one or more of the metabolic processes of glucose metabolism, fatty acid metabolism, insulin action and catecholamine action.

It is additionally preferred that the measuring comprises the steps of introducing a nucleic acid molecule containing the gene into a cell or organism, assaying in a biological sample of the organism or in the organism itself the level of one or more of glucose uptake, non-esterified fatty acid secretion, insulin action or catecholamine action in the cell or organism and in a control cell or organism lacking the nucleic acid molecule, and comparing the levels, wherein a difference in the levels is indicative of an effect of the gene on one or more of the metabolic processes of glucose metabolism, fatty acid metabolism, insulin action and catecholamine action.

It is contemplated that the gene may be either normal or defective. If normal and defective genes are both available, the relative effects of the normal and defective genes can be compared when each, apart from the other, is introduced into a cell or organism and assayed.

As used herein in reference to the level of one or more of glucose uptake, non-esterified fatty acid secretion, insulin action or catecholamine action in the cell or organism to which the gene has been introduced and in a control cell or organism, the term "difference" refers to a change of at least 20, preferably 30%, highly preferably 45% and, more preferably, 50–75% and most preferably 100% or even more than 100%, such as 2- or more fold, up to 100,000-fold.

In a particularly preferred embodiment, the cell or organism has a defect in one or more of said metabolic processes of glucose metabolism, fatty acid metabolism, insulin action and catecholamine action.

The invention further encompasses, in a method of identifying a gene associated with one or more of glucose metabolism, fatty acid metabolism, insulin action or catecholamine action, an improvement comprising comparing the chromosomal map position of a gene with a map position of one or more of an Insulin Resistance locus of a Spontaneously Hypertensive Rat, wherein coincidence between the map positions indicates an association between the gene and one or more of the metabolic processes of glucose metabolism, fatty acid metabolism and catecholamine activity.

The invention also provides, in a method of identifying a gene associated with one or more of glucose metabolism, fatty acid metabolism, insulin action or catecholamine action, an improvement comprising comparing the chromosomal map position of a gene with a map position of one or more of Insulin Resistance loci 1, 2, 3 and 4, wherein coincidence between the map positions indicates an association between the gene and one or more of the metabolic processes of glucose metabolism, fatty acid metabolism and catecholamine activity.

Another aspect of the invention is a method of diagnosing a disease associated with a defect in one or more of the metabolic processes of glucose metabolism, fatty acid metabolism, insulin action and catecholamine action in a mammal, comprising assaying a biological sample from a mammal for the presence of a mutation or polymorphism in a gene which is linked to an Insulin-Resistance locus of a Spontaneously Hypertensive Rat, wherein the presence of a mutation in the gene is indicative of the presence of a disease.

The invention also provides a method of diagnosing a disease associated with a defect in one or more of the metabolic processes of glucose metabolism, fatty acid metabolism, insulin action and catecholamine action in a mammal, comprising assaying a biological sample from a mammal for the presence of a mutation or polymorphism in a gene which is linked to one of Insulin-Resistance loci 1, 2, 3 or 4, wherein the presence of a mutation in the gene is indicative of the presence of a disease.

It is contemplated that the mutation is in a gene corresponding to a rat gene selected from the group that includes Il6, Nos3, Slc4α2, Psmc2, Fgl2, Pgy1, Cd36 and Cacna2, a mouse gene selected from the group that includes Gnai1, Pgy2, Pgy3, Sri, Hgf, Htr5a, Cdk5, Dpp6, Plk, Tyms, Fgfr3, Adra2c, Pparg, ERTD363 and Cd36 or human IPF-1 and CD36, as well as other mammalian genes to which map to chromosomal map positions of Insulin-Resistance loci according to the invention, which genes minimally number in the hundreds.

Preferably, the disease is selected from the group that includes non-insulin-dependent diabetes, metabolic Syndrome X, obesity, familial dyslipidemic hypertension, combined hyperlipidemia (including, but not limited to, familial combined hyperlipidemia) and essential hypertension.

The invention also is based upon the discovery of a mutant or polymorphic gene that maps to the insulin-resistance locus-i in the SHR rat (chromosome 4), and mutations or polymorphisms in the gene. Thus, the invention contemplates the following nucleic acid sequences.

An isolated nucleic acid comprising the nucleotide sequence presented in one or more of the following nucleotide sequences: [SEQ ID NO: 5], [SEQ ID NO: 11], [SEQ ID NO: 17], [SEQ ID NO: 23], [SEQ ID NO: 29], [SEQ ID NO: 35], [SEQ ID NO:41], [SEQ ID NO: 47], [SEQ ID NO: 53], [SEQ ID NO: 59], [SEQ ID NO: 65], [SEQ ID NO: 71], [SEQ ID NO: 77], [SEQ ID NO: 83], and/or [SEQ ID NO:87].

Also encompassed in the invention are the polypeptide sequences encoded by the above nucleic acid sequences.

The nucleic acids are useful according to the invention as nucleic acid probes for detecting mutations described herein. A hybridization probe useful herein may be as small as 10–11 nucleotides (for instance, where the mutant nucleotide is the center nucleotide, the sequence encompassing 5 nucleotides on either side of the mutant nucleotide), 15 nucleotides, 20 nucleotides, 25 nucleotides, 30–40 nucleotides, or larger, such as 75, 80 90, 100, 150, 200, 300, 400, 500, or 1000 nucleotides. A hybridization probe will be useful if it hybridizes to the mutant nucleic acid but not to the wild type nucleic acid under stringent conditions (see below), or if it distinguishes a single nucleotide difference in a given stretch of a nucleic acid.

The invention also contemplates a method of diagnosing a disease associated with a defect in one or more of the metabolic processes of glucose metabolism, fatty acid metabolism, insulin action and catecholamine action in a mammal, comprising assaying a biological sample from a mammal for the presence of a mutation or polymorphism in a gene which is linked to Insulin-Resistance locus 1, wherein the presence of a mutation in the gene is indicative of the presence of a disease.

Preferably, the disease is associated with a defect in one or more of the metabolic processes of glucose metabolism, fatty acid metabolism, insulin action and catecholamine action in a mammal, comprising assaying a biological sample from a mammal for the presence of an alteration in the amino acid sequence of a protein encoded by a gene which is linked to Insulin-Resistance locus 1, wherein the presence of an altered amino acid sequence encoded by the gene is indicative of the presence of the disease.

Preferably, the disease is selected from the group that includes non-insulin-dependent diabetes, metabolic Syndrome X, obesity, familial dyslipidemic hypertension and combined hyperlipidemia (including, but not limited to, familial combined hyperlipidemia).

Preferably, the mutation is selected from the group consisting of nucleotide position 378, 397, 507, 521, 522, 533, 552, 553, 554, 601, 619, 620, 641, 742, 791, and 871 of [SEQ ID NO: 87].

Preferably, the amino acid sequence is encoded by a mutation selected from the group consisting of nucleotide position 378, 397, 507, 521, 522, 533, 552, 553, 554, 601, 619, 620, 641, 742, 791, and 871 of [SEQ ID NO: 87].

As used herein, the term "nucleic acid" refers to RNA or DNA, which may be double- or single-stranded and linear or circular. It is contemplated that a nucleic acid molecule of use in the invention may be selected from the group that includes linear RNA or DNA fragments, bacterial plasmids, episomal vectors, artificial chromosomes, and viral or retroviral chromosomes.

As used herein, the term "organism" refers to a cellular life-form, such as a prokaryote or a eukaryote. It is contemplated that an organism of use in the invention is a multicellular organism, such as a mammal, as defined above. It is further contemplated that a cell of use in the invention is a eukaryotic cell, preferably a mammalian cell.

As used herein, the term "biological sample" refers to a whole organism or a subset of its tissues, cells or component parts (e.g. body fluids, including but not limited to blood, serum, plasma, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as nucleic acid molecules.

As used herein in reference to a nucleic acid molecule of the invention, the term "introducing" refers to transformation, transfection or infection of a cell or organism with the molecule.

As used herein, the term "mutation" refers to a defect in a gene, as defined above, which leads to a loss or reduction of the amount of gene product or the biological activity of the encoded product, or to increased, novel or altered function of the same. Such a mutation may comprise single- or multiple-base substitution, insertion or deletion or, alternatively, translocation of the gene to a chromosomal location other than that at which it normally resides.

A "reduction" in the amount of CD36 gene product refers to a reduction of at least 50%, 60%, 75%, 80%, 90%, 95%, and as much as 98–100% of CD36 gene product (CD36 protein), a determined by one of a number of assays disclosed herein.

As used herein, the term "polymorphism" refers to an allelic variant of a nucleic acid sequence of a gene which may be present either in the majority or, alternatively, in a minority of members of a population. A polymorphism may be silent (i.e., not resulting in an amino acid substitution or change in gene regulation relative to other known allelic variants) or may encode a different amino acid or result in a change of gene regulation relative to other allelic variants.

It is contemplated that genes identified according to the methods described above may be used as targets in drug screening assays, where the drugs being tested are candidate modulators of one or more of the metabolic processes of glucose metabolism, fatty acid metabolism, insulin action and catecholamine action through modulation of the activity of a gene which is linked to an Insulin-Resistance locus. It is envisioned that a change in activity of such a gene in the presence of said the candidate drug is indicative that the drug is an effective modulator of one or more of the metabolic processes of glucose metabolism, fatty acid metabolism, insulin action and catecholamine action and may be used in the treatment of diseases which are associated with disruption of- or dysfunction in one or more of these processes. In particular, testing of such an agent in an animal which models such a disease, and monitoring the animal for improvement in disease-related indicators (e.g. glucose uptake, non-esterified fatty acid secretion, insulin action or catecholamine action), wherein improvement of such an indicator in the presence of the candidate drug relative to its absence is indicative of efficacy of the drug. Target genes believed particularly advantageous in such an assay may be selected from the group that includes rat Il6, Nos3, Slc4α2, Psmc2, Fgl2, PgyI, Cacna2 and Cd36, mouse Gnail, Pgy2, Pgy3, Sri, Hgf, Htr5a, Cdk5, Dpp6, Plk, Tyms, Fgfr3, Adra2c, Pparg and ERTD363 and human IPF-1 and CD36; alternatively, other genes as may be identified by the methods described above may be used.

The invention further provides an isolated nucleic acid molecule comprising a sequence selected from the group consisting of [SEQ ID NO:179], [SEQ ID NO:181], [SEQ ID NO:183], [SEQ ID NO:185], [SEQ ID NO:187], [SEQ ID NO:190], [SEQ ID NO:191], [SEQ ID NO:192], [SEQ ID NO:193], [SEQ ID NO:194], [SEQ ID NO:195], [SEQ ID NO:196], [SEQ ID NO:197], [SEQ ID NO:198], [SEQ ID NO:199], [SEQ ID NO:200], [SEQ ID NO:201], [SEQ ID NO:202], [SEQ ID NO:203], and [SEQ ID NO:204].

The invention also encompasses a mutant CD36 gene having one or more of the mutations set forth in [SEQ ID NO:179], [SEQ ID NO:181], [SEQ ID NO:183], [SEQ ID NO:185], [SEQ ID NO:187], [SEQ ID NO:190], [SEQ ID NO:191], [SEQ ID NO:192], [SEQ ID NO:193], [SEQ ID NO:194], [SEQ ID NO:195], [SEQ ID NO:196], [SEQ ID NO:197], [SEQ ID NO:198], [SEQ ID NO:199], [SEQ ID NO:200], [SEQ ID NO:201], [SEQ ID NO:202], [SEQ ID NO:203], and [SEQ ID NO:204].

The invention additionally encompasses a mutant CD36 protein having one or more of the mutations encoded by [SEQ ID NO:179], [SEQ ID NO:181], [SEQ ID NO:183], [SEQ ID NO:185], [SEQ ID NO:187], [SEQ ID NO:190], [SEQ ID NO:191], [SEQ ID NO:192],[ SEQ ID NO:193], [SEQ ID NO:194], [SEQ ID NO:195], [SEQ ID NO:196], [SEQ ID NO:197], [SEQ ID NO:198], [SEQ ID NO:199], [SEQ ID NO:200], [SEQ ID NO:201], [SEQ ID NO:202], [SEQ ID NO:203], and [SEQ ID NO:204].

The invention further provides for a method of detecting a CD36 protein deficiency in a biological sample, comprising the step of detecting a mutation in the CD36 gene. It is contemplated that said mutation corresponds to a sequence selected from the group consisting of [SEQ ID NO:179], [SEQ ID NO:181], [SEQ ID NO:183], [SEQ ID NO:185], [SEQ ID NO:187], [SEQ ID NO:190], [SEQ ID NO:191], [SEQ ID NO:192], [SEQ ID NO:193], [SEQ ID NO:194], [SEQ ID NO:195], [SEQ ID NO:196], [SEQ ID NO:197], [SEQ ID NO:198], [SEQ ID NO:199], [SEQ ID NO:200], [SEQ ID NO:201], [SEQ ID NO:202], [SEQ ID NO:203], and [SEQ ID NO:204].

The invention encompasses a method of screening a tissue for administration to a mammal, whereby a sample of the tissue is tested for a mutation in the CD36 gene. The tissue sample is labeled based on the presence or absence of said mutation.

Preferably, the labeled tissue is stored.

More preferably, the tissue is blood or a blood product, including platelets.

It is preferred that said mutation corresponds to a sequence selected from the group consisting of [SEQ ID NO:179], [SEQ ID NO:181], [SEQ ID NO:183], [SEQ ID NO:185], [SEQ ID NO:187], [SEQ ID NO:190], [SEQ ID NO:191], [SEQ ID NO:192], [SEQ ID NO:193], [SEQ ID NO:194], [SEQ ID NO:195], [SEQ ID NO:196], [SEQ ID NO:197], [SEQ ID NO:198], [SEQ ID NO:199], [SEQ ID NO:200], [SEQ ID NO:201], [SEQ ID NO:202], [SEQ ID NO:203], and [SEQ ID NO:204].

The invention further encompasses a method of matching a donor with a recipient. A biological sample from a donor or a recipient is tested for a mutation in the CD36 gene, wherein said mutation results in a deficiency of CD36 gene product. The donor and recipient are matched, whereby if the recipient possesses a mutation resulting in a deficiency of CD36 gene product, a donor is selected who also possesses a deficiency of CD36 gene product.

Preferably, the biological sample is blood.

More preferably, the mutation corresponds to a sequence selected from the group consisting of [SEQ ID NO:179], [SEQ ID NO:181], [SEQ ID NO:183], [SEQ ID NO:185], [SEQ ID NO:187], [SEQ ID NO:190], [SEQ ID NO:191], [SEQ ID NO:192], [SEQ ID NO:193], [SEQ ID NO:194], [SEQ ID NO:195], [SEQ ID NO:196], [SEQ ID [NO:197], [SEQ ID NO:198], [SEQ ID NO:199], [SEQ ID NO:200], [SEQ ID NO:201], [SEQ ID NO:202], [SEQ ID NO:203], and [SEQ ID NO:204].

Another aspect of the invention is a method of determining the resistance of a patient to infection by a parasite by testing the patient for a mutation in the CD36 gene, wherein the mutation is indicative of resistance to infection by the parasite.

Preferably the parasite is *Plasmodium falciparum*.

More preferably, the mutation corresponds to a sequence selected from the group consisting of [SEQ ID NO:179], [SEQ ID NO:181], [SEQ ID NO:183], [SEQ ID NO:185], [SEQ ID NO:187], [SEQ ID NO:190], [SEQ ID NO:191], [SEQ ID NO:192], [SEQ ID NO:193], [SEQ ID NO:194], [SEQ ID NO:195], [SEQ ID NO:196], [SEQ ID NO:197], [SEQ ID NO:198], [SEQ ID NO:199], [SEQ ID NO:200], [SEQ ID NO:201], [SEQ ID NO:202], [SEQ ID NO:203], and [SEQ ID NO:204].

The invention further provides a method of treating a parasitic infection. A pharmaceutical composition comprising an inhibitor of CD36 gene expression is administered to a patient in need thereof.

Preferably, the inhibitor is an antisense oligonucleotide which hybridizes to CD36 mNRA.

It is preferred that the parasite causing the infection is *Plasmodium falciparum*.

The invention additionally encompasses a method of diagnosing a disease associated with a defect in insulin action and/or glucose metabolism and/or fatty acid metabolism and/or catecholamine action in a mammal. A mutation in the CD36 gene is detected, whereby said mutation corresponds to a sequence selected from the group consisting of [SEQ ID NO:179], [SEQ ID NO:181], [SEQ ID NO:183], [SEQ ID NO:185], [SEQ ID NO:187], [SEQ ID NO:190], [SEQ ID NO:191], [SEQ ID NO:192], [SEQ ID NO:193], [SEQ ID NO:194], [SEQ ID NO:195], [SEQ ID NO:196], [SEQ ID NO:197], [SEQ ID NO:198], [SEQ ID NO:199], [SEQ ID NO:200], [SEQ ID NO:201], [SEQ ID NO:202], [SEQ ID NO:203], and [SEQ ID NO:204].

Preferably the disease is selected from the group consisting of insulin resistance, impaired glucose tolerance, type 2 diabetes mellitus, combined hyperlipidemia, essential hypertension, cardiomyopathy, and coronary heart disease.

The invention further provides a method of treating a disease associated with a defect in insulin action and/or glucose metabolism and/or fatty acid metabolism and/or catecholamine action in a subject that has been determined to possess a mutation in the CD36 gene. The method provides for the administration of a modulator which increases CD36 activity. The mutation results in a deficiency of a CD36 gene product and corresponds to a sequence selected from the group consisting of [SEQ ID NO:179], [SEQ ID NO:181], [SEQ ID NO:183], [SEQ ID NO:185], [SEQ ID NO:187], [SEQ ID NO:190], [SEQ ID NO:191], [SEQ ID NO:192], [SEQ ID NO:193], [SEQ ID NO:194], [SEQ ID NO:195], [SEQ ID NO:196[, [SEQ ID NO:197], [SEQ ID NO:198], [SEQ ID NO:199], [SEQ ID NO:200], [SEQ ID NO:201], [SEQ ID NO:202], [SEQ ID NO:203], and [SEQ ID NO:204].

Preferably, the modulator is a polypeptide.

More preferably the polypeptide is selected from the group consisting of a CD36 protein and a CD36 peptide.

Even more preferably, the polypeptide is human.

It is preferred that the polypeptide comprises an amino acid sequence encoded by a nucleic acid sequence selected from the group consisting of [SEQ ID NO:101], [SEQ ID NO: 102], [SEQ ID NO:103], [SEQ ID NO:104], [SEQ ID NO:105], [SEQ ID NO:106], [SEQ ID NO:107], [SEQ ID NO:108], [SEQ ID NO:109], [SEQ ID NO:110], [SEQ ID NO:111], [SEQ ID NO:112], [SEQ ID NO:113], [SEQ ID NO:114], [SEQ ID NO:115], [SEQ ID NO: 116], [SEQ ID NO:117], [SEQ ID NO:118], [SEQ ID NO:119], [SEQ ID NO:120], [SEQ ID NO:121], [SEQ ID NO:122], [SEQ ID NO:123], [SEQ ID NO:124], [SEQ ID NO:125], [SEQ ID NO:126], [SEQ ID NO:127], [SEQ ID NO:128] and [SEQ ID NO:129].

It is additionally preferred that the polypeptide is expressed by a recombinant nucleic acid molecule.

Even more preferably the recombinant nucleic acid molecule comprises a sequence selected from the group consisting of [SEQ ID NO:101], [SEQ ID NO:102], [SEQ ID NO: 103], [SEQ ID NO:104], [SEQ ID NO:105], [SEQ ID NO:106], [SEQ ID NO:107], [SEQ ID NO:108], [SEQ ID NO:109], [SEQ ID NO:110], [SEQ ID NO:111], [SEQ ID NO:112], [SEQ ID NO:113], [SEQ ID NO:114], [SEQ ID NO:115], [SEQ ID NO:116], [SEQ ID NO: 117], [SEQ ID NO:118], [SEQ ID NO:119], [SEQ ID NO:120], [SEQ ID NO:121], [SEQ ID NO:122], [SEQ ID NO:123], [SEQ ID NO:124], [SEQ ID NO:125], [SEQ ID NO:126], [SEQ ID NO:127], [SEQ ID NO:128], [SEQ ID NO:129], [SEQ ID NO:132], [SEQ ID NO: 133], [SEQ ID NO:134], [SEQ ID NO:135], [SEQ ID NO:136], [SEQ ID NO:137], [SEQ ID NO:139], [SEQ ID NO:140], [SEQ ID NO:142], [SEQ ID NO:143], [SEQ ID NO:144], [SEQ ID NO:145], [SEQ ID NO:146], [SEQ ID NO:147], [SEQ ID NO:148] and [SEQ ID NO:149].

It is additionally preferred that the modulator is a nucleic acid molecule.

Even more preferably, the nucleic acid molecule comprises a sequence selected from the group consisting of [SEQ ID NO:101], [SEQ ID NO:102], [SEQ ID NO:103], [SEQ ID NO: 104], [SEQ ID NO:105], [SEQ ID NO:106], [SEQ ID NO:107], [SEQ ID NO:108], [SEQ ID NO:109], [SEQ ID NO:110], [SEQ ID NO:111], [SEQ ID NO:112], [SEQ ID NO:113], [SEQ ID NO:114], [SEQ ID NO:115], [SEQ ID NO:116], [SEQ ID NO:117], [SEQ ID NO: 118], [SEQ ID NO:119], [SEQ ID NO:120], [SEQ ID NO:121], [SEQ ID NO:122], [SEQ ID NO:123], [SEQ ID NO:124], [SEQ ID NO:125], [SEQ ID NO:126], [SEQ ID NO:127],

[SEQ ID NO:128], [SEQ ID NO:129], [SEQ ID NO:132], [SEQ ID NO:133], [SEQ ID NO: 134], [SEQ ID NO:135], [SEQ ID NO:136], [SEQ ID NO:137], [SEQ ID NO:139], [SEQ ID NO:140], [SEQ ID NO:142], [SEQ ID NO:143], [SEQ ID NO:144], [SEQ ID NO:145], [SEQ ID NO:146], [SEQ ID NO:147], [SEQ ID NO:148] and [SEQ ID NO:149].

It is additionally preferred that the nucleic acid molecule expresses in a host cell a polypeptide selected from the group consisting of a CD36 protein and a fragment thereof.

It is preferred that the nucleic acid molecule self-replicates in said host cell.

It is even more preferred that a host cell is transformed with said nucleic acid molecule.

Preferably, the modulator is selected from the group consisting of a peptide, a phosphopeptide, a polypeptide, a polysaccharide, a small organic molecule, a small inorganic molecule, an antibody and an epitope-binding fragment of an antibody. As used herein, a peptide, a polypeptide, a polysaccharide, a small inorganic molecule, and a small organic molecule may have a molecular weight of more than 200 and less than about 2,500 daltons, preferably between 500 and 1,000 daltons. A peptide may be between 2 and 100 residues in length, more advantageously between 4 and 40 residues in length, and even between 8 and 20 residues in length, and may comprise either D- or L-amino acids (or equivalents).

It is further preferred that the modulator is selected from the group consisting of an antisense nucleic acid molecule, a ribozyme and a triple helical nucleic acid molecule.

The invention also encompasses a method of screening drugs to treat a parasitic infection, wherein the parasite causing said infection requires CD36 protein as a ligand in order for infection to occur. The method comprises the step of testing a candidate drug for inhibition of CD36 gene expression.

Preferably, the parasite is *Plasmodium falciparum*.

The invention further encompasses a method of screening drugs to treat a parasitic infection, wherein the parasite causing said infection requires CD36 protein as a ligand in order for infection to occur. The method comprising the step of testing a candidate drug for inhibition of a positive regulator gene of the CD36 gene.

Preferably, the positive regulator gene is ppr-gamma.

More preferably, the parasite is *Plasmodium falciparum*.

Further features and advantages of the invention will become more fully apparent in the following description of the embodiments and drawings thereof, and from the claims.

BRIEF DESCRIPTIONS OF THE DRAWINGS

FIG. 1 presents a radiation hybrid map of insulin-resistance locus 1 showing the position of the Cd36 gene.

FIG. 2 presents graphical representations of the Insulin-Resistance Locus 1 and Insulin-Resistance Locus 2 genetic linkage groups.

Figure 3:
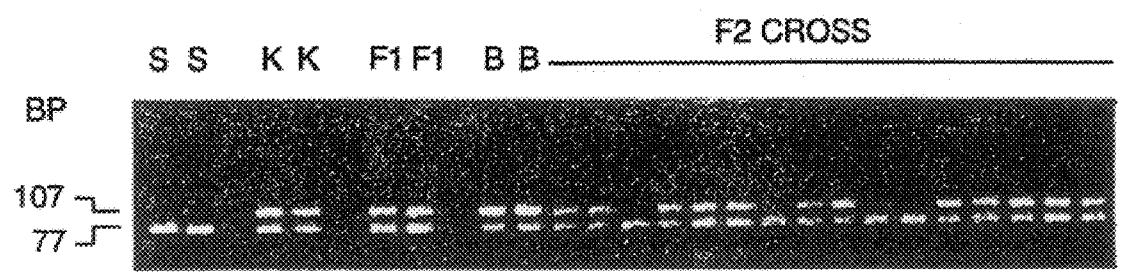

FIG. 3 presents HinfI digests of Cd36 genes from SHR, WKY, BN, (SHR×WKY) F$_1$ and (SHR×WKY) F$_2$ genomic DNA.

Figure 4:
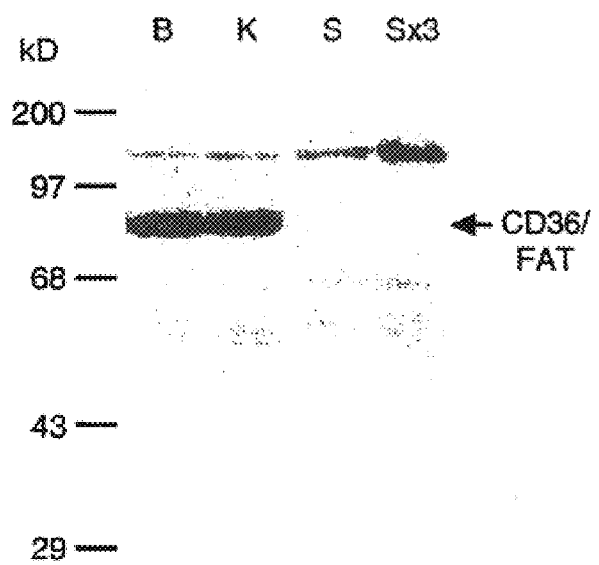

FIG. 4 presents a Western blot of microsomal and plasma membrane proteins in BN, WKY and SHR rats.

Figure 5:
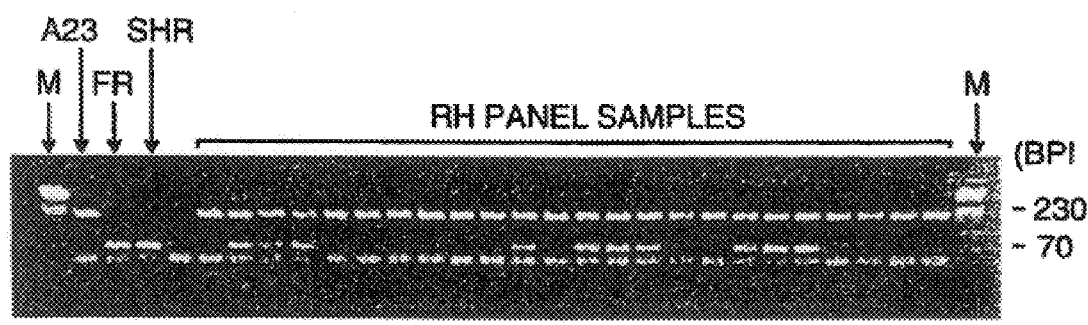

FIG. 5 shows PCR products from amplification of the primers designed from mouse Psmc2.

Figure 6:
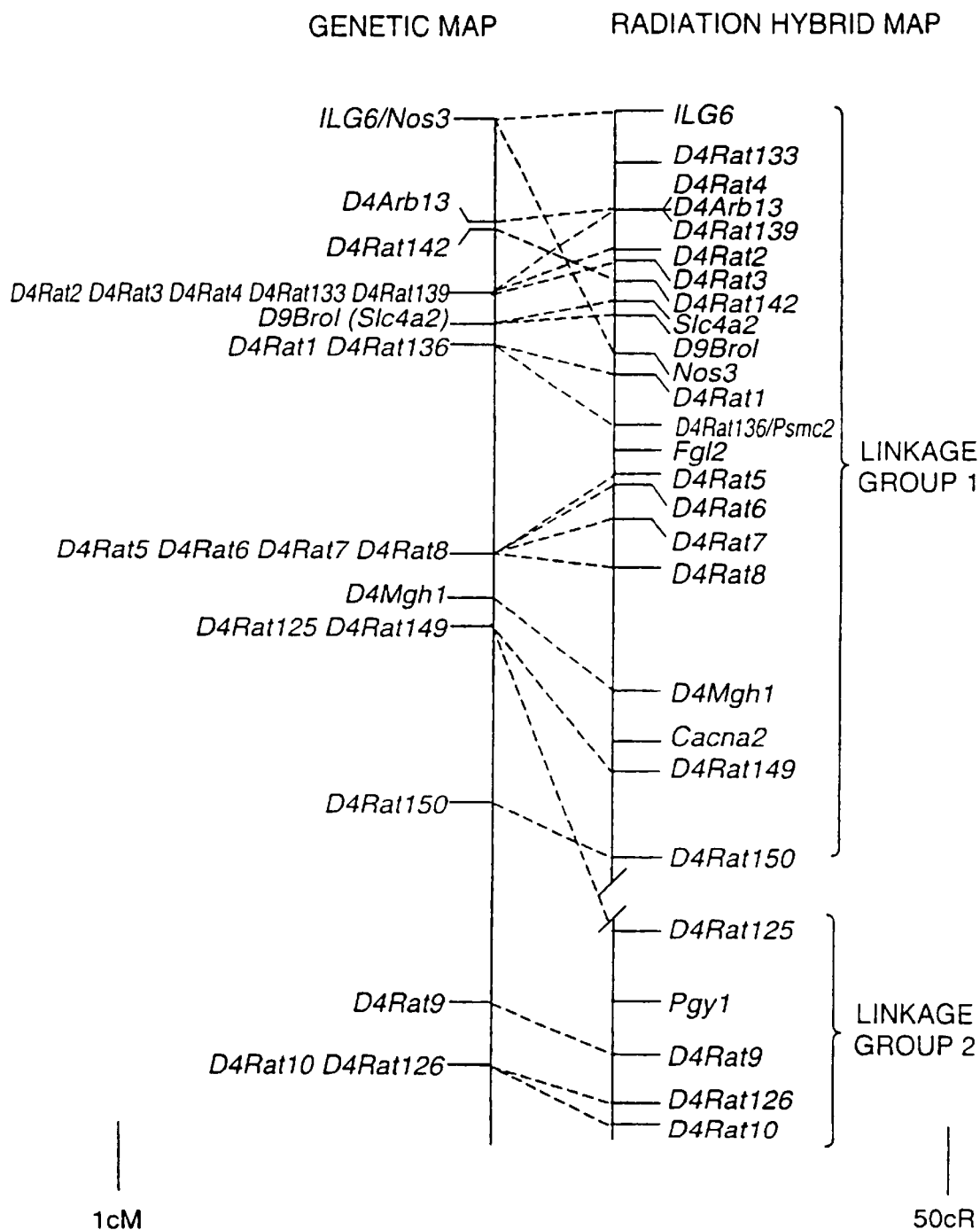

FIG. 6 presents a maximum likelihood radiation hybrid map of proximal rat chromosome 4 (right), compared with an integrated genetic map of the same region (left).

FIG. 7 diagrams the variation in marker order obtained by maximum likelihood analysis.

Figure 8:
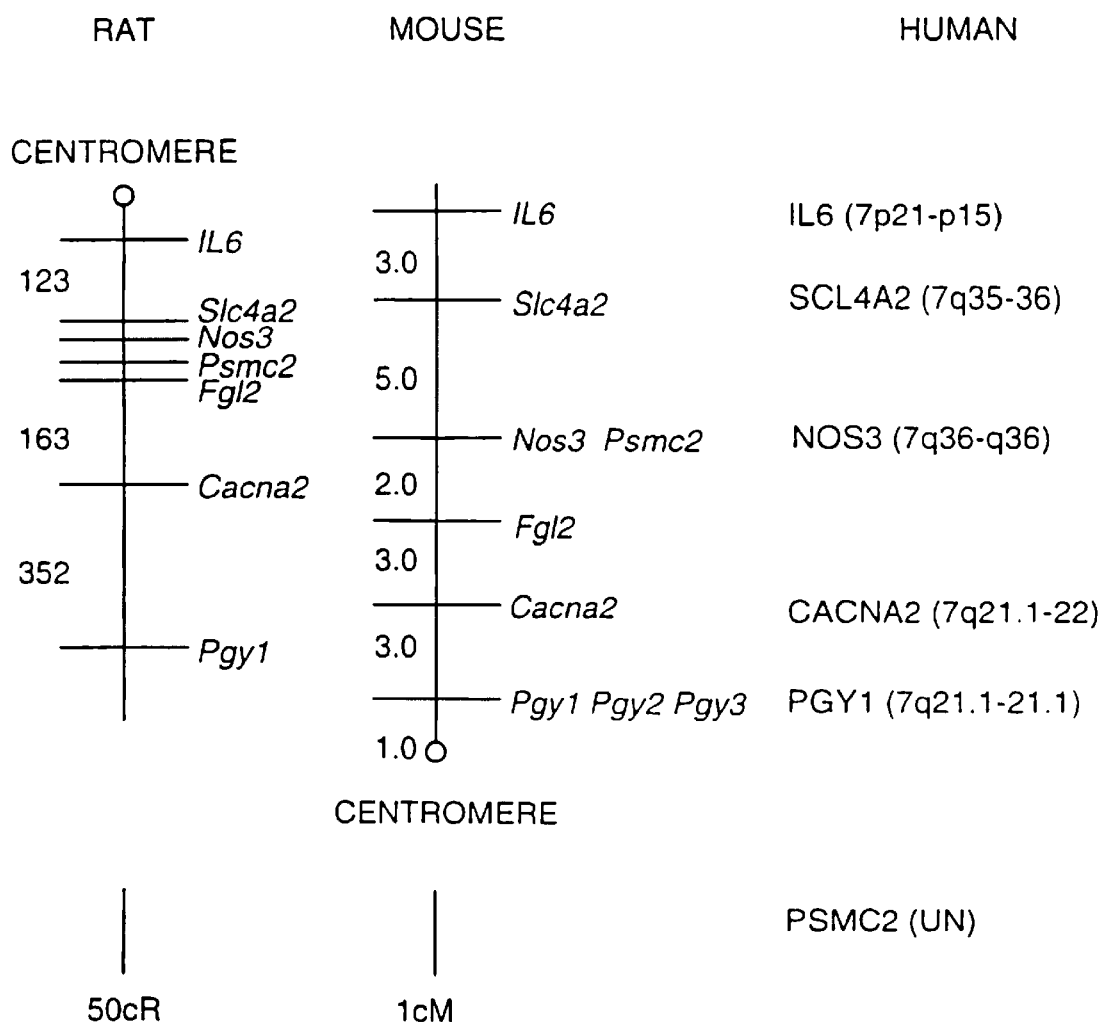

FIG. 8 presents a comparison of the maximum likelihood order of genes on rat chromosome 4 with gene orders on syntenic segments of mouse chromosome 5 and human chromosome 7.

FIG. 9 presents peptide sequences derived from WKY, BN and SHR Cd36 proteins sequences.

FIG. 10 presents wild-type human CD36 nucleic acid sequences.

FIG. 11 presents the complete wild type (Sprague-Dawley) rat CD36 sequence (Genbank accession number L19658; [SEQ ID NO:85]).

FIG. 12 presents the predicted polypeptide sequence of rat CD36 [SEQ ID NO:86].

FIG. 13 presents the complete coding sequence and partial untranslated Cd36 sequence for rat strain SHR [SEQ ID NO:87].

FIG. 14 presents the predicted Cd36 polypeptide sequence of SHR [SEQ ID NO:88].

FIG. 15 presents partial Cd36 sequence from rat strain Wistar Kyoto [SEQ ID NO:89].

FIG. 16 presents the predicted partial Cd36 polypeptide sequence from rat strain Wistar Kyoto [SEQ ID NO:90].

FIG. 17 presents partial Cd36 sequence for rat strain BN [SEQ ID NO:91].

FIG. 18 presents the predicted partial Cd36 polypeptide sequence for rat strain BN [SEQ ID NO:92].

DESCRIPTION OF THE INVENTION

The invention is based upon the discovery in a rat model of four genetic loci in which mutations or variant alleles of a gene or genes are linked with insulin action and fatty acid metabolism. One or more of the four are useful as markers for identification of the genes involved in these diseases. The invention also is based on the discoveries that the rat CD36 gene (rat FAT gene) maps to insulin-resistance locus 1 (chromosome 4), which localization is herein described for the first time, and that the Cd36 gene of the SHR rat contains at least 18 mutations, 11 encoding an amino acid other than the wild type amino acid at the corresponding position, which mutations are linked to the SHR phenotype. A radiation hybrid map of insulin-resistance locus 1 showing the position of the Cd36 gene is shown in FIG. 1. In addition, mutations in the human CD36 gene have been found to correlate with defects in insulin action and fatty acid metabolism. These human CD36 sequence variants, the wild-type nucleic acid sequence and their respective encoded polypeptide sequences are useful in disease diagnosis, as potential candidates for drug targeting, in diagnostic procedures and, ultimately therapeutic regimens aimed at controlling the effects of the disease. The invention also is based upon the discovery that the Cd36 gene transcripts in the SHR rat exhibit sequence variations and size difference relative to the corresponding wild-type mRNA (for wild-type rat Cd36 cDNA sequence, see Genbank accession number L19658 or [SEQ ID NO:85]; for wild-type human CD36 gene sequences, see Genbank accession numbers G18324, Z32753, Z32759, Z32757, Z32756, Z32755, Z32754, Z32764, Z32763, Z32762, Z32761, Z32760, Z32752, Z32758, Z32765, AA360674, AA342353, AA302823, L06849, S67532, S67044, Z32770, Z22924, Z22555, T28585, M98399, M98398, M24795 and L06850, or SEQ ID NO:101, 102, 103, 104, 105, 106, 107, 108, 109, 110, 111, 112, 113,114, 115, 116, 117, 118,119, 120,121, 122, 123, 124,125, 126, 127, 128 and 129, respectively), and thus an aberrantly sized mRNA or mRNA with sequence variants as described herein are diagnostic markers for a phenotype characterized by defective insulin action or fatty acid metabolism. The invention also is based on the correlation of CD36 gene mutations with CD36 deficiency that is present in certain human populations, and thus the detection of such mutations is useful in screening biological tissue samples, such as blood or a blood product. The invention also is based on detecting CD36 gene mutations as an indicator of resistance to infection by certain parasites such as the parasite that causes malaria.

Example 1 describes mapping of a gene and comparison of its map position to that of one of the Insulin-Resistance loci in SHR. Example 2 describes determining that a gene maps to a chromosomal location of an Insulin-Resistance locus in the rat. Example 3 presents screening of a patient for a mutation in an Insulin-Resistance locus-linked gene. Example 4 presents screening of a patient for a mutation in the CD36 gene. Example 5 presents screening of a biological sample from a patient for size polymorphisms in mRNA molecules hybridizing to a nucleic acid probe comprising CD36 sequence. Example 6 presents in vivo screening according to the invention of a candidate therapeutic agent in a rat model.

A. The Insulin-Resistance Genetic Loci

Defects in the metabolism of glucose and fatty acids have been linked to four loci in the rat genome using the spontaneously hypertensive rat (SHR). These four loci are described and defined in detail for the first time herein. The SHR rat is a widely-used animal model of essential hypertension (Yamori, 1984, in *Handbook of Hypertension*, Vol. 4. *Experimental and Genetic Models of Hypertension*, ed. de Jong, Elsevier Science Publishers, NY, pp. 224–239) which has a global defect in insulin action on glucose metabolism (Rao, 1993, *Diabetes*, 42:1364–1371; Reaven et al., 1989c, *Diabeteds*, 38:1155–1160; Paternostro, 1995, *Cardiovasc. Res.*, 30:205–211; Chiappe de Cingolani, 1988, *Metabolism*, 37:318–322) and shows reduced catecholamine action on lipolysis in fat cells (Reaven et al., 1989c, supra; Chiappe de Cingolani, 1988, supra) in genetic crosses with nonhypertensive rats. Spontaneous hypertension, dyslipidemia, insulin resistance, hyperinsulinemia and increased abdominal fat, all displayed by the SHR model, are the defining features of metabolic Syndrome X. SHR may, therefore, be a model for this human condition, and the identification of genes for defective insulin and catecholamine action in SHR may facilitate gene identification in human metabolic Syndrome X and related conditions, such as type 2 diabetes and combined hyperlipidemia (including, but not limited to, familial combined hyperlipidemia).

Genetics and statistical analysis

In order to determine the chromosomal location of genes underlying defects in one or more of the metabolic processes of glucose metabolism, fatty acid metabolism, insulin action and catecholamine action in the spontaneously hypertensive rat, experimental crosses were bred between the SHR strain, which manifests these defects, and control strains which do not display these defects. In these experiments, in which the Insulin-Resistance loci of the invention were characterized, the control strains were the Wistar Kyoto and the Brown Norway strains of rats, although it is expected that other control strains would have been equally effective; other strains are, indeed, useful according to the claimed methods. In segregating offspring from these matings, measurements of the metabolic processes of glucose metabolism, fatty acid metabolism, insulin action and catecholamine action were made, as described below. These measurements in the segregating offspring constituted the phenotypic characterization stage of the linkage study. The offspring scored resulted from one of two types of crosses:$F_1$ individuals were mated either to siblings ("F2 cross") or to animals of the parental control strain ("backcross").

To determine the chromosomal location of genes underlying these defective metabolic processes, DNA was extracted from the liver or spleen of each of the animals in the segregating offspring generation. The DNA of these animals was then genotyped using multiple genetic markers across the genome. The distribution of markers was of sufficient density to detect, by statistical analysis, linkage to genes underlying these defective metabolic processes at any point on any chromosome in the rat genome, thereby allowing the statistical test for linkage to be carried out for all genetic markers against all measured phenotypes. This statistical analysis, which is generally applicable to genetic linkage and mapping methods of the invention, is briefly described as follows:

To test for linkage, a statistical analysis of variance (ANOVA) that tests for differences in metabolic phenotype between the groups of animals in each genotypic class was initially employed. For example, $F_2$ animals that inherited two alleles of a particular genetic marker from the SHR strain were compared phenotypically with all $F_2$ animals that inherited two alleles from the control strain or those that inherited one from either strain. The ANOVA test measured the significance of this result. As is true of statistical tests performed according to the invention, an independent P value of less than 0.0001 in one cross was taken to indicate significant linkage. A confirmatory P value (that is, a value obtained from a second cross identical to the first, which is performed in order to confirm a first-cross result) of less than 0.05 offered supporting evidence of linkage to a given genetic marker which showed linkage on a previous independent experimental cross. The ANOVA test was then extended to a multi-point analysis using a computer program such as Mapmaker/QTL. This software package is generally useful in linkage analysis and gene mapping, in that it allows the intervals between markers to be assessed for linkage to the defective metabolic processes and allows calculation of the lod score, a commonly used measure of the strength of linkage, expressed as a likelihood of the odds ratio in favor of genetic linkage.

According to the invention, in mapping via standard linkage analysis (see below) a candidate gene to an Insulin-Resistance locus, a lod score of 3 is taken as evidence that the candidate gene and a marker that is already mapped to an Insulin-Resistance locus are significantly linked. If, as described in below and in Example 1, mapping via a radiation hybrid panel is instead undertaken, linkage is assumed if a lod score of 4 is obtained.

Genetic crosses and statistical analyses such as those described above may be repeated on any number of experimentals of the same- or different designs which may employ the same- or different strain combinations. When different parental strains are used, linkage to different genetic markers will be demonstrated because different genetic polymorphisms exist and/or have been characterized strain-specifically and the ability to perform linkage analysis to a given marker depends upon the availability of a polymorphism at that locus; however, linkage to the same chromosomal regions should be demonstrated for a given trait or gene being mapped, albeit having a peak of linkage which maps to a different marker within that region depending upon the parental strains chosen to be employed. For example, SHR genes mapped to an Insulin-Resistance locus using different strain combinations may show peak linkage to different genetic markers on the same chromosomal segment even though the underlying SHR gene or genes detected on that particular chromosome segment in different strain combinations or different crosses are the same.

Whether a trait is found to be linked to one or to more than one marker, crosses performed and analyzed as described above indicate the likely location of the underlying gene or genes. The confidence of localization of a gene increases with the number of crosses in which linkage is shown between a particular phenotype and a particular chromosomal segment, and with the strength of the linkage in each experinental cross.

Insulin-Resistance loci 1, 2, 3 and 4

Figure 2A:
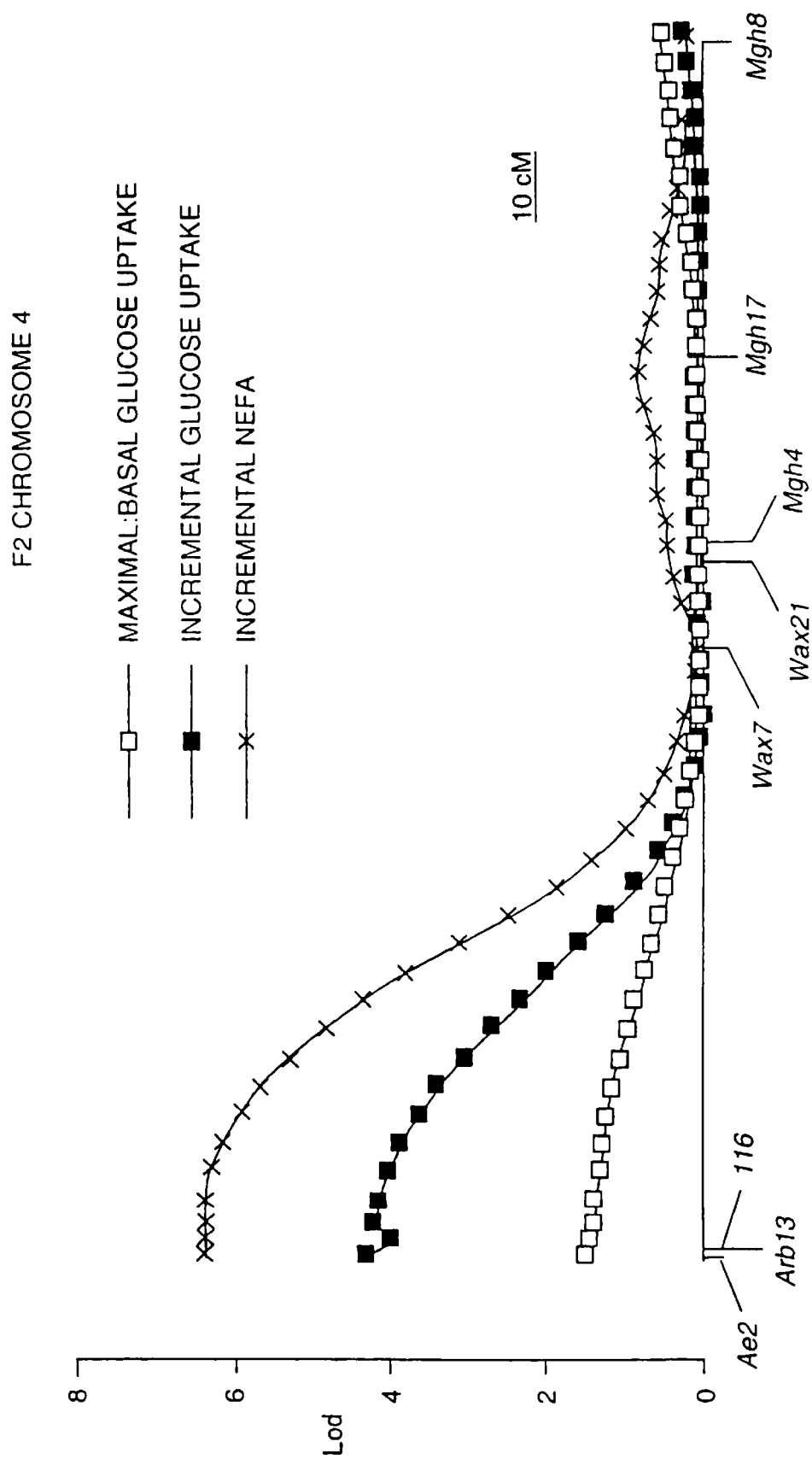
Figure 2B:
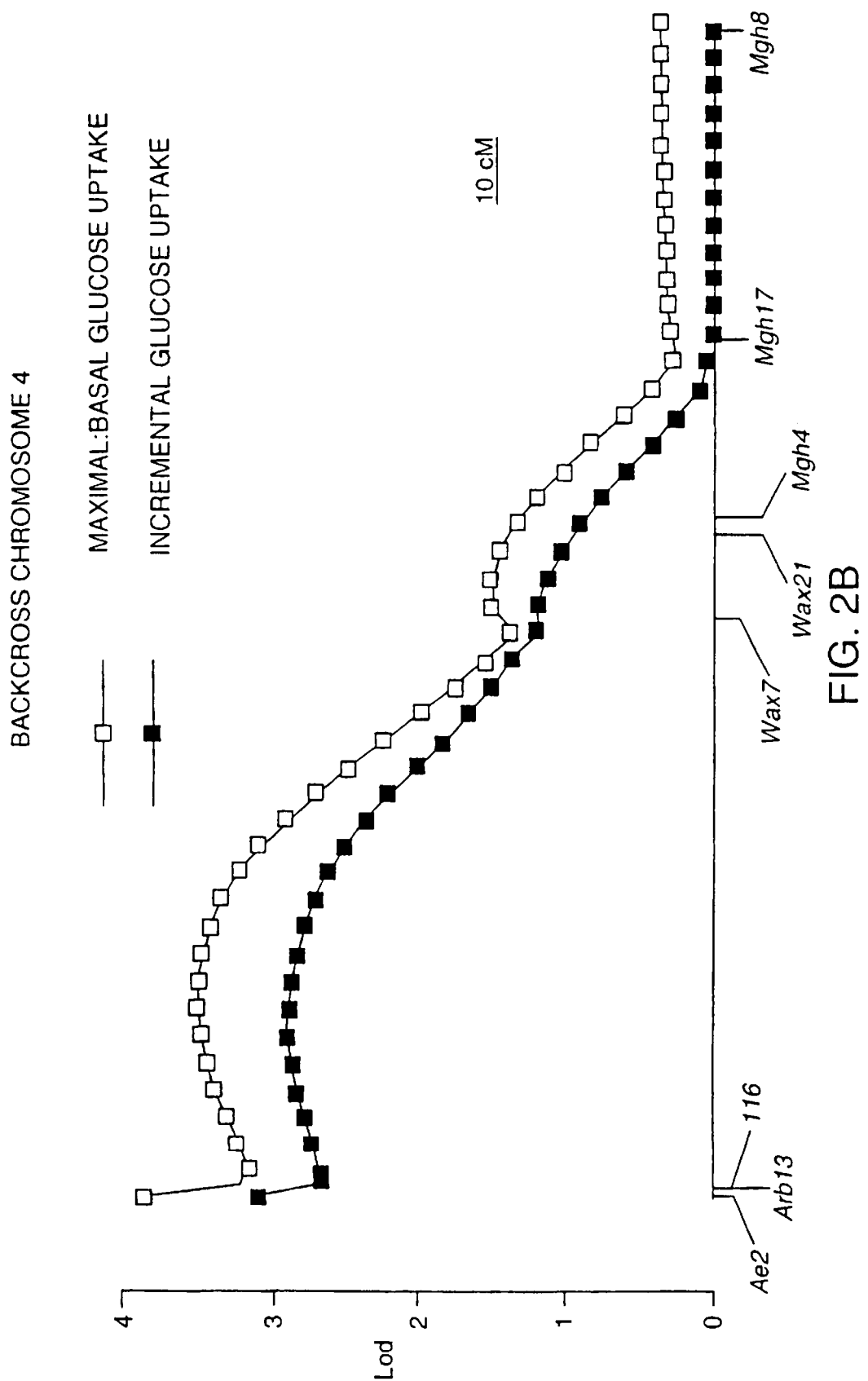

Insulin-Resistance Locus 1 is a site on chromosome 4 to which the regulation of insulin action maps. It is linked with highest certainty to three chromosomal markers, (D4Arb13, D4Ae2 and D4Rt8, all hereinafter referred to without the D4 designation). These markers, which together represent the peak of linkage, are within 4 centi-Morgans (cM) of one another. FIG. 2A shows a graphical representation of the linkage of defects in glucose- and fatty acid metabolism to the Arbl3 and Ae2 markers in F2 crosses in which SHR and Wistar Kyoto rats were used as the mutant and control parental ($F_0$) strains, respectively; this graph, in which Lod score is plotted against chromosomal map position, was generated using the MAPMAKER-QTL program (Paterson et al., 1988, Nature, 335:721–726; cM, centiMorgans). FIG. 2B shows a graphical representation of the linkage of defects in glucose uptake to these markers, instead demonstrated in a backcross experiment, using again the SHR and Wistar Kyoto parental strains.

It is contemplated that genes associated with Insulin-Resistance Locus 1 will map to within 10 cM of either end of this region; however, as the Ae2 marker is believed to be located within 2–3 cM of the end of the chromosome, sequences adjacent to the telomere represent the distal boundary of Insulin-Resistance Locus 1. It is likely that genes linked to Insulin-Resistance Locus 1 may be located within 7 cM of the peak of linkage in the direction of the centromere, possibly within 5 cM or even within 2 cM. Ae2 is strongly linked to incremental glucose uptake, which it appears to control in a recessive manner. This region of chromosome four is also linked to isopreterenol-mediated secretion of non-esterified fatty acids (NEFA); in fact, the major determinant of defective catecholamine action on adipocyte lipolysis in SHR maps to this locus. Insulin-Resistance Locus 1 accounts for 11%–15% of the total phenotypic variance in incremental glucose uptake, and 47% of the total phenotypic variance in incremental NEFA secretion. Heritability of these traits has been calculated to be between 48% and 70%.

The coincident linkage on chromosome 4 to defects in action of both insulin and isoproterenol, a beta-adrenergic agonist, suggests the possibility of a gene defect acting on the pathways that control both glucose and fatty acid metabolism. Several interesting candidates map, either directly or by synteny, to this region of chromosome 4 including endothelial nitric oxide synthase (eNOS; Hubner et al., 1995, Mamm. Genome, 6:758–759), subunit 2A of the L type calcium channel (Beckers et al., 1994, Genonmis, 23:685–690), the type a2c adrenergic receptor (Riess et al., 1994, Genomics, 19:298–302) and the voltage-gated potassium channel KCND2 (Klocke et al., 1993, Genomics, 18:568–574). eNOS is particularly interesting in this regard, as eNOS function is deranged in SHR (Dohi et al., 1996, Hypertension, 28:732–737), NO mediates insulin action in blood vessels (Scherrer, 1994, J. Clin. Invest., 94:2511–2515) and eNOS knockout mice are hypertensive (Huang et al., 1995, Nature, 377:239–242).

Figure 2C:
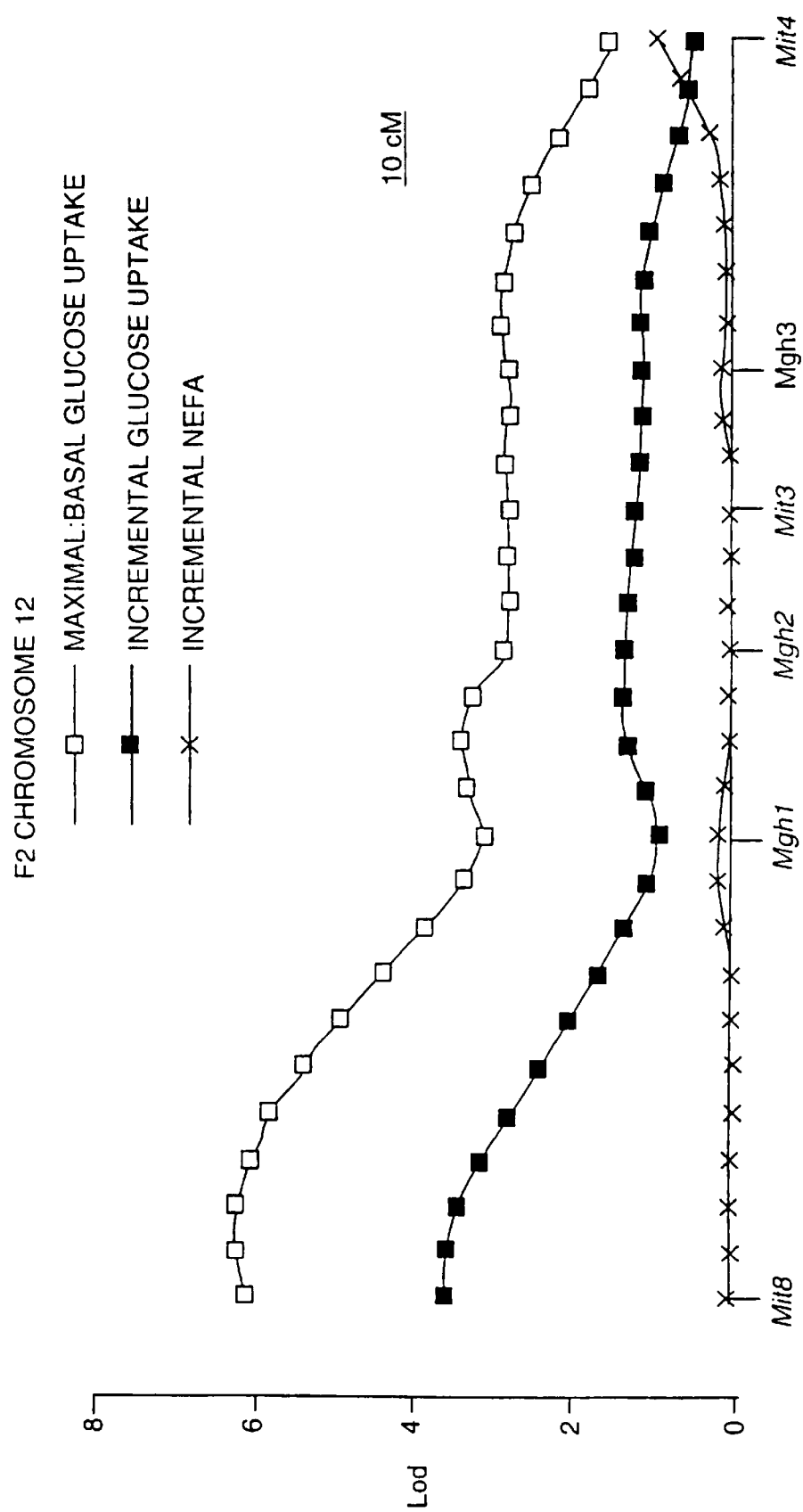

The Insulin-Resistance Locus 2 is found on chromosome 12. This locus, to which effects on incremental glucose uptake and maximal/basal glucose uptake map, shows a peak of linkage within the 20 cM region between the D12Mit8 and D12Mgh1 loci; this linkage correlates most strongly to the 4 cM proximal to D12Mit8 with respect to the centromere. FIG. 2C shows a graphical representation of the linkage of the defects in glucose metabolism to these markers, as determined by F2 crosses using SHR and WKY rats as the mutant and control parental strains, respectively. It is likely that genes linked to Insulin-Resistance Locus 2 may be found within 10 cM of the peak of linkage, possibly within 5 cM or even within 2 cM.

The Insulin-Resistance Locus 3 is found on chromosome 7. This locus, to which an effect on basal glucose uptake maps, displays a peak of linkage at the D7Cebr179s7 marker. A gene associated with Insulin-Resistance Locus 3 may be within 10 cM of the D7Cebr179s7 marker; it is likely that such a gene maps within 5 cM or even 2 cM of this marker.

The Insulin-Resistance Locus 4 is found on chromosome 16. This locus, to which effects on incremental glucose uptake and maximal/basal glucose uptake map, displays a peak of linkage at the D16Mit3 marker. Genes which occupy a map position coincident with that of Insulin-Resistance Locus 4 may be found within 15 cM of this marker, possibly within 10 cM or even within 5 cM.

B. How to Determine that a Candidate Gene Manps to the Chromosomal Map Position of an Insulin-Resistance Locus According to the Invention Linkage analysis According to the invention, it is possible to determine whether a gene to which no map position has been assigned is located within an Insulin-Resistance locus. Such an analysis, in which an unmapped gene may be found to reside within an Insulin-Resistance locus, provides a powerful method by which to determine whether such a candidate gene is suitable for more intensive study which includes, but is not limited to, DNA sequence analysis, in vitro and/or in vivo gene expression studies and gene targeting (either for disease diagnosis or drug discovery). This may be accomplished through linkage analysis, which is a probabilistic determination of the likelihood that a given trait is associated with a particular genetic locus. A linkage analysis experiment may be perfonned as follows:

A genetic cross or series of genetic crosses is performed in an animal model system of a defect in one or more of insulin- or fatty acid metabolism, insulin action or catecholamine action (see below) between individuals having an observable mutant phenotype and normal individuals of a control strain. At least one of the Insulin-Resistance loci is used as a marker in these crosses. If non-random assortment of the mutant trait with an Insulin-Resistance locus is observed, and that non-random assortment is statistically significant (for example, if a Student's t test or ANOVA is applied to the results, as described above) the trait is linked to the marker Insulin-Resistance locus. Limits of significance are discussed below.

Similarly, linkage analysis using an existing human or other mammalian pedigree may be performed. Pedigree analysis is a widely-used tool in identifying those genes for which variant alleles may contribute to the risk, onset or progression of a pathological condition in a family containing multiple individuals afflicted with a disease; this procedure typically entails comparison of numerous genetic loci in between affected and unaffected family members. Non-random assortment of a given genetic marker between affected and unaffected family members relative to the distributions observed for other genetic loci indicates that the marker (for example, a variant isoforms of a gene) either contributes to the disease or is in physical proximity to another that does so. According to the invention, a pedigree containing multiple individuals affected with diseases associated with defects in insulin- or fatty acid metabolism or in catecholamine activity is analyzed for linkage of a defect to one of the four Insulin-Resistance loci described herein.

Taking either approach, non-random assortment of the disease-related phenotype with an Insulin-Resistance locus indicates an association between the gene underlying the defect and that locus. Because the strength of any conclusion drawn from linkage analysis is based in statistics, the confidence level increases in proportion to the number of crosses or family members and genetic loci assayed. If a disease-related gene is found to be linked to one of Insulin-Resistance loci 1 or 2, it is likely that the gene is found within 10 cM, preferably 5 cM or even 2 cM of a peak of linkage for that locus. If a disease-related gene is found to be linked to one of Insulin-Resistance loci 3 or 4, it is likely that the gene is found within 15 cM, preferably 5 cM of the peak of linkage for that locus.

When linkage is confirmed, a molecular analysis of the region in to which the peak of linkage maps is undertaken. This analysis is greatly facilitated by the wide availability of yeast artificial chromosome (YAC) libraries, as described below. The nucleic acid sequence of a region encompassing a gene which is determined to occupy a map location of an Insulin-Resistance locus is examined, and open reading frames are assessed for their probable relationship with the observed phenotype. If desired, initial assessment may be performed with the assistance of bioinformatics databases, such as publicly available databases of expressed sequence tags (e.g., as available at http://www.ncbi.nlm.nih.gov). Cloning of all or a subset of the open reading frames present in the region (e.g., using the polymerase chain reaction, or PCR) from mutant animals or affected family members and from their healthy counterparts (either control animals or unaffected family members) is undertaken, and the sequences of these open reading frames compared. A mutation or other allelic variant which is found to be linked to individuals displaying the disease phenotype (again, in a statistically-significant, non-random fashion), is judged to be associated with the disease phenotype according to the invention. A subcloned nucleic acid fragment bearing this gene can then be labeled and used as a probe in an in situ hybridization to fixed chromosomes of the human or other mammal to establish the precise physical location of the gene. In addition, a gene so mapped and isolated may serve as a candidate target for disease diagnosis according to the invention (see below) and drug targeting.

C. How to Map a Candidate Gene and Compare its Map Position to that of an Insulin-Resistance Locus According to the Invention i. Mapping Molecular and cytogenetic methods are of use in mapping candidate genes. These methods are briefly summarized below.

Linkage analysis

As described above, linkage analysis may be performed between an unmapped candidate gene and one or more chromosomal markers within of the Insulin-Resistance loci. It is also possible to establish a map position for a candidate gene via linkage analysis of it and chromosomal markers, regardless of whether or not the markers are present within an Insulin-Resistance locus, and then to compare the map location so established for the candidate gene with that of markers which are linked to an Insulin-Resistance locus. In such an experiment, the optimal spacing of markers throughout the genome of the test organism is approximately one every 10 cM to ensure complete coverage and enable accurate mapping.

Syntenic similarity

The human and mouse genomes are extensively characterized, as a result of classical genetic studies and, more recently, multi-laboratory genomic sequencing collaborations such as the Human Genome Project and Mouse Genome Project. Significant co-linearity exists among human, mice and rats; that is, the chromosomal map positions of numerous genes and groups of genes are conserved relative to one another among these several species. This facilitates the mapping and identification of genes linked to one or more of the four Insulin-Resistance loci. Examination of the human and/or mouse chromosomal maps in the regions comparable to those to which these several loci map in the rat will yield candidate genes which may be responsible for the observed regulation of insulin- and fatty acid metabolic processes. That genes present in these regions of the human and/or mouse are present in the regions of interest in the rat may be confirmed by employing radiation hybrid mapping (see Example 1, below) or by fluorescence in situ hybridization at low stringency to rat chromosomes using labeled fragments derived from the human or mouse genes.

Radiation hybrid (RH) mapping is a somatic cell hybrid technique that was developed to construct high resolution, contiguous maps of mammalian chromosomes. The technique provides a method for ordering DNA markers spanning millions of base pairs of DNA at a resolution not easily obtained by other mapping methods (Cox et al., 1990, *Science*, 250:245–250; Burmeister et al., 1991, *Genomics*, 9:19–30; Warrington et al., 1992, *Genomics*, 13:803–808; Abel et al., 1993, *Genomics*, 17:632–641). An advantage of radiation hybrid mapping is the ability to map non-polymorphic DNA markers that cannot be used for meiotic mapping.

In this method a lethal dose of X-irradiation is used to break the chromosomes of the donor cell line into numerous fragments. Chromosome fragments from the donor cell line are subsequently retained non-selectively following cell fusion with a recipient cell line. The resulting hybrid clones are then tested for the retention or loss of specific donor chromosome markers. Markers that are further apart on a chromosome are more likely to be broken apart by radiation and to segregate independently in the RH cells than markers that are closer together. By analyzing the co-segregation of various loci in hybrid clones statistically, a map can be constructed giving information about the relative order and distance of markers (Cox et al., 1990, supra; Warrington et al., 1991, *Genomics*, 11:701–708; Ceccherini et al., 1992, *Poc. Natl. Acad. Sci. ISA*, 89:104–108).

Subtractive screening and other tests of differential gene expression

As stated above, the biochemical assays which are most useful in quantitating insulin- or catecholamine activity are performed in an isolated tissue, typically adipose tissue, in order to minimize the number of genes in the genetic background which contribute to strain-specific differences in phenotype (i.e., between SHR rats and normal WKY controls). Given that only a subset of an organism's genes are expressed in a given tissue, there is a high probability that transcripts which differ in expression between cells of the same tissue in a mutant and control animal are responsible for the observed mutant phenotype. One way of testing for differentially-expressed genes is by subtractive cloning.

In a subtractive cloning procedure, mRNA is isolated from a tissue of choice, which tissue is obtained from a first and a second organism, where one organism displays a mutant phenotype with regard to a particular trait while the other is normal in that respect. cDNA is prepared by methods well known in the art from the mRNA derived from the organism. The mRNA template is then degraded, either by hydrolysis under alkaline conditions or by RNAse H-mediated cleavage, after which the cDNA is returned to a buffer in which mRNA is stable, and mixed with a molar excess of mRNA prepared from the second organism under stringent hybridization conditions. The mixture is then passed over a hydroxyapatite column, which binds double-stranded nucleic acids but allows single stranded nucleic acid molecules to pass through. Reverse transcripts of the first sample which do not hybridize to mRNA molecules of the second (in other words, those which represent messages specific to the first tissue sample) are present in the flow-through fraction and are cloned into a vector to form a subtraction library. The reciprocal experiment (in which the CDNA is derived from the second mRNA preparation) is also performed to yield a complete set of transcripts specific to the two starting tissue samples.

The transcripts derived from this procedure may be labeled and used as probes in in situ hybridization to immobilized chromosomes or their chromosomal location determined by other means including genetic linkage analysis or radiation hybrid mapping. Therefore, subtractive screening yields both cloned genes and the means by which to determine whether they co-localize with one of the Insulin-Resistance loci according to the invention. If so, the genes may be analyzed functionally (e.g., in a phenotypic rescue experiment, as described below) and may ultimately serve as targets for drugs or disease diagnostic methods, or even as therapeutic nucleic acids.

Representational Difference Analysis (RDA)

RDA is described in detail in Lisitsyn et al., 1993, *Science*, 259:946, and an adaptation which combines selective breeding with RDA has also been described (Lisitsyn et al., 1993, *Nature Genet.*, 6:57). RDA is an advanced approach to subtractive hybridization (see above). To compare tester and driver genomes, one first creates simplified representation, called amplicons, from both samples (consisting, for example, of those BglII fragments that are small enough to be amplified by PCR). The iterative subtraction step begins with the ligation of a special adaptor to the 5' end of fragments in the tester amplicon. The tester amplicon is then melted and briefly reannealed in the presence of a large excess of competing driver amplicon. Those tester fragments that reanneal (which are preferentially those absent from the driver) can serve as a template for the addition of the adaptor sequence to its partner's 3'-end, which allow those fragments to be exponentially amplified by PCR. This procedure is then repeated to achieve successively higher enrichment.

Micoarray screening

Another way of testing for differentially-expressed genes is the use of gridded cDNA libraries or microarrays of expressed sequences. In these experiments, mRNA is extracted from the tissues of choice from a mutant and control mammal, and the mRNA samples converted by reverse transcription into mutant- and control-specific heterogeneous pools of cDNA molecules. Each strain-specific pool of cDNA is labeled using radioactive, fluorescent, chromogenic, luminescent or other labels such as are known in the art, and the resulting labeled molecules used to probe the gridded library or microarray. Following incubation of the probes with the library or array and washing to remove unbound probe, the intensity of the signal resulting from hybridization of either of the strain-specific cDNA probes to each clone of the library or array is measured by autoradiography, fluorimetry, confocal laser scanning and photometric- or densitometric scanning. The signals resulting from hybridization of the mutant and normal cDNAs to each member sequence of the library or array are quantitatively compared in order to generate a profile of differentially-expressed genes whose map locations can then be determined by in situ hybridization, genetic linkage analysis or radiation hybrid mapping. Genes that are differentially expressed and that map to an Insulin-Resistance locus will be highly important candidate genes for defects in glucose metabolism, fatty acid metabolism, insulin action or catecholamine action.

We compared gene expression in SHR and two control rat strains in the adipose tissue using microarray technology (Scios, Inc.). This technology allows tissue samples to monitor expression levels of thousands of genes simultaneously and to compare individual tissue samples.

The CD36 gene was found to be 5–10 fold under-expressed in SHR adipose tissue. The gene is tightly linked to the major SHR QTL on rat chromosome 4. 15 nucleotide sequence mutations, which translated into 9 amino acid alterations were identified in the SHR CD36 gene.

Mutagenic tranposon mapping

Entrapment vectors, first described in bacteria (Casadaban and Cohen, 1979, *Proc. Natl. Acad. Sci. U.S.A.*, 76:4530; Casadaban et al., 1980, *J. Bacteriol.*, 143:971) permit selection of insertional events that lie within genes (e.g., within its coding or regulatory sequences). In an animal model (e.g., mouse or rat), entrapment vectors can be introduced into pluripotent ES cells in culture (for example, using electroporation or a retrovirus) and then passed into the germline via chimeras (Gossler et al., 1989, *Science*, 244:463; Skames, 1990, *Biotechnology*, 8:827); alternatively, transgenic animals bearing such vectors may be generated via standard oocyte injection techniques.

These DNA integrations are highly mutagenic because they interrupt the endogenous coding sequence. It is estimated that the frequency of obtaining a mutation in some gene of any in the genome using a promoter or gene trap is about 45%. A detailed description of retroviral insertion mutagenesis has been published (see Methods Enzymol., vol. 225, 1990. Using this technique, it is possible to recover animals bearing mutations which result in phenotypic defects in insulin- or fatty acid metabolism.

Candidate genes according to the invention are most advantageously expressed in tissues to which biochemical assays of insulin and lipid metabolism described herein may be applied, for example, adipocytes. Promoter or gene trap vectors often contain a reporter gene, e.g., lacZ, Cat or green fluorescent protein (Gfp), lacking its own promoter and/or splice acceptor sequence upstream, by which one may assay the tissue-specificity of a candidate gene. If the vector falls within a gene and is spliced into the gene product, then the reporter gene is expressed. Enhancer traps have a minimal promoter which requires the activity of an enhancer in order to function, and contain a reporter gene. If the vector inserts near an enhancer (whether in a gene or not), then the reporter gene is expressed. Reporter gene activity in a tissue of interest provides an indicator of which may map to chromosomal map positions of Insulin-Resistance loci of the invention. Methods for detecting reporter gene activity in transfected cells or tissues of a transgenic animal are well known in the art; applicable methods of DNA, RNA and protein detection are described below (see sections E and G).

In testing such a gene to see whether it maps to a chromosomal map position of an Insulin-Resistance locus according to the invention, one may map the mutagenic vector using standard cytogenetic techniques, such as in situ hybridization, in which case a labeled fragment of vector-specific sequence is used as probe. Co-localization of the probe with an Insulin-Resistance locus is indicative that the associated gene is a suitable candidate for further work. Cloning of a gene identified in this manner may be performed as described below.

Candidate genes which may be tested for linkage to the Insulin-Resistance loci

Several genes which are candidates for linkage to Insulin-Resistance locus 1 have already been identified by various of the methods described above. These include rat Il6, Nos3, Slc4 α2, Psmc2, Fgl2, PgyI, and Cacna2 and mouse Gnail, Pgy2, Pgy3, Sri, Hgf, Htr5a, Cdk5, Dpp6, Plk, Tyms, Fgfr3, Adra2c, Pparg, ERTD363 and CD36. An inactivating mutation in the protein-coding sequence of the human gene encoding insulin promoting factor 1 (IPF-1) has been described (Stoffers et al., *Nature Genetics*, 15:106–110. Heterozygosity for this mutation has been linked to mature onset diabetes of the young (MODY), while homozygosity results in congenital pancreatic agenesis. The IPF1 gene is also a candidate gene useful in the invention.

ii. Comparing the chromosomal map position of a candidate gene with that of an Insulin-Resistance locus The map position of a candidate gene established as described above are then compared to those of the Insulin-Resistance loci. If a candidate gene occupies a map position which is within 10 cM of the peak of linkage (see above) of an Insulin-Resistance locus, the map positions of the gene and the locus are judged to be coincident.

D. Confirming a Role in Disease for a Gene Identified According to the Invention i. Administration of a nucleic acid to a cell or organism A nucleic acid may be transfected using a viral or non-viral DNA or RNA vector, where non-viral vectors include, but are not limited to, plasmids, linear nucleic acid molecules, artificial chromosomes and episomal vectors. Expression of heterologous genes has been observed after injection of plasmid DNA into muscle (Wolff et al., 1990, *Science*, 247:1465–1468; Carson et al., U.S. Pat. No. 5,580, 859), thyroid (Sykes et al., 1994, *Human Gene Ther.*, 5:837–844), melanoma (Vile et al., 1993, *Cancer Res.*, 53:962–967), skin (Hengge et al., 1995, *Nature Genet*, 10:161–166), liver (Hickman et al., 1994, *Human Gene Therapy*, 5:1477–1483) and after exposure of airway epithelium (Meyer et al., 1995, *Gene Therapy*, 2:450–460). Most convenient for assaying candidate modulators of Insulin-Resistance locus-associated gene activity are the transfection of cultured mammalian cells and the creation of transgenic animals; methods for cell transfection and for the creation of transgenic animals are well known in the art. Useful cells or animals, the latter either for the production of transgenic individuals or as sources of cells, include mice and rats, particularly those described below. Such animals may be wild-type at the genetic locus whose expression under the influence of the candidate modulator is to be studied; alternatively, an animal useful in gene expression studies in the invention may carry a mutation in the gene of interest.

ii. Animal models

As stated above, the SHR animal model of disease is useful in the study of defects in glucose- and fatty acid metabolism as well as insulin- and catecholamine action. Other animal models also may be of use. For example, The Goto-Kakizaki (GK) rat develops insulin resistance and non-insulin-dependent diabetes, and genes for these defects have been mapped (Gauguier et al., 1996, *Nature Genetics*, 12:38–43; Galli et al., 1996, *Nature Genetics*, 12:31–37). Some of the genes in the GK rat may have homologies to genes underlying the SHR metabolic defects in the SHR strain. Fine localization, identification and characterization of the GK genes may, therefore, throw light on the spectrum of candidate genes underlying the SHR metabolic defects and, after localization of these genes or genes in the same functional or structural family, may aid in identification of the SHR genes. Another animal model which is potentially of use in the invention is the Lyon hypertensive rat (Dubay et al., 1993, *Nature Genetics*, 3:354–357). This rat model also exhibits insulin resistance. Several strains of mice including the obese (ob), diabetic (db), agouti (Ay) strains also develop obesity and diabetes, due either to single-gene mutation or to effects in several genes. The causative genes in these monogenic obesity syndromes have been identified in some cases (reviewed in Chagnon and Bouchard, 1996, *Trends. Genet.*, 12:441–444). Cd36 may act as a modifier of such genes or, alternatively, on other components of pathways in which they are involved, and thereby modulate the accompanying ob, db or Ay phenotype.

Many animal models, both naturally-occurring and experimentally-induced, are known to exhibit a variety of cardiovascular diseases (reviewed by Elsner et al 1995 Curr Opin Card, 10: 253–259; Hongo et al, 1997, Trends Cardiovasc Med, 7:161–167). Such models may be used to confirm a role in disease for a gene identified according to the invention, either as sources of cells or in vivo (e.g., in the testing of the effects of a recombinant gene in a transgenic animal), or in testing candidate modulators of CD36 activity according to the invention. Typically, these models present measurable deficiencies in cardiac output that can serve as indicators of the efficacy of agents in improving cardiovascular function. A rat model of dilated cardiomyopathy is produced by constriction of the coronary artery (Pfeffer et al., 1979, *Circ. Res.*, 44:503–512). Also in the rat, hypertrophic cardiomyopathy can be induced by chronic pressure overload (Feldman et al., 1993, *Circ. Res.*, 73:184–192). Atherosclerosis has been studied in canine, ovine and primate models (for reviews, see Constantinides, *Experimental Atherosclerosis*, New York, Elsevier, 1965; Vesselinovitch and Wissler, 1977, *Adv. Exp. Med. Biol.*, 82:614–622).

These animal models, or cells derived from them, are useful for the expression of genes undergoing functional testing according to the invention as well as for drug targeting/screening according to the invention. For example, when placed on a high fat diet, the animal models described above develop atherosclerotic plaques. A particularly advantageous drug screening assay involves placing the test and control animals on such a diet, administering a candidate modulator of fatty acid metabolism or insulin action to the test animals and then comparing plaque accumulation or reduction in the test animals with control animals who have been similarly fed but have not been given the candidate modulator. A difference of at least 10%, but preferably at least 20%, in plaque accumulation between the test and control populations is indicative of efficacy of the candidate modulator according to the invention. Wild-type animals and cells are also of use in drug screening assays and disease diagnosis and treatment according to the invention. In addition, transgenic animals are of use in gene expression studies and drug targeting/screening experiments; such animals may be derived from individuals having a wild-type or mutant genetic background relative to the gene under consideration.

Alternatively, a candidate modulator is administered to animals which model a disease as described above, which animals have been normally maintained (e.g., not on a high-fat diet). Control animals, also modeling the disease, are given the drug carrier only, administered in the same fashion as is the carrier comprising the candidate modulator. Dosage calculation and administration of a candidate modulator to a test animal are performed as described below. The treated animals are monitored for amelioration of their pathophysiological conditions; improvement in a clinical disease indicator of at least 10%, preferably at least 20%, in treated animals relative to controls is indicative of efficacy of the candidate modulator of CD36-mediated activity according to the invention.

Screening systems which comprise neither whole animals or cells are separately described below. These include assay systems which comprise cell lysates, as well as those which are entirely non-cellular (e.g., having assay components in a medium such as a physiologically compatible buffer or enzyme reaction buffer, or having assay components immobilized on a solid- or semi-solid support (including, but not limited to, a gel, a filter and a silica support).

iii. Enzymatic assay of function

The degree to which a gene which is mapped according to the invention functions in insulin- or fatty acid metabolism may be assessed biochemically by methods which include, but are not limited to, the following techniques, which are equally of use in the assessment of efficacy of a candidate drug in a screening assay carried out in cells or an animal model, as described below, or the success of a regimen of disease treatment according to the invention. Such assays may be performed as described below for animal models or cells on a biological sample obtained from a human subject.

Glucose uptake assay

Adipocytes from retroperitoneal fat pads of a test rat are prepared as described elsewhere (Rodbell, 1964, *J. Biol. Chem.*, 239:375–380), except that a HEPES-based buffer is used that includes $CaCl_2$ (1 mmol/l) and adenosine (200 nmol/l) in all incubations. The volume and number of unfixed adipocytes are measured using a Mulitisizer II (Coulter). Adipocytes are diluted to a fixed cell density around $10^5$ per ml and pre-incubated for 30 minutes to allow cell recovery.

Insulin-mediated glucose uptake is measured in isolated retroperitoneal adipocytes from male rats as has been described (Reaven, 1989c, supra) except that incubations contained adenosine deaminase (1 Unit/ml), phenylisopropyladenosine (25 nmol/l) and tracer (300 nmol/l) amounts of [$^{14}$C]-labeled D-glucose, with- or without insulin (50,000 pmol/l). Incubations are terminated by spinning the incubation medium through silicone oil. Adipocytes are then washed and the incorporated [$^{14}$-C]-glucose counted on a scintillation counter (Beckman).

Control incubations for each pad are performed with cytochalasin B (20 $\mu$M), or [$^{14}$-C] L-glucose instead of [$^{14}$-C] D-glucose. Incubations with cytochalasin B or L-glucose typically show less than 20% of basal D-glucose uptake and no increase with insulin. Basal and maximal glucose uptake are measured in duplicate for each pad and are calculated as the accumulation of [$^{14}$-C] D-glucose per cell after subtracting the value for the cytochalasin control for that fat pad. Typical results are highly correlated for the left and right pads on consecutive animals; therefore, the mean of the left and right pads is taken as the phenotypic value for a given animal.

Lipolysis assay

Adipose tissue is prepared as described above for the glucose uptake assay. In separate reactions adipocytes are incubated with- or without isoproterenol (200 nmolll) for 45 minutes. The NEFA concentration of the infranatant is measured in duplicate by enzymatic colorimetric assay (WAKO NEFA-C kit, Alpha Laboratories, UK) and the mean of the left and right pads taken as the phenotypic value for that animal.

Cell-based screening assays for CD36 activity and modulators thereof

To identify compounds that regulate biological effects of CD36, one can search for compounds that affect the binding of known ligands to CD36. Published data indicate that the CD36 protein is a cellular receptor and transporter for certain free fatty acids (Abumrad et al, 1993, *J. Biol. Chem.*, 24:17665–17668) and certain lipoprotein complexes (Endemann et al, 1993, *J. Biol. Chem.*, 268:11811–11816). Antibodies directed against CD36 have been shown to block the binding and uptake of these ligands. The uptake of these CD36 ligands has been measured in cell lines expressing either endogenous or recombinant CD36 (Abumrad et al., 1993, supra; Endemann et al, 1993, supra). A variety of cell types have been shown to express CD36, including:cardiomyocytes, adipocytes, monocytes, and skeletal muscle cells (Ibrahimi et al., 1996, *Proc. Natl. Acad. Sci. U.S.A.*, 93:2646–2651; van Nieuwenhoven et al., 1995, *BBRC*, 207:747–752). Cell lines devoid of CD36 expression have been transfected with DNA constructs that express CD36, resulting in cells which are more efficient at binding and uptake of fatty acid and lipoprotein ligands (Endemann et al, 1993, supra; Abumrad et al, 1993, supra). Such cell types are of use in cell-based assay systems for the identification of agents that bind to CD36, which agents are thereby modulators or candidate modulators of CD36-mediated activities according to the invention.

In one such assay, test compounds are evaluated for their ability to inhibit binding of oxidized low-density lipoprotein (oxLDL) to CD36-expressing cells. Human 293 cells, which do not express CD36, are transfected with an expression vector that encodes CD36. Expression of mRNA controlled by a number of regulatory elements known in the art, of which one non-limiting example is the LTR promoter of cytomegalovirus (CMV) as previously described (Stanton et al, 1992, *J. Biol. Chem.*, 267:22446–22451). As a control, 293 cells will be transfected with a DNA vector that lacks the CD36 gene. Stably transfected 293 cell lines will be selected by conventional methods to establish clones that express CD36, and a negative (vector only) control cell line. Cells are seeded into 96 well microtiter plates for assays. Radioactively labeled oxLDL ligand will be prepared essentially as described (Stanton et al, 1992, J Biol Chem 267:22446–22451). Briefly, LDL is radioiodinated using the iodine monochloride method (Contreras et al, 1983, *Methods Enzymol.*, 92:277–292) to a specific activity of 100–500 cpm/ng of protein. Oxidation of $^{125}$I-LDL is accomplished by incubation in the presence of 5 $\mu$M $CuSO_4$ at 37° C. for 44 hours to generate $^{125}$I-oxLDL. CD36-expressing cells and control cells are incubated with $^{125}$I-oxLDL in serum-free cell culture medium for 2 hours at 37° C. Test compounds, typically at a 1–100 μM concentration, are co-incubated with the cells and ligand. Cells are then washed three times with PBS to remove unbound ligand. Radioactivity in each well is counted to establish degree of binding of $^{125}$I-oxLDL and determine which compounds inhibit or enhance oxLDL interactions with CD36. A monoclonal antibody specific for human CD36 (e.g., OKM5; see Talle et al., 1983, *Cellular Immunol.*, 78:83–99; also commercially available from Columbia Diagnostics, Pleasanton, CA) serves as a control in the assay for the inhibition of ligand binding.

In another assay of CD36 activity, compounds are tested for their ability to alter the binding and uptake of fatty acids essentially as described by Abumrad et al. (1991, *Am. J. Physiol.*, 261:E76-E86). Human 293 cells transfected with an expression vector which expresses CD36 and control cells transfected with the vector only (i.e., the same vector, but which does not express the CD36 gene) are incubated with an $^3$H-oleate fatty acid ligand. Cells plus this ligand are incubated with test compounds present at 1–100 μM concentrations, for 4 hours at room temperature in Krebs-Ringer HEPES (KRH) buffer pH 7.4. The reaction is terminated by addition of ice-cold KRH buffer and cells are washed twice with KRH, followed by cell lysis in 0.1 N NaOH. Uptake of $^3$H-oleate fatty acid is determined by scintillation counting. Agents that substantially (i.e., by at least 10%, preferably at least 20%) inhibit or enhance fatty acid uptake by cells will be selected for further studies as candidate modulators of CD36 activity according to the invention.

Additional assays for agents that regulate the biological activity mediated by CD36 will look at changes in transcription of genes that are responsive to lipids that have entered the cell via CD36 mediated transport. It has been shown that uptake of oxidized low-density lipoprotein (oxLDL), through CD36, activates PPARγ-dependent transcription (Nagy et al., 1998, *Cell*, 93: 229–240; Tontonoz et al., 1998, *Cell*, 93:241–252). PPARγ is a nuclear receptor that acts as a transcriptional regulator of lipid metabolism (Tontonoz et al., 1994, *Cell*, 79:1147–1156). Several genes have been identified that are regulated by PPARγ, including fatty acid binding protein aP2, phosphoenolpyruvate carboxykinase, lipoprotein lipase, fat uncoupling protein UCP1, and CD36. Lipids that activate PPARγ, including 9-HODE and 13-HODE, are delivered to the cell by CD36, and CD36 expression is elevated by PPARγ activation. The effect of a test compound targeted to CD36 may be monitored by evaluating the response of genes that are regulated by lipid through the PPARγ pathway. Reporter constructs are produced by methods well known in the art, as described elsewhere herein, by fusing gene promoter and regulatory regions of lipid-responsive genes to a reporter gene, for example firefly luciferase gene or chloramphenicol acetyl transferase gene, to facilitate monitoring of changes in gene expression induced by CD36 ligands. Cells that express CD36 are transfected by standard methods with reporter constructs and subsequently used in assays to test agents for their ability to modulate gene expression in a CD36-dependent fashion. These types of transcription assays, which are well known in the art and as described herein, are amenable for rapid screening of thousands of test compounds.

E. Drug Screening According to the Invention
i. Targets in the Invention

As indicated above, the invention is useful for screening (identifying and assaying) candidate therapeutic compounds for efficacy against diseases linked to defects in insulin action, glucose metabolism, lipid metabolism or uptake or catecholamine action, such as are described above. A variety of drug screening methods are performed according to the invention using mutant or wild-type nucleotide sequences, or fragments thereof, of genes linked to one of Insulin Resistance Loci 1 through 4, as well as amino acid sequences encoded by such sequences or fragments.

According to these methods, the target mutant or wild-type nucleic acid, protein product or fragment employed in such a test may either be free in solution, affixed to a solid support, expressed on the surface of a cell, or located intracellularly; this is likewise true of the candidate drug under consideration, whether or not it is a nucleic acid or polypeptide that is linked to an Insulin Resistance Locus. If living cells are employed, they may be cultured or otherwise isolated (e.g., explanted), or may be comprised by a multicellular organism.

Particularly preferred target for drug screening according to the invention are the Cd36 and CD36 genes of rats and humans, respectively. As described below, the rat Cd36 gene is linked to Insulin Resistance Locus 1 and mutations at this locus are linked to defects in lipid metabolism in the Spontaneously Hypertensive Rat. Similarly, mutations have been discovered in the human CD36 gene which are linked to diabetes, insulin resistance and risk of coronary heart disease. Either a mutant or wild-type Cd36 or CD36 nucleic acid sequence or a fragment thereof, or a mutant or wild-type Cd36 or CD36 protein or fragment thereof may be used advantageously in a screening assay of the invention, either as a target or as a candidate drug, by methods including, but not limited to, those described below.

ii. Candidate Drugs of Use in the Invention

Having identified genes within one or more of the Insulin-Resistance loci, as described above, potential therapeutic agents can be tested for their ability to modulate the activity of such a gene or genes or the product(s) thereof. The activity of a gene may be assessed either by measuring its level, distribution or timing of transcription or by measuring the size, sequence, processing or stability of its encoded nucleic acid product (e.g., a messenger- or other RNA molecule) or the presence or absence of an encoded protein (for example, immunologically). In addition, the activity of a protein (e.g., enzymatic activity, role in a signaling cascade, receptor/ligand binding interactions, etc.) may be assayed; numerous enzymatic assays are known in the art. Such a protein may be the product of a target gene identified according to the invention; alternatively, such a protein may be encoded by another gene, but produced or activated in response to the action of the target gene. This may be accomplished either in vivo or in vitro, as described briefly below.

Candidate modulators of Insulin-Resistance locus-associated gene activity which may usefully be encoded by a nucleic acid sequence; alternatively, a protein or other agent may be administered directly (see below). Useful proteins include, but are not limited to, nuclear proteins, cytoplasmic proteins, mitochondrial proteins, secreted proteins, plasmalemma-associated proteins, receptors, enzymes, ligands, regulatory factors, structural proteins, serum proteins, hormones, growth factors, neurotransmitters, enzymes, clotting factors, apolipoproteins, drugs, oncoproteins, tumor antigens, tumor suppressors, viral antigens, bacterial antigens, protozoal antigens and parasitic antigens), lipoproteins, glycoproteins and phosphoproteins. Useful nucleic acids may encode proteins as described above or may instead encode modulators which are themselves nucleic acids (e.g., RNAs such as ribozymes or antisense nucleic acids). The compounds which can be incorporated are only limited by the availability of the nucleic acid sequence encoding a given product. One skilled in the art will readily recognize that as more proteins and polypeptides become identified, their corresponding genes can be cloned into the gene expression vector(s) of choice, administered to a tissue of a recipient organism as described above, such as a mammalian tissue (including human tissue), and expressed in that tissue.

Candidate modulators which may be screened according to the invention include substances for which a test cell or organism might be deficient or that might be clinically effective in higher-than-normal concentration as well as those that are designed to eliminate the translation of unwanted proteins. Nucleic acids of use according to the invention not only may encode the candidate modulators which substitute for or enhance a deficient product or function of the recipient, but may instead eliminate or encode products which eliminate deleterious proteins. Such nucleic acid sequences are antisense RNA and ribozymes, as well as DNA expression constructs that encode them. Antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for a target mRNA. Ribozymes of the hammerhead class are the smallest known, and lend themselves both to in vitro synthesis and delivery to cells (summarized by Sullivan, 1994, *J. Invest. Dermatol.*, 103:85S-98S; Usman et al., 1996, *Curr. pin. Struct. Biol.*, 6:527–533).

In addition, candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fugal, plant and animal extracts are available from e.g., Pan Laboratories (Bothell, Wass.) or MycoSearch (N.C.), or are readily produceable by methods well known in the art. Additionally, natural and synthetically produced libraries and compounds are readily modified through conventional chemical, physical, and biochemical means.

Useful compounds may be found within numerous chemical classes, though typically they are organic compounds, and preferably small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

How to Make a Nucleic Acid, Protein or Peptide Useful in the Invention

The sequence encoding a protein (e.g., a modulator as described above, which may be the product of a gene linked to an Insulin Resistance Locus, another protein or a fragment thereof) or a nucleic acid of interest (e.g., an antisense RNA or ribozyme) may be synthesized, wholly or in part, using chemical methods well known in the art (see Caruthers, et al., 1980, *Nucleic Acids Res. Symp. Ser.*, 7:215; Horn, et al., 1980, *Nucleic Acids Res. Symp. Ser.*, 7:225; and others). The nucleic acid so synthesized, whether alone or ligated to additional regulatory and/or vector sequences (see below), may be administered directly to a recipient mammal, or may be placed in a gene expression system (e.g., a transformed or transfected cell or a cell free system, such as a rabbit reticulocyte lysate) for transcription and/or translation to yield the desired end product. Alternatively, a protein or a portion thereof, can be produced using chemical methods of synthesis. For example, peptide synthesis can be performed using various solid-phase techniques (Roberge, et al., 1995, *Science*, 269:202) and automated synthesis may be achieved, for example, using the ABI 431A Peptide Synthesizer (Perkin Elmer) in accordance with the instructions provided by the manufacturer.

A newly synthesized protein or peptide can be substantially purified by a chromatographic procedure know in the art, such as preparative high performance liquid chromatography (see, e.g., Creighton, 1983, Proteins, Structures and Molecular Principles, WH Freeman and Co., New York, N.Y.) or two-dimensional gel electrophoresis. The composition of the isolated protein is then determined, also by standard methods, such as by mass spectrometry (e.g., liquid chromatography/electrospray ionization/ion trap tandem mass spectrometry) or Edman degradation (see Creighton, 1983, supra). Additionally, the amino acid sequence of interest, or any part thereof, may be altered during direct synthesis and/or combined using chemical methods with sequences from other proteins, or any part thereof, to produce a variant polypeptide.

In order to make a larger amino acid sequence, such as a whole or truncated polypeptide, the nucleotide sequence encoding the protein of interest or its functional equivalent, is inserted into an appropriate expression vector, i.e., a vector which contains the necessary elements for the transcription and translation of the inserted coding sequence.

Methods which are well known to those skilled in the art can be used to construct expression vectors containing a protein-encoding sequence and appropriate transcriptional or translational controls. These methods include, but are not limited to, in vitro cloning methods, in vivo recombination and genetic recombination. Such techniques are well known in the art (see Ausubel et al., 1995, supra; Sambrook et al., 1989, supra).

Dosage

It will be apparent to those of skill in the art that the therapeutically-effective amount of a composition administered in the invention will depend, inter alia, upon the efficiency of cellular uptake of a composition, the administration schedule, the unit dose administered, whether the compositions are administered in combination with other therapeutic agents, the health of the recipient, and the therapeutic activity of the particular protein or other pharmaceutical substance.

As is also true of nucleic acids administered according to the invention, the precise amount of a protein or other pharmaceutical agent required to be administered depends on the judgment of the practitioner and may be peculiar to each subject, within a limited range of values. An appropriate dose of a protein or other substance may be calculated as immediately follows (or see below).

An animal model, such as those described above, may be used to assay the effectiveness of varying doses of a protein or other agent in modulating Insulin-Resistance locus-associated gene activity. For a given therapeutic composition, it is necessary to establish an approximate range of dosages that are useful, yet relatively safe, in a clinical situation. The animal model may be employed to establish a dosage curve prior to use of the invention in human subjects. Alternatively, if a pharmaceutical agent useful according to the invention already has been granted regulatory approval, it stands that acceptable upper limits of dosage tolerance for humans and other mammals already will have been established for these drugs prior to testing, as have systemic concentrations useful for other clinical applications. These known dosages may serve as the basis upon which calculations may be made prior to use of the animal model.

iii. In vivo assay of a candidate modulator of Insulin-Resistance locus-associated gene function In the course of linkage studies in which the Insulin-Resistance loci were identified, several parameters in the SHR model (including overall weight, fat pad weight, fat cell volume, maximal glucose uptake, incremental glucose uptake, maximal/basal glucose uptake, absolute NEFA secretion and incremental glucose secretion) were assayed in isolated adipocytes obtained from these animals and from normal rats of the Wistar Kyoto (WKY) and Brown Norway (BN) strains. Following administration of a candidate modulator to an SHR, one or more of these parameters may be monitored for change in treated animals vs. untreated controls.

Following preliminary testing in cells and/or animal models including, but not limited to, those described above, a candidate modulator of function of CD36 or other gene linked to an Insulin Resistance Locus which appears both safe and effective may be tested in a human subject prior to approval for use in disease treatment according to the invention. Dosages are calculated depending on the body weight of the human subject based upon the mg/kg dosages found to be effective in cells or animal subjects, additionally taking into account factors such as age, sex or physical condition of the human subject as judged by one of skill in the art, e.g., a physician or clinical researcher. Human subjects are then monitored, either by molecular and biochemical criteria described below or for changes in clinical indicators particular to the disease at which the candidate drug is aimed. Such indicators include, but are not limited to, blood levels of insulin, glucose, triglycerides, fatty acids and high-density lipoprotein cholesterol; lipid levels in lipoprotein fractions and subfractions including very low density lipoprotein cholesterol, triglycerides and apoB, and intermediate density lipoproteins; and size and density of low density lipoprotein particles. Lipid, glucose nad insulin variables may be measured in the fasting state, after a glucose 'load' or after a mixed meal. Twenty-four hour profiles of the above variables may be taken, the results of which may be advantageously used according to the invention. Evidence of arteriosclerosis in humans may be detected via ultrasound imaging of arteries, such as carotid arteries, and coronary imaging including, but not limited to, angiography and ultra-fast computerized tomography. In addition, weight, blood pressure or other functions associated with insulin action, glucose metabolism, lipid metabolism or catecholamine action, or general health of the patient may be assessed. Those screening assays which entail the use of human subjects are performed under approved regulatory guidelines, which include obtaining informed consent from the research subjects, complete physical and historical evaluation prior to admittance to the study, clinical monitoring throughout the course of the screening to evaluate both the efficacy and safety (absence of harmful side-effects) of the drug and follow-up examinations to detect long-term effects, if any, of the candidate drug.

It is contemplated that a candidate modulator may be administered by a conventional drug-administration protocol, preferably one following approved guidelines for animal use and care. Methods and dosages of drug-delivery which may be used advantageously to deliver a candidate modulator of insulin- or fatty acid metabolism according to the invention include, but are not limited to, those described below.

Administration of a candidate modulator compound a. Systemic

Methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced modulator or may, instead, comprise cells that produce and secrete the modulatory substance. Injection may be performed either by conventional means (i.e. using a hypodermic needle) or by hypospray (see Clarke and Woodland, 1975, *Rheumatol. Rehabil.*, 14:47–49).

Methods for the introduction of a nucleic acid to a screening assay of the invention include simple addition of a nucleic acid molecule to a cell-free assay system, transfection or transformation into a cell or introduction into a multicellular animal, such as a mammal, by means described above, including by transgenic technology. Methods of delivering a nucleic acid molecule to a cell or whole animal are well known in the art (see, part D., section i., above), as are molecular cloning methods required to join coding sequences of interest with appropriate regulatory signals (see below). As stated above, particularly preferred nucleic acid sequences either for drug targeting or for use as candidate drugs according to the invention are those which encode all or a fragment of wild-type or mutant rat Cd36 or human CD36 protein, as well as nucleic acid sequences which hybridize to Cd36 or CD36 transcripts, such as antisense molecules or ribozymes specific for these sequences, which could be used to block translation of a mutant Cd36 or CD36 mRNA.

b. Topical

Topical compositions comprising a candidate modulator can take any of several physical forms, as summarized below:

A liquid, such as a tincture or lotion, which may be applied by pouring, dropping or "painting" (i.e. spreading manually or with a brush or other applicator such as a spatula).

An ointment or cream, which may be spread either manually or with a brush or other applicator (e.g. a spatula), or may be extruded through a nozzle or other small opening from a container such as a collapsible tube.

A dry powder, which may be shaken or sifted onto the site of potential or actual tumor cell growth or, alternatively, applied as a nebulized spray.

A liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

A carbowax or glycerin preparation, such as a suppository, which may be used for rectal or vaginal administration of an modulator.

Drug delivery by inhalation, whether for topical (i.e., to the inner surface of the lung) or systemic distribution, is well known in the art. In particular, it has been demonstrated that it is possible to deliver a protein via aerosol inhalation such that it retains its native activity in vivo (see Hubbard et al., 1989, *J. Clin. Invest.*, 84:1349–1354).

Dosage of a candidate modulator

Dosage is calculated based upon a systemic dose. Taking into account the half-life of the native activity of a given modulator in blood serum, the mean circulating dosage may range from 10 $\mu$g to 100 $\mu$g per kg of body weight; preferably, it is from 100 $\mu$g to 10 mg per kg. The concentration of modulator in the chosen carrier composition is then adjusted such that the required dosage is delivered in a convenient volume. It is within the knowledge of one of skill in the art to select a starting dosage or range of starting dosages; if no effect is seen, dosages within four orders of magnitude above and below the starting dosage or dosages are attempted.

Generally, nucleic acid molecules are administered in a manner compatible with the dosage formulation, and in such amount as will be prophylactically and/or therapeutically effective. When the end product (e.g., an antisense RNA molecule or ribozyme) is administered directly, the dosage to be administered is directly proportional to the amount needed per cell and the number of cells to be treated, with a correction factor for the efficiency of uptake of the molecules. In cases in which a gene must be expressed from the nucleic acid molecules, the strength of the associated transcriptional regulatory sequences also must be considered in is calculating the number of nucleic acid molecules per target cell that will result in adequate levels of the encoded product. Suitable dosage ranges are on the order of, where a gene expression construct is administered, 0.5–1 $\mu$g, or 1–10 $\mu$g, or optionally 10–100 $\mu$g of nucleic acid in a single dose. It is conceivable that dosages of up to 1mg may be advantageously used. Note that the number of molar equivalents per cell vary with the size of the construct, and that absolute amounts of DNA used should be adjusted accordingly to ensure adequate gene copy number when large constructs are administered to a research subject or patient. As a first approximation, an amount of a nucleic acid molecule equivalent to between 1 and 10 copies thereof per cell should be delivered; one of skill in the art may adjust the ratio of nucleic acid molecules to cells at the target as is necessary to optimize nucleic acid uptake.

When the amount of a protein or other therapeutic agent to be used is considered, the lowest dose that provides the desired degree of activity at the target site, tissue or cell should be used; lower doses may be advantageous in order to minimize the likelihood of possible adverse effects. Useful dosages are typically in the range of about 1 $\mu$g–100 mg/kg body weight. Where the candidate drug is a peptide or polypeptide, it is typically administered in the range of about 100–500 $\mu$g/ml per dose. It will be apparent to those of skill in the art that the biologically- or therapeutically-effective amount of a composition administered in the invention will depend, inter alia, upon the efficiency of cellular uptake of a composition, the administration schedule, the unit dose administered, whether the compositions are administered in combination with other therapeutic agents, the health of the recipient, and the therapeutic activity of the particular protein or other pharmaceutical substance. As is also true of nucleic acids administered for screening or therapy according to the invention, the precise amount of a protein or other pharmaceutical agent required to be administered depends on the judgment of the practitioner and may be peculiar to each subject, within a limited range of values.

If no effect on insulin- or fatty acid metabolism is then observed, the candidate modulator is deemed ineffective. If a change of at least 20% between the basal (pre-treatment) and post-treatment values is observed for one or more of the parameters being assayed, the candidate agent is judged to be efficacious.

Pharmacological formulation of a candidate modulator

In the case of liquids, ointments and liquid-based aerosols, the preferred solvent is an aqueous medium with an ionic balance that mimics physiological salt levels in order to preserve activity of the inhibitor and to avoid changes in osmotic pressure for the cells to be contacted with the composition. An example of such medium is a low-ionic-strength saline solution or other physiologically compatible buffer. As used herein, the term "physiologically compatible buffer" or "physiological buffer" is defined as a liquid composition which, when placed in contact with living cells, permits the cells to remain alive over a period of minutes, hours or days. As such, a physiological buffer is substantially isotonic with the cell, such that cell volume does not change more than 20% due to differences in internal and external ionic strength. Non-limiting examples of physiologically compatible buffers or physiological buffers include dilute saline, which may be buffered (e.g., Hanks' buffered saline or phosphate buffered saline), or other physiological salts (e.g., Ringer's solution), dilute glucose, sucrose or other sugar, dilute glycerol with- or without salts or sugars, cell culture media as are known in the art, serum and plasma.

Lipid-, other hydrocarbon-, fluorocarbon- or halogen-based media also are formulated such that they maintain a physiological salt balance.

Dry powders comprising a protein or carbohydrate may be produced via air-drying of a precipitate or by lyophilization; in some instances, a candidate modulator may be an organic or inorganic salt, commercially known and available as a dry powder or as crystals. In either case, it is desirable to compound the candidate modulator with a bulking agent, such as are commonly known in the art, for ease of handling.

A modulator of the activity of a gene associated with glucose- or fatty acid metabolism or with insulin- or catecholamine action may comprise a protein, carbohydrate, nucleic acid or other bio-degradable substance (e.g. an organic or inorganic compound); therefore, depending upon the route of administration, it may be necessary to encapsulate or buffer it in such a way as to protect it from degradation (for example, by digestive enzymes, acid and base), at least until it reaches its target, by such methods as are well known in the pharmacological art.

i. In vitro assay of a candidate modulator of Insulin-Resistance locus-associated gene function Screening of modulators of genes linked to the Insulin-Resistance loci Genes identified according to the invention may serve as drug targets. Useful screening methods include those in which the transcription of the gene is monitored in the presence or absence of the candidate drug; in such a case, gene activity may be assessed via molecular means (e.g. Northern analysis, in situ hybridization or quantitative PCR of the native gene or a marker gene driven by its regulatory region) or biochemical/immunological techniques (e.g., Western- or immunohistochemical detection of a gene product, or functional assay of the gene product- for example, if the encoded product is an enzyme, receptor, etc.). A selection of these procedures are described below.

Drug-screening assays may be performed in vitro in a cell free gene expression system, in a gene expression system including a cell extract, or in a whole cell expression system, or in vivo. Minimally, an in vitro assay performed according to the invention will contain a gene expression construct containing the regulatory region of a gene identified according to the invention, which region is functionally linked either to the native gene or to a marker gene (see below). The assay is performed in a standard in vitro transcription/translation system under conditions which permit expression of the gene expression construct. The TNT® T7 Quick Coupled Transcription/Translation System (Cat. # L1170; Promega) contains all reagents necessary for in vitro transcription/translation except the DNA of interest and the detection label. The group of available TNT® Coupled Reticulocyte Lysate Systems (comprising a rabbit reticulocyte lysate) includes:TNT® T3 Coupled Reticulocyte Lysate System (Cat. # L4950; Promega); TNT® T7 Coupled Reticulocyte Lysate System (Cat. #L4610; Promega); TNT® SP6 Coupled Reticulocyte Lysate System (Cat. #L4600; Promega); TNT® T7/SP6 Coupled Reticulocyte Lysate System (Cat. #L5020; Promega); and TNT® T7/T3 Coupled Reticulocyte Lysate System (Cat. #L5010; Promega).

An assay involving a cell lysate or a whole cell may be performed in a cell lysate or whole cell preferably eukaryotic in nature (such as yeast; fungi; insect, e.g., Drosophila; mouse; or human). An assay in which a cell lysate is used is peformed in a standard in vitro system under conditions which permit expression of the gene expression construct. A rabbit reticulocyte lysate alone is also available from Promega, either nuclease-treated (Cat. #L4960) or untreated (Cat. # L4151).

Assays in which a whole cell is used are also known, and typically comprise the use of a gene expression construct in which the regulatory region of the gene of interest is functionally linked to a reporter gene; such a construct is transfected into cells in culture, which may be mammalian cells (preferably of a cell type which expresses in vivo the gene identified according to the invention) or, alternatively, yeast or other eukaryotic cells, such as insect cells, may be used. Methods for detecting the function of a marker gene in such a system are described below.

Alternatively, the reporter gene expression system may operate in vivo, i.e., in an intact, living multicellular organism, such the SHR system or other animal models described above. For example, a drug which is directed at modulating the activity of a gene identified according to the invention as being linked to one of the Insulin-Resistance loci is administered to an SHR, and clinical indicators, such as glucose uptake or NEFA secretion, are monitored for improvement by the methods described above.

Binding Assays

One method of drug screening entails performing binding assays, which test for direct physical interaction between a candidate modulator and a target gene or protein, or for interference or enhancement of direct interaction between a wild-type or mutant gene or protein of interest and a second gene, protein or other cellular component. Eukaryotic or prokaryotic host cells, which may be stably transformed with a recombinant polynucleotide expressing a polypeptide, nucleic acid or fragment thereof may be employed in competitive binding assays. Such cells, either in viable or fixed form, can be used for standard binding assays. In particular, these cells can be used to measure formation of a complex comprising the Insulin Resistance Locus linked protein product or fragment and the agent being tested. Alternatively, these cells can be used to determine if the formation of a complex between the IRL-linked protein product or fragment and a known ligand or receptor specific for that protein is interfered with by an agent being tested. In other procedures (e.g., those in which the effect of a candidate modulator on the transcription, mRNA processing or translation of a gene transcript of interest or in which the candidate modulator is, itself, a nucleic acid molecule), the formation of protein:nucleic acid or nucleic acid:nucleic acid complexes may be assayed. Lastly, the ability of a candidate modulator which is neither a protein nor a nucleic acid to bind a target IRL-linked protein or nucleic acid may be assayed.

Thus, the present invention discloses methods useful for drug screening wherein such methods comprise contacting a candidate drug with an mutant or wild-type IRL-linked polypeptide, nucleic acid or fragment thereof and assaying (i) for the presence of a complex between the drug and the mutant IRL-linked polypeptide, nucleic acid or fragment, or (ii) for the presence of a complex between the mutant or wild-type IRL4inked polypeptide, nucleic acid or fragment and a ligand, by methods well known in the art. Preferably, the IRL-linked polypeptide, nucleic acid or fragment is labeled for use in competitive binding assays. Methods for producing a labeled protein or peptide by in vitro translation or chemical synthesis using labeled amino acids or radioiodination of are well known in the art. Free labeled protein, polypeptide or fragment will be separated from that present in a protein:protein or protein:nucleic acid complex, and the amount of free (i.e., uncomplexed) label will be used as a measure of the binding of the candidate drug to the target or its ability to interfere with target protein:ligand or nucleic acid:protein binding.

Another method of drug screening which allows for high throughput screening for compounds exhibiting suitable binding affinity to a mutant or wild-type IRL-linked or other polypeptide has been described in detail (Geysen, WO 84103564). According to this method, large numbers of different small peptide test compounds are synthesized on a solid substrate, such as plastic pins or another suitable surface. The peptide test compounds are reacted with mutant or wild-type IRL-linked protein, peptide, gene or other target which is comlexed to a detectable label, and then washed. Bound target is then detected by methods well known in the art (including, but not limited to, autoradiography, scintillation counting and fluorimetry). As stated above, immobilized libraries of test compounds are commercially available.

As an alternative to procedures in which a test library is immobilized on a support, purified target polypeptide or nucleic acid can be coated directly onto plates for use in the aforementioned drug screening techniques. Alternatively, non-neutralizing antibodies to a polypeptide or other linking molecules, such as oligonucleotides complementary to a site outside the intended drug-binding site of a target nucleic acid can be used to capture the IRL-linked polypeptide, peptide, nucleic acid or fragment thereof and immobilize it on the solid support.

Competitive drug screening assays in which neutralizing antibodies capable of specifically binding a mutant or wild-type IRL-linked polypeptide compete with a test compound for binding to the IRL-linked polypeptide or fragments thereof are also useful according to the invention. According to this method, antibodies can be used to detect the presence of any test peptide which shares one or more antigenic determinants with a CD36 or other polypeptide.

Other methods

An additional technique for drug screening involves the use of host eukaryotic cell lines or cells such as described above which have a mutant IRL-linked gene that produces a defective protein. According to this method, the host cell lines or cells are grown in the presence of a test drug compound. The rate of growth of the host cells is measured to determine if the compound is capable of regulating the growth of cells expressing a nonfunctional IRL-linked protein product. Alternatively, the ability of the test compound to restore the function of the mutant IRL-linked protein can be measured by using an appropriate in vitro assay for IRL-linked protein function, such as those quantitating glucose or lipid metabolism of the cells, as described above. If the host cell lines or cells express an IRL-linked protein that exhibits an aberrant pattern of cellular localization the ability of the test compound to alter the cellular localization of the IRL-linked protein will be determined. Changes in the cellular localization of a protein of interest may be detected by performing cellular fractionation studies with biosynthetically labeled cells. Alternatively, the cellular localization of a protein of interest can be determined by immunocytochemical methods well known in the art (see below).

A method of drug screening may involve the use of host eukaryotic cell lines or cells, described above, which have an altered IRL-linked gene that demonstrates an aberrant pattern of expression. As used herein, the term "aberrant pattern of expression" refers to a level of expression that is either abnormally high or low, or a spatial or temporal pattern of expression different from that of a given wild-type gene. A non-limiting example of such a gene is the SHR rat CD36 gene. The ability of a test drug to alter the expression of a mutant form of CD36 can be measured by binding assays, as described above, or by Northern blot analysis, S1 nuclease analysis, primer extension, RNase protection assays or other molecular techniques, as described hereinbelow. Alternatively, if a mutant form of CD36 contains a mutation in the promoter region of the CD36 gene, cells can be engineered to express a reporter construct comprising a mutant CD36 promoter driving expression of a reporter gene, e.g. CAT, luciferase, green fluorescent protein. These cells can be grown in the presence of a test compound and the ability of a test compound to alter the level of activity of the mutant CD36 promoter can be determined by standard assays for each reporter gene which are well known in the art (see also below).

Reporter Genes

A reporter gene, when employed, is selected such that its expression may be monitored, in terms either of mRNA or protein production, and wherein protein production may be assessed either by the direct measurement of the amount of protein present or by measurement of protein activity (e.g., enzymatic activity). Reporter genes of use in the invention include, but are not limited to, the bacterial genes LacZ, which encodes the enzyme β-galactosidase, and Cat, which encodes the enzyme chloramphenicol acetyltransferase (CAT), Luc, which encodes luciferase (luc), gfp, which encodes green fluorescent protein (gfp, which fluoresces in vivo when exposed to ultraviolet light), hrp, which encodes horseradish peroxidase (hrp). the herpesvirus tk gene, which encodes the enzyme thymidine kinase (tk), and the Drosophila genes Adh, which encodes alcohol dehydrogenase (Adh) and Rosy, which encodes xanthine dehydrogenase (Xdh).

A protein product of a reporter gene may be detected indirectly, through monitoring its activity, such the activity of an enzyme in the presence of its substrate and, if necessary, an indicator compound which generates a signal upon conversion of the substrate by the enzyme. Such an indicator may be a chromogenic or fluorescent indicator which is released or otherwise activated in as a result of the catalytic activity of the reporter gene product; the indicator may be either complexed to or separate from the substrate molecule. Biochemical assays for the activity of the reporter enzymes listed above are well known in the art.

Detection of Insulin-Resistance locus-associated gene expression

As indicated above, the level or nature of the activity of a gene which is linked to one of the Insulin-Resistance loci can be measured according to any of a number of means, including observation of phenotypic indicators when a candidate modulator is assayed in vivo. Alternatively, the measurement of nucleic acid or protein levels or distribution, or protein activity either of the target gene itself or of a reporter gene functionally linked to the regulatory sequences of the target gene may be undertaken in either an in vivo or in vitro system. These numerous detection methods which may be advantageously applied in drug screening protocols according to the invention are summarized as follows:

a. Phenotypic quantitation of the effect of a candidate drug on target Insulin-Resistance locus-linked gene activity To assay the effect of a candidate drug on glucose- or fatty acid metabolism, the glucose uptake or lipolysis assays described above may be performed on cells or a test mammal (e.g. an SHR or GK rat, or other rat or mouse strain), as described above.

b. Protein or mRNA detection

Detection of RNA

Detection of an mRNA transcript may be performed by molecular techniques such as are known in the art; these techniques include, but are not limited to, nucleic acid hybridization (such as Northern analysis), affinity binding to an immobilized nucleic acid molecule having a complementary sequence (i.e., a sequence which will hybridize to the transcript through Watson-Crick base pairing under stringent hybridization conditions), reverse transcription using complementary oligonucleotide primers, and reverse-transcription polymerase chain reaction (RT-PCR).

i. Northern analysis

Molecular methods such as Northern analysis are well known in the art (see Sambrook et al., 1989, *Molecular Cloning. A Laboratory Manual.*, 2nd Edition, Cold Spring Harbor Laboratory Press, Cold Spring Harbor, N.Y.).

ii. RT-PCR

As an alternative to Northern analysis, reverse transcription/polymerase chain reaction (RT-PCR) may be performed. In the reverse transcription (T) step of RT-PCR, the RNA is converted to first strand cDNA, which is relatively stable and is a suitable template for a PCR reaction. In the second step, the cDNA template of interest is amplified using PCR. This is accomplished by repeated rounds of annealing sequence-specific primers to either strand of the template and synthesizing new strands of complementary DNA from them using a thermostable DNA polymerase.

1 $\mu$g of total RNA and 75 pmol random hexamer primer (e.g., Pd(n)6, supplied by Pharmacia; Piscataway, N.J.) are resuspended in a 10 $\mu$l volume with DEPC-treated water in an RNase-free 0.5 $\mu$l tube. This mixture is incubated at 70° C. for 10 minutes and placed on ice for two minutes. The following reagents are added to the 10 $\mu$l reaction; 1 $\mu$l (200U) MMLV-RT (Superscript® reverse transcriptase, BRL, Life Technologies, Gaithersburg, Md.), 4 µl 5× reaction buffer (BRL, Life Technologies, Gaithersburg, Md.), 2 µl 0.1M DTT, 1 µl 10 mM dNTP and 1 µl human placental RNase inhibitor (10 to 50 units per µl; Boehringer Mannheim, Indianapolis, Ind.). In addition, for each RNA sample a second reaction is prepared except that MMLV-RT is omitted (RT negative control). The 19 µreaction is incubated for 50 minutes at 42° C. in a programmable thermal cycler (such as is manufactured by MJ Research; Watertown. Mass.) and inactivated by heating to 90° C. for 5 minutes. After cooling to 37° C., 1 µl RNase H (3 units per µl;BRL, Life Technologies, Gaithersburg, Md.) is added, the reaction is incubated at 37° C. for 20 minutes, then cooled to 4° C. RNA integrity is confirmed by amplification of a transcript of a constitutively-expressed gene (e.g., actin, interleukin-2 or $G_{\alpha s}$); therefore, it is ensured that a negative result subsequently observed on a test sample can be ascribed to a lack of that specific mRNA and not to degradation of the pool of mRNA or failure of the reverse transcription reaction.

The polymerase chain reaction, or PCR, is then performed as previously described (Mullis and Faloona, 1987, *Methods Enzymol*, 155:335–350, herein incorporated by reference). PCR, which uses multiple cycles of DNA replication catalyzed by a thermostable, DNA-dependent DNA polymerase to amplify the target sequence of interest, is well known in the art.

Oligonucleotide primers useful in the invention are single-stranded DNA or RNA molecules that are hybridizable to a nucleic acid template to prime enzymatic synthesis of a second nucleic acid strand. The primer is complementary to a portion of a target molecule present in a pool of nucleic acid molecules. It is contemplated that such a molecule is prepared by synthetic methods, either chemical or enzymatic. Alternatively, such a molecule or a fragment thereof is naturally-occurring, and is isolated from its natural source or purchased from a commercial supplier. Oligonucleotide primers are 15 to 100 nucleotides in length, ideally from 20 to 40 nucleotides, although oligonucleotides of different length are of use.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, *Nucleic Acids Res.* 12:203, incorporated herein by reference. Under stringent annealing conditions, longer hybridization probes (of use, for example, in Northern analysis) or synthesis primers hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of a single factor.

Several techniques for detecting PCR products quantitatively without electrophoresis may be advantageously used with the drug-screening assay of the invention in order to make it more suitable for easy clinical use. One of these techniques, for which there are commercially available kits such as Taqmani (Perkin Elmer, Foster City, Calif.), is performed with a transcript-specific antisense probe. This probe is specific for the PCR product (e.g. a nucleic acid fragment derived from a reporter gene or an Insulin-Resistance locus-linked target gene) and is prepared with a quencher and fluorescent reporter probe complexed to the 5' end of the oligonucleotide. Different fluorescent markers can be attached to different reporters, allowing for measurement of two products in one reaction. When Taq DNA polymerase is activated, it cleaves off the fluorescent reporters by its 5'-to-3' nucleolytic activity. The reporters, now free of the quenchers, fluoresce. The color change is proportional to the amount of each specific product and is measured by fluorometer; therefore, the amount of each color can be measured and the RT-PCR product can be quantified. Detection of reporter gene transcripts may advantageously be performed in a single tube reaction for reverse transcription of RNA and specific amplification of transcripts of interest. Commercial kits such as the Access™ RT-PCR system (Promega; Madison, Wis.) conveniently assemble all materials (except primers) necessary to carry out the method in this way. The single-tube RT-PCR assay according to this technique may be used to assay serum- or other samples.

Alternatively, in situ detection of MnRNA transcripts may be performed using either 'squashed' cellular material or to sectioned tissue samples affixed to glass surfaces, prepared as described below. Either paraffin-, plastic- or frozen (Serrano et al., 1989, *Dev. Biol*, 132:410–418) sections are used in the latter case, prepared as described below. Following preparation of either squashed or sectioned tissue, the RNA molecules of the sample are reverse-transcribed in situ.

Reverse transcription is carried out using reverse transcriptase, (e.g. avian myoblastosis virus reverse transcriptase, AMV-RT; Life Technologies/Gibco-BRL or Moloney Murine Leukemia Virus reverse transcriptase, M-MLV-RT, New England Biolabs, Beverly, Mass.) under the manufacturer's recommended reaction conditions.

Following reverse transcription, reagents are pipetted off and the preparation is rinsed thoroughly with TE buffer in prior to amplification of the resulting cDNA molecules. The amplification reaction is then performed, and the amplification product detected.

Detection of protein

The invention also contemplates screening assays in which a reporter gene protein is detected. Detection of a protein may be performed either directly, such as through purification (for example, affinity purification of the protein using a receptor or ligand which will bind the protein, a dimeric pairing partner of the protein, or an antibody directed against the protein), immunological detection (e.g., on a Western blot or immunohistochemically, by in situ binding of an antibody to proteins of a fixed or frozen cell or tissue preparation) or by measurement of energy absorption (for example, spectrophotometrically or fluorimetrically) of the reporter gene expression system before and after sufficient time for protein production to have occurred.

Reporter protein detection may be accomplished, e.g., using an antibody specific for the reporter gene product (i.e., antigen). Antibodies are prepared according to conventional methods.

i. Preparation of Antibodies

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g. by fusion with an immortalizing fusion partner) to produce monoclonal antibodies.

1. Polyclonal antibodies.

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., 1992, *J. Biol. Chem.*, 267:4815–4823). The serum is titered against protein antigen by ELISA (below) or alternatively by dot or spot blotting (Boersma and Van Leeuwen, 1994, *J. Neurosci, Method*, 51:317). At the same time, the antiserum may be used in tissue sections prepared as described below. The serum is shown to react strongly with the appropriate peptides by ELISA, for example, following the procedures of Green et al., 1982, *Cell*, 28:477–487.

2. Monoclonal antibodies.

Techniques for preparing monoclonal antibodies are well known, and monoclonal antibodies may be prepared using a candidate antigen whose level is to be measured or which is to be either inactivated or affinity-purified, preferably bound to a carrier, as described by Amheiter et al., *Nature*, 294, 278–280 (1981).

Monoclonal antibodies are typically obtained from hybridoma tissue cultures or from ascites fluid obtained from animals into which the hybridoma tissue is introduced. Nevertheless, monoclonal antibodies may be described as being "raised to" or "induced by" a protein.

Monoclonal antibody-producing hybridomas (or polyclonal sera) can be screened for antibody binding to the target protein. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

ii. Immunological detection methods

Particularly preferred immunological tests rely on the use of either monoclonal or polyclonal antibodies and include enzyme-linked immunoassays (ELISA), immunoblotting and immunoprecipitation (see Voller, 1978, *Diagnostic Horizons*, 2:1–7, Microbiological Associates Quarterly Publication, Walkersville, Md.; Voller et al., 1978, *J. Clin. Pathol.*, 31:507–520; U.S. Reissue Pat. No. 31,006; UK Patent 2,019,408; Butler, 1981, *Methods Enzymol.*, 73:482–523; Maggio, E. (ed.), 1980, *Enzyme Immunoassay*, CRC Press, Boca Raton, Fla.) or radioimmunoassays (RIA) (Weintraub, B., *Principles of radioimmunoassays*, Seventh Training Course on Radioligand Assay Techniques, The Endocrine Society, March 1986, pp. 1–5, 46–49 and 68–78). For analyzing tissues for the presence or absence of a protein in the present invention, immunohistochemistry techniques may be used. Tissue samples to be assayed by these methods are prepared as described below. It will be apparent to one skilled in the art that the antibody molecule will have to be labeled to facilitate easy detection of a target protein. Techniques for labeling antibody molecules are well known to those skilled in the art (see Harlour and Lane, 1989, Antibodies, Cold Spring Harbor Laboratory, pp. 1–726).

Alternatively, other techniques can be used to detect the target proteins, including chromatographic methods such as SDS PAGE, isoelectric focusing, Western blotting, HPLC and capillary electrophoresis.

Preparation of histological samples

Tissue samples intended for use in in situ detection of DNA, RNA or protein are obtained as described above and are fixed either by freezing or the use of conventional reagents; such samples may comprise whole or squashed cells, or may instead comprise sectioned tissue. Fixatives adequate for such procedures include, but are not limited to, formalin, 4% paraformaldehyde in an isotonic buffer, formaldehyde (each of which confers a measure of RNAase resistance to the nucleic acid molecules of the sample) or a multi-component fixative, such as FAAG (85% ethanol, 4% formaldehyde, 5% acetic acid, 1% EM grade glutaraldehyde). Note that for RNA detection, water used in the preparation of an aqueous component of a solution to which the tissue is exposed until it is embedded is RNAase-free, i.e. treated with 0.1% diethylprocarbonate (DEPC) at room temperature overnight and subsequently autoclaved for 1.5 to 2 hours. Tissue is fixed at 4° C., either on a sample roller or a rocking platform, for 12 to 48 hours in order to allow fixative to reach the center of the sample.

Prior to embedding, samples are purged of fixative and dehydrated; this is accomplished through a series of two- to ten-minute washes in increasingly high concentrations of ethanol, beginning at 60%- and ending with two washes in 95%- and another two in 100% ethanol, followed two ten-minute washes in xylene. Samples are embedded in one of a variety of sectioning supports, e.g. paraffin, plastic polymers or a mixed paraffin/polymer medium (e.g. Paraplast®Plus Tissue Embedding Medium, supplied by Oxford Labware). For example, fixed, dehydrated tissue is transferred from the second xylene wash to paraffin or a paraffin/polymer resin in the liquid-phase at about 58° C., then replace three to six times over a period of approximately three hours to dilute out residual xylene, followed by overnight incubation at 58° C. under a vacuum, in order to optimize infiltration of the embedding medium in to the tissue. The next day, following several more changes of medium at 20 minute to one hour intervals, also at 58° C., the tissue sample is positioned in a sectioning mold, the mold is surrounded by ice water and the medium is allowed to harden. Sections of 6pm thickness are taken and affixed to 'subbed' slides, which are those coated with a proteinaceous substrate material, usually bovine serum albumin (BSA), to promote adhesion. Other methods of fixation and embedding are also applicable for use according to the methods of the invention; examples of these are found in Humason, G.L., 1979, *Animal Tissue Tecniques*, 4th. (W.H. Freeman & Co., San Francisco), as is frozen sectioning (Serrano et al., 1989, supra).

F. How to Diagnose a Disease According to the Invention

Disease diagnosis according to the invention comprises the detection in a biological sample from a patient a mutation in a gene linked with an Insulin Resistance Locus, particularly the CD36 gene. Mutations in this human gene and in its rat homologue, Cd36, have been found to be linked with defects in insulin-mediated glucose uptake, catecholamine-mediated lipolysis, blood triglyceride and lipoprotein levels and hypertension; several such mutations are disclosed below. These findings represent the first recognition of linkage between these variables and CD36 deficiency. Methods by which mutations in a gene of interest may be detected are described briefly as follows:

i. Preparation of a biological sample for use in the invention

Biological fluids and cell lysates according to the invention

Of use for the detection of a mutation according to the invention are body fluids which comprise cells, whether such cells are normally resident in the fluid (such as lymphocytes in blood) or are shed into the fluid from solid tissues through which the fluid passes. Fluids of use in the invention include blood, serum, plasma, mucus, lymphatic fluid, synovial fluid, cerebrospinal fluid, saliva, amniotic fluid, amniotic cord blood, urine, vaginal fluid and semen. The assay of biological fluids according to the invention is particularly advantageous, as obtaining such samples is relatively non-invasive, typically requiring at most a standard phlebotomy (drawing of blood).

Cells of a biological fluid may be assayed whole or may be lysed. Methods of preparing DNA from a cell lysate typically include disruption of the plasma membrane with a detergent such as Nonidet P-40 or the comparable reagent, Ipegal CA-630 (Cat. # I 3021, Sigma; St. Louis, Mont.), which will not dissolve the nuclear envelope, followed by centrifugation to isolate nuclei and the disruption of the nuclear envelope in a buffer containing a detergent such as Triton X-100 (e.g., Cat. # T 9284; Sigma). Alternatively, a protocol employing a hypotonic buffer as a cell-disruption agent may be employed, such as has been previously described (see Unit 12.1, "Preparation of Nuclear and Cytoplasmic Extracts from Mammalian Cells, in *Short Protocols in Molecular Tiology*, eds. Ausubel et al., 1995, John Wiley & Sons, Inc.). A cell lysate may be prepared by comparable methods from cultured mammalian cells or from cells obtained from a solid tissue of a mammal. Such tissue may be harvested from a mammal via surgical biopsy, or may be obtained by scraping or swabbing (for example, of the lining of the mouth or other body cavity). A protocol for the isolation of DNA from tissue is described below.

ii. Detecting a mutation in a biological sample from a mammal

A DNA sample may be prepared from any tissue or cell line, and preparative procedures are well-known in the art. The preparation of genomic DNA from tissue is performed as follows. Approximately 100mg of tissue is placed in 500 $\mu$l TB buffer (50 mM Tris-HCI, pH 8.0, 100 mM NaCl, 1% SDS, 600 $\mu$g/ml proteinase K) and incubated overnight at 55° C. The sample is then extracted with 500 $\mu$l 1:1 (w/w) phenol/chloroform and precipitated with two volumes ethanol. The DNA pellet is then resuspended in 500 $\mu$l H$_2$O.

cDNA samples may also be used in the detection of mutations in genes identified according to the invention. As stated above, the preparation of cDNA is well-known and well-documented in the prior art.

Tissues which are useful for obtaining a DNA sample according to the invention include but are not limited to blood cells, gametes, brain, gonad, liver, heart, kidney, adrenal, spleen, and muscle, while an RNA sample is best obtained from a tissue that expresses the gene of interest. The mRNA expression pattern of a gene may be determined by methods such as Northern analysis performed on different tissues, in situ hybridization or in vivo studies in which the expression of a marker gene driven by the regulatory region of the gene of interest is studied in transfected cells in culture or in a transgenic animal.

A probe useful according to the invention is a nucleic acid having a sequence that is unique to the gene of interest and which is preferably no longer than 30–40 nucleotides, and optimally less than 25 nucleotides, e.g., 18–22 nucleotides, with a minimum of 10 nucleotides. The preparation and labeling of nucleic acid probes, as well as methods of probe detection, are well-known and well-documented in the prior art.

Single Strand Conformation Polymorpbism (SSCP) Screening and Fluorescent SSCP Screening One approach to detecting DNA mutations in an organism is single strand conformation polymorphism (SSCP) (Glavac et al., 1993, *Hum. Mut.*, 2:404; Sheffield et al., 1993, *Genomics*, 16:325). SSCP is a simple and effective technique for the detection of single base mutations. This technique is based on the principle that single-stranded DNA molecules take on specific sequence-based secondary structures (conformers) under nondenaturing conditions. The detection of point mutations by single stranded conformation polymorphism is believed to be due to an alteration in the structure of single stranded DNA. Molecules differing by as little as a single base substitution may form different conformers and migrate differently in a nondenaturing polyacrylamide gel. Mutant single stranded DNAs are identified by an abnormal mobility on polyacrylamide gels. All types of point mutations and short insertions or deletions lying within the probe region (between the PCR primers) can be detected and with apparently equal efficiency. This technique has proven useful for detection of multiple mutations and polymorphisms. SSCP sensitivity varies dramatically with the size of the DNA fragment being analyzed. The optimal size fragment for sensitive detection by SSCP is approximately 150–300bp. Methods of preparing labeled PCR products, such as are detectable on a gel according to this procedure, are well known in the art.

SSCP analysis is performed as follows. Ten $\mu$l of formamide dye (95% formamide, 20mM EDTA, 0.05% bromophenol blue, 0.05% xylene cyanol) are added to 10 $\mu$l of radiolabeled PCR products. The reactions are denatured at 100° C. for 5 min, then placed on ice. Two $\mu$l are loaded onto 8% acrylamide:bisacrylamide (37.5:1), 0.5×TBE (45 mM Tris-borate, 1 mM EDTA), 5% glycerol gels. Electrophoresis is carried out at 25W at 4° C. for 8 hours in 0.5×TBE. Dried gels are exposed to X-OMAT AR film (Kodak) and the autoradiographs are scored for aberrant migration of bands (band shifts). SSCP may be optimized, as desired, as taught in Glavac et al., 1993, Hum Mut,2:404.

fSSCP Analysis

DNA samples may be assayed for mutations in genes mapped and identified according to the invention using fluorescent SSCP (fSSCP) assays (Malino et al., 1992, PCR Methods Appl. 2:10; Ellison et al., 1993, Biotechniques 15:684). PCR products are visualized and analyzed using an ABI fluorescent DNA sequencing machine. Different color fluorochromes (e.g., HEX, FAM, TET and JOE) can be used for different primer pairs. The advantages of FSSCP over SSCP is that the latter requires handling of radioactive materials whereas fSSCP does not. Data collection is automated, and data analysis programs can be used to flag aberrant migrating samples, whereas SSCP evaluation involves visual examination, and correction for lane to lane variations in electrophoretic conditions is not possible; useful data collection and analysis software include, but are not limited to, the Genescan and Genotype programs (ABI).

The SSCP procedure identifies regions of 150–300 base pairs containing a mutation. To specifically identify the sequence change, the fragment which shows the aberrant migration is amplified again from the mutation-bearing mammalian DNA using non fluorescent primers and the sequence determined using standard DNA sequencing technology Denaturing Gradient Gel Electrophoresis Denaturing gradient gel electrophoresis (DGGE) is a gel system which allows electrophoretic separation of DNA fragments differing in sequence by as little as 1 base pair. The separation is based upon differences in the temperature of strand dissociation of the wild-type and mutant molecules. As the fragments migrate down the gel, they are exposed to an increasing concentration of denaturant in the gel. When the molecules reach a critical denaturant level, the DNA strands begin to dissociate. This causes a significant reduction in the fragment's mobility. The position of this critical point is a function of the $T_m$, the point at which mobility retardation for wild-type and mutant molecules will be different, thus resulting in their separation. Fragment sizes are limited to between 100 and 800 bp due to the resolution limit of polyacrylamide gels. For a method of efficient transfer of genomic DNA fragments from the gel following DGGE, see U.S. Pat. No. 5,190,856.

Chemical Cleavage of Mismatches

The detection of mutations by chemical cleavage of mismatch (CCM) is another mutation scanning techniques useful in identifying a mutation in a gene which is linked to an Insulin-Resistance locus. It relies upon the chemicals hydroxylamine and osmium tetroxide to react with the mismatch in a DNA heteroduplex. Subsequent treatment with piperidine cleaves the heteroduplex at the point of mismatch. Mutations are detected as fragments smaller than the untreated heteroduplex on denaturing polyacrylamide gels. The probable 100% detection rate, coupled with the ability to scan DNA fragments up to 1kb in size, make CCM seem an ideal mutation detection method. CCM is particularly useful where it is desired that all mutations in a fragment of DNA are detected or where it is desired to detect a mutation-free piece of DNA.

Constant Denaturant Capillary Electrophoresis (CDCE) Analysis

CDCE analysis is particularly useful in high throughput screening, i.e., wherein large numbers of DNA samples are analyzed (for example, in attempting to process samples from members of a family whose pedigree reveals linkage of defects in insulin- or fatty acid metabolism to a gene or chromosomal region with an Insulin-Resistance locus). The method is described in detail by Khrapko et al., (1994, Nucleic Acids Res., 22[3]:364), and involves the use of a zone of constant temperature and a denaturant concentration in capillary electrophoresis. The relative limit of detection is about 3/10,000, i.e., 100,000 mutant sequences are recognized among $3 \times 10^8$ wild type sequences.

RNase Cleavage

Various ribonuclease enzymes, including RNase A, RNase T1 and RNase T2 specifically digest single stranded RNA. When RNA is annealed to form double stranded RNA or an RNA/DNA duplex, it can no longer be digested with these enzymes. However, when a mismatch is present in the double stranded molecule, cleavage at the point of mismatch may occur.

Ribonuclease A specifically digests single-stranded RNA. The enzyme can also cleave heteroduplex molecules at the point of mismatch. The technique is based upon forming a heteroduplex between a radiolabeled single stranded RNA probe (riboprobe) and a PCR product derived from a mutant mammal. The resulting heteroduplex is an RNA/DNA hybrid duplex. When treated with RNase A, if a point mutation is present, the RNA strand of the duplex may be cleaved. The sample is then heated to denature and run on a denaturing polyacrylamide gel. If a the RNA probe has been cleaved, its size will be smaller than the PCR product. Deletions as small as 1bp are easily detectable.

Heteroduplex Analysis

Heteroduplex molecules, i.e., double-stranded DNA molecules containing a mismatch, can be separated from homoduplex molecules on ordinary gels. Mismatches in the middle of DNA fragments are detected most easily. Although heteroduplex analysis lacks sensitivity, it may be considered useful according to the invention due to its simplicity.

Mismatch Repair Detection (MRD)

MRD is an in vivo method that utilizes a change in bacterial colony color to detect DNA sequence variation. DNA fragments to be screened for variation are cloned into two MRD plasmids, and bacteria are transformed with heteroduplexes of these constructs. The resulting colonies are blue in the absence of a mismatch and white in the presence of a mismatch. MRD is capable of detecting a single mismatch in a DNA fragment as large as 10 kb in size. MRD permits high-throughput screening of genetic mutations, and has been described in detail (Faham et al., 1995, Genome Res, 5:474), and is useful in a procedure such as pedigree analysis.

Mismatch Recognition by DNA Repair Enzymes

DNA repair is another system which has the potential for exploitation in mutation detection. The *E. coli* mismatch correction systems are well-understood. Three of the proteins required for the methyl-directed DNA repair pathway:MutS, MutL and MutH are sufficient to recognize 7 of the possible 8 single base-pair mismatches (not C/C mismatches) and cut/nick the DNA at the nearest GATC sequence. The MutY protein, which is involved in a different repair system, can also be used to detect A/G and A/C mismatches. Some mammalian enzymes are also useful:thymidine glycosylase can recognize all types of T mismatch and 'all-type endonuclease' or Topoisomerase I is capable of detecting all 8 mismatches, but does so with varying efficiencies, depending on both the type of mismatch and the neighboring sequence. The MutS gene product is the methyl-directed repair protein which binds to a mismatch one or more base pairs in length. Gel mobility assays can be performed in which DNA bound to the MutS protein migrates more slowly through an acrylamide gel than free DNA.

An alternative version of MutS mismatch recognition, which does not require gel electrophoresis, involves the immobilization of MutS protein on nitrocellulose membranes. Labeled heteroduplexed DNA is used to probe the membrane in a dot-blot format. When both DNA strands are used, all mismatches can be recognized by binding of the DNA to the protein attached to the membrane.

Sequencing by Hybridization

In Sequencing by Hybridization (SBH, also called Sequencing-by-Hybridization-to-an-Oligonucleotide-Matrix, or SHOM; Dnnanac et al., 1993, Science, 260(5114):1649–52; Khrapko, et al. 1991, supra; Mugasimangalam et al., 1997, Nucleic Acids Res., 25:800–805), arrays of short (8–10 base long) oligonucleotides are immobilized on a solid support in a manner similar to the reverse dot-blot and probed with a target DNA fragment. The system is based on advanced chemistry in which the oligonucleotides are synthesized together directly on the support. Thirty-two cycles of specific additions (i.e., 8 additions of each of the four nucleotides) should enable the production of all 65,536 possible 8-mer oh gonucleotides at defined positions on the chip. When the chip is probed with a DNA molecule, e.g., a fluorescently-labeled PCR product, fully matched hybrids should give a high intensity of fluorescence and hybrids with one or more mismatches should give substantially less intense fluorescence. The combination of the position and intensity of the signals on the chip enables computers to derive the sequence.

Allele-Specific Oligonucleotide Hybridization

Under specific hybridization conditions, an oligonucleotide will only bind to a PCR product if the two are fully matched. A single base pair mismatch is sufficient to prevent hybridization. The use of a pair of oligonucleotides, one carrying the mutant base and the other carrying the wild type base can be used to determine a PCR product as being homozygous wild type, heterozygous wild type mutant or homozygous mutant for a particular known mutation. This is termed allele-specific oligonucleotide (ASO) hybridization or a 'dot-blot'. In conventional dot blots, the PCR product is fixed onto a nylon membrane and probed with a labeled oligonucleotide. In the 'reverse dot blot', an oligonucleotide is fixed to a membrane and probed with a labeled PCR product. The probe may be isotopically labeled or non-isotopically labeled. In addition, a number of PCR-amplified samples may be typed for a single known mutation.

Allele-Specific PCR

In the allele-specific polymerase chain reaction (also called the amplification refractory mutation system or ARMS) the detection assay occurs within the PCR reaction itself. Sequence-specific PCR primers which differ from each other at their terminal 3' nucleotide are used to amplify only the normal allele in one reaction, and only the mutant allele in another reaction. This is especially useful when a specific mutation has been discovered to be linked to disease or the risk thereof according to the invention, and an individual is being tested for the presence or absence of that particular mutation. When the 3' end of a specific primer is fully matched, amplification occurs. When the 3' end of a specific primer is mismatched, amplification fails to occur. Amplification is scored by agarose gel electrophoresis analysis of several known mutations. The genotype of a (homozygous) wild-type sample is characterized by amplification products in both reactions, and a homozygous mutant sample generates product in only the mutant reaction. In a variation of this assay, the 5' ends of the allele-specific primers are labeled with different fluorescent labels, and the 5' end of the common primers are biotin labeled. The wild-type specific and the mutant-specific reactions then may be performed in a single tube. The advantages of this approach is that gel electrophoresis is not required and the method is amenable to automation.

Primer-Introduced Restriction Analysis

Primer-introduced restriction analysis (PIRA) is a technique which allows known mutations to be diagnosed by restriction digestion. By introducing a base change close to the position of a known mutation by a mismatch in the PCR primer, it is possible to create a restriction endonuclease recognition site that is diagnostic for the mutation. The combination of the altered base in the primer sequence and the altered base at the mutation site, has the effect of creating a new restriction target site. The approach may be used to create a new target site on either the wild-type allele or the mutant allele. In such a situation, the homozygous wild-type form would be characterized by a single band of the full-length size. The homozygous mutant form is characterized by a single band of the reduced size and the heterozygous form by bands of both sizes. The different size wild-type vs. mutant PCR fragments following restriction digestion, are analyzed by gel electrophoresis.

Oligo-nucleotide Ligation Assay

When two oligonucleotides, annealed to a strand of DNA are exactly juxtaposed, they can be joined by the enzyme DNA ligase. A single base pair mismatch at the junction of the two oligonucleotides is sufficient to prevent ligation. Rather than assaying ligation by gel electrophoresis and visualization of a new larger sized DNA fragment, ligation is scored by assaying for labels on the two oligonucleotides becoming present on a single molecule. When ligation is scored by ELISA and reactions are conducted in 96-well microtiter plates, the oligonucleotide ligation assay can be performed by robot and the results analyzed by plate reader and fed directly into a computer. The method is therefore excellent for scoring of a known mutation in a large number of samples. The assay comes in two main forms:the oligo-nucleotide ligation assay, which is performed on PCR-amplified DNA, and the ligase chain reaction, which is performed on genornic DNA and amplified with a thermostable DNA ligase.

Direct DNA Sequencing

Mutation detection according to the invention also may be carried out by directly sequencing the mutant DNA sample in the region of the gene identified according to the invention, using DNA sequencing procedures well-known in the art.

Mini-Sequencing

The technique of mini-sequencing (also known as single nucleotide primer extension) can be used to diagnose any known point mutation, deletion or insertion. Obtaining sequence information at just a single base pair only requires the sequencing of that particular base. This can be done by including only one base in the sequencing reaction rather than all four. When this base is labeled and complementary to the first base immediately 3' to the primer (on the target strand), the label will not be incorporated. Thus, a given base pair can be sequenced on the basis of label incorporation or failure of incorporation without the need for electrophoreticsize separation.

5' Nuclease Assay

The 5' nuclease assay is a technique that monitors the extent of amplification in a PCR reaction on the basis of the degree of fluorescence of the reaction mix. Low fluorescence indicates no or very poor amplification and high fluorescence indicates good amplification. This system can be adapted for identification of known mutations in a gene found to be linked with one of the Insulin-Resistance loci, without the need for any post-PCR analysis other than fluorescence emission analysis. The 5' to 3' exonuclease activity of Taq polymerase is utilized to assay for PCR amplification. The enzyme cleaves 5' terminal nucleotides of double stranded DNA. Its preferred substrate is a partially double-stranded molecule, cleaving the strand with the closest free 5' end. In the 5' nuclease assay, an oligonucleotide 'probe' which is phosphorylated at its 3' end so that it cannot act as a DNA synthesis primer is included in the PCR reaction. The probe is designed to anneal to a position between the two amplification primers. When an actively extending Taq polymerase molecule reaches the probe molecule, it partially displaces it and then cleaves the probe at or near the single stranded/double stranded cleavage until the entire probe is broken up and removed from the template. The polymerase continues this process of displacement and cleavage until the entire probe is broken up and removed from the template. The labeling system monitors removal of the probe.

Restriction Fragment Length Polymorhism (RFLP):

Differences in the restriction maps between wild-type DNA sequences and DNA sequences containing mutations can be used to characterize mutant DNA sequences. Wild-type DNA sequences are isolated and subjected to cleavage by restriction enzymes which are known to provide restriction fragments which differentiate between the wild-type and mutant DNA sequences. Restriction patterns are then identified. Restriction enzymes are used that provide a characteristic pattern of restriction fragments, so that a restriction site is either missing or an additional restriction site is introduced into the mutant DNA sequence.

Polymerase Chain Reaction-Restriction Fragment Length Polymorphism (PCR-RFLP)

In the PCR-RFLP method of mutation analysis base pair changes, deletions and insertions are detected which are located in a restriction enzyme recognition sequence and render the site resistant to cleavage by the corresponding restriction endonuclease. The resistant DNA sequence containing the mutated site is amplified by PCR after wild-type DNA has been eliminated by restriction digestion. Amplified DNA is directly sequenced or cloned and mutants are identified. Felley-Bosco, E. et al., Nucleic Acids Res. 1991, 19: 2913–2919; Pourzand C, Cerutti P, Mutat Res 1993 Jul; 288(1):113–21.

G. Mapping and Characterization of the Rat Cd36/ FAT Gene and Mutations Associated with the Insulin-Resistance Phenotype Once a map position has been established for a gene according to the invention, it is possible to clone the gene of interest underlying the observed phenotype. The identification of such a gene may follow the conventional route of fine genetic mapping in further experimental crosses, followed by physical isolation and mapping of the chromosomal segment upon which the gene resides and, subsequently, recovery of the gene itself. Gene cloning may be performed as describe below.

We have pursued investigation of insulin and catecholamine action in the spontaneously hypertensive rat or SHR. We have found that the rat Cd36 gene (the chromosomal locus previously defined as insulin-resistance locus 1, on rat chromosome 4, also known as the rat FAT gene (rat Cd36 gene). GenBank accession number L19658. All nucleotide positions indicated below refer to this GenBank accession number, Li9658. Nucleic acid sequence encompassing the entire coding region and a portion of the 3' untranslated region of the Cd36 gene from the SHR rat has been submitted to Genbank under accession number AF1 1 1268; this submission is confidential until Jan. 1, 1999, as of which date the sequence is publicly available.

A search for differentially expressed genes in the adipose tissue of SHR and control strains (Scios Inc.) permitted screening of tissue samples to monitor expression levels of thousands of genes simultaneously and to compare the level of expression of these genes in two or more tissue samples.

Comparison of gene expression in SHR and two control strains revealed a 5–10 fold reduced Cd36 hybridization signal on a microarray in SHR. This indicates aberrant expression of the Cd36 gene in SHR.

The invention is based in part upon the discovery that:
1. The Cd36 gene maps to insulin-resistance locus 1 on rat chromosome 4;
2. The Cd36 gene in SHR contains at least 18 changes in cDNA sequence that result in 11 changes in the predicted amino acid sequence of the SHR Cd36 protein. These sequence differences are detailed below as sequence variant numbers, where each sequence variant number refers to the sequence changes that occur in a given triplet codon. (Sequence variant number 4 contains two altered nucleotides; these are given together as they occur in the same triplet codon).
3. Cd36 mRNA in the SHR rat comprises molecules which exhibit length polymorphisms relative to the length of a wild-type Cd36 transcript.

Thus, the invention contemplates that alteration of the sequence of the Cd36 gene and/or level of expression and/or length of the Cd36 gene product gives rise to some or all of the phenotypic characteristics in the SHR strain that have been linked to the insulin-resistance locus on rat chromosome 4, namely defective insulin-mediated glucose uptake in adipose tissue, (Aitman et al., 1997; *Nature Genetics*, 16:197–201); defective isoproterenol-mediated control of lipolysis or fat breakdown (Aitman et al., 1997, supra); hypertension (Pravenec et al., 1995, *J. Clin. Ivest.*, 96:1973–1978); and dyslipidaemia (Bottger et al., 1996, *J. Clin. Invest.*, 98:856–862; Kovacs and Kloting, 1998, *Arch. Biochem Biophys*, 354:139–143).

The invention also contemplates use of the rat and corresponding human CD36 mutant sequences for related human conditions, including type 2 diabetes mellitus and the dyslipidaemia of type 2 diabetes mellitus, essential hypertension, combined hyperlipdemia (including, but not limited to, familial combined hyperlipdemia) and predisposition to coronary heart disease, some of which could in part be caused by mutations in the human CD36 gene.

The finding that defective regulation or structure or function of rat Cd36 may cause insulin and catecholamine resistance and hypertension and dyslipidaemia in the rat may be of use in prevention, detection and treatment of human diseases characterized by these abnormalities. The human CD36 gene and mutants thereof also are contemplated for diagnostic tests of these human disorders and drug development aimed at treating them.

Listed below are the sequence alterations disclosed herein in the SHR Cd36 cDNA sequence. For each numbered sequence variant, the first listed sequence is that of Wistar Kyoto (WKY, the first control strain); the second is that of Brown Norway (BN, the second control strain) and the third is that of SHR.

Each numbered sequence variant represents the nucleotide changes in a single codon. Bold type represents nucleotide differences in SHR compared to both WKY and BN. Amino acid changes are listed using standard single letter amino acid symbols. The peptide sequences encoded by the following WKY, BN and SHR variant nucleic acid sequences are presented in FIG. 9.

Sequence variant number 1
[SEQ ID NO: 1]
362 tatttagcc aaggaaaata taactcagga 390

[SEQ ID NO: 3]
362 tatttagcc aaggaaaata taactcagga 390

[SEQ ID NO: 5]
362 tatttagcc aaggaaagta taactcagga 390
Amino acid change: N → S
Sequence variant number 2
[SEQ ID NO: 7]
381 taactcagga ccccaaggac agcactgtct 410

[SEQ ID NO: 9]
381 taactcagga ccccaaggac agcactgtct 410

[SEQ ID NO: 11]
381 taactcagga ccccaaagac agcactgtct 410
Silent polymorphism: K → K
Sequence variant number 3
[SEQ ID NO: 13]
491 ctggctgtgg cagctgcacc acatatctac 520

[SEQ ID NO: 15]
491 ctggctgtgg cagctgcacc acatatctac 520

[SEQ ID NO: 17]
491 ctggctgtgg cagctgtacc acatatctac 520
Amino acid change: A → V
Sequence variant number 4
[SEQ ID NO: 19]
511 acatatctac acaaactcat ttgttcaagg 540

[SEQ ID NO: 21]
511 acatatctac acaaactcat ttgttcaagg 540

[SEQ ID NO: 23]
511 acatatctac caaaactcat tttttcaagg 540
Amino acid change: T → Q
Sequence variant number 5
[SEQ ID NO: 25]
521 acaaactcat ttgttcaagg tgtgctcaac 550

[SEQ ID NO: 27]
521 acaaactcat ttgttcaagg tgtgctcaac 550

[SEQ ID NO: 29]
521 caaaactcat tttttcaagg tgtgctcaac 550
Amino acid change: V → F
Sequence variant number 6
[SEQ ID NO: 31]
541 tgtgctcaac agccttatca aaaagtccaa 570

[SEQ ID NO: 33]
541 tgtgctcaac agccttatca aaaagtccaa 570

[SEQ ID NO: 35]
541 tgtgctcaac atatttatca aaaagtccaa 570
Amino acid change: S → I
Sequence variant number 7
[SEQ ID NO: 37]

-continued 541 tgtgctcaac agccttatca aaaagtccaa 570

[SEQ ID NO: 39]
541 tgtgctcaac agccttatca aaaagtccaa 570

[SEQ ID NO: 41]
541 tgtgctcaac atatttatca aaaagtccaa 570
Amino acid change: L → F
Sequence variant number 8
[SEQ ID NO: 43]
581 ttccaaacac gaagtttgaa ggaactcttg 610

[SEQ ID NO: 45]
581 ttccaaacac gaagtttgaa ggaactcttg 610

[SEQ ID NO: 47]
581 ttccaaacac gaagtttgaa agaactcttg 610
Silent polymorphism: K → K
Sequence variant number 9
[SEQ ID NO: 49]
601 ggaactcttg tggggttaca aagatccatt 630

[SEQ ID NO: 51]
601 ggaactcttg tggggttaca aagatccatt 630

[SEQ ID NO: 53]
601 agaactcttg tggggttatg aagatccatt 630
Silent polymorphism: Y → Y
Sequence variant number 10
[SEQ ID NO: 55]
601 ggaactcttg tggggttaca aagatccatt 630

[SEQ ID NO: 57]
601 ggaactcttg tggggttaca aagatccatt 630

[SEQ ID NO: 59]
601 agaactcttg tggggttatg aagatccatt 630
Amino acid change: K → E
Sequence variant number 11
[SEQ ID NO: 61]
631 cttgagtttg gttccatatc ctataagtac 660

[SEQ ID NO: 63]
631 cttgagtttg gttccatatc ctataagtac 660

[SEQ ID NO: 65]
631 cttgagtttg attccatatc ctataagtac 660
Amino acid change: V → I
Sequence variant number 12
[SEQ ID NO: 67]
721 tggaaaggat aacataagca aggttgccat 750

[SEQ ID NO: 69]
721 tggaaaggat aacataagca aggttgccat 750

[SEQ ID NO: 71]
721 tggaaaggat aacataagca aagttgccat 750
Silent polymorphism: K -> K
Sequence variant number 13
[SEQ ID NO: 73]
781 gtcctattgg gaaagttatt gcgacatgat 810

[SEQ ID NO: 74]
781 gtcctattgg gaaagttatt gcgacatgat 810

[SEQ ID NO: 77]
781 gtcctattgg aaaagttatt gcgacatgat 810

-continued

Amino acid change: E → K

Sequence variant number 14

[SEQ ID NO: 79]
851 aaatctcaaa cactgaggtt cttttcctct 880

[SEQ ID NO: 81]
851 aagtctcgaa cactgaggtt cttttcctct 880

[SEQ ID NO: 83]
851 aagtctcaaa cactgaggtt tttttcctct 880

Silent polymorphism: F → F

Sequence variant number 15

[SEQ ID NO: 164]
1261 tagaaaaata gaagcactga agaatctgaa 1290 [SEQ

[SEQ ID NO: 165]
1261 tagaaaaata gaagcactga agaatctgaa 1290

[SEQ ID NO: 167]
1261 tagaaaaata gaaccactga agaatctgaa 1290

Amino acid change: A → P

The amino acid sequence encoded by [SEQ ID NO:164] and [SEQ ID NO:165] is presented in [SEQ ID NO:166], while the SHR variant 15 amino acid sequence is presented in [SEQ ID NO:168].

Sequence variant number 16

[SEQ ID NO: 169]
1321 aaatgagact gggaccatcg gcgatgagaa 1350

[SEQ ID NO: 170]
1321 aaatgagact gggaccatcg gcgatgagaa 1350

[SEQ ID NO: 171]
1321 aaatgagact gggaccattg gcgatgagaa 1350

Silent polymorphism: I -> I

Sequence variant number 17

[SEQ ID NO: 172]
1441 tgttgctttt atgatttcat actgtgcttg 1470

[SEQ ID NO: 173]
1441 tgttgctttt atgatttcat actgtgcttg 1470

[SEQ ID NO: 174]
1441 tgttgctttc atgatttcat actgtgcttg 1470

Silent polymorphism: F → F

Sequence variant number 18

[SEQ ID NO: 175]
1461 actgtgcttg cagatctaag aatggaaaat 1490

[SEQ ID NO: 176]
1461 actgtgcttg cagatctaag aatggaaaat 1490

[SEQ ID NO: 138]
1461 actgtgcttg cagatttaag aatggaaaat 1490

Amino acid change: S → F

The amino acid sequence encoded by [SEQ ID NO:175] and [SEQ ID NO:176] is presented in [SEQ ID NO:177], while the SHR variant 18 amino acid sequence is presented in [SEQ ID NO:141].

The predicted amino acid sequences for the above-described nucleic acid sequences are contained in the sequence ID listing, and are numbered accordingly after each nucleotide sequence number (that is, using even numbers 2, 4, 6, 8, etc.). The complete wild type rat Cd36 sequence (Genbank accession number L19658) is presented in [SEQ ID NO:85] (FIG. 11). The predicted polypeptide sequence is presented in [SEQ ID NO:86] (FIG. 12). The complete rat Cd36 coding sequence and partial untranslated sequence for rat strain SHR disclosed herein is presented in [SEQ ID NO:87] (FIG. 13). The predicted polypeptide sequence is presented in [SEQ ID NO:88] (FIG. 14). The partial rat Cd36 sequence rat strain Wistar Kyoto disclosed herein is presented in [SEQ ID NO:89] (FIG. 15). The predicted polypeptide sequence is presented in [SEQ ID NO:90] (FIG. 16). The partial rat Cd36 sequence for rat strain BN is presented in [SEQ ID NO:91] (FIG. 17). The predicted polypeptide sequence is presented in [SEQ ID NO:92] (FIG. 18).

In addition to these sequence alterations, we have detected evidence for length polymorphisms the Cd36 mRNA in SHR. The large number of sequence variants in two such closely related strains as SHR and VKY, together with an unexpected 77 base pair HinfI restriction fragment in WKY and BN genomic DNA (FIG. 3), suggested the possibility of a genomic duplication of Cd36 in WKY and BN, and of a deletion in SHR.

To pursue this, direct sequencing of the genomic fragment amplified by the Hin3F/3R primers that flank the HinfI RFLP (a HinfI cleavage site present at nucleotides 640–645 of the SHR Cd36 gene, but absent in WKY cDNA) was carried out. The primer sequences were as follows:

Hin3F: 5'- ACAKMYTTATCAAAGAGTCCAAGTCT-TCTATGTTC -3' [SEQ ID NO:130], and

Hin3R: 5'- ACCAACTGTGGTACTTATCG -3' [SEQ ID NO:131].

These primers amplify across this RFLP, giving a 122 bp product. Primer Hin3F is degenerate containing K(G/T), M (A/C) and Y (C/T) to account for differences between the SHR and WKY DNA sequences. Primer Hin3F contains an engineered HinfI site, shown in bold, to indicate complete digestion. PCR products were digested to completion with HinfI and resolved on a 4% Nusieve/agarose gel. This showed that there are two copies of the Hin3F/3R fragment in WKY and BN genomic DNA, manifested by apparent heterozygosity in the WKY and BN genomic sequences. The second copy of the Hin3F/3R fragment in WKY and BN genomic DNA corresponds exactly to the sequence obtained from SHR DNA, but is not transcribed in WKY or BN, as it is undetectable in adipose tissue DNA from these strains. The presence of only a single Hin3F/3R sequence in SHR genomic DNA suggests that one of the two genomic copies from WKY has been deleted from SHR genomic DNA.

To confirm this result, Southern analysis was performed on genomic DNA from SHR, WKY and BN rats. Probes from the region of the putative exon 6, and from the WKY 3' UTR, detected single restriction fragments in SHR genomic DNA digested with Hinfi, EcoRI and PstI. WKY and BN contained restriction fragments that were identical- or nearly identical in size to those seen in SHR, but additional bands indicated the presence of at least one further copy of the gene in both WKY and BN.

To test for duplication at the 5' end of the gene, direct sequence analysis was carried out. This again showed apparent heterozygosity in WKY and BN genomic DNA at nucleotides 46, 82, 87, and 113 (of Genbank sequence L19658; [SEQ ID NO:85]), but only a single sequence in SHR genomic DNA. The SHR genomic sequence was identical to the cDNA sequence of all three strains. This indicates that the 5' end of the gene is transcribed from the same transcription unit in SHR, WKY and BN. Transcription of exon 6 in SHR from the normally untranscribed copy of the gene suggests that a deletion event has occurred in SHR, creating a single chimeric transcription unit in this strain. Since the majority of this chimeric gene derives from the second, normally untranscribed copy of the Cd36 gene, this accounts for the multiple DNA sequence variants and divergent 3' tail seen in SHR.

According to the invention, the presence of mRNA size variants in a biological sample from subject under diagnostic evaluation may be used as an indicator of the insulin-resistant phenotype in the rat or human.

Functional analys is of Cd36 in SHR rats

To determine whether the SHR transcript results in production of a functional, mature protein, we performed Western blot analysis of SHR microsomal pellets, that were prepared to include the plasma membrane fraction in which the Cd36 protein normally resides. Plasma membrane from WKY and BN adipose tissue contained substantial quantities of Cd36, whereas no Cd36 protein was detectable in SHR (FIG. 4). A similar result was observed in heart microsomes, although the level of expression was lower in controls. Assuming that the SHR transcript is translated, the data indicated failure of normal Cd36 processing in SHR, resulting in functional deficiency of Cd36, at least in fat and heart, in the SHR strain.

Fatty acid and lipoprotein phenotypes in a Cd36 transgenic mouse

To investigate the effects of Cd36 on lipid metabolism in the intact organism, blood triglycerides and non-esterified fatty acids (NEFA) were examined in a transgenic mouse that overexpresses Cd36 in heart and skeletal muscle. A minigene, referred to as MCK-CD36 minigene, with 1.7kb DNA fragment containing 1.3 kb of Cd36 coding sequence and polyadenylation signal under the control of the mouse creatine kinase gene(3.3 kb), was constructed, as described previously (Levak-Frank et al., 1995, *J. Clin, Invest.*, 96:976–986), and injected into the male pronucleus of fertilized eggs from superovulated FVB female mice. Eggs were transferred into oviducts of surrogate FVB females. Transgenic mice were identified by screening of genomic DNA isolated from tail biopsy, with radiolabeled Cd36 DNA (1.3 kb fragment). Northern and Western blotting, performed by standard methods, confirmed overexpression of Cd36 in heart and skeletal muscle tissues from transgenic mice. Blood was collected from the tail vein, and triglycerides and NEFA measured on freshly drawn blood from animals fasted overnight, using kits available from Sigma and Wako, respectively.

Table 1 shows blood triglycerides and non-esterified fatty acids (NEFA) in transgenic MCK-Cd36 mice and in control mice (age and sex-matched) from the same genetic (FVB) background. Transgenic mice showed marked reduction in blood triglycerides and NEFA establishing a critical physiological role for Cd36 in whole body lipid homeostasis.

The ability to a Cd36 transgene to influence lipid metabolism in a subject mammal illustrates the usefulness of animal models in the testing of therapeutic agents (in this case, the Cd36 gene and/or its expressed protein product) according to the invention, as well as the operability of treating disease in a subject mammal using a gene or protein linked to an Insulin Resistance Locus.

H. Human CD36 Polymorphisms Associated with the Insulin Resistant Phenotype

Sequence analysis was performed on the CD36 genes of twelve individuals with coronary heart disease. Sequence variants which were observed are presented below. For each number sequence variant, the first listed sequence is that of a published sequence; the second is from the sequence analysis disclosed herein. Bold type represents nucleotide differences in individuals whose DNA was sequenced in these experiments compared to the published sequence. For sequence variant numbers 1 and 2, the base positions refer to the sequence published by Armesilla and Vega (1994, *J. Biol. Chem.*, 264:18385–18991). The base positions for sequence variant number 3 refer to Genbank Accession number Z32753, while those for sequence variant number 4 refer to Genbank Accession number Z32764. Sequence variants numbered 1 and 2 are in the promoter region, sequence variant 3 is in the 5' untranslated region and sequence variant number 4 is in the 3' untranslated region. The remaining variants are positioned as indicated below. None encodes a change in CD36 amino acid sequence.

```
Sequence variant number 1
                                            [SEQ ID NO: 132]
-73 gctttctctt ctctttttttt ggggggggga -44

[SEQ ID NO: 133]
-73 gctttctctt ctc-tttttt ggggggggga -44

Sequence variant number 2
                                            [SEQ ID NO: 134]
-73 gctttctctt ctctttttttt ggggggggga -44

[SEQ ID NO: 135]
-73 gctttctctt ctctttttttt tggggggga -44

Sequence variant number 3
                                            [SEQ ID NO: 136]
 65 ctgtgactca tcagttcctt tcctgtaaaa 94

[SEQ ID NO: 137]
 65 ctgtgactca tcagttcatt tcctgtaaaa 94

Sequence variant number 4
                                            [SEQ ID NO: 139]
421 attgtaacaa tagcacaaat aaagcacttg tgccaaagtt 460

[SEQ ID NO: 140]
421 attgtaacaa ta-------- --------tg tgccaaagtt 460
```

Hyphens/solid lines represent deletions in the sequence.

A silent nucleic acid substitution was observed in coding sequence in exon 10, relative to a published human cDNA sequence (Annesilla et al., 1994, *J. Biol. Chem.*, 269:18985–18991; Genbank accession no. Z32760). The published sequence is shown above the sequence variant disclosed herein. Sequences are numbered according to Anmesilla et al. (1994, supra).

```
                                            [SEQ ID NO: 142]
1149 gaatccctgt gtatagattt gttcttccat 1178
```

```
                                                     [SEQ ID NO: 143]
1149 gaatccctgt gtatagattc gttcttccat 1178
```

An additional sequence variant relative to the sequence of Armesilla et al. (1994, supra), was discovered in non-coding sequence and is shown below, again below the published sequence (exon 2, 5' untranslated cDNA sequence; Genbank accession no. Z32753).

```
                                                     [SEQ ID NO: 144]
141 ctgtgactca tcagttcctt tcctgtaaaa 170

[SEQ ID NO: 145]
141 ctgtgactca tcagttcatt tcctgtaaaa 170
```

Two sequence variants were identified in intron 2 (downstream sequence of exon 2), by sequencing between exons 2 and 3. The first is more commonly observed than is the second, which is relatively rare.

```
                                                     [SEQ ID NO: 146]
5' tgatacgttt cagtgggtgt tttctttgta 3'
```

```
                                                     [SEQ ID NO: 147]
5' tgatacgttt cagtggatgt tttctttgta 3'
```

The variant nucleotide in the above sequences is 73 base pairs downstream of the intron2/exon 3 boundary.

A final site at which sequence variants were discovered in human CD36, located in intron 12, was obtained by sequencing between exons 12 and 13. Two sequences were obtained. The first is the common sequence, while the second is the rare sequence.

```
                                                     [SEQ ID NO: 148]
5' ggttattttg atatgatctg tagtatcgta 3'

[SEQ ID NO: 149]
5' ggttattttg atatgatcta tagtatcgta 3'
```

The variant nucleotide in these sequences is 37 base pairs upstream of the exon12/intron12 boundary.

Five additional mutations were found in five Afro-Caribbeans and one African American with phenotypic CD36 deficiency. A sixth mutation was found in an Afro-Caribbean with diabetes. Of these mutations, four are discrete nonsense or frame-shift mutations that prevent translation of functional CD36 protein. One of these mutations ([SEQ ID NO:179]) is a single nucleotide deletion at nucleotide 1145 in exon 10 of a cDNA sequence reported in Armisilla et al. (Genbank Z32760, [SEQ ID NO:178]). This point deletion causes a shift in the reading frame and abolishes the ability of a CD36 allele containing this mutation to encode a functional CD36 protein.

```
                                                     [SEQ ID NO: 178]
1127 gaatccgacg ttaatctgaa aggaatccct 1156

[SEQ ID NO: 179]
1127 gaatccgacg ttaatct-aa aggaatccct 1156
```

SEQ ID NOs:190, 191 and 192 comprise nucleotides containing the same point mutation. However, these sequences are 8, 12, and 16 nucleotides in length. The point mutation is in the center of each of these nucleotides. The point mutation, however, may occur at any position within an 8, 12, or 16 nucleotide sequence. For example, the mutation may occur at each of positions 1 through 8 in a sequence of 8 nucleotides.

```
1127 gaatccgacg ttaatctgaa aggaatccct 1156    [SEQ ID NO: 178]
                atct-aa ag                    [SEQ ID NO: 190]

1127 gaatccgacg ttaatctgaa aggaatccct 1156    [SEQ ID NO: 178]
               taatct-aa agga                 [SEQ ID NO: 191]

1127 gaatccgacg ttaatctgaa aggaatccct 1156    [SEQ ID NO: 178]
              g ttaatct-aa aggaat             [SEQ ID NO: 192]
```

In the second of these mutations ([SEQ ID NO:181]), nucleotide 1264 in exon 10 of the same CD36 gene (Genbank Z32760, [SEQ ID NO:180]) is mutated from T to G. This mutation was found in homozygous form in three of the five Afro-Caribbean subjects with phenotypic CD36 deficiency; it was found in heterozygous form in the remaining two subjects.

```
                                                     [SEQ ID NO: 180]
1247 aaaaattgta catcatatgg tgtgctagac 1276

[SEQ ID NO: 181]
1247 aaaaattgta catcataggg tgtgctagac 1276
```

SEQ ID NOs:193, 194 and 195 comprise nucleotides containing the same T to G mutation. However, these sequences are 9, 13, and 17 nucleotides in length. The T to G mutation is in the center of each of these nucleotides. The mutation, however, may occur at any position within an 9, 13, or 17 nucleotide sequence.

```
1247 aaaaattgta catcatatgg tgtgctagac 1276    [SEQ ID NO: 180]
                cataggg tg                    [SEQ ID NO: 193]

1247 aaaaattgta catcatatgg tgtgctagac 1276    [SEQ ID NO: 180]
               atcataggg tgtg                 [SEQ ID NO: 194]
```

```
1247 aaaaattgta catcatatgg tgtgctagac 1276   [SEQ ID NO: 180]
           a catcataggg tgtgct               [SEQ ID NO: 195]
```

The third mutation ([SEQ ID NO:183]) discovered in this group of subjects is a four base insertion beginning after nucleotide 996 in exon 7 of Genbank Z32757 ([SEQ ID NO: 182]). The insertion causes a frame-shift and is predicted to abolish the expression of functional CD36 protein from the allele containing the mutation. This mutation was present in only one subject, who also was homozygous for the mutation shown in [SEQ ID NO:181].

```
                                             [SEQ ID NO: 182]
979 taaaggtaaa aggtaagt    attctggt aaaa
                                             [SEQ ID NO: 183]
979 taaaggtaaa aggtaagtaa gtattctggt aaaa
```

SEQ ID NOs:196, 197 and 198 comprise nucleotides containing the same 4 base insertion. However, these sequences are 8, 12, and 16 nucleotides in length. The 4 base insertion is in the center of each of these nucleotides. The insertion, however, may occur at any position within an 8, 12, or 16 nucleotide sequence.

```
979 taaaggtaaa aggtaagt    attctggt aaaa     [SEQ ID NO: 182]
                     gtaa gtat               [SEQ ID NO: 196]

979 taaaggtaaa aggtaagt    attctggt aaaa     [SEQ ID NO: 182]
                   aagtaa gtattc             [SEQ ID NO: 197]

979 taaaggtaaa aggtaagt    attctggt aaaa     [SEQ ID NO: 182]
                 gtaagtaa gtattctg           [SEQ ID NO: 198]
```

A fourth mutation ([SEQ ID NO:185]) was found in one of the five phenotypically CD3 6-deficient AfroCaribbean subjects. This mutation is a point deletion within intron 2 of Genbank Z32753 ([SEQ ID NO:184]). It is uncertain whether this mutation has any significant effect on the production of functional CD36 protein.

```
                                             [SEQ ID NO: 184]
tctatttacc catgcttttc ttattttcac aga 107

[SEQ ID NO: 185]
-ctatttacc catgcttttc ttattttcac aga 107
```

SEQ ID NOs:199, 200 and 201 comprise nucleotides containing the same point deletion. However, these sequences are 8, 12, and 16 nucleotides in length. The deletion is positioned at the beginning of each of these nucleotides. The deletion, however, may occur at any position within an 8, 12, or 16 nucleotide sequence.

```
                                             [SEQ ID NO: 184]
tctatttacc catgcttttc ttattttcac aga 107
                                             [SEQ ID NO: 199]
-ctatttac
                                             [SEQ ID NO: 184]
tctatttacc catgcttttc ttattttcac aga 107
                                             [SEQ ID NO: 200]
-ctatttacc cat
                                             [SEQ ID NO: 184]
tctatttacc catgcttttc ttattttcac aga 107
                                             [SEQ ID NO: 201]
-ctatttacc catgctt
```

A fifth mutation ([SEQ ID NO:187]) was found in an African American with phenotypic CD36 deficiency. The mutation is an insertion of 14 nucleotides in exon 13 ([SEQ ID NO:186]) resulting from a novel repeat of 14 nucleotides. The 14 nucleotide insert occurs after nucleotide 1530 and contains a repeated sequence for nucleotides 1517–1530. The mutation is a functionally significant mutation that predicts a frameshift in the open reading frame which will abolish the normal C terminal end of the protein, including the C terminal transmembrane domain which is essential for CD36 location and function.

```
                                             [SEQ ID NO: 186]
1511 cctattct              ttggctta

[SEQ ID NO: 187]
1511 cctattctat tgtgcctatt ctttggctta
```

SEQ ID NOs:202, 203 and 204 comprise nucleotides containing the same 14 base insertion. However, these sequences are 14, 22, and 26 nucleotides in length. The 14 base insertion mutation is in the center of each of the 22 and 26 base nucleotides. The insertion, however, may occur at any position within a 22 or 26 nucleotide sequence.

```
1511 cctattct                    ttggctta    [SEQ ID NO: 186]
         at tgtgcctatt ct                     [SEQ ID NO: 202]

1511 cctattct                    ttggctta    [SEQ ID NO: 186]
         ttctat tgtgcctatt ctttgg             [SEQ ID NO: 203]

1511 cctattct                    ttggctta    [SEQ ID NO: 186]
       tattctat tgtgcctatt ctttggct           [SEQ ID NO: 204]
```

The sixth mutation ([SEQ ID NO:189]) was found in an AfroCaribbean with diabetes. The mutation is a silent substitution of T to C in exon 10 ([SEQ ID NO:188]). The mutation does not predict a change in the amino acid sequence of the protein.

```
tccctgtgta tagatttgtt cttccatcca    [SEQ ID NO: 188]

tccctgtgta tagattcgtt cttccatcca    [SEQ ID NO: 189]
```

SEQ ID NOs:205, 206 and 207 comprise nucleotides containing the same T to C mutation. However, these sequences are 9, 13, and 17 nucleotides in length. The T to C mutation is in the center of each of these nucleotides. The mutation, however, may occur at any position within an 9, 13, or 17 nucleotide sequence.

```
tccctgtgta tagatttgtt cttccatcca    [SEQ ID NO: 188]
              gattcgtt c             [SEQ ID NO: 205]

tccctgtgta tagatttgtt cttccatcca    [SEQ ID NO: 188]
             tagattcgtt ctt          [SEQ ID NO: 206]

tccctgtgta tagatttgtt cttccatcca    [SEQ ID NO: 188]
            ta tagattcgtt cttcc      [SEQ ID NO: 207]
```

The human CD36 polymorphisms described herein, in particular [SEQ ID NO:133] and [SEQ ID NO:135], which are in the CD36 promoter region, may be primary causes of insulin resistance, diabetes and coronary heart disease in certain populations, notably the Punjabi Sikhs and others from South Asia and elsewhere; such populations include, but not limited to, other Indian Asians. The sequence polymorphisms found in [SEQ ID NO:133] and [SEQ ID NO:135] are within a phorbol ester response element in the promoter, and are also within a region of nuclease hypersensitivity. These elements may control CD36 regulation; the CD36 gene is known to be transcribed at high levels and to be subject to a high degree of transcriptional control. One or both of these variants may be present in up to 60% of these populations and may, therefore, account for their two- to four-fold greater risk of diabetes and coronary heart disease when compared to that of Caucasian subjects in the United Kingdom or United States. As such, these variants are useful markers in the diagnosis, risk assessment, prevention and treatment of insulin resistance, type BI diabetes and coronary heart disease.

In a separate experiment, a significant association was observed between a dinucleotide repeat (a very informative type of gene marker) in the CD36 gene of obese Punjabi Sikh males (n=46) and diabetes, impaired glucose tolerance, coronary heart disease, fasting and two-hour (post glucose load) glucose levels in the glucose tolerance test and, lastly, fasting and two-hour (post glucose load) insulin levels (i.e., where a subject first fasts, the receives an oral glucose load and is tested two hours later for blood insulin and glucose levels). That these results represent an actual linkage between the mutation and the observed phenotypes is supported by statistical analysis, in which p values are as low as $p=0.005$ were observed.

These experiments, using a microsatellite marker for human CD36 described by Lipsky et al., (1994, *Hum. Mol. Genet.*, 3:217), were performed on a test population of Punjabi Sikh males. An association with glucose intolerance was observed, where the two common alleles of the gene, designated herein as alleles 3 and 4, correspond to alleles A1 and A4 (Lipsky et al., 1994, supra). Table 2 presents allele 3 associations, where the values are expressed as numbers of individuals (per cent of total).

TABLE 2

|  | Allele 3 +ve | Allele 3 −ve |
| --- | --- | --- |
| Normal | 15 (44) | 10 (83) |
| IGT | 3 (9) | 1 (8) |
| Diabetic | 16 (47) | 1 (8) |

Abbreviations:
IGT, impaired glucose tolerance; Allele3 +ve indicates individuals possessing at least one copy (i.e., one or two copies) of allele 3; Allele 3 −ve indicates individuals who do not possess a copy of allele 3.

These data demonstrate a 6-fold increased relative risk of diabetes in Punjabi Sikhs possessing at least one copy of allele 3 over those not found to possess allele 3. The statistical significance of the linkage between allele 3 and diabetes is:Allele 3 +ve versus Allele 3 −ve: $p=0.01$.

Table 3 presents the association between Allele 4 and risk of IGT or diabetes.

TABLE 3

|  | Allele 4 +ve | Allele 4 −ve |
| --- | --- | --- |
| Normal | 17 (74) | 8 (35) |
| IGT | 2 (9) | 2 (9) |
| Diabetic | 4 (17) | 13 (57) |

The data of Table 3 demonstrate a 3-fold reduced risk of diabetes in Punjabi Sikh males possessing at least one copy of allele 4 relative to those possessing none (statistical significance:$p=0.004$ for Allele 4 +ve versus Allele 4 −ve).

The association between sequence variants and coronary heart disease (CHD) was also examined. Table 4 shows data regarding the correlation between allele 3 variants and CHD.

TABLE 4

|  | Allele 3 +ve | Allele −ve | Not typed |
|---|---|---|---|
| CHD −ve | 29 (85) | 12 (100) | 650 (95) |
| CHD +ve | 5 (15) | 0 (0) | 38 (5) |

Abbreviations are as above.

This demonstrates an increased relative risk of CHD in Punjabi Sikhs possessing at least one copy of allele 3 (statistical significance:p=0.2 for Allele 3 +ve versus Allele 3 −ve). As a result of the 0 value observed for CHD in individuals lacking allele 3, this risk cannot be quantified absolutely, but may indicate a large relative risk of up to 15-fold.

Changes in risk associated with the presence or absence of allele 4 were also determined; the results are presented in Table 5.

TABLE 5

|  | Allele 4 +ve | Allele 4 −ve | Not typed |
|---|---|---|---|
| CHD −ve | 23 (100) | 18 (78) | 650 (95) |
| CHD +ve | 0 (0) | 5 (22) | 38 (5) |

This result demonstrates a reduced relative risk of CHD in Punjabi Sikhs possessing one copy of allele 4 (statistical significance:p=0.02 for Allele 4 +ve versus Allele 4 −ve). This risk is not quantified, owing to the 0 value in allele 4 +ve individuals with CHD, but could indicate a large relative risk of up to 15-fold over individuals lacking this allele.

Other significant results of note are elevated levels of insuling during fasting and 2 hours after a glucose load in Punjabi Sikhs who are homozygous for allele 3 (p<0.009 for both). This indicates predisposition to insulin resistance in individuals homozygous for allele 3.

Although it is unlikely that the microsatellite alleles themselves are the cause of the genetic predisposition toward the above-mentioned disorders, such a remotely possible result has been observed for type 1 diabetes at the insulin gene locus, where a minisatellite which affects insulin gene transcription confers risk of disease; therefore, linkage between either of alleles 3 and 4 and diabetes, IGT or CHD may be observed in other populations. In Punjabi Sikhs at least, and possibly in other populations, these markers may be important diagnostic markers of predisposition to diabetes, insulin resistance and risk of coronary heart disease. Alternatively, these alleles may not, themselves, represent the underlying cause of disease, but may instead be in linkage disequilibrium (i.e., tight genetic linkage) to other alleles within the CD36 gene that are the primary cause of differences in disease risk among individuals. The polymorphisms disclosed herein, as well as other as-yet-unidentified mutations or polymorphisms, are candidates for the genetic defects which underlie the observed disease associations. They may, therefore, be advantageously employed in screening individual for predisposition toward these disorders, as well as in drug screening and as targets for disease treatment according to the invention in individuals possessing these alleles.

Allelic variation of the CD36 gene represents a major source of susceptibility in Punjabi Sikhs, and possibly in other populations, for insulin resistance, diabetes and coronary heart disease. Such a result is significant for public health, and for disease prevention and treatment. As indicated above, disease-linked allelic variants can be detected in diagnostic methods according to the invention, for example using oligonucleotide probes comprising either mutant or wild-type sequences which encompass the sites of observed polymorphisms, including, but not limited to, those shown above. Other applicable techniques include, but are not limited to, direct DNA sequencing, single-strand conformation polymorphism analysis, allele-specific PCR, microarray hybridization analysis or mismatch analysis via enzymatic cleavage or electrophoretic methods (e.g., gradient denaturing gels). In addition, the proteins encoded by these variants may be detected for diagnostic purposes (e.g., with variant-specific labeled antibodies), provided a variant of interest is immunologically distinct from non-disease-associated variants. Lastly, these results offer support for drug screening protocols which utilize the human CD36 gene or its protein product as a target.

T. Cloning of Candidate Disease-Linked Genes According to the Invention

Positional cloning methods
i. Physical mapping and isolation of chromosomal segments using yeast artificial chromosomes The first step to identifying by this method a gene which is maps to an Insulin-Resistance locus of the invention is the isolation of genomic fragments which cover the region encompassing the particular Insulin-Resistance locus. Yeast artificial chromosomes (YACs) are advantageously employed in terms of insert length, since these chromosomes carry up to 2 mega-base pairs (Mb) of insert DNA, requiring few clones to cover a given genomic region, e.g., relative to bacterial artificial chromosomes (BACs), which have insert sizes of up to 150 kb. In that BACs are less prone to chimerism and rearrangements than are YACs, they are also useful in subcloning segments from YACs and in bridging gaps in- or junction regions of YAC contigs. A combination of YAC and BAC contigs is, therefore, useful in physically mapping the chromosomal segments of interest.

Rat, mouse and human YAC and BAC libraries are commercially available (e.g., through Research Genetics; Huntsville, AL). End-fragment sequences can be isolated from YACs in the YAC contig, and clones derived from these and used as probes to order clones with respect to each other. Restriction mapping with partial digestion using rare-cutting enzymes and pulse-field gel electrophoresis can be used to determine the extent of overlap between TACs in a contig and the actual length of a contig. Molecular methods involved in gene localization procedures (e.g., restriction mapping, gel electrophoresis, nucleic acid hybridization and subcloning) may be performed by methods well known in the art (see Sambrook et al., 1989, *Molecular Cloning, A Laboratory Manual.*, 2nd Edition Cold Spring Harbor Laboratory Press, Cold Spring Harbor, N.Y.). Candidate gene identification from physically-isolated DNA can be approached using several techniques in combination, including direct YAC hybridization, direct cDNA selection, exon trapping and long-range sequencing, again by methods known in the art. One or a combination of these methods may be used in the isolation of a given gene. For example, a gene of an Insulin-Resistance locus may be identified by fine genetic mapping, followed by a combination of physical mapping, long-range sequencing and exon trapping. Each of these steps facilitates performance of the next. The final step is to identify mutation(s) in the gene by DNA sequence analysis or a method described below (see section E) to show that mutations co-segregate with the relevant mutant phenotype and to define the effect of the mutant- and/or corresponding wild-type gene in cells, cell lines or animals, also as described above (see section D).

ii. Plasmid rescue

As described above, it is possible to map a gene of interest using a mutagenic vector, such as a retroviral vector, plasmid or mobile genetic element (e.g., a transposon). A specialized subclass of such mutagenic nucleic acids enables recovery of chromosomal sequences adjacent to the vector integration site in the host (i.e., the test animal) through a technique known as "plasmid rescue", first described in Drosophila, but equally applicable to mammalian model systems (Pirotta, 1986, in *Drosophila:A practical approach*, ed. Roberts, IRL Press, Oxford and Washington, D.C.). According to this procedure, the mutagenic construct comprises both a bacterial origin of replication and a selection marker, such as a drug resistance gene, which together constitute a minimal plasmid. On either side of the minimal plasmid cassette is a unique recognition site for a restriction endonuclease and, typically, more than one such site. Genomic DNA from an organism bearing the mutagenic construct is restricted with one of these unique restriction enzymes, circularized (e.g., by self-ligation) and transformed into bacteria. Only the minimal plasmid, along with chromosomal sequences extending to the nearest genomic cleavage site for the enzyme employed, can be propagated in bacteria.

iii. Microcloning

A gene of interest can, once mapped, be cloned from an enriched library derived from the physical excision of a region of a chromosome which is affixed to a support substrate (e.g., a glass microscope slide) which is then randomly cloned into a vector and propagated, although this technique is somewhat obsolete, given the availability of YAC libraries spanning the entire genome of numerous organisms.

J. Disease Treatment According to the Invention

The invention provides methods for the diagnosis of diseases associated with defects in insulin action, catecolamine action, glucose metabolism or fatty acid metabolism or transport, as well as for the identification and assay of candidate drugs which may be of use in the treatment of such diseases. Defects in insulin action or fatty acid metabolism or transport give rise to insulin resistance syndrome (metabolic syndrome X) or cardiomyopathy. Diseases associated with insulin resistance syndrome include, but are not limited to, non-insulin-dependent diabetes mellitus (NIDDM) and essential hypertension, while those associated with cardiomyopathy include, but are not limited to, hereditary hypertrophic-, dilated-, pressure-overload- or idiopathic cardiomyopathy. The invention additionally provides methods by which a drug identified and found to be efficacious in modulating functions related to glucose- or lipid metabolism, is administered to a patient having a defect in such a function, wherein the target of the drug regulates the function of interest and is linked to an Insulin Resistance Locus, as defined above.

One method of treating a patient possessing a CD36 protein deficiency, such as patients harboring one of the mutations disclosed in SEQ ID NO:179, 181, 183, and 187 or other mutations resulting in CD36 protein deficiency, involves gene therapy to introduce wild type CD36 gene or other recombinant nucleic acid which results in expression of functional CD36 protein. Gene therapy can be carried out by any of the methods listed above in section D.i., or any suitable method known in the art. A CD36 protein deficiency can be treated by the introduction of any nucleic acid sequence encoding a functional CD36 protein, such as the sequences disclosed in [SEQ ID NO:101], [SEQ ID NO:102], [SEQ ID NO:103], [SEQ ID NO:104], [SEQ ID NO:105], [SEQ ID NO:106], [SEQ ID NO:107], [SEQ ID NO:108], [SEQ ID NO:109], [SEQ ID NO:110], [SEQ ID NO:111], [SEQ ID NO:112], [SEQ ID NO: 113], [SEQ ID NO:114], [SEQ ID NO:115], [SEQ ID NO:116], [SEQ ID NO:117], [ SEQ ID NO:118], [SEQ ID NO:119], [SEQ ID NO:120], [SEQ ID NO:121], [SEQ ID NO:122], [SEQ ID NO:123], [SEQ ID NO:124], [SEQ ID NO:125], [SEQ ID NO:126], [SEQ ID NO: 127], [SEQ ID NO:128], [SEQ ID NO:129], [SEQ ID NO:132], [SEQ ID NO:133], [SEQ ID NO:134], [SEQ ID NO:135], [SEQ ID NO:136], [SEQ ID NO:137], [SEQ ID NO:139], [SEQ ID NO:140], [SEQ ID NO:142], [SEQ ID NO:143], [SEQ ID NO:144], [SEQ ID NO: 145], [SEQ ID NO:146], [SEQ ID NO:147], [SEQ ID NO:148] and [SEQ ID NO:149].

Dosages and methods of administration of a drug which modulates glucose- or lipid metabolism according to the invention are as described above for screening methods involving an animal model or human subject. Such a drug may be administered in a single dose or on a multi-dose schedule at the discretion of one of skill in the art, such as a physician, depending on the physical needs and condition of the patient. Treatment is judged efficacious based upon the monitoring of clinical indicators or biochemical indices, as described above; generally, a percent change, where quantifiable, of at least 10%, preferably 20% or more, is indicative of efficacy.

K. Screening Biological Samples for Donation According to the Invention

The invention provides methods for screening blood or other cells, tissues, organs, or bodily fluids from a human or a mammal for donation to another human or mammal. The screening methods comprise methods of testing for mutations in a CD36 gene, or the homologous gene of a non-human mammalian species, and methods for the detection of a CD36 protein deficiency, or a deficiency of a homologous protein of a non-human mammalian species.

A human or mammal which has a CD36 protein deficiency and is the recipient of cells, tissue (such as blood or blood products including platelets), an organ, or bodily fluid from a human or mammal which does not have a CD36 protein deficiency is subject to developing a harmful immune reaction such as the production of antibodies to CD36 protein. When seeking donor materials such as cells, tissues, organs, or bodily fluids prior to donation or transplantation to a human or mammal with a deficiency of CD36 or a homologous protein it may therefore be desirable to screen potential donors and select those who bear a compatible CD36 deficiency, rejecting potential donors whose cells, tissues, organs, or bodily fluids contain wild type CD36 protein. Such screening can be particularly important when the material to be donated or transplanted is whole blood or a blood product such as packed cells, erythrocytes, platelets, or any other material prepared from blood which potentially contains a type of CD36 protein that could stimulate an immune response in the recipient.

Screening of donor materials can be performed by testing any biological sample, including blood, from potential donors for either a mutation in the CD36 gene or a CD36 protein deficiency. The material tested can be the donor materials themselves or another biological sample, such as blood, obtained from the donor. Detection of mutations can be performed by any of the methods described above. Detection of a CD36 protein deficiency can be performed either by testing for mutations in the CD36 gene or by testing for variants of the CD36 protein not found in the recipient, for example using Western blotting, ELISA, or another technique capable of distinguishing among CD36 protein variants. It is preferred that methods for screening for CD36 deficiency or CD36 gene mutations indicative of such deficiency test for commonly occurring mutations such as those described in SEQ ID NOS:179, 181, 183, 185, and 187 or other mutations known to result in or be indicative of CD36 protein deficiency. After testing, donor materials such as cells, tissues (including blood and blood products), organs, or bodily fluids are labeled in any way appropriate to convey the results to end users (e.g., physicians or their associates) or recipients of such donor materials. For example, the container in which the donor materials are stored can be labeled with a designation of the CD36 genotype or phenotype of the donor material, or similar information can be transmitted using a specifications sheet or in electronic form which accompanies or is associated with the shipment of donor material to the end user or recipient.

The invention also provides methods of matching a donor with a recipient based on CD36 deficiency. A recipient of cells, tissue (including blood or blood products), an organ, or a bodily fluid is tested to determine whether the recipient has either a CD36 gene product deficiency or a mutation in a CD36 gene resulting in such a deficiency. If the recipient possesses such a deficiency, then the recipient is matched with a donor who possesses a similar deficiency, or one which is compatible with the recipient's deficiency. The donor's CD36 deficiency is compatible with the recipient's deficiency if the donated material is not likely to cause an immune response in the recipient because of a CD36 gene product expressed in the donor material. The likelihood of such an immune response can be predicted by one of skill in the art by comparing the result of testing the recipient for a deficiency in a CD36 gene product or for a mutation in a CD36 gene with the results of a screening of the donor material performed as described above.

L. Resistance to and Treatment of Parasitic Infections A

The invention provides methods for determining whether a patient is genetically predisposed to be resistant to certain parasitic infections. Any parasitic disease that requires functional CD36 or a homologous protein in the course of the infection of a human or other animal subject is appropriate for use with these methods. Examples of such diseases include falciparum malaria, cerebral malaria, and black water fever.

Of the CD36 mutations described herein, four (SEQ ID NOS:179, 181, 183 and 187) are associated with complete CD36 protein deficiency in homozygous individuals. These mutations and others yet to be discovered can be used to identify patients who are likely to be resistant to falciparum malaria and other parasitic infections involving CD36 protein. Testing of patients at risk for such parasitic infections by determimng whether they harbor a mutation such as those disclosed in SEQ ID NOS:179, 181, 183 and 187 or another mutation resulting in or indicative of CD36 protein deficiency can enable these patients to take appropriate precautions such as preventive medication or to avoid the risk of infection if they do not harbor a mutation indicative of CD36 protein deficiency.

Furthermore, the invention provides methods of prevention and treatment of parasitic infections such as falciparum malaria, cerebral malaria, blackwater fever, and other diseases that involve CD36 protein as a ligand for the parasitic agent. The methods involve the inhibition of CD36 gene expression. Inhibition of CD36 gene expression can result in an induced CD36 protein deficiency, which can inhibit the process of infection by *Plasmodium falciparum* or other parasites that use CD36 as a ligand. Therefore, in order to practice these methods, a pharmaceutical composition comprising an inhibitor of CD36 gene expression is administered to a patient in need thereof. A patient is in need of such a pharmaceutical composition if the patient is infected with such a parasite or is at risk of infection by such a parasite. An inhibitor of CD36 gene expression can be any of the agents disclosed above, such as an antibody to CD36 protein, an antisense nucleic acid which binds CD36 mRNA, a vector which incorporates into cells of the host and produces such an antisense nucleic acid, a ribozyme, or a small molecule which inhibits any aspect of CD36 gene expression. Such an agent is administered in a dose that inhibits at least 30%, at least 50%, at least 60%, at least 70%, at least 80%, at least 90%, at least 95%, at least 98%, or at least 99% of CD36 protein expression in cells of the patient. A reduction in the amount of CD36 gene product may be determined via inhibition of rosette formation by erythrocytes (which bear C36), as described in Handunnetti et al., 1992, Blood 80:2097, hereby incorporated by reference, or via inhibition of binding of oxidized low density lipoprotein to cells bearing CD36, e.g., platelets, as described in Endemann et al., 1993, Jour. Biol. Chem. 268:11811, hereby incorporated by reference.

The invention also provides methods for screening drugs for their effectiveness in preventing or treating parasitic infections involving binding of the parasite to CD36 protein. Candidate drugs can be tested for their ability to disrupt the expression of the CD36 gene so as to produce a deficiency of CD36 protein, and thus indicate efficacy of a drug to prevent or treat infection by the parasite. By disrupting or inhibiting the binding of the parasite to CD36 protein, the drug can prevent cells or tissues from becoming infected or prevent infection from spreading within the host. In such a drug screening assay, the CD36 gene can be tested in a transcriptional and/or a transcriptional/translational assay, or a whole cell assay, and level of inhibition of CD36 gene expression in the presence of the drug can be compared to the level of gene expression by a CD36 mutant gene as disclosed herein. Binding of a candidate drug to CD36 protein can predict the efficacy of the drug in preventing binding of the parasite to CD36 protein, and therefore its efficacy in preventing or treating infection by the parasite. Potential drugs for the treatment of parasitic infections may also be screened by assaying the level of inhibition of CD36 transcriptional activator gene expression produced by the drug. Genes that are such positive regulators of the CD36 gene include the ppr-gamma gene. Any assay known in the art which is capable of qualitatively or quantitatively measuring CD36 gene expression is useful according to this aspect of the invention. Varying concentrations of the candidate drug may be tested in order to determine the effective concentration for treatment which also is easily reversible once treatment is no longer needed.

Drugs that have been identified as candidate anti-malarial drugs can be further tested in the SHR (Spontaneously Hypertensive Rat) animal model. The SHR rat lacks the CD36 protein because part of the CD36 gene is missing on both chromosomes of this rat. The candidate anti-malaria drug would be tested in both CD36 transgenic SHR rats and in SHR rats.

M. Kits According to the Invention

A kit according to the invention may include a nucleic acid comprising or consisting of any one of the mutant sequences of CD36 disclosed herein, and packaging therefor.

A kit according to the invention also may comprise a drug selected from those screened and found to be efficacious in the treatment of disease according to the invention, a carrier (e.g., a buffer or other agent, as described above in the description of drug screening) and packaging therefor. A drug supplied in a kit of the invention may comprise one or more than one agent screened according to the methods disclosed herein. The drug component is provided as a protein, nucleic acid comprising a gene expression construct encoding a protein or other nucleic acid (e.g., a ribozyme or antisense molecule), and are either in solution (preferably refrigerated or frozen) or other agent, as described above (see "Candidate modulators"), in a buffer which inhibits degradation and maintains the biological activity of the drug. If such a buffer is a storage buffer rather than a physiologically compatible buffer, as defined above, a physiologically compatible buffer must be used for dilution and/or delivery of the drug. A physiologically compatible buffer is optionally supplied with such a kit. Alternatively, the drug is provided in dried form, i.e., lyophilized, in which case, the components are resuspended prior to administration in a physiologically compatible buffer, which buffer is supplied with the kit; such a buffer preserves the biological activity of the drug to be admixed with it and permits safe administration to a patient. Each of these components is supplied separately contained or in admixture with one or more of the others in a container selected from the group that includes, but is not limited to, a tube, vial, syringe or bottle. All components may be shipped and/or stored at a single temperature; alternatively, different components may be maintained at separate temperatures such that the shelf-life of each is optimized.

Optionally, the kit includes cells. Such cells may optionally comprise a drug to be delivered to a patient in a treatment protocol according to the invention. Eukaryotic or prokaryotic cells, as described above, are supplied in- or on a liquid or solid physiological buffer or culture medium (e.g. in suspension, in a stab culture or on a culture plate, e.g. a Petri dish). For ease of shipping, the cells are typically refrigerated, frozen or lyophilized in a bottle, tube or vial. Methods of cell preservation are widely known in the art; suitable buffers and media are widely known in the art, and are obtained from commerical suppliers (e.g., Gibco/ LifeTechnologies) or made by standard methods (see, for example Sambrook et al., 1989, *Molecular Cloning. A Laboratory Manual.*, 2nd Edition, Cold Spring Harbor Laboratory Press, Cold Spring Harbor, N.Y.).

EXAMPLE 1

This Example demonstrates the chromosomal mapping of a candidate gene and the comparison of its map position to that of an Insulin-Resistance locus according to the invention. A radiation hybrid (RH) map of the proximal region of rat chromosome 4 is constructed using microsatellite and gene markers from this region and is used to localize markers for five genes not previously mapped in the rat. This represents one of the first applications of RH mapping to the rat. The map facilitates identification according to the invention of the genes underlying cardiovascular and metabolic functions known to map to Insulin-Resistance Locus 1 on chromosome 4 and provides a basis for physical map construction of this chromosomal segment. The methods employed and the results obtained are as follows:

The whole genome rat/hamster RH panel of 106 hybrid DNAs used in these experiments was purchased from Research Genetics (Huntsville, Alabama). The panel was constructed by fusing irradiated cells from a Sprague Dawley fibroblast line (RatFR) with a recipient hamster line (A23). FR donor cells were irradiated with 3,000 rad prior to fusion with A23 recipient cells.

Twenty four rat microsatellite markers from various sources (Jacob et al., 1995, *Cell*, 67: 213–224; Goldmuntz et al., 1995, *Mamm. Genome*, 6:459–463; http://www-genome.wi.mit.edu/rat/public/) were used to screen donor and recipient DNA for variability between FR and A23 (Table 6). The primer sequences for ILG6 were obtained from Research Genetics:ILG6F 5'-TGAGTTCCAGGATACCCAGG-3' [SEQ ID NO:93]; ILG6R 5'-AAGCGGAGTCAAAATACTTTGC-3' [SEQ ID NO:94]. The primers for the Nos3 microsatellite were designed from the rat genome sequence for Nos3 (Hubner et al., 1995, Mamm. Genome 6:758–759):Nos3F:5'-ACGTTCCTCCTCAGCCCTGG-3' [SEQ ID NO:95]; Nos3R:5'-GTGCATGTCTGCATAAACATG-3' [SEQ ID NO:96]. The primers designated as D9Bro1 (Research Genetics) correspond to the Ae2 gene (Jacob et al., 1995, supra, Simon et al, 1996, *Mamm. Genorne*, 7:380–382) and have retained the designation D9Bro1 for this study. Oligonucleotide primers were synthesized commercially by Genosys Biotechnology (Cambridge, UK). Oil-free PCR was carried out on a TouchDown sub-ambient thermal cycler (Hybaid, Teddington, UK) with an initial denaturation at 94° C. for 3 minutes, followed by 35 cycles of denaturation at 94° C. for 30 seconds, annealing at the appropriate temperature (Table 6) for 45 seconds, and extension at 72° C. for 1 minute, with a final extension at 72° C. for 8 minutes. Each reaction had a total volume of 10 µl containing 50 ng of hybrid cell line DNA in 10 mM Tris-HCl, 0.1 mM EDTA (pH 7.5) and 0.5 units of Taq DNA polymerase. Final concentration of other reagents were as follows:each oligonucleotide primer 0.66 µM, dNTPs 0.2 mM and 1×PCR reaction buffer. $MgCl_2$ concentration and annealing temperature were optimized for each primer pair (Table 6).

PCR products were resolved on 3% agarose gels (2% Nusieve:1% agarose) in 1×TBE and visualized by ethidium bromide staining. Where size differences between A23 and FR were not detected on agarose gel electrophoresis, PCR products were tested for size difference on an ABI 377 automated sequencer (Perkin Elmer) with products visualized by incorporation of fluorescence-labeled dUTP (Perkin Elmer).

Of 24 microsatellites tested by this method, all showed either length variation between FR and A23 DNA or gave a PCR product with FR DNA but no product for A23. The microsatellite marker D4Rat117 gave inconsistent amplification and was excluded from the data analysis. Twenty three microsatellites were, therefore, used to score the RH cell lines, for retention of FR chromosomal fragments. Separate duplicate PCR reactions for each locus were scored independently by two observers as present or absent. Typically 95%–99% concordance was obtained between duplicate PCR reactions. Results from hybrids showing discordant results for a given marker were discarded.

Where possible, control hamster primers were used in the PCR reaction together with the rat-specific primers, to give a hamster-specific band in all PCR reactions. The following primers derived from the hamster sequence for the DHFR gene were used for amplification of hamster genomic DNA:

HAM1F:5'-TATAGGTGGAGCCTAATGAG-3' [SEQ ID NO:97];
HAM1R:5'-ACTCACGACTGATCAAAGTG-3' [SEQ ID NO:98];
HAM2F:5'-AGCTGCTGTGAGCTTGTGAG-3' [SEQ ID NO:99]; and
HAM2R:5'-GACAGCAGTCAGCATGGAGA-3' [SEQ ID NO:100].

HAM2F and HAM2R were used with D4Arb13, D4Rat2, D4Rat5, D4Rat117, D4Mgh1, Nos3, Fin13, Pgy1, and Psmc2; HAM1F and HAM2R were used for D4Rat1, D4Rat3, D4Rat4, D4Rat6, D4Rat7, D4Rat9, D4Rat 10, D4Rat125, D4Rat126, D4Rat133, D4Rat136, D4Rat139, D4Rat142, D4Rat149, D4Rat150, D9Brol, ILG6, Slc4a2, and Cacna2; HAM1F and HAM1R were used for D4Rat150. HAM2F/2R gave a product size of 230 bp, HAM1F/2R a product size of 300 bp and HAM1F/1R a product size of 280 bp.

To place new genes on the rat RH map, PCR assays were developed for mouse and human genes that map to mouse chromosome 5 and human chromosome 7, which are syntenic to rat chromosome 4 (Yamada et al., 1994, *Mamm. Genome*, 5:63–83). Primers were designed for each mouse and human gene from both coding sequences and 3' untranslated sequences. In order to maximize the likelihood of specific amplification with primers designed from coding sequence, the last two 3' bases of each oligonucleotide corresponded to the first and second bases of a codon, where cross-species conservation of sequence is likely to be greatest. PCR primer pairs were also designed from the rat cDNA sequence for the L-type calcium channel gene (GenBank accession No:M86621), the mouse homolog of which maps to mouse chromosome 5 (Chin et al., 1992, (Genomics, 13:1325–1327).

Retention patterns were analyzed by two-point and multipoint methods using the programs RH2PT, RHMINBRK and RHMAXLIK of the RHEMAP package (Boehnke et al., 20 1991; Lange et al., 1995; RHMAP, Version 3.0, September 1996; http://www.sph.umich.edu/group/statgen/software). The model of maximum likelihood employed in these experiments assumed that radiation-induced breaks occur at random. A further assumption was that the expected retention frequencies were equal along the chromosome. However, in view of the observed variation in retention frequencies, maximum likelihood analysis under a left-endpoint retention model (Boehnke et al.,1991; Bishop and Crockford, 1992; Boehnke et aL, 1992) was also performed. The branch and bound method was used to compute the overall minimum breakage number. But if the branch and bound algorithm could not be applied (for example, due to too great a number of loci under consideration), a set of best orders regarding obligate chromosome breaks was established with the stepwise algorithms of program RHMINBRK. The result was then checked with 10 simulated annealing runs starting with random orders. The maximum likelihood method was used to estimate map distances, measured in Centirays (cR) where 1 $cR_{30000}$ is equivalent to a 1% probability of breakage between markers after exposure to 3000 rad of X-rays. Breakage frequencies, P, were transformed to map distance estimates, d, by:$d=-Ln(1-P)$ (Cox, et al., 1990, supra).

106 RH cell lines were initially scored for 24 rat microsatellites markers that had previously been mapped to the proximal region of rat chromosome 4 (Table 6). Mapping of genes from syntenic regions of the mouse and human genomes onto our framework RH map was then attempted. Using primers designed from 19 mouse genes on mouse chromosome 5 and 10 human genes from human chromosome 7, successful amplification of FR genomic DNA, defined as a single band of the correct size on agarose gel electrophoresis, was achieved for 10 mouse genes and 3 human genes. Length variation between FR and A23 was detected for 6 mouse genes but for no human genes. The RH cell lines were, therefore, scored for these 6 mouse genes (Table 7). The retention pattern of PCR products derived from the marker for the Psmc2 gene is shown in FIG. 5. The observed size of 70 bp is close to the expected fragment size of 74 bp. A 230 bp hamster product, resulting from hamster primers included in each reaction as a positive control, is present in all samples. ("SHR" denotes the PCR product from spontaneously hypertensive rat genomic DNA.)

Two of the mouse-derived PCR markers, Fin13 and Tyms, were loosely linked to each other (two-point lod score 2.4)

but were not linked to any other marker on rat chromosome 4. The remaining four markers, Psmc2, Fgl2, Slc4a2 and Pgy1, were all linked on the RH panel to existing chromosome 4 markers with lod scores greater than 6. The retention pattern for Psmc2 showed identity to that of D4Rat136, demonstrating total linkage (lod score 28.4) between these two markers.

The marker Fgl2 was linked to D4Rat136 with a lod score of 19.6; Slc4a2 to Nos3 (lod score 22.5) and to D9Brol (lod score 19.0); and PgY1 to D4Rat9 (lod score 7.0). The results indicate that the rat homologs of Psmc2, Fgl2, Slc4a2 and Pgy] reside on rat chromosome 4. These four markers were, therefore, integrated into the chromosome 4 RH map. Using primers designed from the rat gene Cacna2 (Table 7), tight linkage between Cacna2 and the microsatellite D4Rat149 was observed (lod score 15.7), establishing its location on chromosome 4.

Based on an initial pairwise analysis with the program RH2PT using a lod score threshold of 6, the 28 markers were divided into two linkage groups (FIG. 6). Marker locations on this genetic map were based on the Whitehead Institute maps (http://www-genome.wi.mit.edu/). Additional markers were placed on the genetic map using the Oxford map (http://www.well.ox.ac.uk/-bihoreau/key.html) and data from Hubner et al. (1995, supra). (cM, centiMorgans; cR, centiRays). The two linkage groups covered a total distance of 730 $cR_{3000}$ corresponding to a genetic distance of 15 centiMorgans (cM). Therefore, on this region of rat chromosome 4, one cM corresponds to around 50 $cR_{3000}$.

The maximum likelihood order of markers and a comparison with existing genetic maps are shown in FIG. 6. The distances between markers are shown in Table 8. Marker order was determined for the two linkage groups separately and the orientation of the linkage groups determined by reference to the genetic map and the results of the two-point analysis. The variation of orders obtained by maximum likelihood analysis is shown in FIG. 7, in which the observed orders are indicated at three levels of log likelihood ratio (1, 2 and 3) for either of the two linkage groups. The inclusion of the four mouse genes did not influence the order of the maximum likelihood estimate of the 24 rat loci, except that variation of likely orders was reduced by inclusion of the four mouse genes.

The mean retention frequency of the 28 chromosome 4 markers was 36%, with a marked gradient from the most centromeric marker ILG6, with retention frequency 65%, to more distal markers with retention frequency down to 11% (Table 8).

The conservation of synteny groups was considerably stronger between rat and mouse and between rat and human, as shown in FIG. 8, which presents the maximum likelihood order of genes on rat chromosome 4 compared with gene orders on syntenic segments of mouse chromosome 5 and human chromosome 7. Distances between genes on rat chromosome 4 were calculated from the RHMAXLIK analysis. Human and mouse gene locations were derived from the mouse genome database (http://mgd.hgmp.mrc.ac.ulk/) and the human genome database (http:I/www.hgmp.mrc.ac.ud/gdb). Distances between markers on the rat map are in $cRays_{3000}$ and on the mouse map in cMorgans. (UN, unknown). The order of genes on the RH map corresponded exactly to that on mouse chromosome 5, except that the genes are inverted with respect to the centromere. Furthermore the genes in both rat and mouse are limited to a single 20 cM segment of their respective chromosomes. In contrast, the homologs of these genes in the human are distributed across the long and short arms of human chromosome 7, with at least one inversion of gene order breaking the synteny relationship.

Importantly, the map locations for the genes for Psmc2, Fgl2, Slc4a2 and Pgy1 are based on PCR primers designed from the mouse sequences of these genes. These products are likely to be markers for the homologs of the mouse genes. First, the observed size of the PCR products for all of these primer pairs is within ten base pairs of that predicted from the mouse sequence (Table 7; FIG. 5). Second, the location of these mouse genes on chromosome 5, within the synteny group for proximal rat chromosome 4, offers prior support for the localization of their homologs on rat chromosome 4. Third, the marker designed from the mouse Slc4a2 sequence has been mapped to a distance of less than 10 $cR_{3000}$ from D9Brol, which is a microsatellite marker on chromosome 4 for the rat gene Slc4a2, formerly called Ae2. Fourth, the rat gene for Pgy1 has previously been mapped by somatic cell hybrid analysis to rat chromosome 4 (Hanson et al., 1988, Abstract, *BioScience*, MalmÜ, Sweden). The map location determined in the experiments described in this Example therefore confirms and refines the previous chromosomal location of rat Pgy1.

Because this strategy was as successful for primers designed from 3' untranslated sequence as from coding sequence, it also may be applied to the large number of available anonymous mouse- or other heterologous (e.g., human) expressed sequence tags (ESTs), as well as to recognized heterologous genes.

The mouse gene for the L-type calcium channel, Cacna2, resides on mouse chromosome 5 in a region of synteny to rat chromosome 4 (Chin et al., 1992, supra), but had not been mapped in the rat prior to the experiments presented herein, in which tight linkage between Cacna2 and the microsatellite D4Rat149 indicated that Cacna2 resides on rat chromosome 4 near D4Rat149.

The rat/hamster RH panel provided a high resolution map of 28 markers spanning approximately 15 cM of rat chromosome 4, corresponding to a physical distance of approximately 730 $cR_{3000}$. As shown in FIG. 6, the resolution of the RH map is considerably higher than that of existing genetic maps. The resolution offered by the rat RH map is similar to that of a 3000 rad RH panel in the mouse (Schmitt et al., 1996, *Genomics*, 34:193–197), but apparently higher than that of a human RH panel constructed using the same radiation dose (Ahlbom et al., 1997, *Hum. Genet.*, 99:186–190).

In general, the order of markers is consistent with previous mapping studies. The major differences relate either to markers that previously were imprecisely mapped, such as Nos3, or to markers not previously separated on genetic maps (FIG. 6). However, the strong linkage between D4Rat150 and D4Rat149 and the support for this order with $\log_{10}$-likelihood-ratio difference>3 (FIG. 7) suggests that this placement of D4Rat150 with respect to other chromosome 4 markers is correct and an improvement on previously suggested orders. Confirmation of this should await genetic mapping on a larger cross or data from physical mapping studies.

The results show a remarkable locus retention frequency gradient. Loci at or near the centromere were retained with a much higher frequency than those that mapped more distally (Table 7). Similar, but smaller gradients have been observed in other RH panels and may be due to preferential retention of centromeric sequences (Benham et al., 1989, *Genomics*, 4:509–517; Cox et al., 1990, supra; Richard et al., 1991, *Am, J. Hum Genet*, 49:1189–1196). In view of the marked gradient, multipoint analysis was performed under models which assumed either equal or unequal retention frequencies along the chromosome. No substantive differences were seen when the data were analyzed under these two models.

In summary, we have demonstrated in this Example a strategy for determining that a gene maps to a map position that is coincident with that of an Insulin-Resistance locus, in this case, Insulin-Resistance locus 1 on chromosome 4 of the rat. Using the technique of RH mapping, a high resolution map of proximal rat chromosome 4 has been constructed, and genes which may serve as targets for drugs or diagnostic procedures aimed at metabolic disorders associated with defects in glucose or fatty acid metabolism, such as those diseases described above, have been identified. The presence in a mammal of a mutation in one of these genes that is found in mammals having a disorder relating to glucose or fatty acid metabolism, which mutation is not found in mammals which do not suffer from such a disorder, is indicative of either the presence of- or the predisposition for such a disease in the mammal. Genes identified in this Example, as well as others similarly identified in Insulin-Resistance locus, such as Insulin-Resistance locus 1, 2, 3, 4 or another such locus as may be identified, may additionally serve as targets for drug screening according to methods described above.

EXAMPLE 2

In this Example, an unmapped gene is demonstrated to be linked to a map position of an Insulin-Resistance locus according to the invention.

As described above, a candidate gene is selected based either upon a mutant phenotype related to a defect in one or more of insulin action or fatty acid metabolism or transport. A linkage study is carried out in a genetic scheme in which a member of a family of rats (e.g., a GK rat) presenting diabetes is crossed with normal control animals.

Each of the three markers (D4Arb13, Ae2 and D4Rt8) located within the peak of linkage of defects characteristic of Insulin Resistance Locus 1 is assayed for linkage to this phenotype. These markers are polymorphic between strains of rats; therefore, a strain known to differ from that in which the diabetic phenotype has been observed is crossed to the diabetic strain. Offspring of the F. generation are self-crossed (i.e., crossed to siblings, rather than to members of either parental strain or of an unrelated strain), and the F2 generation scored for assortment of the allelic variant of each of the three markers present in the $F_0$ diabetic parent. This may be accomplished by PCR amplification and sequence comparison of each of the three markers in $F_2$ individuals, correlation of the alleles present in each rat with the presence or absence of diabetes and application of an ANOVA to the results. A value of P <0.0001 between the observed diabetic phenotype and at least one of the markers is considered to indicate significant linkage of trait to Insulin-Resistance Locus 1; the gene responsible for diabetes in the test rats is judged to map to the chromosomal map position of Insulin-Resistance Locus 1 if its distance from one or more of the markers is 15 cM or less or, preferably, 10 cM or less from the center of linkage of the locus to the metabolic defects of the SHR model described above.

EXAMPLE 3

This example demonstrates disease diagnosis according to the invention.

As a first step, one or more genes which are found to map to a chromosomal map position of an Insulin-Resistance locus and subsequently cloned, both as described above, are examined (e.g. by nucleic acid sequencing) for the presence of allelic polymorphisms between individuals. Pedigree analysis, also as described above, is performed on families in which numerous individuals are affected with metabolic disorders associated with a defect in one or more of the metabolic processes of insulin action and fatty acid metabolism and/or transport to determine whether the disease state is linked to a particular allelic variant of the gene(s) in any of the affected families.

Once statistically-significant linkage between a mutation in a gene which maps to an Insulin-Resistance locus and such a metabolic disease is uncovered, that gene serves as a diagnostic tool. Clinical patients who are at risk of the disease, based upon family history or environmental factors, are assayed for the disease linked mutation (e.g., by PCR amplification and sequencing of the gene, which are undertaken either separately or in a coupled reaction using methods and reagents well known in the art). Presence of the mutation is indicative of a predisposition for the disease. Such testing permits early medical intervention, as discussed above, and is most advantageously performed early in the life of the individual, even before birth.

EXAMPLE 4

Example 4 presents screening the DNA (genomic or cDNA) of a patient suspected of having a condition, i.e., one of type 2 diabetes mellitus, dyslipidaemia of type 2 diabetes, essential hypertension, combined hyperlipidaemia, and/or predisposition to heart disease, for a mutation in the CD36 gene as described herein.

A DNA sample may be prepared from any tissue or cell line, and preparative procedures are well-known in the art. The preparation of genomic DNA from tissue may be performed as follows. Approximately 100 mg of tissue is placed in 500 $\mu$l TB buffer (50 mM Tris-HCl, pH 8.0, 100 mM NaCl, 1% SDS, 600 $\mu$g/ml proteinase K) and incubated overnight at 55° C. The sample is then extracted with 500 $\mu$l 1:1 (w/w) phenolchloroform and precipitated with two volumes ethanol. The DNA pellet is then resuspended in 500 $\mu$l $H_2O$ .

cDNA samples may also be used in the detection of mutations in genes identified according to the invention.

Tissues which are useful for obtaining a DNA sample according to the invention include but are not limited to blood cells, gametes, brain, gonad, liver, heart, kidney, adrenal, spleen, and muscle, while an RNA sample is best obtained from a tissue that expresses the gene of interest, for example, adipose tissue.

A nucleic acid probe useful in this example is described in any one or more of [SEQ ID NO:5], [SEQ ID NO:11], [SEQ ID NO:17], [SEQ ID NO:23], [SEQ ID NO:29], [SEQ ID NO:35], [SEQ ID NO:41], [SEQ ID NO:47], [SEQ ID NO:53], [SEQ ID NO:59], [SEQ ID NO:65], [SEQ ID NO:71], [SEQ ID NO:77], [SEQ ID NO:83], [SEQ ID NO:87], [SEQ ID NO:164], [SEQ ID NO:165], [SEQ ID NO:167], [SEQ ID NO:169], [SEQ ID NO:170], [SEQ ID NO:171], [SEQ ID NO:172], [SEQ ID NO:173], [SEQ ID NO:174], [SEQ ID NO: 175], [SEQ ID NO:176] and [SEQ ID NO:138] or simply using one or more of the mutations selected from the group consisting of nucleotide position 378, 397, 507, 521, 522, 533, 552, 553, 554, 601, 619, 620, 641,742, 791, and 871 of [SEQ ID NO:87]. The probe encompasses a nucleic acid having a sequence that is unique to the gene of interest. Although the complete SHR Cd36 gene may be used as a probe for the mutant phenotype [SEQ ID NO:87], with either the SHR Cd36 gene containing silent mutations (see above) or the wild type Cd36 [SEQ ID NO:85] gene being used as a control probe, optimally, the probe is preferably no longer than 30–40 nucleotides, and optimally less than 25 nucleotides, e.g., 18–22 nucleotides, with a minimum of nucleotides. The probe is used in any one of the DNA detection assays described hereinabove. The results are contemplated to establish an association between the mutant sequences identified herein, particularly those sequences associated with an amino acid sequence alteration (i.e., a non-silent change), and the disease presence or predisposition, for those human diseases relating to defecting insulin action or fatty acid metabolism or transport, which give rise to insulin resistance syndrome (metabolic syndrome X) or cardiomyopathy, respectively. In addition, platelet abnormalities may be associated with CD36 defects. Diseases associated with insulin resistance syndrome include, but are not limited to, non-insulin-dependent diabetes mellitus (NIDDM), combined hyperlipidemia and essential hypertension, while those associated with cardiomyopathy include, but are not limited to, hereditary hypertrophic-, dilated-, pressure-overload- or idiopathic cardiomyopathy.

Alternatively, an antibody may be made that is specific for the mutant CD36 protein but not to the wild type CD36 protein, as described using techniques disclosed herein above, using either a peptide containing an altered amino acid or the complete mutant protein. The antibody may be used to detect the protein product of a CD36 mRNA length variant or the protein product of a mutant CD36 MnRNA of normal length as an indicator of disease.

EXAMPLE 5

Example 5 presents screening of a biological sample of a patient for a mRNA transcripts of polymorphic length, which transcripts hybridize to a nucleic acid probe comprising sequence of the CD36 gene. The patient, suspected of having a condition as described above, is screened for a mutation in the CD36 gene as described herein.

Tissue is selected as described in Example 4, and the mRNA expression profile of the CD36 gene is determined by a method such as Northern analysis or other technique which allows for size determination of detected mRNA molecules, which method is performed on biological samples derived from one or more different tissues or body fluids of the subject under evaluation.

The detection of mRNA varying in size from that observed for wild-type CD36 transcripts (i.e., those of an individual who is normal in terms of insulin resistance or the associated conditions described herein) is expected to correlate with the presence of predisposition to one or more of the diseases described herein.

USE

The invention is of use in the discovery of the mechanisms underlying non-insulin-dependent diabetes, hypertension, combined hyperlipidemia, obesity and other pathological conditions which are linked to defects in insulin action and fatty acid metabolism or uptake. Knowledge gained according to the invention of the genes responsible for these conditions enables methods of diagnosing the presence of disease or the propensity therefor in a patient who may be carrying a mutation in a said gene. In addition, the invention is useful in the screening of candidate drugs directed against defects in insulin action or fatty acid metabolism or transport, which give rise to insulin resistance syndrome (metabolic syndrome X), cardiomyopathy or platelet defects. Diseases associated with insulin resistance syndrome include, but are not limited to, non-insulin-dependent diabetes mellitus (NIDDM), combined hyperlipidemia and essential hypertension, while those associated with cardiomyopathy include, but are not limited to, hereditary hypertrophic-, dilated-, pressure-overload- or idiopathic cardiomyopathy. Drugs screened according to the invention are, if determined to be efficacious, useful in the treatment of diseases linked to defects in insulin action and fatty acid metabolism or uptake, as described above. Lastly, the invention is useful in providing kits for the treatment of diseases linked to defects in insulin action and fatty acid metabolism or uptake, as described above, thereby facilitating distribution and clinical use of therapeutic agents identified according to the screening methods of the invention.

TABLE 1

| | Triglycerides (mg/dl) | NEFA (mEg/l) |
|---|---|---|
| Control | 106.7 ± 5.6** | 1.10 ± 0.08* |
| Transgenic | 62.8 ± 4.3 | 0.74 ± 0.07 |

**P < 0.0001
*P < 0.005
n = 6 for each group. Values are means ± SEM

TABLE 6

Rat Microsatellite Markers and PCR Conditions

| Marker Name | Annealing Temp (° C.) | Magnesium Concentration mM/L |
|---|---|---|
| D4Arb13 | 55 | 1.0 |
| D4Mgh1 | 55 | 1.5 |
| D4Rat1 | 63 | 1.5 |
| D4Rat2 | 63 | 1.5 |
| D4Rat3 | 63 | 1.5 |
| D4Rat4 | 55 | 1.5 |
| D4Rat5 | 55 | 1.0 |
| D4Rat6 | 55 | 1.5 |
| D4Rat7 | 55 | 1.5 |
| D4Rat8 | 55 | 1.0 |
| D4Rat9 | 55 | 1.0 |
| D4Rat10 | 55 | 1.5 |
| D4Rat117 | 62 | 1.5 |
| D4Rat125 | 55 | 1.5 |
| D4Rat126 | 55 | 1.0 |
| D4Rat133 | 63 | 2.0 |
| D4Rat136 | 63 | 2.0 |
| D4Rat139 | 63 | 2.0 |
| D4Rat142 | 63 | 2.0 |
| D4Rat149 | 55 | 1.0 |
| D4Rat150 | 55 | 1.5 |
| D9Brol | 55 | 1.5 |
| JLG6 | 55 | 1.5 |
| Nos3 | 63 | 1.0 |

TABLE 8

Marker Name, Retention Frequencies and the Distance Between Adjacent Markers

| Marker | Retention Frequency | Distance cR$_{3000}$ |
|---|---|---|
| ILG6 | 0.65 | 53.8 |
| D4Rat133 | 0.54 | 4.1 |
| D4Rat4 | 0.52 | 1.9 |
| D4Arb13 | 0.51 | 4.3 |
| D4Rat139 | 0.47 | 35.4 |
| D4Rat2 | 0.46 | 6.2 |
| D4Rat3 | 0.42 | 2.1 |
| D4Rat142 | 0.44 | 15.0 |
| Slo4a2 | 0.41 | 9.8 |
| D9Brol | 0.43 | 21.4 |
| Nos3 | 0.46 | 12.8 |
| D4Rat1 | 0.41 | 35.7 |
| D4Rat136 | 0.38 | 0.0 |
| Psmc2 | 0.38 | 11.4 |
| Fg12 | 0.31 | 12.7 |
| D4Rat5 | 0.35 | 6.2 |
| D4Rat6 | 0.35 | 25.6 |
| D4Rat7 | 0.22 | 22.0 |
| D4Rat8 | 0.15 | 68.7 |
| D4Mghl | 0.24 | 27.3 |
| Cacna2 | 0.27 | 16.2 |
| D4Rat149 | 0.30 | 50.0 |
| D4Rat150 | 0.45 | 156.7 |
| D4Rat125 | 0.11 | 45.1 |
| Pgyl | 0.11 | 37.3 |
| D4Rat9 | 0.12 | 37.3 |
| D4Rat126 | 0.18 | 9.0 |
| D4Rat10 | 0.11 | |

All distances are calculated from the RHMAXLIK analysis, except for the distance between the two linkage groups (D4Rat150 - D4Rat125), which is calculated from the RH2PT analysis.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

TABLE 7

Mouse and Rat Genes Used in the Present Study

| Gene | Gene Symbol (Accession no) | Sequence (Origin) | Anneal Temp (° C.) | Fragment Size *observed •expected (bp) | Primer Sequence 5' → 3' | SEQ ID NO: |
|---|---|---|---|---|---|---|
| Anion exchange member 2 | Slc4a2 (J04O36) | cDNA (Mouse) | 63 | 70* 71• | CTCCTCCTGCCCTCCTCATT TTGAAGCACTTTACTGCAGG | 150 151 |
| Fibroblast growth factor inducible 13 | Fin13 (U42383) | cDNA (Mouse) | 60 | 70* 79• | TCTGCTGTCCTCTTAAGCCT TCCAACACAACAGAGCACAG | 152 153 |
| Fibrinogen-like protein | Fg12 (M1576)1 | Genomic (Mouse) | 60 | 70* 68• | CAGGAACTGGAGAGTCAGGT GCCCCTGGATCTGGTCCTTT | 154 155 |
| Multidrug resistance protein | Pgy1 (M30697) | cDNA (Mouse) | 55 | 60* 56• | GAACTTGAAGAGGACCTTAA TTGCCCATCTTTGAGAAGTT | 156 157 |
| Thymidylate synthase | Tyms (M29309) | Genomic (Mouse) | 60 | 160* 157• | TGCCTTGCAAGCTGTAACCA GTCTGGCAGCAGTGTAGTCA | 158 159 |
| Proteasome 28S subunit ATPase 2 | Psmc2 (U61283) | cDNA (Mouse) | 65 | 70* 74• | CCGGATTACCTAGGTGCGGA TCCAGAGCTCGGATGGGCTT | 160 161 |
| Calcium channel | Cacna2 (M86621) | cDNA (Rat) | 55 | 70* 70• | CAGGAATATCTAGATGTTCTGTGG TCCACTGGACTTGCTTTGC | 162 163 |

What is claimed is:

1. An isolated nucleic acid molecule comprising a sequence selected from the group consisting of SEQ ID NO. 179, SEQ ID NO. 181, SEQ ID NO. 183, SEQ ID NO. 187, SEQ ID NO. 195, SEQ ID NO. 203, and SEQ ID NO. 204.

2. An isolated mutant CD36 coding region comprising the mutation set forth in SEQ ID. NO. 179.

3. An isolated mutant CD36 coding region comprising the mutation set forth in SEQ ID. NO. 181.

4. An isolated mutant CD36 coming region comprising the mutation set forth in SEQ ID. NO. 183.

5. An isolated mutant CD36 coding region comprising the mutation set forth in SEQ ID. NO. 187.

6. An isolated mutant CD36 coding region comprising the mutation set forth in SEQ ID. NO. 195.

7. An isolated mutant CD36 coding region comprising the mutation set forth in SEQ ID. NO. 203.

8. An isolated mutant CD36 coding region comprising the mutation set forth in SEQ ID. NO. 204.

9. An isolated CD36 nucleic acid sequence of at least 10 nucleotides comprising SEQ ID NO. 190.

10. An isolated CD36 nucleic acid sequence of at least 15 nucleotides comprising SEQ ID NO. 191.

11. An isolated CD36 nucleic acid sequence of at least 20 nucleotides comprising SEQ ID NO. 192.

12. An isolated CD36 nucleic acid sequence of at lest 15 nucleotides comprising SEQ ID NO. 194.

13. An isolated CD36 nucleic acid sequence of at least 15 nucleotides comprising SEQ ID NO 197.

14. An isolated CD36 nucleic acid sequence of at least 15 nucleotides comprising SEQ ID NO. 198.

15. An isolated CD36 nucleic acid sequence of at least 10 nucleotides comprising SEQ ID NO. 199.

16. An isolated CD36 nucleic acid sequence of at least 15 nucleotides comprising SEQ ID NO. 200.

17. An isolated CD36 nucleic acid sequence of at least 20 nucleotides comprising SEQ ID NO. 201.

18. An isolated CD36 nucleic acid sequence of at least 15 nucleotides comprising SEQ ID NO. 202.

* * * * *